(12) United States Patent
Catania et al.

(10) Patent No.: US 12,077,601 B2
(45) Date of Patent: Sep. 3, 2024

(54) ANTIBODIES TO UBIQUITIN C-TERMINAL HYDROLASE L1 (UCH-L1) AND GLIAL FIBRILLARY ACIDIC PROTEIN (GFAP) AND RELATED METHODS

(71) Applicant: Banyan Biomarkers, Inc., San Diego, CA (US)

(72) Inventors: Michael Catania, San Diego, CA (US); Ronald L. Hayes, San Diego, CA (US)

(73) Assignee: BANYAN BIOMARKERS, INC., San Diego, CA (US)

( * ) Notice: Subject to any disclaimer, the term of this patent is extended or adjusted under 35 U.S.C. 154(b) by 103 days.

(21) Appl. No.: 17/379,739

(22) Filed: Jul. 19, 2021

(65) Prior Publication Data

US 2021/0347914 A1    Nov. 11, 2021

Related U.S. Application Data

(62) Division of application No. 16/345,562, filed as application No. PCT/US2017/058881 on Oct. 27, 2017, now Pat. No. 11,078,298.

(60) Provisional application No. 62/414,569, filed on Oct. 28, 2016.

(51) Int. Cl.

| | | |
|---|---|---|
| *C07K 16/40* | (2006.01) | |
| *A61B 5/00* | (2006.01) | |
| *A61B 5/055* | (2006.01) | |
| *A61B 6/03* | (2006.01) | |
| *A61B 6/50* | (2024.01) | |
| *A61P 25/00* | (2006.01) | |
| *C07K 16/18* | (2006.01) | |
| *G01N 33/68* | (2006.01) | |
| *A61B 6/00* | (2024.01) | |

(52) U.S. Cl.
CPC ............ *C07K 16/40* (2013.01); *A61B 5/0042* (2013.01); *A61B 5/055* (2013.01); *A61B 6/032* (2013.01); *A61B 6/501* (2013.01); *A61P 25/00* (2018.01); *C07K 16/18* (2013.01); *G01N 33/6896* (2013.01); *C07K 2317/20* (2013.01); *C07K 2317/21* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search
CPC ............... C07K 16/40; C07K 2317/34; C07K 2317/52; C07K 2317/565; C07K 2317/76; C07K 2317/92; A61B 5/0042; A61B 6/501; A61P 25/00; A61P 9/00; A61P 9/10; A61P 17/02; A61P 21/04; A61P 25/16; A61P 25/28; A61P 29/00; A61P 31/00; A61P 31/04; A61P 31/12; A61P 31/14; A61P 31/20; A61P 31/22; A61P 33/14; A61P 39/02; A61P 43/00; G01N 33/6896; G01N 33/53
See application file for complete search history.

(56) References Cited

U.S. PATENT DOCUMENTS

| | | |
|---|---|---|
| 1,120,148 A | 12/1914 | Hull et al. |
| 1,146,000 A | 7/1915 | Koons |
| 2,172,896 A | 9/1939 | Walker |
| 4,275,149 A | 6/1981 | Litman et al. |
| 4,366,241 A | 12/1982 | Tom et al. |
| 4,376,110 A | 3/1983 | David et al. |
| 4,419,446 A | 12/1983 | Howley et al. |
| 4,517,288 A | 5/1985 | Geigel et al. |
| 4,560,655 A | 12/1985 | Baker et al. |
| 4,601,978 A | 7/1986 | Karin |
| 4,657,866 A | 4/1987 | Kumar |
| 4,676,980 A | 6/1987 | Segal et al. |
| 4,702,909 A | 10/1987 | Villarejos et al. |
| 4,743,542 A | 5/1988 | Graham et al. |
| 4,767,704 A | 8/1988 | Cleveland et al. |
| 4,816,567 A | 3/1989 | Cabilly et al. |
| 4,837,168 A | 6/1989 | de Jaeger et al. |
| 4,927,762 A | 5/1990 | Darfler |
| 4,965,199 A | 10/1990 | Capon et al. |
| 5,045,694 A | 9/1991 | Beavis et al. |
| 5,118,606 A | 6/1992 | Lynch et al. |
| 5,118,937 A | 6/1992 | Hillenkamp et al. |

(Continued)

FOREIGN PATENT DOCUMENTS

| | | |
|---|---|---|
| EP | 0732399 | 9/1996 |
| EP | 0789578 | 8/1997 |

(Continued)

OTHER PUBLICATIONS

Rudikoff et al, Proc Natl Acad Sci USA 1982 vol. 79 p. 1979 (Year: 1982).*
Rudikoff et al. Proc Natl Acad Sci USA vol. 79 p. 1979, (1982 ) (Year: 1982).*
MacCallum et al. J. Mol. Biol. 262, 732-745, (1996) (Year: 1996).*
Pascalis et al. The Journal of Immunology 169, 3076-3084 (2002) (Year: 2002).*
Casset et al. BBRC 307, 198-205, (2003) (Year: 2003).*
Vajdos et al. 320, 415-428 (2002) (Year: 2002).*

(Continued)

*Primary Examiner* — Kimberly Ballard
*Assistant Examiner* — Stacey N MacFarlane
(74) *Attorney, Agent, or Firm* — Oliff PLC

(57) ABSTRACT

The invention provides anti-UCH-L1 antibodies and anti-GFAP antibodies and their use in in vitro detection of UCH-L1 and GFAP, respectively, in a sample from an individual, such as an individual known or suspected of having a brain injury or damage, for example, neurological damage such as mild traumatic brain injury. Also provided are methods, systems and kits for diagnosing brain injury or damage, such as neurological damage, in an individual with the aforementioned antibodies as well as compositions comprising the anti-UCH-L1 antibodies and anti-GFAP antibodies.

20 Claims, No Drawings

Specification includes a Sequence Listing.

(56) References Cited

U.S. PATENT DOCUMENTS

| | | |
|---|---|---|
| 5,122,464 A | 6/1992 | Wilson et al. |
| 5,122,469 A | 6/1992 | Mather et al. |
| 5,231,000 A | 7/1993 | Majocha et al. |
| 5,234,814 A | 8/1993 | Card et al. |
| 5,252,463 A | 10/1993 | Nelson et al. |
| 5,264,365 A | 11/1993 | Georgiou et al. |
| 5,270,163 A | 12/1993 | Gold et al. |
| 5,380,650 A | 1/1995 | Barnard et al. |
| 5,475,096 A | 12/1995 | Gold et al. |
| 5,492,812 A | 2/1996 | Vooheis |
| 5,508,192 A | 4/1996 | Georgiou et al. |
| 5,536,639 A | 7/1996 | Siman et al. |
| 5,567,588 A | 10/1996 | Gold et al. |
| 5,571,894 A | 11/1996 | Wels et al. |
| 5,587,458 A | 12/1996 | King et al. |
| 5,595,877 A | 1/1997 | Gold et al. |
| 5,614,649 A | 3/1997 | Iqbal et al. |
| 5,637,459 A | 6/1997 | Burke et al. |
| 5,639,635 A | 6/1997 | Joly et al. |
| 5,641,870 A | 6/1997 | Rinderknecht et al. |
| 5,648,237 A | 7/1997 | Carter |
| 5,660,985 A | 8/1997 | Pieken et al. |
| 5,670,637 A | 9/1997 | Gold et al. |
| 5,683,867 A | 11/1997 | Biesecker et al. |
| 5,696,249 A | 12/1997 | Gold et al. |
| 5,707,796 A | 1/1998 | Gold et al. |
| 5,710,132 A | 1/1998 | Moller et al. |
| 5,719,060 A | 2/1998 | Hutchens et al. |
| 5,733,721 A | 3/1998 | Hemstreet et al. |
| 5,750,345 A | 5/1998 | Bowie |
| 5,777,194 A | 7/1998 | Scott et al. |
| 5,792,664 A | 8/1998 | Chait et al. |
| 5,830,870 A | 11/1998 | Iqbal et al. |
| 5,840,523 A | 11/1998 | Simmons et al. |
| 5,869,046 A | 2/1999 | Presta et al. |
| 5,869,336 A | 2/1999 | Mever et al. |
| 5,871,712 A | 2/1999 | Siman |
| 5,891,693 A | 4/1999 | Bebbington et al. |
| 5,990,083 A | 11/1999 | Iqbal et al. |
| 6,011,020 A | 1/2000 | Gold et al. |
| 6,027,888 A | 2/2000 | Georgiou et al. |
| 6,048,703 A | 4/2000 | Siman et al. |
| 6,057,143 A | 5/2000 | Meyer et al. |
| 6,083,715 A | 7/2000 | Georgiou et al. |
| 6,183,977 B1 | 2/2001 | Doyle et al. |
| 6,225,047 B1 | 5/2001 | Hutchens et al. |
| 6,235,489 B1 | 5/2001 | Jackowski |
| 6,248,516 B1 | 6/2001 | Winter et al. |
| 6,449,562 B1 | 9/2002 | Chandler et al. |
| 6,589,746 B1 | 7/2003 | Zemlan |
| 6,664,442 B2 | 12/2003 | McConlogue et al. |
| 6,884,591 B2 | 4/2005 | Janigro et al. |
| 6,982,321 B2 | 1/2006 | Winter |
| 7,014,854 B2 | 3/2006 | Jackowski et al. |
| 7,087,409 B2 | 8/2006 | Barbas et al. |
| 7,144,708 B2 | 12/2006 | Janigro et al. |
| 7,229,619 B1 | 6/2007 | Young et al. |
| 7,256,252 B1 | 8/2007 | Siman et al. |
| 7,291,495 B2 | 11/2007 | Bejanin et al. |
| 7,291,497 B2 | 11/2007 | Holmes et al. |
| 7,291,710 B2 | 11/2007 | Hayes et al. |
| 7,371,582 B2 | 5/2008 | Nahm et al. |
| 7,396,654 B2 | 7/2008 | Hayes et al. |
| 7,396,689 B2 | 7/2008 | Dowd et al. |
| 7,419,821 B2 | 9/2008 | Davis et al. |
| 7,456,027 B2 | 11/2008 | Wang et al. |
| 7,645,584 B2 | 1/2010 | Svetlov et al. |
| 7,682,833 B2 | 3/2010 | Miller et al. |
| 7,723,099 B2 | 5/2010 | Miller et al. |
| 7,910,352 B2 | 3/2011 | Miller et al. |
| 7,981,843 B2 | 7/2011 | Flynn et al. |
| 8,017,382 B2 | 9/2011 | Davis et al. |
| 8,048,638 B2 | 11/2011 | Svetlov et al. |
| 8,168,439 B2 | 5/2012 | Miller et al. |
| 8,298,835 B2 | 10/2012 | Wang et al. |
| 8,309,364 B2 | 11/2012 | Miller et al. |
| 8,492,107 B2 | 7/2013 | Wang et al. |
| 8,557,526 B2 | 10/2013 | Ottens et al. |
| 8,642,558 B2 | 2/2014 | Anagli et al. |
| 9,023,651 B2 | 5/2015 | Evers et al. |
| 9,074,019 B2 | 7/2015 | Anagli et al. |
| 9,664,694 B2 | 5/2017 | Wang et al. |
| 9,810,698 B2 | 11/2017 | Wang et al. |
| 10,041,959 B2 | 8/2018 | Wang et al. |
| 10,330,689 B2 | 6/2019 | Wang et al. |
| 10,794,918 B2 | 10/2020 | Curdt et al. |
| 11,078,298 B2 | 8/2021 | Catania et al. |
| 2001/0001285 A1 | 5/2001 | Moh |
| 2002/0123059 A1 | 9/2002 | Ho |
| 2002/0147998 A1 | 10/2002 | McConlogue et al. |
| 2003/0040660 A1 | 2/2003 | Jackowski et al. |
| 2003/0119064 A1 | 6/2003 | Valkirs et al. |
| 2003/0129134 A1 | 7/2003 | Chenard et al. |
| 2003/0199000 A1 | 10/2003 | Valkirs et al. |
| 2004/0121343 A1 | 6/2004 | Buechler et al. |
| 2004/0203083 A1 | 10/2004 | Buechler et al. |
| 2004/0253637 A1 | 12/2004 | Buechler et al. |
| 2005/0063942 A1 | 3/2005 | Clark et al. |
| 2005/0112585 A1 | 5/2005 | Zichi et al. |
| 2005/0130226 A1 | 6/2005 | Ahn |
| 2005/0136489 A1 | 6/2005 | Tseng et al. |
| 2005/0244890 A1 | 11/2005 | Davies |
| 2005/0260654 A1 | 11/2005 | Wang et al. |
| 2005/0260697 A1 | 11/2005 | Wang et al. |
| 2006/0094064 A1 | 5/2006 | Ray et al. |
| 2006/0099593 A1 | 5/2006 | Nawa et al. |
| 2006/0134098 A1 | 6/2006 | Bebbington et al. |
| 2006/0240480 A1 | 10/2006 | Curdt et al. |
| 2006/0246489 A1 | 11/2006 | Svetlov et al. |
| 2006/0292558 A1 | 12/2006 | O'Neill |
| 2007/0003982 A1 | 1/2007 | Hayes et al. |
| 2007/0027634 A1 | 2/2007 | Mendrick et al. |
| 2007/0042425 A1 | 2/2007 | Hochstrasser et al. |
| 2007/0074972 A1 | 4/2007 | Nassef |
| 2007/0255113 A1 | 11/2007 | Grimes |
| 2007/0298433 A1 | 12/2007 | Sia et al. |
| 2009/0041626 A1 | 2/2009 | Atkin |
| 2009/0068691 A1 | 3/2009 | Dave et al. |
| 2009/0087868 A1 | 4/2009 | Wang et al. |
| 2009/0130658 A1 | 5/2009 | Barlag |
| 2009/0317805 A1 | 12/2009 | Wang et al. |
| 2010/0047817 A1 | 2/2010 | Ottens et al. |
| 2010/0198142 A1 | 8/2010 | Sloan et al. |
| 2010/0317041 A1 | 12/2010 | Wang et al. |
| 2011/0082203 A1 | 4/2011 | Wang et al. |
| 2011/0097392 A1 | 4/2011 | Wang et al. |
| 2011/0143375 A1 | 6/2011 | Wang et al. |
| 2011/0177974 A1 | 7/2011 | Wang et al. |
| 2012/0028904 A1 | 2/2012 | Anagli et al. |
| 2012/0196307 A1 | 2/2012 | Ottens et al. |
| 2012/0168305 A1 | 7/2012 | Hunter et al. |
| 2012/0178186 A1 | 7/2012 | Nieuwennhuis et al. |
| 2012/0202231 A1 | 8/2012 | Wang et al. |
| 2013/0022982 A1 | 1/2013 | Wang et al. |
| 2013/0029362 A1 | 1/2013 | Jeromin et al. |
| 2013/0029859 A1 | 1/2013 | Svetlov et al. |
| 2014/0018299 A1 | 1/2014 | Mondello et al. |
| 2014/0024053 A1 | 1/2014 | Kobeissy et al. |
| 2014/0178351 A1 | 6/2014 | Svetlov et al. |
| 2014/0228298 A1 | 8/2014 | Anagli et al. |
| 2014/0275294 A1 | 9/2014 | Svetlov et al. |
| 2014/0303041 A1 | 10/2014 | Hayes et al. |
| 2014/0342381 A1 | 11/2014 | Hayes |
| 2014/0370583 A1 | 12/2014 | Miller |
| 2015/0141528 A1 | 5/2015 | Larner |
| 2015/0247867 A1 | 9/2015 | Curdt et al. |
| 2015/0259740 A1 | 9/2015 | Pollard et al. |
| 2015/0268252 A1 | 9/2015 | Svetlov et al. |
| 2017/0045534 A1 | 2/2017 | Wang et al. |
| 2017/0146555 A1 | 5/2017 | Wang et al. |
| 2017/0176460 A1 | 6/2017 | Larner |
| 2017/0242036 A1 | 8/2017 | Pollard et al. |
| 2017/0242041 A1 | 8/2017 | Wang et al. |
| 2017/0281738 A1 | 10/2017 | Svetlov et al. |

(56) References Cited

U.S. PATENT DOCUMENTS

| | | |
|---|---|---|
| 2017/0307640 A1 | 10/2017 | Kobaissy et al. |
| 2018/0031577 A1 | 2/2018 | Wang et al. |
| 2018/0059123 A1 | 3/2018 | Wang et al. |
| 2019/0064187 A1 | 2/2019 | Svetlov et al. |
| 2019/0064188 A1 | 2/2019 | Wang et al. |
| 2020/0003789 A1 | 1/2020 | Wang et al. |
| 2020/0165355 A1 | 5/2020 | Catania et al. |
| 2021/0011028 A1 | 1/2021 | Wang et al. |
| 2021/0102958 A1 | 4/2021 | Curdt et al. |
| 2022/0113321 A1 | 4/2022 | Wang et al. |

FOREIGN PATENT DOCUMENTS

| | | |
|---|---|---|
| EP | 1037626 | 9/2000 |
| EP | 1310797 | 5/2003 |
| EP | 1519194 | 3/2005 |
| EP | 2143735 | 1/2010 |
| EP | 2245466 | 11/2010 |
| JP | 2000-505544 | 5/2000 |
| JP | 2003-070498 | 3/2003 |
| JP | 2007-532915 | 11/2007 |
| JP | 2007-535318 | 12/2007 |
| WO | WO-1987/000195 | 1/1987 |
| WO | WO-1990/003430 | 4/1990 |
| WO | WO-1990/015331 | 12/1990 |
| WO | WO-1991/013904 | 9/1991 |
| WO | WO-1992/00374 | 1/1992 |
| WO | WO-1993/006213 | 4/1993 |
| WO | WO-1993/008829 | 5/1993 |
| WO | WO-1993/016185 | 8/1993 |
| WO | WO-1993/024834 | 12/1993 |
| WO | WO-1995/026506 | 10/1995 |
| WO | WO-1996/02634 | 2/1996 |
| WO | WO-1996/14857 | 5/1996 |
| WO | WO-1996/34097 | 10/1996 |
| WO | WO-1998/021590 | 5/1998 |
| WO | WO-1999/030707 | 6/1999 |
| WO | WO-1999/051773 | 10/1999 |
| WO | WO-2000/004389 | 1/2000 |
| WO | WO-2000/014546 | 3/2000 |
| WO | WO-2000/056934 | 9/2000 |
| WO | WO-2000/078807 | 12/2000 |
| WO | WO-2002/093174 | 11/2002 |
| WO | WO-2003/016910 | 2/2003 |
| WO | WO-2003/019181 | 3/2003 |
| WO | WO-2003/032894 | 4/2003 |
| WO | WO/2003/032894 | 4/2003 |
| WO | WO-2003/062824 | 7/2003 |
| WO | WO-2003/085083 | 10/2003 |
| WO | WO-2004/025298 | 3/2004 |
| WO | WO-2004/059293 | 7/2004 |
| WO | WO-2004/078204 | 9/2004 |
| WO | WO-2005/004794 | 1/2005 |
| WO | WO-2005/029087 | 3/2005 |
| WO | WO-2005/029088 | 3/2005 |
| WO | WO-2005/106038 | 11/2005 |
| WO | WO-2005/113798 | 12/2005 |
| WO | WO-2007/007129 | 1/2007 |
| WO | WO-2007/046811 | 4/2007 |
| WO | WO-2007/140188 | 12/2007 |
| WO | WO-2008/008819 | 1/2008 |
| WO | WO-2008/063369 | 5/2008 |
| WO | WO-2008/095136 | 8/2008 |
| WO | WO-2008/097618 | 8/2008 |
| WO | WO-2007/094395 | 7/2009 |
| WO | WO-2009/100131 | 8/2009 |
| WO | WO-2009/129476 | 10/2009 |
| WO | WO-2010/019553 | 2/2010 |
| WO | WO-2010/033912 | 3/2010 |
| WO | WO-2010/148391 | 12/2010 |
| WO | WO-2011/011334 | 1/2011 |
| WO | WO-2011/032155 | 3/2011 |
| WO | WO-2011/077333 | 6/2011 |
| WO | WO-2021/123844 | 10/2011 |
| WO | WO-2011/160096 | 12/2011 |
| WO | WO-2012/051519 | 4/2012 |
| WO | WO-2012/141674 | 10/2012 |
| WO | WO-2013/040502 | 3/2013 |
| WO | WO-2014/194329 | 12/2014 |
| WO | WO-2015/143387 | 9/2015 |
| WO | WO-2015/157300 | 10/2015 |
| WO | WO-2015/157390 | 12/2016 |

OTHER PUBLICATIONS

Holm et al. 44, 1075-1084 (2007) (Year: 2007).*
Chen et al. J. Mol. Bio. 293, 865-881 (1999) (Year: 1999).*
Wu et al. J. Mol. Biol. 294, 151-162 (1999) (Year: 1999).*
"Anti-PGP9.5 antibody [13C4/13C4]ab 8189 11," Abcam online catalogue, Jan. 1, 1988, Retrieved from the Internet: URL:http://www.abcam.com/PGP95-antibody-13 C4-I3C4-ab8189.pdf, retrieved on Jan. 4, 2018, 6 pages.
"Cerebral contusion" published by Wikipedia online on Sep. 13, 2006. Retrieved from http://en.wikipedia.org/wik/Cerebral_contusion. Retrieved on Mar. 20, 2017 1:54:09 PM.
"Recommendations of the German Society for Clinical Chemistry," Z. klin. Chem. u. klin. Biochem., 1972, pp. 182-192.
Adams et al., "The neuropathology of the vegetative state after an acute brain insult," Brain (2000) 123:1327-1338.
Al-Lazikani et al., "Standard conformations for the canonical structures of immunoglobulins," J Mol Biol (1997) 273(4):927-948.
André et al., "NMDA Receptor Alterations in Neurons from Pediatric Cortical Dysplasia Tissue," Cereb Cortex (2004) 14(6):634-646.
Ankeny et al., "Mechanisms and implications of adaptive immune responses after traumatic spinal cord injury," Neuroscience (2009) 158:1112-1121; Epub Jul. 4, 2008.
Araki et al., "Developmentally regulated expression of Neuro-p24 and its possible function in neurite extension," Neurosci Res (2002) 44(4):379-389.
Arie et al., "Chaperone function of FkpA, a heat shock prolyl isomerase, in the periplasm of *Escherichia coli*," Mol Microbiol (2001) 39(1):199-210.
Arnaud et al., "Proteasome-caspase-cathepsin sequence leading to tau pathology induced by prostaglandin J2 in neuronal cells," J Neurochem (2009) 110(1):328-342.
Aurell et al., "Determination of S-100 and glial fibrillary acidic protein concentrations in cerebrospinal fluid after brain infarction," Stroke (1991) 22(10):1254-1258.
Authoritative Dictionary of IEEE Standard Terms. Seventh Edition. 2000. Excerpt of definitions of "parallel" and "serial".
Baldwin et al., "Intermediate filament change in astrocytes following mild cortical contusion," Glia (1996) 16(3):266-275.
Barnes et al., "Methods for growth of cultured cells in serum-free medium," Anal Biochem (1980) 102(2):255-270.
Bartus et al., "Time-related neuronal changes following middle cerebral artery occlusion: implications for therapeutic intervention and the role of calpain," J Cereb Blood Flow Metab (1995) 15(6):969-979.
Bass et al., "Hormone phage: an enrichment method for variant proteins with altered binding properties," Proteins (1990) 8(4):309-314.
Bauman et al., "An introductory characterization of a combat-casualty-care relevant swine model of closed head injury resulting from exposure to explosive blast*," Journal of Neurotrauma (2009) 26:841-860.
Beer et al., "Temporal Profile and Cell Subtype Distribution of Activated Caspase-3 Following Experimental Traumatic Brain Injury," J Neurochem (2000) 75:1264-1273.
Belay et al., "Creutzfeldt-Jakob Disease in Unusually Young Patients Who Consumed Venison," Arch. Neurol (2001) 58(10): 1673-1678.
Berger et al., "Serum Concentrations of Ubiquitin C-Terminal Hydrolase-L1 and αII-Spectrin Breakdown Product 145 kDa Correlate with Outcome after Pediatric Tbi," J Neurotrauma (2012) 29(1): 162-167.
Binder et al., "The Distribution of Tau in the Mammalian Central Nervous System," J Cell Biol (1985)101:1371-1378.

(56) References Cited

OTHER PUBLICATIONS

Bitsch et al., "Serum Tau Protein Level as a Marker of Axonal Damage in Acute Ischemic Stroke," Eur Neurol (2002) 47(1):45-51.
Blennow "Cerebrospinal Fluid Protein Biomarkers for Alzheimer's Disease," NeuroRx (2004) 1(2):213-225.
Boerner et al., "Production of antigen-specific human monoclonal antibodies from in vitro-primed human splenocytes," J Immunol (1991) 147(1):86-95.
Borghi et al., "Full length alpha-synuclein is present in cerebrospinal fluid from Parkinson's disease and normal subjects," Neurosci Lett (2000) 287(1):65-67.
Bornstein et al., "Antibodies to brain antigens following stroke," Neurology (2001) 56(4):529-530.
Bothmann et al., "The Periplasmic *Escherichia coli* Peptidylprolyl cis, trans-Isomerase FkpA I. Increased Functional Expression of Antibody Fragments With and Without cis-Prolines," J Biol Chem (2000) 275:17100-17105.
Bramlett et al., "Quantitative structural changes in white and gray matter 1 year following traumatic brain injury in rats," Acta Neuropathologica (2002) 103:607-614.
Brennan et al., "Preparation of bispecific antibodies by chemical recombination of monoclonal immunoglobulin G1 fragments," Science (1985) 229(4708):81-83.
Brief Communication granting Extension of Time for EP 09807153.3, dated Mar. 18, 2019. 4 pages.
Brief Communication Notifications (Proprietor and Opponent) concerning the date of oral proceedings for EP 09807153.3, dated Aug. 19, 2020; 2 pages.
Brief Communication Notifications (Proprietor and Opponent) concerning the date of oral proceedings for EP 09807153.3, dated Feb. 24, 2021; 6 pages.
Brief Communication Notifiy Proprietor re Written Submissions for EP 09807153.3, dated Apr. 22, 2021; 10 pages.
Brief Communication Postponing Oral Proceedings for EP 09807153.3, dated Jun. 8, 2020. 2 pages.
Brief Communication re Letter from Proprietor for EP 09807153.3, dated Jan. 9, 2020; 57 pages.
Brodeur et al., Monoclonal Antibody Production Techniques and Applications, pp. 51-63 (Marcel Dekker, Inc., New York, 1987); BOOK.
Brophy et al., "AlphaII-Spectrin breakdown product cerebrospinal fluid exposure metrics suggest differences in cellular injury mechanisms after severe traumatic brain injury," J Neurotrauma (2009) 26:471-479.
Brophy et al., "Biokinetic Analysis of Ubiquitin C-Terminal Hydrolase-L1 (UCH-L1) in Severe Traumatic Brain Injury Patient Biofluids," J Neurotrauma (2011) 28(6):861-870.
Buki et al., "Cytochrome c Release and Caspase Activation in Traumatic Axonal Injury," J Neurosci (2000) 20(8):2825-2834.
Canu et al., "Tau Cleavage and Dephosphorylation in Cerebellar Granule Neurons Undergoing Apoptosis," J Neurosci (1998) 18(18):7061-7074.
Cao et al., "Cleavage of Bax to p18 Bax accelerates stress-induced apoptosis, and a cathespin-like protease may rapidly degrade p18 Bax," Blood (2003) 102(7):2605-2614.
Carrillo et al., "The Multiple Sequence Alignment Problem in Biology," SIAM J. Appl Math (1987) 48(5):1073-1082.
Carter et al., "High Level *Escherichia coli* Expression and Production of a Bivalent Humanized Antibody Fragment," Bio/Technology (1992) 10:163-167.
Carter et al., "Humanization of an anti-p185HER2 antibody for human cancer therapy," PNAS USA (1992) 89(10):4285-4289.
Casset et al., "A peptide mimetic of an anti-CD4 monoclonal antibody by rational design," Biochem Biophys Res Commun. (2003) 307(1): 198-205.
CDC, Glasgow Coma Scale, published Apr. 19, 2004 [online] Retrieved from https://www.cdc.gov/masstrauma/resources/gcs.pdf; Retrieved on Feb. 7, 2020. (Year: 2004).

Chekhonin et al., "Enzyme immunoassay of antibodies to neurospecific proteins in examination of blood-brain barrier function," Immunologiya (1996) 0(2):67-69.
Chen et al., "Chaperone Activity of DsbC*," The Journal of Biological Chemistry (1999) 274:19601-19605.
Chen et al., "Selection and analysis of an optimized anti-VEGF antibody: crystal structure of an affinity-matured Fab in complex with antigen," J Mol Biol (1999) 293(4):865-881.
Chothia et al., "Canonical structures for the hypervariable regions of immunoglobulins," J Mol Biol (1987) 196(4):901-917.
Christman et al., "Ultrastructural Studies of Diffuse Axonal Injury in Humans." J Neurotrauma (2009) 11:173-186.
Chung et al., "Proapoptotic Effects of Tau Cleavage Product Generated by Caspase-3," Neurobiol Dis (2001) 8(1):162-172.
Clark et al., "Caspase-3 Mediated Neuronal Death After Traumatic Brain Injury in Rats," J Neurochem (2000) 74(2):740-753.
Communication Notifications (Proprietor and Opponent) concerning reference File No. for Notice of Appeal proceedings for EP 09807153.3, dated Oct. 12, 2021; 4 pages.
Communication of Amended Entries Representative EP 09807153.3, dated Feb. 4, 2019. 1 page.
Communication of Notice of Opposition for EP 09807153.3, dated Nov. 7, 2018, 116 pages.
Communication of Notice of Opposition Request for Observations for EP 09807153.3, dated Nov. 16, 2018, 1 page.
Cookson, "Parkin's substrates and the pathways leading to neuronal damage," Neuromolecular Med (2003) 3(1):1-13.
Cotman et al., "The Role of Caspase Cleavage of Tau in Alzheimer Disease Neuropathology," J Neuropathol Exp Neurol (2005) 64(2): 104-112.
Cox et al., "Dicyclomine, an M1 Muscarinic Antagonist, Reduces Biomarker Levels, But Not Neuronal Degeneration, in Fluid Percussion Brain Injury," J Neurotrauma (2008) 25(11):1355-1365.
Cunningham et al., "High-resolution epitope mapping of hGH-receptor interactions by alanine-scanning mutagenesis," Science (1989) 244(4908):1081-1085.
Cutler et al., "Review of the Next Generation of Alzheimer's Disease Therapeutics: Challenges for Drug Development," Prog Neuropsychopharmacol Biol Psychiatry (2001) 25(1):27-57.
Dambinova et al., "Blood Test Detecting Autoantibodies to N-Methyl-D-aspartate Neuroreceptors for Evaluation of Patients with Transient Ischemic Attack and Stroke," Clin Chem (2003) 49(10):1752-1762.
Dambinova et al., "The presence of autoantibodies to N-terminus domain of GluR1 subunit of AMPA receptor in the blood serum of patients with epilepsy," J Neurol Sci (1997) 152(1):93-97.
Dash et al., "Biomarkers for the Diagnosis, Prognosis, and Evaluation of Treatment Efficacy for Traumatic Brain Injury," Neurotherapeutics (2010) 7(1):100-114.
De Kruijk et al., "S-100B and neuron-specific enolase in serum of mild traumatic brain injury patients," Acta Neurol. Scand. (2001) 103:175-179.
Decision in Opposition Proceeding (Opponent) for EP 09807153.3, dated Jul. 15, 2021; 94 pages.
Decision in Opposition Proceeding (Proprietor) for EP 09807153.3, dated Jul. 15, 2021; 94 pages.
Dekosky et al., "Looking Backward to Move Forward: Early Detection of Neurodegenerative Disorders," Science (2003) 302(5646):830-834.
Del Prete et al., "Migration of dendritic cells across blood and lymphatic endothelial barriers," Thromb Haemost (2006) 95(1):22-28.
Delobel et al., "Proteasome inhibition and Tau proteolysis: an unexpected regulation," FEBS Lett (2005) 579(1):1-5.
Denning et al., "Protein Kinase Cdelta Is Activated by Capase-dependent Proteolysis during Ultraviolet Radiation-induced Apoptosis of Human Keratinocytes," J Biol Chem (1998) 273(45):29995-30002.
Dixon et al., "A controlled cortical impact model of traumatic brain injury in the rat," J Neurosci Methods (1991) 39(3):253-262.
Drubin et al., "Tau Protein Function in Living Cells," J Cell Biol (1986) 103(6):2739-2746.

(56) References Cited

OTHER PUBLICATIONS

Dvorak et al., "Characterisation of the diagnostic window of serum glial fibrillary acidic protein for the differentiation of intracerebral haemorrhage and ischaemic stroke," Cerebrovasc Dis (2009) 27:37-41.
Dykman et al., "Gold Nanoparticles in Biology and Medicine: Recent Advances and Prospects," Acta Naturae (2011) 3(2):34-55.
ECG Guidelines, "Part 7: The Era of Reperfusion, Section 2: Acute Stroke", Circulation 2000;102(suppl 1):1-204-1-216, https://doi.org/10.1161/01.CIR.102.suppl_1.1-204 (Year: 2000).
Eikelenboom et al., "Multiple sclerosis, Neurofilament light chain antibodies are correlated to cerebral atrophy," Neurology (2003) 60(2):219-223.
El-Fawal et al., "Autoantibodies to neurotypic and gliotypic proteins as biomarkers of neurotoxicity: assessment of trimethyltin (TMT)," Neurotoxicology (2008) 29(1):109-115.
Englebienne et al., "Use of colloidal gold surface plasmon resonance peak shift to infer affinity constants from the interactions between protein antigens and antibodies specific for single or multiple epitopes," Analyst (1998) 123:1599.
Esselman et al., "Review of subject: Classification of the spectrum of mild traumatic brain injury," Brain Injury (1995) 9(4):417-424.
Estrov et al., "Caspase 2 and Caspase 3 Protein Levels as Predictors of Survival in Acute Myelogenous Leukemia," Blood (1998) 92(9):3090-3097.
Everbroeck et al., "A Prospective Study of CSF Markers in 250 Patients with Possible Creutzfeldt-Jakob Disease," J Neurol Neurosurg Psychiatry (2003) 74:1210-1214.
Finfer et al., "A comparison of albumin and saline for fluid resuscitation in the intensive care unit," N Engl J Med (2004) 350(22):2247-2256.
Foerch et al., "Serum glial fibrillary acidic protein as a biomarker for intracerebral hemorrhage in patients with acute stroke," J Neurol Neurosurg Psychiatry (2006) 77:181-184.
Franz et al., "Amyloid beta 1-42 and tau in cerebrospinal fluid after severe traumatic brain injury," Neurology (2003) 60(9):1457-1461.
Frijns et al., "Inflammatory Cell Adhesion Molecules in Ischemic Cerebrovascular Disease," Stroke (2002) 33(8):2115-2122.
Gabbita et al., "Cleaved-Tau: A Biomarker of Neuronal Damage after Traumatic Brain Injury," J Neurotrauma (2005) 22(1):83-94.
Gamblin et al., "Caspase cleavage of tau: Linking amyloid and neurofibrillary tangles in Alzheimer's disease," Proc Natl Acad Sci USA (2003) 100(17):10032-10037.
Garcia et al., "Going new places using an old MAP: tau, microtubules and human neurodegenerative disease" Curr Opin Cell Biol (2001) 13(1):41-48.
Garcia-Sierra et al., "Truncation of Tau Protein and its Pathological Significance in Alzheimer's Disease," J Alzheimers Dis (2008) 14(4):401-409.
Gaskin et al., "Patients with clinically diagnosed senile dementia of the Alzheimer type make autoantibodies that react with neurofibrillary tangles," Clinical Research (1986) 34(2): 669A.
Giza et al., "The Neurometabolic Cascade of Concussion," J Athl Train (2001) 36(3):228-235.
Goryunova et al., "Glutamate Receptor Autoantibody Concentrations in Children with Chronic Post-Traumatic Headache," Neuroscience and Behavioral Physiology (2007) 37(8):761-764.
Graham et al., "Characteristics of a human cell line transformed by DNA from human adenovirus type 5," J Gen Virol (1977) 36(1):59-74.
Gruden et al., "Differential neuroimmune markers to the onset of Alzheimer's disease neurodegeneration and dementia: autoantibodies to Abeta((25-35)) oligomers, S100b and neurotransmitters," J Neuroimmunol (2007) 186(1-2):181-192.
Grus et al., "Analysis of complex autoantibody repertoires by surface-enhanced laser desorption/ionization-time of flight mass spectrometry," Proteomics (2003) 3(6):957-961.
Guillozet-Bongaarts et al., "Tau truncation during neurofibrillary tangle evolution in Alzheimer's disease," Neurobiol Aging (2005) 26(7):1015-1022.

Guss et al., "Structure of the lgG-binding regions of streptococcal protein G," EMBO J (1986) 5(7):1567-1575.
Hailer., "Immunosuppression after traumatic or ischemic CNS damage: It is neuroprotective and illuminates the role of microglial cells," Progres Neurobiol. (2008) 84:211-233.
Hajimohammadreza et al., "A Specific Inhibitor of Calcium/Calmodulin-Dependent Protein Kinase-II Provides Neuroprotection Against NMDA- and Hypoxia/Hypoglycemia-Induced Cell Death," J Neurosci (1995) 15(5):4093-4101.
Hajimohammadreza et al., "Neuronal Nitric Oxide Synthase and Calmodulin-Dependent Protein Kinase II alpha Undergo Neurotoxin-Induced Proteolysis," J Neurochem (1997) 69(3):1006-1013.
Ham et al., "[5] Media and growth requirements," Methods in Enzymology (1979) 58:44-93.
Hamaoui et al., "Real-Time Quantitative PCR Measurement of Circulatory Rhodopsin mRNA in Healthy Subjects and Patients with Diabetic Retinopathy," Annals of the New York Academy of Sciences (2004) 1022:152-156.
Hansen et al., "Frontal cortical synaptophysin in Lewy body diseases: relation to Alzheimer's disease and dementia" J Neurol Neurosurg Psychiatry (1998) 64(5): 653-656.
Hara et al., "Overproduction of Penicillin-Binding Protein 7 Suppresses Thermosensitive Growth Defect at Low Osmolarity due to an spr Mutation of *Escherichia coli*," Microbial Drug Resistance (1996) 2(1):63-72.
Harris, "Therapeutic Monoclonals," Biochem. Soc. Transactions 23:1035-1038 (1995).
Hasselmann et. al., "Extracellular Tyrosinase mRNA within Apoptotic Bodies is Protected from Degradations in Human Serum," Clinical Chemistry (2001) 47(8):1488-1489.
Hayakawa, T. et al., "Astroprotein (GFAP) Levels in Cerebrospinal Fluid of Stroke Patients," Neurol Med Chir (Tokyo)24, 13-18, 1984.
Herrmann et al., "Release of Glial Tissue-Specific Proteins After Acute Stroke: A comparative analysis of serum concentrations of protein S-100B and glial fibrillary acidic protein," Stroke (2000) 31(11):2670-2677.
Hesselink, "Imaging of Stroke and Cerebral Ischemia", Aug. 2003, 9 pages, retrieved from https://web.archive.org/web/20030826111030/http://spinwarp.ucsd.edu/neuroweb/Text/br-71 0.htm on May 6, 2018 (Year: 2003).
Higuchi et al., "Tau and axonopathy in neurodegenerative disorders," Neuromolecular Med (2002) 2(2):131-150.
Hinkle et al., "GFAP and S100β Expression in the Cortex and Hippocampus in Response to Mild Cortical Contusion," J Neurotrama (1997) 14(10):729-738.
Holm et al.,, "Functional mapping and single chain construction of the anti-cytokeratin 8 monoclonal antibody TS1," Mol Immunol. (2007) 44(6): 1075-1084.
Honda et al., "Serum glial fibrillary acidic protein is a highly specific biomarker for traumatic brain injury in humans compared with S-100B and neuron-specific enolase," J. Trauma (2010) 69:104-109.
Honegger et al., "Yet another numbering scheme for immunoglobulin variable domains: an automatic modeling and analysis tool," J Mol Biol (2001) 309(3):657-670.
Hozumi et al., "GFAP mRNA levels following stab wounds in rat brain," Brain Res (1990) 534(1-2):291-294.
Hudson et al., "Engineered antibodies," Nat Med (2003) 9(1):129-134.
Hurle et al., "Protein engineering techniques for antibody humanization," Curr Opin in Biotechnol (1994) 5(4):428-433.
Inden et al., "Proteasome Inhibitors Protect Against Degeneration of Nigral Dopaminergic Neurons in Hemiparkinsonian Rats," J Pharmacol Sci (2005) 97:203-211.
Information Results from Oral proceedings for EP 09807153.3, dated Jun. 18, 2021; 22 pages.
Ingebrigsten et al., "Biochemical serum markers for brain damage: A short review with emphasis on clinical utility in mild head injury," Restorative Neurology and Neuroscience (2003) 21(3):171-176.
Jakowec et al., "The native form of alpha-synuclein is not found in the cerebrospinal fluid of patients with Parkinson's disease or normal controls," Neurosci Lett (1998) 253(1):13-16.

(56) References Cited

OTHER PUBLICATIONS

Jefferis et al., "Human immunoglobulin allotypes," mAbs (2009) 1(4):1-7.
Johnson et al., "Proteolysis of Tau by Calpain," Biochem Biophys Res Commun (1989) 163(3):1505-1511.
Jones et al., "Replacing the complementarity-determining regions in a human antibody with those from a mouse," Nature (1986) 321(6069):522-525.
Junghans et al., "Anti-Tac-H, a humanized antibody to the interleukin 2 receptor with new features for immunotherapy in malignant and immune disorders," Cancer Res (1990) 50(5):1495-1502.
Kadota et al., "A Newly Identified Membrane Protein Localized Exclusively in Intracellular Organelles of Neurons," Mol Brain Res (1997) 46(1-2):265-273.
Kampfl et al., "Mechanisms of Calpain Proteolysis Following Traumatic Brain Injury: Implications for Pathology and Therapy: A Review and Update," J Neurotrauma (1997) 14(3):121-134.
Kim et al., "Comparison of Proteome Between Hepatitis B Virus- and Hepatitis C VirusAssociated Hepatocellular Carcinoma," Clin Cancer Res (2003) 9(15):5493-5500.
Kiraly et al., "Traumatic Brain Injury and Delayed Sequelae: A Review—Traumatic Brain Injury and Mild Traumatic Brain Injury (Concussion) are Precursors to Later-Onset Brain Disorders, Including Early-Onset Dementia," Scientific World Journal (2007) 12(7):1768-1776.
Knoblach et al., "Multiple Caspases Are Activated after Traumatic Brain Injury: Evidence for Involvement in Functional Outcome," J Neurotrama (2002) 19(10):1155-1170.
Kobeissy et al. "Novel differential neuroproteomics analysis of traumatic brain injury in rats," Mol Cell Proteomics (2006) 5(10):1887-1898.
Kohler et al., "Continuous Cultures of Fused Cells Secreting Antibody of Predefined Specificity," Nature (1975) 256(5517):495-497.
Koriyama et al., "Proteolytic Activation of Protein Kinase C delta and epsilon by Capase-3 in U937 Cells During Chemotherapeutic Agent-Induced Apoptosis," Cell Signal (1999) 11(11):831-838.
Kosik et al., "MAP2 and Tau Segregate into Dendritic and Axonal Domains After the Elaboration of Morphologically Distinct Neurites: An Immunocytochemical Study of Cultured Rat Cerebrum," J Neurosci (1987) 7(10):3142-3153.
Kovesdi et al., "Update on protein biomarkers in traumatic brain injury with emphasis on clinical use in adults and pediatrics", Acta Neurochirurgica (2010) 152(1):1-17.
Kozbor et al., "A human hybrid myeloma for production of human monoclonal antibodies," J Immunol (1984) 133(6):3001-3005.
Krishnamurthy et al., "Molecular and biologic markers of premalignant lesions of human breast," Adv Anat Pathol (2002) 9(3):185-197.
Kronborg et al., "Pre-symptomatic increase in urine-orosomucoid excretion in preeclamptic women," Acta Obstet Gynecol Scand (2007) 86(8):930-937.
Lamers et al., "Protein S-100b, Neuron-Specific Enolase (NSE), Myelin Basic Protein (MBP) and Glial Fibrillary Acidic Protein (GFAP) in Cerebrospinal Fluid (CSF) and Blood of Neurological Patients," Brain Res Bull (2003) 61(3): 261-264.
Le Prince et al., "Alterations of glial fibrillary acidic protein mRNA level in the aging brain and in senile dementia of the Alzheimer type," Neurosci Lett (1993) 151(1):71-73.
Lee et al., "Fit-for-Purpose Method Development and Validation for Successful Biomarker Measurement," Pharm Res (2006) 23(2):312-328.
Lee et al., "Neuroimaging in traumatic brain imaging," NeuroRx (2005) 2(2):372-383.
Lee et al., "Rapid increase in immunoreactivitiy to GFAP in astrocytes in vitro induced by acidic pH is mediated by calcium influx and calpain I," Brain Research (2000) 864(2): 220-229.
Lefranc et al., "IMGT unique numbering for immunoglobulin and T cell receptor variable domains and Ig superfamily V-like domains," Dev Comp Immunol (2003) 27(1):55-77.
Leon et al., "Free DNA in the Serum of Cancer Patients and the Effect of Therapy," Patients Cancer Research (1977) 37:646-650.
Letter Regarding Additional Attendess for Oral proceedings for EP 09807153.3, dated Jun. 7, 2021; 3 pages.
Letter Regarding Notice of Appeal of Opponent for Oral proceedings for EP 09807153.3, dated Jun. 7, 2021; 5 pages.
Letter Regarding Transfer of Representation of Opponent for Oral proceedings for EP 09807153.3, dated Jun. 7, 2021; 4 pages.
Letter Reply to date proposed for Oral proceedings for EP 09807153. 3, dated Aug. 6, 2020, 4 pages.
Letter Reply to date proposed for Oral proceedings for EP 09807153. 3, dated Aug. 7, 2020, 3 pages.
Letter Requesting Interpreter of Oral Proceedings for EP 09807153. 3, dated Apr. 16, 2021, 4 pages.
Letter Requesting Interpreter of Oral Proceedings for EP 09807153. 3, dated Apr. 22, 2020, 3 pages.
Letter Requesting Postponement of Oral Proceedings for EP 09807153. 3, dated Apr. 2, 2020, 4 pages.
Lewis et al., "Alpha-II spectrin breakdown products in aneurysmal subarachnoid hemorrhage: a novel biomarker of proteolytic injury," J Neurosurg (2007) 107(4):792-796.
Lewis et al., "Utility of Serum Biomarkers in the Diagnosis and Stratification of Mild Traumatic Brain Injury," Acad Emerg Med. (2017) 24(6):710-720.
Li et al., "Expression of the ubiquitin carboxyl-terminal hydrolase PGP 9.5 in axons following spinal cord compression trauma. An immunohistochemical study in the rat," APMIS (1997) 105(5):384-390.
Li et al., "Peptide alpha-Keto Ester, alpha-Keto Amide, and alpha-Keto Acid Inhibitors of Calpains and Other Cysteine Proteases," J Med Chem (1993) 36(22):3472-3480.
Lindmark et al., "Binding of immunoglobulins to protein A and immunoglobulin levels in mammalian sera," J Immunol Methods (1983) 62:1-13.
Litersky et al., "Phophorylation, calpain proteolysis and tubulin binding of recombinant human tau isoforms," Brain Res (1993) 604:32-40.
Liu et al., "The UCH-L1 Gene Encodes Two Opposing Enzymatic Activities that Affect α-Synuclein Degradation and Parkinson's Disease Susceptibility," Cell (2002) 111(2):209-218.
Liu et al., "Ubiquitin C-terminal hydrolase-L1 as a biomarker for ischemic and traumatic brain injury in rats," Eur J Neurosci (2010) 31(4):722-732.
Lo et al., "Pediatric brain trauma outcome prediction using paired serum levels of inflammatory mediators and brain-specific proteins," Journal of Neurotrauma (2009) 26:1479-1487.
Lo et al., "Presence of fetal DNA in maternal plasma and serum," The Lancet (1997) 350:485-487.
Lowe et al., "Ubiquitin carboxyl-terminal hydrolase (PGP 9.5) is selectively present in ubiquitinated inclusion bodies characteristic of human neurodegenerative diseases," J Pathol (1990) 161(2):153-160.
Lumpkins et al., "Glial Fibrillary Acidic Protein is Highly Correlated With Brain Injury," J Trauma (2008) 65(4):778-782.
MacCallum et al., "Antibody-antigen interactions: contact analysis and binding site topography," J Mol Biol (1996) 262(5):732-745.
Malmqvist "Biacore: an affinity biosensor system for characterization of biomolecular interactions," Biochem. Soc. Trans. (2000) 27:335.
Mao et al., "The value of serum myelin basic protein in assessment of severity of acute closed head trauma," Hua Xi Yi Ke Da Xue Bao (1995) 26(2):135-137 (Abstract).
Mao et al., "Electrochemiluminescence assay for basic carboxypeptidases: inhibition of basic carboxypeptidases and activation of thrombin-activatable fibrinolysis inhibitor," Anal Biochem (2003) 319(1):159-170.
Martin et al., "Modeling antibody hypervariable loops: a combined algorithm," PNAS (1989) 86(23):9268-9272.
Martinez et al., Granulomatous Amebic Encephalitis in a Patient with AIDS: Isolation of *Acanthamoeba* sp. Group II from Brain Tissue and Successful Treatment with Sulfadiazine and Fluconazole, J Clin Microbiol (2000) 38(10):3892-3895.

(56) References Cited

OTHER PUBLICATIONS

Matevossian et al., "Neuronal Nuclei Isolation from Human Postmortem Brain Tissue," J Vis Exp (2008) 20:pii 914.
Mather et al., "Culture of testicular cells in hormone-supplemented serum-free medium," Ann N Y Acad Sci (1982) 383:44-68.
Mather et al., "Establishment and characterization of two distinct mouse testicular epithelial cell lines," Biol Reprod (1980) 23:243-251.
Maynard et al., "Excess placental soluble fms-like tyrosine kinase 1 (sFlt1) may contribute to endothelial dysfunction, hypertension, and proteinuria in preeclampsia," J Clin Invest (2003) 111(5): 649-658.
McAllister, "Neuropsychiatric sequelae of head injuries," Psychiatric Clinics of North America (1992) 15(2):395-413.
McComb et al., "Alkaline Phosphatase," 1979, Plenum Press, New York, D Bibliography pages only.
McCraken et al., "Calpain activation and cytoskeletal protein breakdown in the corpus callosum of head-injured patients," J Neurotrauma (1999) 16(9):749-761.
McGinnis et al., "Alterations of Extracellular Calcium Elicit Selective Modes of Cell Death and Protease Activation in SH-SY5Y Human Neuroblastoma Cells," J Neurochem (1999) 72(5):1853-1863.
McGinnis et al., "Calcium/Calmodulin-dependent Protein Kinase IV Is Cleaved by Caspase-3 and Calpain in SH-SY5Y Human Neuroblastoma Cells Undergoing Apoptosis," J Biol Chem (1998) 273(32):19993-20000.
McKee et al., "Chronic traumatic encephalopathy in athletes: progressive tauopathy following repetitive head injury," J Neuropathol Exp Neurol (2009) 68(7):709-735.
McKnight et al., "Serum antibodies in epilepsy and seizure-associated disorders," Neurology (2005) 65(11):1730-1736.
McLendon et al., "Immunohistochemistry of the glial fibrillary acidic protein: basic and applied considerations," Brain Pathol (1994) 4(3):221-228.
McMahon et al., "Measurement of the glial fibrillary acidic protein and its breakdown products GFAP-BDP biomarker for the detection of traumatic brain injury compared to computed tomography and magnetic resonance imaging," J Neutrotrauma (2015) 32(8):527-533.
Medana et al., "Axonal damage: a key predictor of outcome in human CNS diseases," Brain (2003) 126(3):515-530.
Menke et al., "Improved Conditions for Isolation and Quantification of RNA in Urine Specimens," Annals of the New York Academy of Sciences (2004) 1022:185-189.
Miller et al., "Excitatory amino acid receptor subtype binding following traumatic brain injury" Brain Res (1990) 526(1):103-107.
Miller et al., "Utilizing clinical factors to reduce head CT scan ordering for minor head trauma patients," J. Emerg. Med. (1997) 15(4):453-457.
Milstein et al., "Hybrid hybridomas and their use in immunohistochemistry," Nature (1983) 305(5934):537-540.
Missler et al., "Measurement of Glial Fibrillary Acidic Protein in Human Blood: Analytical Method and Preliminary Clinical Results," Clin Chem (1999) 45(1):138-141.
Miura et al., "An Enzymatic Method for the Assay of Serum Argininosuccinate Lyase," Anal Biochem (1987) 164(2):482-487.
Mohideen, "Brain natriuretic peptide is more than a marker," Ceylon Medical Journal, September (2002) 47(3):81-82.
Mondello et al., "Clinical Utility Of Serum Levels Of Ubiquitin C-Terminal Hydrolase As A Biomarker For Severe Traumatic Brain Injury," Neurosurgery (2012) 70(3):666-675.
Mondello et al., "Neuronal and glial markers are differently associated with computed tomography findings and outcome in patients with severe traumatic brain injury: a case control study," Crit Care (2011) 15(3):R156.
Mondello et al., "all-Spectrin Breakdown Products (SBDPs): Diagnosis and Outcome in Severe Traumatic Brain Injury Patients," J Neurotrauma (2010) 27(7):1203-1213.
Moniem et al., "Autoantibodies to neurofilaments (NF), glial fibrillary acidic protein (GFAP) and myelin basic protein (MBP) in workers exposed to lead," J. Egyptian Public Health Assoc (1999) 74 (1-2): 121-138.
Morimoto et al., "Single-step purification of F(ab')2 fragments of mouse monoclonal antibodies (immunoglobulins G1) by hydrophobic interaction high performance liquid Chromatography using TSKgel Phenyl-5PW," J Biochem Biophys Methods (1992) 24(1-2):107-117.
Morozov et al., "Autoantibodies against nerve tissue proteins long after cranio-cerebral injury," Vopr Med Khim (1996) 42(2):147-152.
Morrison et al., "Chimeric human antibody molecules: mouse antigen-binding domains with human constant region domains," PNAS USA (1984) 81(21):6851-6855.
Mouser et al., "Caspase-Mediated Cleavage of Glial Fibrillary Acidic Protein within Degenerating Astrocytes of the Alzheimer's Disease Brain, "Am J Pathol (2003 168(3): 936-946.
Mukerjee et al., "Caspase-Mediated Calcineurin Activation Contributes to IL-2 Release during T Cell Activation," Biochem Biophys Res Commun (2001,) 285(5):1192-1199.
Muller et al., "Methylated DNA as a possible screening marker for neoplastic disease in several body fluids," Expert Review of Molecular Diagnostics (2003) 3(4):443-458.
N.N.: "Catalogue# MCA-BH7: Mouse Monoclonal Antibody to Ubiquitin C-Terminal Hydrolase 1," Online catalogue of EnCor Biotechnology, Jun. 23, 2014, Retrieved from the Internet: URL:http://encorbio.com/Datasheet/MCA-BH7 Product Data Sheet.pdf, retrieved on Jan. 27, 2018, 2 pages.
Nakanishi et al., "Molecular Characterization of a Transport Vesicle Protein Neurensin-2, a homologue of Neurensin-1, expressed in neural cells," Brain Res (2006) 1081(1):1-8.
Nath et al., "Activation of apoptosis-linked caspase(s) in NMDA-injured brains in neonatal rats," Neurochem Int (2000) 36(2):119-126.
Nath et al., "Development and characterization of antibodies specific to caspase-3-produced alpha II-spectrin 120 kDa breakdown product: marker for neuronal apoptosis," Neurochem Int (2000) 37(4):351-361.
Nath et al., "Effects of ICE-like protease and calpain inhibitors on neuronal apoptosis," Neuroreport (1996) 8(1):249-255.
Nath et al., "Evidence for Activation of Caspase-3-Like Protease in Excitotoxin- and Hypoxia/Hypoglycemia-Injured Neurons," J Neurochem (1998) 71:186-195.
Nath et al., "Non-erythroid a-spectrin breakdown by calpain and interleukin 1β-converting-enzyme-like protease(s) in apoptotic cells: contributory roles of both proteasefamilies in neuronal apoptosis," Biochem J (1996) 319(Pt 3):683-690.
Nawashiro et al., "Selective vulnerability of hippocampal CA3 neurons to hypoxia after mild concussion in the rat," Neurol Res (1995) 17(6):455-460.
Newcomb et al., "Immunohistochemical study of calpain-mediated breakdown products to alpha-spectrin following controlled cortical impact injury in the rat," J Neurotrauma (1997) 14(6):369-383.
Ng et. al., "The pathological spectrum of diffuse axonal injury in blunt head trauma: assessment with axon and myelin stains," Clin Neurol Neurosurg (1994) 96:24-31.
Niebroj-Dobosz et al., "Immunochemical analysis of some proteins in cerebrospinal fluid and serum of patients with ischemic strokes," Folia Neuropathol (1994) 32(3):129-137.
Notice of Appeal, for Opposition for EP 09807153.3, dated Sep. 24, 2021, 5 pages.
Nylen et al., "Increased serum-GFAP in patients with severe traumatic brain injury is related to outcome," J Neurol Sci (2006) 240(1-2):85-91.
Ohta et al., "Clinical and Analytical Evaluation of an Enzyme Immunoassay for Myelin Basic Protein in Cerebrospinal Fluid," Clin Chem (2000)46(9):1326-1330.
Okazaki et al., "Pathogenic roles of cardiac autoantibodies in dilated cardiomyopathy," Trends in Molecular Medicine (2005) 11(7):322-326.

(56) References Cited

OTHER PUBLICATIONS

Ontario Neurotrauma Foundation, Guideline for Concussion/Mild Traumatic Brain Injury & Persistent Symptoms, May 2018. (Year: 2018).
Papa et al., "Biomarkers improve clinical outcome predictors of mortality following non-penetrating severe traumatic brain injury," Neurocrit Care (2015) 22(1):52-64.
Papa et al., "Elevated Levels of Serum Glial Fibrillary Acidic Protein Breakdown Products in Mild and Moderate Traumatic Brain Injury are Associated With Intracranial Lesions and Neurosurgical Intervention," Ann Emerg Med (2011) 59(6):471-483.
Papa et al., "GFAP Out-Performs S100ß in Detecting Traumatic Intracranial Lesions on Computed Tomography in Trauma Patients with Mild Traumatic Brain Injury and Those with Extracranial Lesions," J Neurotrauma (2014) 31(22):1815-1822.
Papa et al., "Serum levels of ubiquitin C-terminal hydrolase distinguish mild traumatic brain injury from trauma controls and are elevated in mild and moderate traumatic brain injury patients with intracranial lesions and neurosurgical intervention," J Trauma Acute Care Surg (2012) 72(5):1335-1344.
Papa et al., "Time Course and Diagnostic Accuracy of Glial and Neuronal Blood Biomarkers GFAP and UCH-L1 in a Large Cohort of Trauma Patients With and Without Mild Traumatic Brain Injury," JAMA Neurol (2016) 73(5):551-560.
Papa et al., "Use of biomarkers for diagnosis and management of traumatic brain injury patients," Expert Opin Med Diagn (2008) 2(8):937-945.
Papa et al. "Ubiquitin C-terminal hydrolase is a novel biomarker in humans for severe traumatic brain injury," Crit Care Med (2010) 38(1):138-144.
Park et al., "The generation of a 17 kDa neurotoxic fragment: an alternative mechanism by which tau mediates beta-amyloid-induced neurodegeneration," J Neurosci (2005) 25(22):5365-5375.
Pearl et al., "Clinical Aspects of the Disorders of GABA Metabolism in Children," Curr Opin Neurol (2004) 17(2):107-113.
Pekny et al., "The Role of Astrocytes and Complement System in Neural Plasticity," Int Rev Neurobiol (2007) 82:95-111.
Pelinka et al., "GFAP Versus S100B in Serum After Traumatic Brain Injury: Relationship to Brain Damage and Outcome," J Neurotrama (2004) 21(11):1553-1561.
Pelinka et al., "Glial Fibrillary Acidic Protein in Serum After Traumatic Brain Injury and Multiple Trauma," J Trauma (2004) 57(5):1006-1012.
Petricoin et al., "Clinical proteomics: translating benchside promise into bedside reality," Nat Rev Drug Discov (2002) 1(9):683-695.
Pettigrew et al., "Microtubular Proteolysis in Focal Cerebral Ischema," J Cereb Blood Flow Metab (1996) 16(6):1189-1201.
Pettus et al., "Traumatically induced altered membrane permeability: its relationship to traumatically induced reactive axonal change," J Neurotrauma (1994) 11(5):507-522.
Petzold et al., "An ELISA for glial fibrillary acidic protein." J Immunol Methods (2004) 287(1-2):169-177.
Petzold et al., "Role of Serum S100B as an Early Predictor of High Intracranial Pressure and Mortality in Brain Injury: A Pilot Study," Crit Care Med. (2002) 30(12), 2705-2710.
Pike et al., "Accumulation of Calpain and Caspase-3 Proteolytic Fragments of Brain-Derived alpha-II-Spectrin in Cerebral Spinal Fluid After Middle Cerebral Artery Occlusion in Rats, " J Cereb Blood Flow Metab (2004) 24(1):98-106.
Pike et al., "Accumulation of non-erythroid alpha II-spectrin and calpain-cleaved alpha II- spectrin breakdown products in cerebrospinal fluid after traumatic brain injury in rats," J Neurochem (2001) 78(6):1297-1306.
Pike et al., "Regional calpain and caspase-3 proteolysis of alpha-spectrin after traumatic brain injury," NeuroReport (1998) 9(11):2437-2442.
Pike et al., "Temporal relationships between de novo protein synthesis, calpain and caspase 3-like protease activation, and DNA fragmentation during apoptosis," J. Neurosci Res (1998) 52(5):505-520.
Pineda et al., "Clinical significance of alphaII-spectrin breakdown products in cerebrospinal fluid after severe traumatic brain injury," J Neurotrauma (2007) 24(2)354-366.
Poletaev et al., "Serum anti-S100b, anti-GFAP and anti-NGF autoantibodies of IgG class in healthy persons and patients with mental and neurological disorders," Autoimmunity (2000) 32(1):33-38.
Posmantur et al. "A calpain inhibitor attenuates cortical cytoskeletal protein loss after experimental traumatic brain injury in the rat," Neuroscience (1997) 77(3):875-888.
Presta et al., "Antibody engineering," Curr Opin Struct Biol (1992) 2:593-596.
Presta et al., "Humanization of an antibody directed against IgE," J Immunol (1993) 151(5):2623-2632.
Proba et al., "Functional antibody single-chain fragments from the cytoplasm of *Escherichia coli*: influence of thioredoxin reductase (TrxB)," Gene (1995) 159(2):203-207.
Quintana et al., "Antigen microarrays identify CNS-produced autoantibodies in RRMS," Neurology (2012) 78(8):532-539.
Raabe et al., "Serum markers of brain damage and outcome prediction in patients after severe head injury," Br J Neurosurg (1999) 56-59.
Rainer et al., "Effects of Filtration on Glyceraldehyde-3-Phosphate Dehydrogenase mRNA in the Plasma of Trauma Patients and Healthy Individuals," Clinical Chemistry (2004) 50(1):206-208.
Rainer et al., "Prognostic Use of Circulating Plasma Nucleic Acid Concentrations in Patients with Acute Stroke," Clinical Chemistry (2003) 49(4):562-569.
Ramm et al., "The Periplasmic *Escherichia coli* Peptidylprolyl cis, trans-Isomerase FkpA II. Isomerase-Independent Chaperone Activity in Vitro*," J Biol Chem (2000) 275:17106-17113.
Rao et al., "Marked calpastatin (CAST) depletion in Alzheimer's disease accelerates cytoskeleton disruption and neurodegeneration: neuroprotection by CAST overexpression," J Neurosci (2008) 28(47):12241-12254.
Redell et al., "Traumatic brain injury alters expression of hippocampal microRNAs: Potential regulators of multiple pathophysiological processes," J Neurosci Res (2009) 87(6):1435-1448.
Response to Appeal, for Opposition for EP 09807153.3, dated Apr. 19, 2022, 89 pages.
Response to Opposition for EP 09807153.3, dated May 24, 2019; 75 pages.
Reyes et al., "Expression of human B-interferon cDNA under the control of a thymidine kinase promoter from herpes simplex virus," Nature (1982) 297:598-601.
Rich et al., "Advances in surface plasmon resonance biosensor analysis," Curr Opin Biotechnol (2000) 11(1):54-61.
Riechmann et al., "Reshaping human antibodies for therapy," Nature (1988) 332:323-327.
Ringger et al., "A novel marker for traumatic brain injury: CSF alphaII-spectrin breakdown product levels," J Neurotrauma (2004) 21(10):1443-1456.
Rissman et al., "Caspase-cleavage of tau is an early event in Alzheimer disease tangle pathology," J Clin Invest (2004) 114:121-130.
Roche, Instruction Manual for "DIG Detection ELISA (Abts)" and "DIG Detection ELISA (TMB)", Version 2, Nov. 1999, retrieved from http://jenobiotech.com/techsupport/protocol/ELISA1-17.pdf on Apr. 25, 2014, 18 pages.
Rohn et al., "Caspase-9 Activation and Caspase Cleavage of tau in the Alzheimer's Disease Brain," Neurobiol Dis (2002) 11(2):341-354.
Rosengren, L. et al. "Patients with Amyotrophic Lateral Sclerosis and Other Neurodegenerative Diseases Have Increased Levels of Neurofilament Protein in CSF", Journal of Neurochemistry, 1996, pp. 2013-2018, vol. 67, No. 5.
Rudehill et al., "Autoreactive antibodies against neurons and basal lamina found in serum following experimental brain contusion in rats," Acta Neurochirurgica (2006) 148(2):199-205.
Rudikoff et al., "Single amino acid substitution altering antigen-binding specificity," Proc Natl Acad Sci U S A. (1982) 79(6): 1979-1983.

(56) References Cited

OTHER PUBLICATIONS

Saatman et al., "Behavioral efficacy of posttraumatic calpain inhibition is not accompanied by reduced spectrin proteolysis, cortical lesion, or apoptosis," J Cereb Blood Flow Metab (2000) 20(1):66-73.
Saatman et al., "Calpain inhibitor AK295 attenuates motor and cognitive deficits following experimental brain injury in the rat," Proc Natl Acad Sci (1996) 93(8):3428-3433.
Saido et al., "Spatial Resolution of Fodrin Proteolysis in Postischemic Brain," J Biol Chem (1993) 268(33):25239-25243.
Sanchez et al., "Cystatin C as a Potential Cerebrospinal Fluid Marker for the Diagnosis of Creutzfeldt-Jakob Disease," Proteomics (2004) 4(8):2229-2233.
Sankiewicz et al., "Development of surface plasmon resonance imaging biosensors for detection of ubiquitin carboxyl-terminal hydrolase L1," Anal Biochem (2015) 469:4-11.
Scatchard, "The Attractions of Protelns for Small Molecules and Ions," Ann N. Y. Acad Sci (1947) 51:660-672.
Schwab et al., "Cleavage of plasma membrane calcium pumps by caspases: a link between apoptosis and necrosis," Cell Death Differ (2002) 9(8):818-831.
Shea, T. et al. "Calcium Influx into Human Neuroblastoma Cells Induces ALZ-50 Immunoreactivity: Involvement of Calpain-Mediated Hydrolysis of Protein Kinase C", Journal of Neurochemistry, 1996, pp. 1539-1549, vol. 66, No. 4.
Shigeta, K. et al. "Fragmentation of a 70000-dalton calpastatin molecule upon its complex formation with calpain", Biochem. Int., 1984, pp. 327-333, vol. 9, No. 3. Abstract only.
Shimohama et al., "Changes in caspase expression in Alzheimer's disease: comparison with development and aging," Biochem Biophys Res Commun (1999) 256(2):381-384.
Sienbenlist et al., "*E. coli* RNA polymerase interacts homologously with two different promoters," Cell (1982) 20:269-281.
Silber et al., "Patients with progressive multiple sclerosis have elevated antibodies to neurofilament subunit," Neurology (2002) 58:1372-1381.
Silva et al., "Presence of Tumor DNA in Plasma of Breast Cancer Patients: Clinicopathological Correlations," Cancer Research (1999) 59:3251-3256.
Siman et al., "Biomarker evidence for mild central nervous system injury after surgically-induced circulation arrest," Brain Research, 1213:1-11, Jun. 5, 2008.
Siman et al., "Proteins released from degenerating neurons are surrogate markers for acute brain damage," Neurobiol Dis (2004) 16(2):311-320.
Simmons et al., "Expression of full-length immunoglobulins in *Escherichia coli*: rapid and efficient production of aglycosylated antibodies," J Immunol Methods (2002) 263(1-2):133-147.
Sims et al., "A humanized CD18 antibody can block function without cell destruction," J Immunol (1993) 151(4):2296-2308.
Singh et al., "Detection of brain autoantibodies in the serum of patients with Alzheimer's disease but not Down's syndrome," Immunol Lett (1986) 12(5-6):277-280.
Sinjoanu et al., "The novel calpain inhibitor A-705253 potently inhibits oligomeric beta-amyloid-induced dyanmin 1 and tau cleavage in hippocampal neurons," Neurochem Int (2008) 53(3-4):79-88.
Sjögren et al., "Neurofilament Protein in Cerebrospinal Fluid: A Marker of White Matter Changes," J Neurosci Res (2001) 66(3):510-516.
Skoda et al., "Antibody formation against beta-tubulin class III in response to brain trauma," Brain Research Bulletin (2006) 68(4):213-216.
Smith et al., "Protein Accumulation in Traumatic Brain Injury," NeuroMolecular Med (2003) 4(1-2):59-72.
Smith et al., "Functional subsets of human helper-inducer cells defined by a new monoclonal antibody, UCHL1," Immunology. (1986) 58(1): 63-70.

Sorokina et al., "Autoantibodies to glutamate receptors and metabolic products of nitric oxide in blood serum of children in the acute period of brain trauma," Zh Nevrol Psikhiatr Im S S Korsakova (2008) 108(3):67-72.
Spinal Cord Injury Journal, Contusion vs. Concussion: Understanding the Difference by Zawn Villines. Pulbished online Nov. 23, 2015. Retrieved from <https://web-beta.archive.org/web/20151202013742/http://www.spinalcord.com/blog/contusion-vs.-concussion-understanding-the-difference>. Retrieved on May 4, 2017 12:31:00 PM.
Stagg et al., "Autoantibodies to glutamic acid decarboxylase in patients with epilepsy are associated with low cortical GABA levels," Epilepsia (2010) 51(9):1989-1901.
Statement for Grounds of Appeal for EP 09807153.3, dated Nov. 24, 2021; 39 pages.
Summons to Attend Oral Proceedings—OPPO for EP 09807153.3, dated Jan. 1, 2021; 22 pgs.
Summons to Attend Oral Proceedings—OPPO for EP 09807153.3, dated Jul. 6, 2020, 14 pgs.
Summons to Attend Oral Proceedings for EP 09807153.3, dated Jan. 1, 2021; 22 pgs.
Summons to Attend Oral Proceedings for EP 09807153.3, dated Jul. 6, 2020, 14 pgs.
Summons to Attend Oral Proceedings for EP 09807153.3, dated Oct. 17, 2019, 18 pgs.
Suresh et al., "Bispecific Monoclonal Antibodies from Hybrid Hybridomas," Methods in Enzymology, (1986) 121:210.
Svetlov et al., "Biomarkers of Blast-induced neurotrauma: profiling molecular and cellular mechanisms of Blast brain injury," Journal of Neurotrauma (2009) 26:913-921.
Svetlov et al., "Title: Pathological Fingerprints, Systems Biology and Biomarkers of Blast Brain Injury", 2010, Retrieved from the Internet: URL:http:jwww.dtic.mil/dticjtr/fulltextju2/a548699.pdf, p. 4-6.
Taback et al., "Circulating Nucleic Acids and Proteomics of Plasma/Serum Clinical Utility," Annals of the New York Academy of Sciences (2004) 1022:1-8.
Tabuchi et al., "Regulation of Genes for Inducible Nitric Oxide Synthase and Urea Cycle Enzymes in Rat Liver in Endotoxin Shock," Biochem Biophys Res Commun (2000) 268(1):221-224.
Taheri et al. "The Role of Hypocretins (Orexins) in Sleep Regulation and Narcolepsy," Annu Rev Neurosci (2002) 25:283-313.
Tan et al., "Deoxyribonucleic Acid (DNA) and Antibodies to DNA in the Serum of Patients with Systemic Lupus Erythematosus," Journal of Clinical Investigation (1966) 45(11):1732-1740.
Tanriverdi et al., "Antipituitary antibodies after traumatic brain injury: is head trauma-induced pituitary dysfunction associated with autoimmunity?" Eur J of Endocrinol (2008) 159(1):7-13.
Terryberry et al., "Autoantibodies in Neurodegenerative Diseases: Antigen-Specific Frequencies and Intrathecal Analysis," Neurobiology of Aging (1998) 19(3):205-216.
Terryberry et al., "Clinical Utility of Autoantibodies in Guillain-Barre Syndrome and Its Variants," Clinical Reviews in Allergy and Immunology (1998) 16:265-273.
Teunissen et al., "Biochemical Markers Related to Alzheimer's Dementia in Serum and Cerebrospinal Fluid," Neurobiol Aging (2002) 23(4):485-508.
The Safe Study Investigators, "Saline or Albumin for Fluid Resuscitation in Patients with Traumatic Brain Injury," N Engl J Med (2007) 357:874-884.
Tobias et al., Biomolecular Binding Kinetic Assays in the Octet Platform, Application Note 14, ForteBio, Div. of Pall Life Sciences, 2013.
Tooney et al., "Neurons Expressing Calcium-binding Proteins in the Prefrontal Cortex in Schizophrenia", Prog Neuropsychopharmacol Biol Psychiatry (2004) 28(2):273-278.
Toth et al., "Lateral Ventricle vol. Asymmetry Predicts Midline Shift in Severe Traumatic Brain Injury," J Neurotrauma (2015) 32(17):1307-1311.
Toyota et al., "Calpain-induced Bax-cleavage product is a more potent inducer of cell death than wild-type Bax," Cancer Lett (2003) 189(2):221-230.

(56) References Cited

OTHER PUBLICATIONS

Traunecker et al., "Bispecific single chain molecules (Janusins) target cytotoxic lymphocytes on HIV infected cells," EMBO J (1991) 10(12):3655-3659.
Trowern et al., "Detection of neuron-specific protein gene product (PGP) 9.5 in the rat and zebrafish using anti-human PGP9.5 antibodies," Neurosci Lett (1996) 210(1)21-24.
Turner et al., "Expression of COX2, HO1, and GFAP following collagenase-induced intracerebral hemorrhage," Neurology (2000) 54:A299.
Urlaub et al., "Isolation of Chinese hamster cell mutants deficient in dihydrofolate reductase activity," PNAS USA (1980) 77(7):4216-4220.
Urrea et al., "Widespread cellular proliferation and focal neurogenesis after traumatic brain injury in the rat," Restor Neurol and Neurosci (2007) 25(1):65-76.
Uryu et al., "Multiple proteins implicated in neurodegenerative diseases accumulate in axons after brain trauma in humans", Exp Neurol (2007) 208(2):185-192.
Van Geel et al., "Measurement of glial fibrillary acidic protein in blood: an analytical method," Clin Chim Acta (2002) 326(1-2):151-154.
Van Geel et al., :An enzyme immunoassay to quantify neurofilament light chain in cerebrospinal fluid, J. Immunol. Methods (2005) 296:179-185.
Van Voorhis et al., "Understanding Power and Rules of Thumb for Determining Sample Sizes," Tutorials | Quantitative Methods for Psychology (2007) 3(2):43-50.
Vaswani et al., "Humainzed antibodies as potential therapeutic drugs," Ann. Allergy, Asthma & Immunol. 1:105-115 (1998).
Verbeek et al., "Accumulation of intercellular adhesion loecule-1 in senile plaques in brain tissue of patients with Alzheimer's disease," American Journal of Pathology (1994) 144(1):104-116.
Vercauteren, "Proteomic approaches in brain research and neuropharmacology," European Journal of Pharmacology, Oct. 1, 2004, vol. 500, No. 1-3, p. 385-398, Elsevier Science, NL.
Verhoeyen et al., "Reshaping human antibodies: grafting an antilysozyme activity," Science (1988) 239(4847):1534-1536.
Villines, "Contusion vs. Concussion: Understanding the Difference," Published on Nov. 23, 2015. Retrieved from https://www.spinalcord.com/blog/contusion-vs.-concussion-understanding-the-difference and retrieved on Jan. 3, 2018.
Vissers et al., "Rapid immunoassay for the determination of glial fibrillary acidic protein (GFAP) in serum," Clin Chim Acta (2006) 366(1-2):336-340.
Vos et al., "Glial and neuronal proteins in serum predict outcome after severe traumatic brain injury," Neurology (2004) 62(8):1303-1310.
Vos et al., "Increased GFAP and S100β but not NSE serum levels after subarachnoid haemorrhage are associated with clinical severity" Eur J Neurol (2006) 13(6):632-638.
Walker et al., "DNA-based molecular diagnostic techniques: research needs for standardization and validation of the detection of aquatic animal pathogen and diseases," Report and proceedings of the joint FAO/NACA/CSIRO/ACIAR/DFID expert workshop. Bangkok, Thailand, Feb. 7-9, 1999. FAO Fisheries Technical Paper No. 395 Rome, FAO, 2000, pp. i-iv & 30-37.
Wang et al., "Calpain and caspase: can you tell the difference?" Trends Neurosci (2000) 23(1):20-26.
Wang et al., "Simultaneous Degradation of aII and βII-Spectrin by Caspase 3 (CPP32) in Apoptotic Cells," J Biol Chem (1998) 273(35):22490-22497.
Wang et al.," A study of HSP70 and NF in brain contusion timing," Fa Yi Xue Za Zhi (2000) 16(3):132-134 (Abstract).
Wang, et al., "Proteomic identification of biomarkers of traumatic brain injury," Expert Rev Proteomics (2005) 2(4):603-614.
Ward et al., "Binding Activities of a Repertoire of Single Immunoglobulin Variable Domains Secreted from *Escherichia coli*," Nature (1989) 341 (6242):544-546.

Warren et al., "Calpain-and caspase-mediated aII-spectrin and tau proteolysis in rat cerebrocortical neuronal cultures after ecstasy or methamphetamine exposure," Intl J Neuro-Psychopharmacology, (2007) 10(4):479-489.
Warren et al., "Concurrent calpain and caspase-3 mediated proteolysis of alphaII-spectrin and tau in rat brain after methamphetamine exposure: A similar profile to traumatic brain injury," Life Sciences (2005) 78(3):301-309.
Wilhelm et al., "Immune reactivity towards insulin, its amyloid and protein S100B in blood sera of Parkinson's disease patients," Eur J Neurol (2007) 14(3):327-334.
Wilson et al., "Functional Genomics and Proteomics: Application in Neurosciences," J Neurol Neurosurg Psychiatry (2004) 75(4):529-538.
Woertgen et al., "Glial and neuronal serum markers after controlled cortical impact injury in the rat," Acta Neurochir Suppl. (2002) 81:205-7.
Written Submissions for EP 09807153.3, dated Apr. 16, 2021, 11 pgs.
Written Submissions for EP 09807153.3, dated Apr. 24, 2020, 15 pgs.
Written Submissions for EP 09807153.3, dated Dec. 31, 2019, 60 pgs.
Xu et al., "Facilitated Sprouting in a Peripheral Nerve Injury," Neuroscience (2008) 152(4):877-887.
Yamauchi et al., "Ubiquitin-Mediated Stress Response in the Spinal Cord After Transient Ischemia," Stroke (2008) 39(6):1883-1889.
Yang et al., "Calpain-Induced Proteolysis of Normal Human Tau and Tau Associated with Paired Helical Filaments," Eur J Biochem (1995) 223(1):9-17.
Yang et al., "Electrochemiluminescence: A New Diagnostics and Research Tool," Bio/Technology, vol. 12, Feb. 1994, p. 193-194.
Yaniv, "Enhancing elements for activation of eukaryotic promoters," Nature (1982) 297(5861):17-18.
Yansura et al., "Nucleotide sequence selection for increased expression of heterologous genes in *Escherichia coli*," Methods (1992) 4(2):151-158.
Yen et al., "FTDP-17 tau mutations decrease the susceptibility of tau to calpain I digestion," FEBS Lett (1999) 461(1):91-95.
Yohrling et al., "Inhibition of Tryptophan Hydroxylase Activity and Decreased 5-HT1A Receptor Binding in a Mouse Model of Huntington's Disease," J Neurochem (2002) 82(6):1416-1423.
Yokota et al., "Three distinct phases offodrin proteolysis induced in postischemic hippocampus-involvement of calpain and unidentified protease," Stroke (1995) 26(10):1901-1907.
Yoshiyama et al., "Enhanced neurofibrillary tangle formation, cerebral atrophy, and cognitive deficits induced by repetitive mild brain injury in a transgenic tauopathy mouse model" J Neurotrama (2005) 22(10):1134-1141.
Yu et al., "Accumulation of immunoreactivity to ubiquitin carboxyl-terminal hydrolase PGP 9.5 in axons of human cases with spinal cord lesions," APMIS (1998) 106(11):1081-1087.
Zaffaroni "Biological Indicators of the Neurodegenerative Phase of Multiple Sclerosis", Neurol Sci (2003) 24:S279-S282.
Zapata et al., "Engineering linear F(ab')2 fragments for efficient production in *Escherichia coli* and enhanced antiproliferative activity," Protein Eng (1995) 8(10):1057-1062.
Zemlan et al., "C-tau biomarker of neuronal damage in severe brain injured patients: association with elevated intracranial pressure and clinical outcome," Brain Res (2002) 947(1):131-139.
Zemlan et al., "Quantification and localization of kainic acid-induced neurotoxicity employing a new biomarker of cell death: cleaved microtubule associated protein-tau (C-tau)," Neuroscience (2003) 121(2):399-409.
Zemlan et al., "Quantification of axonal damage in traumatic brain injury: affinity purification and characterization of cerebrospinal fluid tau proteins," J Neurochem (1999) 72(2):741-750.
Zhang et al., "Inhibition of autophagy causes tau proteolysis by activating calpain in rat brain," J Alzheimers Dis (2009)16(1):39-47.
Zhang et al., "Multiple alphaII-spectrin breakdown products distinguish calpain and caspase dominated necrotic and apoptotic cell death pathways," Apoptosis (2009) 14(11):1289-1298.

(56) References Cited

OTHER PUBLICATIONS

Zhang et al., "Phenotypes of T Cells Infiltrating the Eyes in Autoimmune Anterior Uveitis Associated with EAE," Invest Ophthalmol Vis Sci (2002) 43(5):1499-1508.
Zhang et al., "Roles of autoantibodies in central nervous system injury," Discov Med (2011) 11(60):395-402.
Zhang et al., "Expression of glial fibrillary acidic protein in pericerebral hemorrhage foci," Journal of the Fourth Military Medical University (Di-si Junyi Daxue Xuebao) (2003) 24(17):1586-1588.
Zhang et al., "The Expression of GFAP after Brain Concussion in Rats," J of Forensic Medicine. 22(2):88-92, Apr. 2006 (certified translation) (Year: 2006).
Zhao et al., "Maitotoxin Induces Calpain But Not Caspase-3 Activation and Necrotic Cell Death in Primary Septo-Hippocampal Cultures," Neurochem Res (1999) 24(3):371-382.
Zhu et al., "Non-invasive imaging of GFAP expression after neuronal damage in mice," Neurosci Letters (2004) 367(2):210-212.

\* cited by examiner

ANTIBODIES TO UBIQUITIN C-TERMINAL HYDROLASE L1 (UCH-L1) AND GLIAL FIBRILLARY ACIDIC PROTEIN (GFAP) AND RELATED METHODS

CROSS-REFERENCE TO RELATED APPLICATIONS

This application is a divisional of U.S. patent application Ser. No. 16/345,562, filed Apr. 26, 2019, which is a National Stage application under 35 U.S.C. § 371 of International Application No. PCT/US2017/058881, filed on Oct. 27, 2017, which claims priority from U.S. provisional application No. 62/414,569 filed Oct. 28, 2016, entitled "Antibodies to Ubiquitin C-Terminal Hydrolase (UCH-L1) and Glial Fibrillary Acidic Protein (GFAP) and Related Methods," the contents of which are incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750582000110SeqList.txt, date recorded: Jul. 16, 2021, size: 133,365 bytes).

FIELD OF THE INVENTION

The present disclosure relates to anti-UCH-L1 antibodies and anti-GFAP antibodies as well as methods, systems and kits for detection of UCH-L1 and GFAP, for example, in a sample from an individual with or suspected of having a brain injury, such as for diagnosing a brain injury in an individual.

BACKGROUND OF THE INVENTION

Numerous types of injuries, diseases and disorders can lead to neurological damage that, if not detected quickly, can lead to more severe damage. For example, initial injuries resulting from traumatic, ischemic, and neurotoxic chemical insult can lead to neurological damage. Diseases or disorders affecting nerve cells (or other brain cells such as glial cells) can also result in injury or damage that leads to the development of a neurological condition. Common methods for diagnosing a neurological condition usually involve a neurological examination and assigning a Glasgow Coma Score to an individual. These methods are of limited value and often preclude a nuanced diagnosis due to the subjectivity of the testing, and the ability of a patient to knowingly alter their true response to achieve a desired result. In order to obtain a diagnosis of a neurological condition resulting from damage or injury, neuroimaging, such as computed tomography (CT) and magnetic resonance imaging (MRI), is widely used to help determine the scope of injury and potential for intervention. However, these tests are costly, time consuming and likely not as sensitive as a biomarker test.

Thus there remains a need for reagents, devices and methods of detecting damage or injury in an individual that has a neurological condition, is suspected of having a neurological condition, or will develop a neurological condition. In particular, reagents, devices and methods that allow for rapid and/or early in vitro detection of damage in an individual can facilitate diagnosis and treatment that prevents or lessens the progression of a neurological condition. Provided herein are embodiments that meet such needs.

SUMMARY OF THE INVENTION

Provided herein are anti-ubiquitin c-terminal hydrolase L1 (UCH-L1) antibodies and glial fibrillary acidic protein (GFAP) antibodies, including antigen-binding fragments thereof, compositions containing such antibodies or antigen-binding fragments, combinations of such antibodies or antigen-binding fragments and methods of use thereof. In particular embodiments, the antibodies or antigen-binding fragments are used in methods of predicting if a subject is in need of neuroimaging and/or of diagnosing brain injury or damage in a subject.

Provided herein are antibodies or antigen-binding fragments thereof, including those that specifically bind to a UCH-L1, such as a human UCH-L1, wherein the antibodies or antigen-binding fragments contain particular complementarity determining regions (CDRs), including heavy chain CDRs (i.e., CDR-H1, CDR-H2, and/or CDR-H3) and light chain CDRs (i.e., CDR-L1, CDR-L2, and/or CDR-L3), such as any described herein. In some embodiments, the antibody or antigen-binding fragment thereof includes a heavy chain variable region and a light chain variable region, such as any described herein.

In some embodiments, provided herein are antibodies or antigen-binding fragments thereof that specifically binds to a UCH-L1 (e.g., human UCH-L1), wherein the antibody or antigen-binding fragment comprises a heavy chain variable region comprising an amino acid sequence having at least 85% identity to an amino acid sequence selected from any one of SEQ ID NOs:51-63; and/or a light chain variable region comprising an amino acid sequence having at least 85% identity to an amino acid sequence selected from any one of SEQ ID NOs:64-76. In some embodiments, the heavy chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs:51-63; or has the amino acid sequence selected from any one of SEQ ID NOs:51-63. In some of any of the embodiments herein, the light chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from SEQ ID NOs:64-76 or has the amino acid sequence selected from any one of SEQ ID NOs:64-76. In some of any of the embodiments herein, the heavy chain variable region comprises: (i) a CDR-H1 comprising the amino acid sequence selected from SEQ ID NOs:1-8; (ii) a CDR-H2 comprising the amino acid sequence selected from SEQ ID NOs:9-19; and (iii) a CDR-H3 comprising the amino acid sequence selected from SEQ ID NOs:20-27; and/or the light chain variable region comprises: (i) a CDR-L1 comprising the amino acid sequence selected from SEQ ID NOs:28-36; (ii) a CDR-L2 comprising the amino acid sequence selected from SEQ ID NOs:37-44; and (iii) a CDR-L3 comprising the amino acid sequence selected from SEQ ID NOs:45-50. In some of any of the embodiments herein, the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:51-63; and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:64-76.

In some embodiments, provided herein are antibodies or antigen-binding fragments thereof that specifically binds to a UCH-L1 (e.g., human UCH-L1), wherein the antibody or antigen-binding fragment comprises a heavy chain variable region comprising an amino acid sequence having at least 85% identity to an amino acid sequence selected from any one of SEQ ID NOs: 53-62; and/or a light chain variable region comprising an amino acid sequence having at least 85% identity to an amino acid sequence selected from any one of SEQ ID NOs:66-75. In some embodiments, the heavy chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs: 53-62 or comprises the amino acid sequence set forth in any of SEQ ID NOs: 53-62; and/or the light chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs: 66-75 or comprises the light chain variable region comprises the amino acid sequence set forth in any one of SEQ ID NOs: 66-75. In some of any of the embodiments herein, the heavy chain variable region comprises: (i) a CDR-H1 comprising the amino acid sequence selected from SEQ ID NOs:3-8; (ii) a CDR-H2 comprising the amino acid sequence selected from SEQ ID NOs:11-18; and (iii) a CDR-H3 comprising the amino acid sequence selected from SEQ ID NOs:20-27; and/or the light chain variable region comprises: (i) a CDR-L1 comprising the amino acid sequence selected from SEQ ID NOs:30-36; (ii) a CDR-L2 comprising the amino acid sequence selected from SEQ ID NOs:37-44; and (iii) a CDR-L3 comprising the amino acid sequence selected from SEQ ID NOs:45-49; or the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:53-62 and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:66-75.

In some embodiments, provided herein are antibodies or antigen-binding fragments thereof that specifically binds to a UCH-L1 (e.g., human UCH-L1), wherein the antibody or antigen-binding fragment comprises a heavy chain variable region and a light chain variable region, wherein the heavy chain variable region comprises: (i) a CDR-H1 comprising the amino acid sequence selected from SEQ ID NOs:1-8; (ii) a CDR-H2 comprising the amino acid sequence selected from SEQ ID NOs:9-18; and (iii) a CDR-H3 comprising the amino acid sequence selected from SEQ ID NOs:20-27; and/or wherein the light chain variable region comprises: (i) a CDR-L1 comprising the amino acid sequence selected from SEQ ID NOs:28-36; (ii) a CDR-L2 comprising the amino acid sequence selected from SEQ ID NOs:37-44; and (iii) a CDR-L3 comprising the amino acid sequence selected from SEQ ID NOs:45-49.

In some of any of the embodiments herein, the antibody or antigen-binding fragment thereof that specifically binds to a UCH-L1 comprises (a) a heavy chain variable region comprising CDR-H1, CDR-H2 and CDR-H3 amino acid sequences of SEQ ID NO: 1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively; (b) a heavy chain variable region comprising CDR-H1, CDR-H2 and CDR-H3 amino acid sequences of SEQ ID NO:2, SEQ ID NO:10, SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively; (c) a heavy chain variable region comprising CDR-H1, CDR-H2 and CDR-H3 amino acid sequences of SEQ ID NO:3, SEQ ID NO: 11 and SEQ ID NO:20, respectively and/or a light chain variable region comprising CDR-L1, CDR-L2 and CDR-L3 amino acid sequences of SEQ ID NO:30, SEQ ID NO:37 and SEQ ID NO:45, respectively; (d) a heavy chain variable region comprising CDR-H1, CDR-H2 and CDR-H3 amino acid sequences of SEQ ID NO:4, SEQ ID NO:12 and SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively; (e) a heavy chain variable region comprising CDR-H1, CDR-H2 and CDR-H3 amino acid sequences of SEQ ID NO:5, SEQ ID NO:13 and SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively; (f) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:33, SEQ ID NO:40, SEQ ID NO:48, respectively; (g) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:34, SEQ ID NO:41 and SEQ ID NO:48, respectively; (h) a heavy chain variable region comprising CDR-H1, CDR-H2 and CDR-H3 amino acid sequences of SEQ ID NO:6, SEQ ID NO:15 and SEQ ID NO:24, respectively and/or a light chain variable region comprising CDR-L1, CDR-L2 and CDR-L3 amino acid sequences of SEQ ID NO:34, SEQ ID NO:42 and SEQ ID NO:48, respectively; (i) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:35, SEQ ID NO:41 and SEQ ID NO:48, respectively; (j) a heavy chain variable region comprising CDR-H1, CDR-H2 and CDR-H3 amino acid sequences of SEQ ID NO:6, SEQ ID NO:16 and SEQ ID NO:25, respectively and/or a light chain variable region comprising CDR-L1, CDR-L2 and CDR-L3 amino acid sequences of SEQ ID NO:34, SEQ ID NO:42 and SEQ ID NO:48, respectively; (k) a heavy chain variable region comprising CDR-H1, CDR-H2 and CDR-H3 amino acid sequences of SEQ ID NO:7, SEQ ID NO:17 and SEQ ID NO:26, respectively and/or a light chain variable region comprising CDR-L1, CDR-L2 and CDR-L3 amino acid sequences of SEQ ID NO:36, SEQ ID NO:43 and SEQ ID NO:49, respectively; (1) a heavy chain variable region comprising CDR-H1, CDR-H2 and CDR-H3 amino acid sequences of SEQ ID NO:8, SEQ ID NO: 18 and SEQ ID NO:27, respectively and/or a light chain variable region comprising CDR-L1, CDR-L2 and CDR-L3 amino acid sequences of SEQ ID NO:36, SEQ ID NO:44 and SEQ ID NO:49, respectively; or (m) a heavy chain variable region comprising CDR-H1, CDR-H2 and CDR-H3 amino acid sequences of SEQ ID NO:1, SEQ ID NO:19 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:50, respectively.

In some of any of the embodiments herein, the antibody or antigen-binding fragment thereof that specifically binds to a UCH-L1 comprises (a) a heavy chain variable region comprising the amino acid sequence of SEQ ID NO:51 or an amino acid sequence having at least 85% identity to an amino acid sequence of SEQ ID NO:51; and/or a light chain variable region comprising the amino acid sequence of SEQ ID NO:64 or an amino acid sequence having at least 85% identity to the amino acid sequence of SEQ ID NO:64; (b) a heavy chain variable region comprising the amino acid sequence of SEQ ID NO:52 or an amino acid sequence having at least 85% identity to an amino acid sequence of SEQ ID NO:52; and/or a light chain variable region comprising the amino acid sequence of SEQ ID NO:65 or an amino acid sequence having at least 85% identity to an amino acid sequence of SEQ ID NO:65; (c) a heavy chain variable region comprising the amino acid sequence of SEQ ID NO:53 or an amino acid sequence having at least 85% identity to an amino acid sequence of SEQ ID NO:53; and/or a light chain variable region comprising the amino acid sequence of SEQ ID NO:66 or an amino acid sequence having at least 85% identity to an amino acid sequence of SEQ ID NO:66; (d) a heavy chain variable region comprising the amino acid sequence of SEQ ID NO:54 or an amino acid sequence having at least 85% identity to an amino acid sequence of SEQ ID NO:54; and/or a light chain variable region comprising the amino acid sequence of SEQ ID NO:67 or an amino acid sequence having at least 85% identity to an amino acid sequence of SEQ ID NO:67; (e) a heavy chain variable region comprising the amino acid sequence of SEQ ID NO:55 or an amino acid sequence having at least 85% identity to an amino acid sequence of SEQ ID NO:55; and/or a light chain variable region comprising the amino acid sequence of SEQ ID NO:68 or an amino acid sequence having at least 85% identity to an amino acid sequence of SEQ ID NO:68; (f) a heavy chain variable region comprising the amino acid sequence of SEQ ID NO:56 or an amino acid sequence having at least 85% identity to an amino acid sequence of SEQ ID NO:56; and/or a light chain variable region comprising the amino acid sequence of SEQ ID NO:69 or an amino acid sequence having at least 85% identity to an amino acid sequence of SEQ ID NO:69; (g) a heavy chain variable region comprising the amino acid sequence of SEQ ID NO:57 or an amino acid sequence having at least 85% identity to an amino acid sequence of SEQ ID NO:57; and/or a light chain variable region comprising the amino acid sequence of SEQ ID NO:70 or an amino acid sequence having at least 85% identity to an amino acid sequence of SEQ ID NO:70; (h) a heavy chain variable region comprising the amino acid sequence of SEQ ID NO:58 or an amino acid sequence having at least 85% identity to an amino acid sequence of SEQ ID NO:58; and/or a light chain variable region comprising the amino acid sequence of SEQ ID NO:71 or comprising an amino acid sequence having at least 85% identity to an amino acid sequence of SEQ ID NO:71; (i) a heavy chain variable region comprising the amino acid sequence of SEQ ID NO:59 or an amino acid sequence having at least 85% identity to an amino acid sequence of SEQ ID NO:59; and/or a light chain variable region comprising the amino acid sequence of SEQ ID NO:72 or an amino acid sequence having at least 85% identity to an amino acid sequence of SEQ ID NO:72; (j) a heavy chain variable region comprising the amino acid sequence of SEQ ID NO:60 or an amino acid sequence having at least 85% identity to an amino acid sequence of SEQ ID NO:60; and/or a light chain variable region comprising the amino acid sequence of SEQ ID NO:73 or an amino acid sequence having at least 85% identity to an amino acid sequence of SEQ ID NO:73; (k) a heavy chain variable region comprising the amino acid sequence of SEQ ID NO:61 or an amino acid sequence having at least 85% identity to an amino acid sequence of SEQ ID NO:61; and/or a light chain variable region comprising the amino acid sequence of SEQ ID NO:74 or an amino acid sequence having at least 85% identity to an amino acid sequence of SEQ ID NO:74; (l) a heavy chain variable region comprising the amino acid sequence of SEQ ID NO:62 or an amino acid sequence having at least 85% identity to an amino acid sequence of SEQ ID NO:62; and/or a light chain variable region comprising the amino acid sequence of SEQ ID NO:75 or an amino acid sequence having at least 85% identity to an amino acid sequence of SEQ ID NO:75; or (m) a heavy chain variable region comprising the amino acid sequence of SEQ ID NO:63 or an amino acid sequence having at least 85% identity to an amino acid sequence of SEQ ID NO:63; and/or a light chain variable region comprising the amino acid sequence of SEQ ID NO:76 or an amino acid sequence having at least 85% identity to an amino acid sequence of SEQ ID NO:76. In some of any of the embodiments herein, the antibody or antigen-binding fragment thereof that specifically binds to a UCH-L1 comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the sequence of any of the above recited SEQ ID NO and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the sequence of any of the above recited SEQ ID NO.

In some of any of the embodiments herein, the antibody or antigen-binding fragment thereof that specifically binds to a UCH-L1 comprises (a) a heavy chain variable region comprising CDR-H1, CDR-H2 and CDR-H3 amino acid sequences of SEQ ID NO: 1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively; (b) a heavy chain variable region comprising CDR-H1, CDR-H2 and CDR-H3 amino acid sequences of SEQ ID NO:2, SEQ ID NO:10, SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively; (c) a heavy chain variable region comprising CDR-H1, CDR-H2 and CDR-H3 amino acid sequences of SEQ ID NO:4, SEQ ID NO: 12, SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively; (d) a heavy chain variable region comprising CDR-H1, CDR-H2 and CDR-H3 amino acid sequences of SEQ ID NO:6, SEQ ID NO:14, SEQ ID NO:24, respectively and/or a light chain variable region comprising CDR-L1, CDR-L2 and CDR-L3 amino acid sequences of SEQ ID NO:33, SEQ ID NO:40 and SEQ ID NO:48, respectively; or (e) a heavy chain variable region comprising CDR-H1, CDR-H2 and CDR-H3 amino acid sequences of SEQ ID NO:5, SEQ ID NO:13, SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively.

In some of any of the embodiments herein, the antibody or antigen-binding fragment thereof that specifically binds to a UCH-L1 comprises (a) a heavy chain variable region comprising the amino acid sequence of SEQ ID NO:51 or an amino acid sequence having at least 85% identity to an amino acid sequence of SEQ ID NO:51; and/or a light chain variable region comprising the amino acid sequence of SEQ ID NO:64 or an amino acid sequence having at least 85% identity to the amino acid sequence of SEQ ID NO:64; (b) a heavy chain variable region comprising the amino acid sequence of SEQ ID NO:52 or an amino acid sequence having at least 85% identity to an amino acid sequence of SEQ ID NO:52; and/or a light chain variable region comprising the amino acid sequence of SEQ ID NO:65 or an amino acid sequence having at least 85% identity to an amino acid sequence of SEQ ID NO:65; (c) a heavy chain variable region comprising the amino acid sequence of SEQ ID NO:54 or an amino acid sequence having at least 85% identity to an amino acid sequence of SEQ ID NO:54; and/or a light chain variable region comprising the amino acid sequence of SEQ ID NO:67 or an amino acid sequence having at least 85% identity to an amino acid sequence of SEQ ID NO:67; (d) a heavy chain variable region comprising the amino acid sequence of SEQ ID NO:56 or an amino acid sequence having at least 85% identity to an amino acid sequence of SEQ ID NO:56; and/or a light chain variable region comprising the amino acid sequence of SEQ ID NO:69 or an amino acid sequence having at least 85% identity to an amino acid sequence of SEQ ID NO:69; or (e) a heavy chain variable region comprising the amino acid sequence of SEQ ID NO:55 or an amino acid sequence having at least 85% identity to an amino acid sequence of SEQ ID NO:55; and/or a light chain variable region comprising the amino acid sequence of SEQ ID NO:68 or an amino acid sequence having at least 85% identity to an amino acid sequence of SEQ ID NO:68. In some of any of the embodiments herein, the antibody or antigen-binding fragment thereof that specifically binds to a UCH-L1 comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of any of the above recited SEQ ID NO and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of any of the above recited SEQ ID NO.

In some of any of the embodiments herein, the antibody or antigen-binding fragment thereof that specifically binds to a UCH-L1 comprises (a) a heavy chain variable region comprising the amino acid sequence of SEQ ID NO:51 or an amino acid sequence having at least 85% identity to an amino acid sequence of SEQ ID NO:51; and/or a light chain variable region comprising the amino acid sequence of SEQ ID NO:64 or an amino acid sequence having at least 85% identity to the amino acid sequence of SEQ ID NO:64; or (b) a heavy chain variable region comprising the amino acid sequence of SEQ ID NO:52 or an amino acid sequence having at least 85% identity to an amino acid sequence of SEQ ID NO:52; and/or a light chain variable region comprising the amino acid sequence of SEQ ID NO:65 or an amino acid sequence having at least 85% identity to an amino acid sequence of SEQ ID NO:65. In some of any of the embodiments herein, the antibody or antigen-binding fragment thereof that specifically binds to a UCH-L1 comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of any of the above recited SEQ ID NO and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of any of the above recited SEQ ID NO.

In some of any of the embodiments herein, the antibody or antigen-binding fragment thereof that specifically binds to a UCH-L1 comprises a heavy chain variable region comprising CDR-H1, CDR-H2 and CDR-H3 amino acid sequences of SEQ ID NO:1, SEQ ID NO:19 and SEQ ID NO:20 and/or a light chain variable region comprising CDR-L1, CDR-L2 and CDR-L3 amino acid sequences of SEQ ID NO:28, SEQ ID NO:37 and SEQ ID NO:50, respectively.

In some of any of the embodiments herein, the antibody or antigen-binding fragment thereof that specifically binds to a UCH-L1 comprises a heavy chain variable region comprising the amino acid sequence of SEQ ID NO:63 or an amino acid sequence having at least 85% identity to an amino acid sequence of SEQ ID NO:63; and/or a light chain variable region comprising the amino acid sequence of SEQ ID NO:76 or an amino acid sequence having at least 85% identity to an amino acid sequence of SEQ ID NO:76. In some of any of the embodiments herein, the antibody or antigen-binding fragment thereof that specifically binds to a UCH-L1 comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of SEQ ID NO:63 and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of SEQ ID NO:76.

In some of any of the embodiments herein, the antibody or antigen-binding fragment thereof that specifically binds to a UCH-L1 comprises (a) a heavy chain variable region comprising CDR-H1, CDR-H2 and CDR-H3 amino acid sequences of SEQ ID NO:3, SEQ ID NO:11 and SEQ ID NO:20, respectively and/or a light chain variable region comprising CDR-L1, CDR-L2 and CDR-L3 amino acid sequences of SEQ ID NO:30, SEQ ID NO:37 and SEQ ID NO:45, respectively; or (b) a heavy chain variable region comprising CDR-H1, CDR-H2 and CDR-H3 amino acid sequences of SEQ ID NO:4, SEQ ID NO:12 and SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively; or (c) a heavy chain variable region comprising CDR-H1, CDR-H2 and CDR-H3 amino acid sequences of SEQ ID NO:5, SEQ ID NO:13 and SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively; or (d) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:33, SEQ ID NO:40, SEQ ID NO:48, respectively; or (e) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:34, SEQ ID NO:41 and SEQ ID NO:48, respectively; or (f) a heavy chain variable region comprising CDR-H1, CDR-H2 and CDR-H3 amino acid sequences of SEQ ID NO:6, SEQ ID NO:15 and SEQ ID NO:24, respectively and/or a light chain variable region comprising CDR-L1, CDR-L2 and CDR-L3 amino acid sequences of SEQ ID NO:34, SEQ ID NO:42 and SEQ ID NO:48, respectively; or (g) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:35, SEQ ID NO:41 and SEQ ID NO:48, respectively; or (h) a heavy chain variable region comprising CDR-H1, CDR-H2 and CDR-H3 amino acid sequences of SEQ ID NO:6, SEQ ID NO:16 and SEQ ID NO:25, respectively and/or a light chain variable region comprising CDR-L1, CDR-L2 and CDR-L3 amino acid sequences of SEQ ID NO:34, SEQ ID NO:42 and SEQ ID NO:48, respectively; or (i) a heavy chain variable region comprising CDR-H1, CDR-H2 and CDR-H3 amino acid sequences of SEQ ID NO:7, SEQ ID NO:17 and SEQ ID NO:26, respectively and/or a light chain variable region comprising CDR-L1, CDR-L2 and CDR-L3 amino acid sequences of SEQ ID NO:36, SEQ ID NO:43 and SEQ ID NO:49, respectively; or (j) a heavy chain variable region comprising CDR-H1, CDR-H2 and CDR-H3 amino acid sequences of SEQ ID NO:8, SEQ ID NO:18 and SEQ ID NO:27, respectively and/or a light chain variable region comprising CDR-L1, CDR-L2 and CDR-L3 amino acid sequences of SEQ ID NO:36, SEQ ID NO:44 and SEQ ID NO:49, respectively.

In some of any of the embodiments herein, the antibody or antigen-binding fragment thereof that specifically binds to a UCH-L1 comprises (a) a heavy chain variable region comprising the amino acid sequence of SEQ ID NO:53 or an amino acid sequence having at least 85% identity to an amino acid sequence of SEQ ID NO:53; and/or a light chain variable region comprising the amino acid sequence of SEQ ID NO:66 or an amino acid sequence having at least 85% identity to an amino acid sequence of SEQ ID NO:66; or (b) a heavy chain variable region comprising the amino acid sequence of SEQ ID NO:54 or an amino acid sequence having at least 85% identity to an amino acid sequence of SEQ ID NO:54; and/or a light chain variable region comprising the amino acid sequence of SEQ ID NO:67 or an amino acid sequence having at least 85% identity to an amino acid sequence of SEQ ID NO:67; or (c) a heavy chain variable region comprising the amino acid sequence of SEQ ID NO:55 or an amino acid sequence having at least 85% identity to an amino acid sequence of SEQ ID NO:55; and/or a light chain variable region comprising the amino acid sequence of SEQ ID NO:68 or an amino acid sequence having at least 85% identity to an amino acid sequence of SEQ ID NO:68; (d) a heavy chain variable region comprising the amino acid sequence of SEQ ID NO:56 or an amino acid sequence having at least 85% identity to an amino acid sequence of SEQ ID NO:56; and/or a light chain variable region comprising the amino acid sequence of SEQ ID NO:69 or an amino acid sequence having at least 85% identity to an amino acid sequence of SEQ ID NO:69; (e) a heavy chain variable region comprising the amino acid sequence of SEQ ID NO:57 or an amino acid sequence having at least 85% identity to an amino acid sequence of SEQ ID NO:57; and/or a light chain variable region comprising the amino acid sequence of SEQ ID NO:70 or an amino acid sequence having at least 85% identity to an amino acid sequence of SEQ ID NO:70; (f) a heavy chain variable region comprising the amino acid sequence of SEQ ID NO:58 or an amino acid sequence having at least 85% identity to an amino acid sequence of SEQ ID NO:58; and/or a light chain variable region the amino acid sequence of SEQ ID NO:71 or comprising an amino acid sequence having at least 85% identity to an amino acid sequence of SEQ ID NO:71; (g) a heavy chain variable region comprising the amino acid sequence of SEQ ID NO:59 or an amino acid sequence having at least 85% identity to an amino acid sequence of SEQ ID NO:59; and/or a light chain variable region comprising the amino acid sequence of SEQ ID NO:72 or an amino acid sequence having at least 85% identity to an amino acid sequence of SEQ ID NO:72; (h) a heavy chain variable region comprising the amino acid sequence of SEQ ID NO:60 or an amino acid sequence having at least 85% identity to an amino acid sequence of SEQ ID NO:60; and/or a light chain variable region comprising the amino acid sequence of SEQ ID NO:73 or an amino acid sequence having at least 85% identity to an amino acid sequence of SEQ ID NO:73; (i) a heavy chain variable region comprising the amino acid sequence of SEQ ID NO:61 or an amino acid sequence having at least 85% identity to an amino acid sequence of SEQ ID NO:61; and/or a light chain variable region comprising the amino acid sequence of SEQ ID NO:74 or an amino acid sequence having at least 85% identity to an amino acid sequence of SEQ ID NO:74; or (k) a heavy chain variable region comprising the amino acid sequence of SEQ ID NO:62 or an amino acid sequence having at least 85% identity to an amino acid sequence of SEQ ID NO:62; and/or a light chain variable region comprising the amino acid sequence of SEQ ID NO:75 or an amino acid sequence having at least 85% identity to an amino acid sequence of SEQ ID NO:75. In some of any of the embodiments herein, the antibody or antigen-binding fragment thereof that specifically binds to a UCH-L1 comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence set forth in any of the above recited SEQ ID NO and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence set forth in any of the above recited SEQ ID NO.

In some of any such embodiments herein, the antibody or antigen-binding fragment binds UCH-L1 with a binding affinity having a dissociation constant ($K_D$) of less than or less than about $1.0\times10^{-10}$ M, $2.0\times10^{-10}$ M, $3.0\times10^{-10}$ M, $4.0\times10^{-10}$ M, $5.0\times10^{-10}$ M, $6.0\times10^{-10}$ M, $7.0\times10^{-10}$ M, $8.0\times10^{-10}$ M, $9.0\times10^{-10}$ M, $1.0\times10^{-1}$ M, $2.0\times10^{-1}$ M, $3.0\times10^{-1}$ M, $4.0\times10^{-1}$ M, $5.0\times10^{-1}$ M, $6.0\times10^{-1}$ M, $7.0\times10^{-1}$ M, $8.0\times10^{-1}$ M, $9.0\times10^{-1}$ M, $1.0\times10^{-12}$ M or less; or the antibody or antigen-binding fragment binds UCH-L1 with a dissociation constant ($K_D$) from or from about $2.0\times10^{-10}$ M to $5.0\times10^{-12}$ M, such as from or from about $2.0\times10^{-10}$ M to $1.0\times10^{-12}$ M, $2.0\times10^{-10}$ M to $5.0\times10^{-1}$ M, $2.0\times10^{-10}$ M to $1.0\times10^{-1}$ M, $2.0\times10^{-10}$ M to $5.0\times10^{-10}$ M, $5.0\times10^{-10}$ M to $1.0\times10^{-12}$ M, $5.0\times10^{-10}$ M to $5.0\times10^{-11}$ M, $5.0\times10^{-10}$ M to $1.0\times10^{-11}$ M, $1.0\times10^{-11}$ M to $1.0\times10^{-12}$ M, $1.0\times10^{-11}$ M to $5.0\times10^{-11}$ M or $5.0\times10^{-11}$ M to $1.0\times10^{-12}$ M, for example, from or from about $2.0\times10^{-10}$ M $2.0\times10^{-10}$ M to $4.0\times10^{-10}$ M, $1.0\times10^{-11}$ M to $9.0\times10^{-11}$ M, $1.0\times10^{-12}$ M to $5.0\times10^{-12}$ M, or $1.0\times10^{-12}$ M, $2.0\times10^{-10}$ M.

In some of any such embodiments herein, the antibody or antigen-binding fragment binds to an epitope within or that is or includes residues 28-36 of UCH-L1 protein, residues 98-106 of UCH-L1 protein, residues 138-145 of UCH-L1 protein, and/or residues 142-149 of UCH-L1 protein corresponding to amino acid positions set forth in SEQ ID NO:207.

In some aspects, provided herein are antibodies or antigen-binding fragments that specifically binds to a UCH-L1 (e.g., human UCH-L1), wherein the antibody or antigen-binding fragment binds to an epitope within or that is or includes residues 98-106 of UCH-L1 protein corresponding to amino acid positions set forth in SEQ ID NO:207. In some embodiments, the antibody or antigen-binding fragment comprises (a) a heavy chain variable region comprising CDR-H1, CDR-H2 and CDR-H3 amino acid sequences of SEQ ID NO:1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively; (b) a heavy chain variable region comprising CDR-H1, CDR-H2 and CDR-H3 amino acid sequences of SEQ ID NO:3, SEQ ID NO:11 and SEQ ID NO:20, respectively and/or a light chain variable region comprising CDR-L1, CDR-L2 and CDR-L3 amino acid sequences of SEQ ID NO:30, SEQ ID NO:37 and SEQ ID NO:45, respectively; or (c) heavy chain variable region comprising CDR-H1, CDR-H2 and CDR-H3 amino acid sequences of SEQ ID NO:1, SEQ ID NO:19 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:50, respectively.

In some aspects, provided herein are antibodies or antigen-binding fragments that specifically binds to a UCH-L1 (e.g., human UCH-L1), wherein the antibody or antigen-binding fragment binds to an epitope within or that is or includes residues 28-36 UCH-L1 corresponding to amino acid positions of UCH-L1 set forth in SEQ ID NO:207. In some embodiments, the antibody or antigen-binding fragment comprises (a) a heavy chain variable region comprising CDR-H1, CDR-H2 and CDR-H3 amino acid sequences of SEQ ID NO:2, SEQ ID NO:10 and SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively; (b) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:33, SEQ ID NO:40 and SEQ ID NO:48, respectively; (c) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:34, SEQ ID NO:41 and SEQ ID NO:48, respectively; (d) a heavy chain variable region comprising CDR-H1, CDR-H2 and CDR-H3 amino acid sequences of SEQ ID NO:6, SEQ ID NO:15 and SEQ ID NO:24, respectively and/or a light chain variable region comprising CDR-L1, CDR-L2 and CDR-L3 amino acid sequences of SEQ ID NO:34, SEQ ID NO:42 and SEQ ID NO:48, respectively; (e) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:35, SEQ ID NO:41 and SEQ ID NO:48, respectively; (f) a heavy chain variable region comprising CDR-H1, CDR-H2 and CDR-H3 amino acid sequences of SEQ ID NO:6, SEQ ID NO:16 and SEQ ID NO:25, respectively and/or a light chain variable region comprising CDR-L1, CDR-L2 and CDR-L3 amino acid sequences of SEQ ID NO:34, SEQ ID NO:42 and SEQ ID NO:48, respectively; (g) a heavy chain variable region comprising CDR-H1, CDR-H2 and CDR-H3 amino acid sequences of SEQ ID NO:7, SEQ ID NO:17 and SEQ ID NO:26, respectively and/or a light chain variable region comprising CDR-L1, CDR-L2 and CDR-L3 amino acid sequences of SEQ ID NO:36, SEQ ID NO:43 and SEQ ID NO:49, respectively; or (h) a heavy chain variable region comprising CDR-H1, CDR-H2 and CDR-H3 amino acid sequences of SEQ ID NO:8, SEQ ID NO:18 and SEQ ID NO:27, respectively and/or a light chain variable region comprising CDR-L1, CDR-L2 and CDR-L3 amino acid sequences of SEQ ID NO:36, SEQ ID NO:44 and SEQ ID NO:49, respectively.

In some aspects, provided herein are antibodies or antigen-binding fragments that specifically binds to a UCH-L1 (e.g., human UCH-L1), wherein the antibody or antigen-binding fragment binds to an epitope within or that is or includes residues 138-145 of UCH-L1 protein corresponding to amino acid positions set forth in SEQ ID NO:207. In some embodiments, the antibody or antigen-binding fragment comprises a heavy chain variable region comprising CDR-H1, CDR-H2 and CDR-H3 amino acid sequences of SEQ ID NO:4, SEQ ID NO: 12 and SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively.

In some aspects, provided herein are antibodies or antigen-binding fragments that specifically binds to a UCH-L1 (e.g., human UCH-L1), wherein the antibody or antigen-binding fragment binds to an epitope within or that is or includes residues 142-149 of UCH-L1 protein corresponding to amino acid positions set forth in SEQ ID NO:207. In some embodiments, the antibody or antigen-binding fragment comprises a heavy chain variable region comprising CDR-H1, CDR-H2 and CDR-H3 amino acid sequences of SEQ ID NO:5, SEQ ID NO:13 and SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively.

In some of any of the embodiments herein, the UCH-L1 (e.g., human UCH-L1) is recombinant UCH-L1 (e.g., recombinant human UCH-L1). In some of any of the embodiments herein, the UCH-L1 (e.g., human UCH-L1) is native UCH-L1 (e.g., native human UCH-L1). In some further embodiments, the native UCH-L1 is present in or obtained from serum, plasma, blood, cerebrospinal fluid (CSF), urine, sweat, or saliva.

Provided herein are antibodies or antigen-binding fragments thereof, including those that specifically bind to a GFAP, such as a human GFAP, wherein the antibodies or antigen-binding fragments contain particular complementarity determining regions (CDRs), including heavy chain CDRs (i.e., CDR-H1, CDR-H2, and/or CDR-H3) and light chain CDRs (i.e., CDR-L1, CDR-L2, and/or CDR-L3), such as any described herein. In some embodiments, the antibody or antigen-binding fragment thereof includes a heavy chain variable region and a light chain variable region, such as any described herein.

In some embodiments, provided herein are antibodies or antigen-binding fragments thereof that specifically binds to a GFAP (e.g., human GFAP), wherein the antibody or antigen-binding fragment comprises a heavy chain variable region comprising an amino acid sequence having at least 85% identity to an amino acid sequence selected from any one of SEQ ID NOs:172-188; and/or a light chain variable region comprising an amino acid sequence having at least 85% identity to an amino acid sequence selected from any one of SEQ ID NOs:189-206. In some embodiments, the heavy chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs:172-188 or has the amino acid sequence selected from any one of SEQ ID NOs:172-188. In some of any of the embodiments herein, the light chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs:189-206 or has the amino acid sequence selected from any one of SEQ ID NOs:189-206. In some embodiments, the heavy chain variable region comprises: (i) a CDR-H1 comprising the amino acid sequence selected from SEQ ID NOs:77-90; (ii) a CDR-H2 comprising the amino acid sequence selected from SEQ ID NOs:91-107; and (iii) a CDR-H3 comprising the amino acid sequence selected from SEQ ID NOs:108-124; and/or wherein the light chain variable region comprises: (i) a CDR-L1 comprising the amino acid sequence selected from SEQ ID NOs:125-141; (ii) a CDR-L2 comprising the amino acid sequence selected from SEQ ID NOs:142-156; and (iii) a CDR-L3 comprising the amino acid sequence selected from SEQ ID NOs:157-171. In some of the embodiments, the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:172-188; and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:189-206.

In some embodiments, provided herein are antibodies or antigen-binding fragments thereof that specifically binds to a GFAP (e.g., human GFAP), wherein the antibody or antigen-binding fragment comprises an amino acid sequence having at least 85% identity to an amino acid sequence selected from any one of SEQ ID NOS:174-188; and/or a light chain variable region comprising an amino acid sequence having at least 85% identity to an amino acid sequence selected from any one of SEQ ID NO: 191-206. In some embodiments, the heavy chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOS: 174-188 or comprises the amino acid sequence set forth in any of SEQ ID NOS: 174-188; and/or the light chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOS: 191-206 or comprises the light chain variable region comprises the amino acid sequence set forth in any one of SEQ ID NOS:191-206. In some embodiments, the heavy chain variable region comprises: (i) a CDR-H1 comprising the amino acid sequence selected from SEQ ID NOs:79-90; (ii) a CDR-H2 comprising the amino acid sequence selected from SEQ ID NOs:93-107; and (iii) a CDR-H3 comprising the amino acid sequence selected from SEQ ID NOs:110-124; and/or the light chain variable region comprises: (i) a CDR-L1 comprising the amino acid sequence selected from SEQ ID NOs:127-141; (ii) a CDR-L2 comprising the amino acid sequence selected from SEQ ID NOs:144-156; and (iii) a CDR-L3 comprising the amino acid sequence selected from SEQ ID NOs:159-171; or the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:174-188 and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:191-206.

In some embodiments, provided herein are antibodies or antigen-binding fragments thereof that specifically binds to a GFAP (e.g., human GFAP), wherein the antibody or antigen-binding fragment comprises a heavy chain variable region and a light chain variable region, wherein the heavy chain variable region comprises: (i) CDR-H1 comprising the amino acid sequence selected from SEQ ID NOs:77-90; (ii) CDR-H2 comprising the amino acid sequence selected from SEQ ID NOs:91-107; and (iii) CDR-H3 comprising the amino acid sequence selected from SEQ ID NOs:108-124;

and/or the light chain variable region comprises: (i) CDR-L1 comprising the amino acid sequence selected from SEQ ID NOs:125-141; (ii) CDR-L2 comprising the amino acid sequence selected from SEQ ID NOs:142-156; and (iii) CDR-L3 comprising the amino acid sequence selected from SEQ ID NOs:157-171.

In some of any such embodiments herein, the antibody or antigen-binding fragment that specifically binds to a GFAP comprises (a) a heavy chain variable region comprising CDR-H1, CDR-H2 and CDR-H3 amino acid sequences of SEQ ID NO:77, SEQ ID NO:91 and SEQ ID NO:108, respectively and/or a light chain variable region comprising CDR-L1, CDR-L2 and CDR-L3 amino acid sequences of SEQ ID NO:125, SEQ ID NO:142 and SEQ ID NO:157, respectively; (b) a heavy chain variable region comprising CDR-H1, CDR-H2 and CDR-H3 amino acid sequences of SEQ ID NO:78, SEQ ID NO:92 and SEQ ID NO:109, respectively and/or a light chain variable region comprising CDR-L1, CDR-L2 and CDR-L3 amino acid sequences of SEQ ID NO:126, SEQ ID NO:143 and SEQ ID NO:158, respectively; (c) a heavy chain variable region comprising CDR-H1, CDR-H2 and CDR-H3 amino acid sequences of SEQ ID NO:79, SEQ ID NO:93 and SEQ ID NO:110, respectively and/or a light chain variable region comprising CDR-L1, CDR-L2 and CDR-L3 amino acid sequences of SEQ ID NO:127, SEQ ID NO:144 and SEQ ID NO:159, respectively; (d) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:128, SEQ ID NO:145 and SEQ ID NO:160, respectively; (e) a heavy chain variable region comprising CDR-H1, CDR-H2 and CDR-H3 amino acid sequences of SEQ ID NO:80, SEQ ID NO:95 and SEQ ID NO:112, respectively and/or a light chain variable region comprising CDR-L1, CDR-L2 and CDR-L3 amino acid sequences of SEQ ID NO:126, SEQ ID NO:142 and SEQ ID NO:158, respectively; (f) a heavy chain variable region comprising CDR-H1, CDR-H2 and CDR-H3 amino acid sequences of SEQ ID NO:81, SEQ ID NO:96 and SEQ ID NO:113, respectively and/or a light chain variable region comprising CDR-L1, CDR-L2 and CDR-L3 amino acid sequences of SEQ ID NO:129, SEQ ID NO:146 and SEQ ID NO:161, respectively; (g) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:130, SEQ ID NO:145 and SEQ ID NO:160, respectively; (h) a heavy chain variable region comprising CDR-H1, CDR-H2 and CDR-H3 amino acid sequences of SEQ ID NO:82, SEQ ID NO:97 and SEQ ID NO:114, respectively and/or a light chain variable region comprising CDR-L1, CDR-L2 and CDR-L3 amino acid sequences of SEQ ID NO:131, SEQ ID NO:147 and SEQ ID NO: 162, respectively; (i) a heavy chain variable region comprising CDR-H1, CDR-H2 and CDR-H3 amino acid sequences of SEQ ID NO:83, SEQ ID NO:98 and SEQ ID NO:115, respectively and/or a light chain variable region comprising CDR-L1, CDR-L2 and CDR-L3 amino acid sequences of SEQ ID NO:132, SEQ ID NO:148 and SEQ ID NO:163, respectively; (j) a heavy chain variable region comprising CDR-H1, CDR-H2 and CDR-H3 amino acid sequences of SEQ ID NO:84, SEQ ID NO:99 and SEQ ID NO:116, respectively and/or a light chain variable region comprising CDR-L1, CDR-L2 and CDR-L3 amino acid sequences of SEQ ID NO:133, SEQ ID NO:149 and SEQ ID NO:164, respectively; (k) a heavy chain variable region comprising CDR-H1, CDR-H2 and CDR-H3 amino acid sequences of SEQ ID NO:85, SEQ ID NO:100 and SEQ ID NO:117, respectively and/or a light chain variable region comprising CDR-L1, CDR-L2 and CDR-L3 amino acid sequences of SEQ ID NO: 134, SEQ ID NO:150 and SEQ ID NO:165, respectively; (l) a heavy chain variable region comprising CDR-H1, CDR-H2 and CDR-H3 amino acid sequences of SEQ ID NO:86, SEQ ID NO:101 and SEQ ID NO:118, respectively and/or a light chain variable region comprising CDR-L1, CDR-L2 and CDR-L3 amino acid sequences of SEQ ID NO:135, SEQ ID NO:151 and SEQ ID NO:166, respectively; (m) a heavy chain variable region comprising CDR-H1, CDR-H2 and CDR-H3 amino acid sequences of SEQ ID NO:78, SEQ ID NO:102 and SEQ ID NO:119, respectively and/or a light chain variable region comprising CDR-L1, CDR-L2 and CDR-L3 amino acid sequences of SEQ ID NO:136, SEQ ID NO:152 and SEQ ID NO:167, respectively; (n) a heavy chain variable region comprising CDR-H1, CDR-H2 and CDR-H3 amino acid sequences of SEQ ID NO:78, SEQ ID NO:103 and SEQ ID NO:120, respectively and/or a light chain variable region comprising CDR-L1, CDR-L2 and CDR-L3 amino acid sequences of SEQ ID NO:137, SEQ ID NO:142 and SEQ ID NO:158, respectively; (o) a heavy chain variable region comprising CDR-H1, CDR-H2 and CDR-H3 amino acid sequences of SEQ ID NO:87, SEQ ID NO:104 and SEQ ID NO:121, respectively and/or a light chain variable region comprising CDR-L1, CDR-L2 and CDR-L3 amino acid sequences of SEQ ID NO: 138, SEQ ID NO:153 and SEQ ID NO:168, respectively; (p) a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO: 169, respectively; (q) a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:140, SEQ ID NO:155 and SEQ ID NO:170, respectively; or (r) a heavy chain variable region comprising CDR-H1, CDR-H2 and CDR-H3 amino acid sequences of SEQ ID NO:90, SEQ ID NO:107 and SEQ ID NO:124, respectively and/or a light chain variable region comprising CDR-L1, CDR-L2 and CDR-L3 amino acid sequences of SEQ ID NO:141, SEQ ID NO:156 and SEQ ID NO:171, respectively.

In some of any such embodiments herein, the antibody or antigen-binding fragment that specifically binds to a GFAP comprises (a) a heavy chain variable region comprising the amino acid sequence of SEQ ID NO:172 or an amino acid sequence having at least 85% identity to an amino acid sequence of SEQ ID NO:172; and/or a light chain variable region comprising the amino acid sequence of SEQ ID NO:189 or an amino acid sequence having at least 85% identity to an amino acid sequence of SEQ ID NO:189; (b) a heavy chain variable region comprising the amino acid sequence of SEQ ID NO:173 or an amino acid sequence having at least 85% identity to an amino acid sequence of SEQ ID NO:173; and/or a light chain variable region comprising the amino acid sequence of SEQ ID NO:190 or an amino acid sequence having at least 85% identity to an amino acid sequence of SEQ ID NO:190; (c) a heavy chain variable region comprising the amino acid sequence of SEQ ID NO:174 or an amino acid sequence having at least 85% identity to an amino acid sequence of SEQ ID NO: 174; and/or a light chain variable region comprising the amino acid sequence of SEQ ID NO:191 or an amino acid sequence having at least 85% identity to an amino acid sequence of SEQ ID NO:191; (d) a heavy chain variable region comprising the amino acid sequence of SEQ ID NO:175 or an amino acid sequence having at least 85% identity to an amino acid sequence of SEQ ID NO:175; and/or a light chain variable region comprising the amino acid sequence of SEQ ID NO:192 or an amino acid sequence having at least 85% identity to an amino acid sequence of SEQ ID NO:192; (e) a heavy chain variable region comprising the amino acid sequence of SEQ ID NO:176 or an amino acid sequence having at least 85% identity to an amino acid sequence of SEQ ID NO:176; and/or a light chain variable region comprising the amino acid sequence of SEQ ID NO: 193 or an amino acid sequence having at least 85% identity to an amino acid sequence of SEQ ID NO:193; (f) a heavy chain variable region comprising the amino acid sequence of SEQ ID NO: 177 or an amino acid sequence having at least 85% identity to an amino acid sequence of SEQ ID NO:177; and/or a light chain variable region comprising the amino acid sequence of SEQ ID NO:194 or an amino acid sequence having at least 85% identity to an amino acid sequence of SEQ ID NO:194; (g) a heavy chain variable region comprising the amino acid sequence of SEQ ID NO:175 or an amino acid sequence having at least 85% identity to an amino acid sequence of SEQ ID NO:175; and/or a light chain variable region comprising the amino acid sequence of SEQ ID NO:195 or an amino acid sequence having at least 85% identity to an amino acid sequence of SEQ ID NO:195; (h) a heavy chain variable region comprising the amino acid sequence of SEQ ID NO:178 or an amino acid sequence having at least 85% identity to an amino acid sequence of SEQ ID NO:178; and/or a light chain variable region comprising the amino acid sequence of SEQ ID NO: 196 or an amino acid sequence having at least 85% identity to an amino acid sequence of SEQ ID NO:196; (i) a heavy chain variable region comprising the amino acid sequence of SEQ ID NO:179 or an amino acid sequence having at least 85% identity to an amino acid sequence of SEQ ID NO: 179; and/or a light chain variable region comprising the amino acid sequence of SEQ ID NO: 197 or an amino acid sequence having at least 85% identity to an amino acid sequence of SEQ ID NO:197; (j) a heavy chain variable region comprising the amino acid sequence of SEQ ID NO:180 or an amino acid sequence having at least 85% identity to an amino acid sequence of SEQ ID NO:180; and/or a light chain variable region comprising the amino acid sequence of SEQ ID NO:198 or an amino acid sequence having at least 85% identity to an amino acid sequence of SEQ ID NO:198; (k) a heavy chain variable region comprising the amino acid sequence of SEQ ID NO:181 or an amino acid sequence having at least 85% identity to an amino acid sequence of SEQ ID NO:181; and/or a light chain variable region comprising the amino acid sequence of SEQ ID NO: 199 or an amino acid sequence having at least 85% identity to an amino acid sequence of SEQ ID NO: 199; (l) a heavy chain variable region comprising the amino acid sequence of SEQ ID NO: 182 or an amino acid sequence having at least 85% identity to an amino acid sequence of SEQ ID NO:182; and/or a light chain variable region comprising the amino acid sequence of SEQ ID NO:200 or an amino acid sequence having at least 85% identity to an amino acid sequence of SEQ ID NO:200; (m) a heavy chain variable region comprising the amino acid sequence of SEQ ID NO:183 or an amino acid sequence having at least 85% identity to an amino acid sequence of SEQ ID NO:183; and/or a light chain variable region comprising the amino acid sequence of SEQ ID NO:201 or an amino acid sequence having at least 85% identity to an amino acid sequence of SEQ ID NO:201; (n) a heavy chain variable region comprising the amino acid sequence of SEQ ID NO:184 or an amino acid sequence having at least 85% identity to an amino acid sequence of SEQ ID NO:184; and/or a light chain variable region comprising the amino acid sequence of SEQ ID NO:202 or an amino acid sequence having at least 85% identity to an amino acid sequence of SEQ ID NO:202; (o) a heavy chain variable region comprising the amino acid sequence of SEQ ID NO:185 or an amino acid sequence having at least 85% identity to an amino acid sequence of SEQ ID NO: 185; and/or a light chain variable region comprising the amino acid sequence of SEQ ID NO:203 or an amino acid sequence having at least 85% identity to an amino acid sequence of SEQ ID NO:203; (p) a heavy chain variable region comprising the amino acid sequence of SEQ ID NO:186 or an amino acid sequence having at least 85% identity to an amino acid sequence of SEQ ID NO: 186; and/or a light chain variable region comprising the amino acid sequence of SEQ ID NO:204 or an amino acid sequence having at least 85% identity to an amino acid sequence of SEQ ID NO:204; (q) a heavy chain variable region comprising the amino acid sequence of SEQ ID NO:187 or an amino acid sequence having at least 85% identity to an amino acid sequence of SEQ ID NO:187; and/or a light chain variable region comprising the amino acid sequence of SEQ ID NO:205 an amino acid sequence having at least 85% identity to an amino acid sequence of SEQ ID NO:205; or (r) a heavy chain variable region comprising the amino acid sequence of SEQ ID NO:188 or an amino acid sequence having at least 85% identity to an amino acid sequence of SEQ ID NO:188; and/or a light chain variable region comprising the amino acid sequence of SEQ ID NO:206 or an amino acid sequence having at least 85% identity to an amino acid sequence of SEQ ID NO:206. In some of any of the embodiments herein, the antibody or antigen-binding fragment thereof that specifically binds to a GFAP comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of any of the above recited SEQ ID NO and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence set forth in any of the above recited SEQ ID NO.

In some of any such embodiments herein, the antibody or antigen-binding fragment that specifically binds to a GFAP comprises a heavy chain variable region comprising CDR-H1, CDR-H2 and CDR-H3 amino acid sequences of SEQ ID NO:77, SEQ ID NO:91 and SEQ ID NO:108, respectively and/or a light chain variable region comprising CDR-L1, CDR-L2 and CDR-L3 amino acid sequences of SEQ ID NO:125, SEQ ID NO:142 and SEQ ID NO:157, respectively.

In some of any such embodiments herein, the antibody or antigen-binding fragment that specifically binds to a GFAP comprises a heavy chain variable region comprising the amino acid sequence of SEQ ID NO:172 or an amino acid sequence having at least 85% identity to an amino acid sequence of SEQ ID NO:172; and/or a light chain variable region comprising the amino acid sequence of SEQ ID NO:189 or an amino acid sequence having at least 85% identity to an amino acid sequence of SEQ ID NO:189. In some of any of the embodiments herein, the antibody or antigen-binding fragment thereof that specifically binds to a GFAP comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of SEQ ID NO:172 and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of SEQ ID NO:189.

In some of any such embodiments herein, the antibody or antigen-binding fragment that specifically binds to a GFAP comprises a heavy chain variable region comprising CDR-H1, CDR-H2 and CDR-H3 amino acid sequences of SEQ ID NO:78, SEQ ID NO:92 and SEQ ID NO:109, respectively and/or a light chain variable region comprising CDR-L1, CDR-L2 and CDR-L3 amino acid sequences of SEQ ID NO:126, SEQ ID NO:143 and SEQ ID NO:158, respectively.

In some of any such embodiments herein, the antibody or antigen-binding fragment that specifically binds to a GFAP comprises a heavy chain variable region comprising the amino acid sequence of SEQ ID NO:173 or an amino acid sequence having at least 85% identity to an amino acid sequence of SEQ ID NO:173; and/or a light chain variable region comprising the amino acid sequence of SEQ ID NO:190 or an amino acid sequence having at least 85% identity to an amino acid sequence of SEQ ID NO:190. In some of any of the embodiments herein, the antibody or antigen-binding fragment thereof that specifically binds to a GFAP comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence of SEQ ID NO:173 and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence provided of SEQ ID NO:190.

In some of any such embodiments herein, the antibody or antigen-binding fragment that specifically binds to a GFAP comprises (a) a heavy chain variable region comprising CDR-H1, CDR-H2 and CDR-H3 amino acid sequences of SEQ ID NO:79, SEQ ID NO:93 and SEQ ID NO:110, respectively and/or a light chain variable region comprising CDR-L1, CDR-L2 and CDR-L3 amino acid sequences of SEQ ID NO:127, SEQ ID NO:144 and SEQ ID NO:159, respectively; (b) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:128, SEQ ID NO:145 and SEQ ID NO:160, respectively; (c) a heavy chain variable region comprising CDR-H1, CDR-H2 and CDR-H3 amino acid sequences of SEQ ID NO:80, SEQ ID NO:95 and SEQ ID NO:112, respectively and/or a light chain variable region comprising CDR-L1, CDR-L2 and CDR-L3 amino acid sequences of SEQ ID NO:126, SEQ ID NO:142 and SEQ ID NO: 158, respectively; (d) a heavy chain variable region comprising CDR-H1, CDR-H2 and CDR-H3 amino acid sequences of SEQ ID NO:81, SEQ ID NO:96 and SEQ ID NO:113, respectively and/or a light chain variable region comprising CDR-L1, CDR-L2 and CDR-L3 amino acid sequences of SEQ ID NO:129, SEQ ID NO:146 and SEQ ID NO:161, respectively; (e) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:130, SEQ ID NO:145 and SEQ ID NO:160, respectively; (f) a heavy chain variable region comprising CDR-H1, CDR-H2 and CDR-H3 amino acid sequences of SEQ ID NO:82, SEQ ID NO:97 and SEQ ID NO:114, respectively and/or a light chain variable region comprising CDR-L1, CDR-L2 and CDR-L3 amino acid sequences of SEQ ID NO:131, SEQ ID NO:147 and SEQ ID NO:162, respectively; (g) a heavy chain variable region comprising CDR-H1, CDR-H2 and CDR-H3 amino acid sequences of SEQ ID NO:83, SEQ ID NO:98 and SEQ ID NO:115, respectively and/or a light chain variable region comprising CDR-L1, CDR-L2 and CDR-L3 amino acid sequences of SEQ ID NO:132, SEQ ID NO:148 and SEQ ID NO:163, respectively; (h) a heavy chain variable region comprising CDR-H1, CDR-H2 and CDR-H3 amino acid sequences of SEQ ID NO:84, SEQ ID NO:99 and SEQ ID NO:116, respectively and/or a light chain variable region comprising CDR-L1, CDR-L2 and CDR-L3 amino acid sequences of SEQ ID NO:133, SEQ ID NO:149 and SEQ ID NO: 164, respectively; (i) a heavy chain variable region comprising CDR-H1, CDR-H2 and CDR-H3 amino acid sequences of SEQ ID NO:85, SEQ ID NO:100 and SEQ ID NO:117, respectively and/or a light chain variable region comprising CDR-L1, CDR-L2 and CDR-L3 amino acid sequences of SEQ ID NO:134, SEQ ID NO:150 and SEQ ID NO:165, respectively; (j) a heavy chain variable region comprising CDR-H1, CDR-H2 and CDR-H3 amino acid sequences of SEQ ID NO:86, SEQ ID NO:101 and SEQ ID NO:118, respectively and/or a light chain variable region comprising CDR-L1, CDR-L2 and CDR-L3 amino acid sequences of SEQ ID NO:135, SEQ ID NO:151 and SEQ ID NO:166, respectively; (k) a heavy chain variable region comprising CDR-H1, CDR-H2 and CDR-H3 amino acid sequences of SEQ ID NO:78, SEQ ID NO:102 and SEQ ID NO:119, respectively and/or a light chain variable region comprising CDR-L1, CDR-L2 and CDR-L3 amino acid sequences of SEQ ID NO: 136, SEQ ID NO:152 and SEQ ID NO:167, respectively; (l) a heavy chain variable region comprising CDR-H1, CDR-H2 and CDR-H3 amino acid sequences of SEQ ID NO:78, SEQ ID NO:103 and SEQ ID NO:120, respectively and/or a light chain variable region comprising CDR-L1, CDR-L2 and CDR-L3 amino acid sequences of SEQ ID NO:137, SEQ ID NO:142 and SEQ ID NO:158, respectively; (n) a heavy chain variable region comprising CDR-H1, CDR-H2 and CDR-H3 amino acid sequences of SEQ ID NO:87, SEQ ID NO:104 and SEQ ID NO:121, respectively and/or a light chain variable region comprising CDR-L1, CDR-L2 and CDR-L3 amino acid sequences of SEQ ID NO:138, SEQ ID NO:153 and SEQ ID NO:168, respectively; (o) a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO:169, respectively; (p) a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO: 140, SEQ ID NO:155 and SEQ ID NO:170, respectively; or (q) a heavy chain variable region comprising CDR-H1, CDR-H2 and CDR-H3 amino acid sequences of SEQ ID NO:90, SEQ ID NO:107 and SEQ ID NO:124, respectively and/or a light chain variable region comprising CDR-L1, CDR-L2 and CDR-L3 amino acid sequences of SEQ ID NO:141, SEQ ID NO:156 and SEQ ID NO:171, respectively.

In some of any such embodiments herein, the antibody or antigen-binding fragment that specifically binds to a GFAP comprises (a) a heavy chain variable region comprising the amino acid sequence of SEQ ID NO:174 or an amino acid sequence having at least 85% identity to an amino acid sequence of SEQ ID NO:174; and/or a light chain variable region comprising the amino acid sequence of SEQ ID NO:191 or an amino acid sequence having at least 85% identity to an amino acid sequence of SEQ ID NO:191; (b) a heavy chain variable region comprising the amino acid sequence of SEQ ID NO:175 or an amino acid sequence having at least 85% identity to an amino acid sequence of SEQ ID NO:175; and/or a light chain variable region comprising the amino acid sequence of SEQ ID NO:192 or an amino acid sequence having at least 85% identity to an amino acid sequence of SEQ ID NO:192; (c) a heavy chain variable region comprising the amino acid sequence of SEQ ID NO:176 or an amino acid sequence having at least 85% identity to an amino acid sequence of SEQ ID NO: 176; and/or a light chain variable region comprising the amino acid sequence of SEQ ID NO:193 or an amino acid sequence having at least 85% identity to an amino acid sequence of SEQ ID NO:193; (d) a heavy chain variable region comprising the amino acid sequence of SEQ ID NO:177 or an amino acid sequence having at least 85% identity to an amino acid sequence of SEQ ID NO:177; and/or a light chain variable region comprising the amino acid sequence of SEQ ID NO:194 or an amino acid sequence having at least 85% identity to an amino acid sequence of SEQ ID NO:194; (e) a heavy chain variable region comprising the amino acid sequence of SEQ ID NO:175 or an amino acid sequence having at least 85% identity to an amino acid sequence of SEQ ID NO:175; and/or a light chain variable region comprising the amino acid sequence of SEQ ID NO:195 or an amino acid sequence having at least 85% identity to an amino acid sequence of SEQ ID NO:195; (f) a heavy chain variable region comprising the amino acid sequence of SEQ ID NO: 178 or an amino acid sequence having at least 85% identity to an amino acid sequence of SEQ ID NO:178; and/or a light chain variable region comprising the amino acid sequence of SEQ ID NO:196 or an amino acid sequence having at least 85% identity to an amino acid sequence of SEQ ID NO:196; (g) a heavy chain variable region comprising the amino acid sequence of SEQ ID NO:179 or an amino acid sequence having at least 85% identity to an amino acid sequence of SEQ ID NO:179; and/or a light chain variable region comprising the amino acid sequence of SEQ ID NO:197 or an amino acid sequence having at least 85% identity to an amino acid sequence of SEQ ID NO:197; (h) a heavy chain variable region comprising the amino acid sequence of SEQ ID NO:180 or an amino acid sequence having at least 85% identity to an amino acid sequence of SEQ ID NO:180; and/or a light chain variable region comprising the amino acid sequence of SEQ ID NO:198 or an amino acid sequence having at least 85% identity to an amino acid sequence of SEQ ID NO:198; (i) a heavy chain variable region comprising the amino acid sequence of SEQ ID NO:181 or an amino acid sequence having at least 85% identity to an amino acid sequence of SEQ ID NO: 181; and/or a light chain variable region comprising the amino acid sequence of SEQ ID NO:199 or an amino acid sequence having at least 85% identity to an amino acid sequence of SEQ ID NO:199; (j) a heavy chain variable region comprising the amino acid sequence of SEQ ID NO:182 or an amino acid sequence having at least 85% identity to an amino acid sequence of SEQ ID NO:182; and/or a light chain variable region comprising the amino acid sequence of SEQ ID NO:200 or an amino acid sequence having at least 85% identity to an amino acid sequence of SEQ ID NO:200; (k) a heavy chain variable region comprising the amino acid sequence of SEQ ID NO:183 or an amino acid sequence having at least 85% identity to an amino acid sequence of SEQ ID NO:183; and/or a light chain variable region comprising the amino acid sequence of SEQ ID NO:201 or an amino acid sequence having at least 85% identity to an amino acid sequence of SEQ ID NO:201; (l) a heavy chain variable region comprising the amino acid sequence of SEQ ID NO: 184 or an amino acid sequence having at least 85% identity to an amino acid sequence of SEQ ID NO:184; and/or a light chain variable region comprising the amino acid sequence of SEQ ID NO:202 or an amino acid sequence having at least 85% identity to an amino acid sequence of SEQ ID NO:202; (n) a heavy chain variable region comprising the amino acid sequence of SEQ ID NO:185 or an amino acid sequence having at least 85% identity to an amino acid sequence of SEQ ID NO:185; and/or a light chain variable region comprising the amino acid sequence of SEQ ID NO:203 or an amino acid sequence having at least 85% identity to an amino acid sequence of SEQ ID NO:203; (o) a heavy chain variable region comprising the amino acid sequence of SEQ ID NO:186 or an amino acid sequence having at least 85% identity to an amino acid sequence of SEQ ID NO:186; and/or a light chain variable region comprising the amino acid sequence of SEQ ID NO:204 or an amino acid sequence having at least 85% identity to an amino acid sequence of SEQ ID NO:204; (p) a heavy chain variable region comprising the amino acid sequence of SEQ ID NO:187 or an amino acid sequence having at least 85% identity to an amino acid sequence of SEQ ID NO: 187; and/or a light chain variable region comprising the amino acid sequence of SEQ ID NO:205 an amino acid sequence having at least 85% identity to an amino acid sequence of SEQ ID NO:205; or (q) a heavy chain variable region comprising the amino acid sequence of SEQ ID NO:188 or an amino acid sequence having at least 85% identity to an amino acid sequence of SEQ ID NO:188; and/or a light chain variable region comprising the amino acid sequence of SEQ ID NO:206 or an amino acid sequence having at least 85% identity to an amino acid sequence of SEQ ID NO:206.

In some of any of the embodiments herein, the antibody or antigen-binding fragment thereof that specifically binds to a GFAP comprises (a) a heavy chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence set forth in any of the recited SEQ ID NO and/or a light chain variable region comprising an amino acid sequence having at least 86%, at least 87%, at least 88%, at least 89%, at least 90%, at least 91%, at least 92%, at least 93%, at least 94%, at least 95%, at least 96%, at least 97%, at least 98%, or at least 99% identity to the amino acid sequence set forth in any of the recited SEQ ID NO.

In some of any such embodiments herein, the antibody or antigen-binding fragment binds GFAP with a binding affinity having a dissociation constant ($K_D$) of less than or less than about $1.0 \times 10^{-8}$ M, $2.0 \times 10^{-8}$ M, $3.0 \times 10^{-8}$ M, $4.0 \times 10^{-8}$ M, $5.0 \times 10^{-8}$ M, $6.0 \times 10^{-8}$ M, $7.0 \times 10^{-8}$ M, $8.0 \times 10^{-8}$ M, $9.0 \times 10^{-8}$ M, $1.0 \times 10^{-9}$ M, $2.0 \times 10^{-9}$ M, $3.0 \times 10^{-9}$ M, $4.0 \times 10^{-9}$ M, $5.0 \times 10^{-9}$ M, $6.0 \times 10^{-9}$ M, $7.0 \times 10^{-9}$ M, $8.0 \times 10^{-9}$ M, $9.0 \times 10^{-9}$ M, $1.0 \times 10^{-10}$ M, $2.0 \times 10^{-10}$ M, $3.0 \times 10^{-10}$ M, $4.0 \times 10^{-10}$ M, $5.0 \times 10^{-10}$ M, $6.0 \times 10^{-10}$ M, $7.0 \times 10^{-10}$ M, $8.0 \times 10^{-10}$ M, $9.0 \times 10^{-10}$ M, $1.0 \times 10^{-11}$ M, $2.0 \times 10^{-11}$ M, $3.0 \times 10^{-11}$ M, $4.0 \times 10^{-1}$ M, $5.0 \times 10^{-11}$ M, $6.0 \times 10^{-11}$ M, $7.0 \times 10^{-11}$ M, $8.0 \times 10^{-11}$ M, $9.0 \times 10^{-11}$ M, or $1.0 \times 10^{-12}$ M; or the antibody or antigen-binding fragment binds GFAP with a dissociation constant ($K_D$) from or from about $1.0 \times 10^{-8}$ M to $5.0 \times 10^{-12}$ M, such as from or from about $1.0 \times 10^{-8}$ M to $1.0 \times 10^{-12}$ M, $1.0 \times 10^{-8}$ M to $1.0 \times 10^{-11}$ M, $1.0 \times 10^{-8}$ M to $1.0 \times 10^{-11}$ M, $1.0 \times 10^{-8}$ M to $1.0 \times 10^{-10}$ M, $1.0 \times 10^{-10}$ M to $1.0 \times 10^{-12}$ M, $1.0 \times 10^{-10}$ M to $1.0 \times 10^{-11}$ M, $1.0 \times 10^{-11}$ M to $1.0 \times 10^{-12}$ M, for example, from or from about $1.0 \times 10^{-8}$ M to $2.0 \times 10^{-8}$ M, $1.0 \times 10^{-9}$ M to $6.0 \times 10^{-9}$ M, $2.0 \times 10^{-10}$ M to $9.0 \times 10^{-10}$ M, $1.0 \times 10^{-11}$ M to $8.0 \times 10^{-11}$ M, $1.0 \times 10^{-12}$ M to $5.0 \times 10^{-12}$ M, or $1.0 \times 10^{-8}$ M to $1.0 \times 10^{-12}$ M.

In some of any such embodiments herein, the antibody or antigen-binding fragment binds GFAP binds to an epitope within or that is or includes residues 92-106 of GFAP protein, residues 190-202 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or within residues 138-149 of GFAP protein corresponding to amino acid positions set forth in SEQ ID NO:212.

In some aspects, provided herein are antibodies or antigen-binding fragments thereof that specifically binds to human GFAP, wherein the antibody or antigen-binding fragment binds to an epitope within residues 92-106 of a GFAP protein corresponding to amino acid positions set forth in SEQ ID NO:212. In some embodiments, the antibody or antigen-binding fragment comprises a heavy chain variable region comprising CDR-H1, CDR-H2 and CDR-H3 amino acid sequences of SEQ ID NO:77, SEQ ID NO:91 and SEQ ID NO:108, respectively and/or a light chain variable region comprising CDR-L1, CDR-L2 and CDR-L3 amino acid sequences of SEQ ID NO:125, SEQ ID NO:142 and SEQ ID NO:157, respectively.

In some aspects, provided herein are antibodies or antigen-binding fragments thereof that specifically binds to human GFAP, wherein the antibody or antigen-binding fragment binds to an epitope within residues 190-202 of a GFAP protein corresponding to amino acid positions set forth in SEQ ID NO:212. In some embodiments, the antibody or antigen-binding fragment comprises a heavy chain variable region comprising CDR-H1, CDR-H2 and CDR-H3 amino acid sequences of SEQ ID NO:78, SEQ ID NO:92 and SEQ ID NO:109, respectively and/or a light chain variable region comprising CDR-L1, CDR-L2 and CDR-L3 amino acid sequences of SEQ ID NO:126, SEQ ID NO:143 and SEQ ID NO:158, respectively.

In some aspects, provided herein are antibodies or antigen-binding fragments thereof that specifically binds to human GFAP, wherein the antibody or antigen-binding fragment binds to an epitope within residues 16-35 and/or 380 of a GFAP protein corresponding to amino acid positions set forth in SEQ ID NO:212. In some embodiments, the antibody or antigen-binding fragment comprises a heavy chain variable region comprising CDR-H1, CDR-H2 and CDR-H3 amino acid sequences of SEQ ID NO:79, SEQ ID NO:93 and SEQ ID NO:110, respectively and/or a light chain variable region comprising CDR-L1, CDR-L2 and CDR-L3 amino acid sequences of SEQ ID NO:127, SEQ ID NO:144 and SEQ ID NO:159, respectively.

In some aspects, provided herein are antibodies or antigen-binding fragments thereof that specifically binds to human GFAP, wherein the antibody or antigen-binding fragment binds to an epitope within residues 119 and/or 190 of a GFAP protein corresponding to amino acid positions set forth in SEQ ID NO:212. In some embodiments, the antibody or antigen-binding fragment comprises a heavy chain variable region comprising CDR-H1, CDR-H2 and CDR-H3 amino acid sequences of SEQ ID NO:80, SEQ ID NO:95 and SEQ ID NO:112 respectively and/or a light chain variable region comprising CDR-L1, CDR-L2 and CDR-L3 amino acid sequences of SEQ ID NO:126, SEQ ID NO:142 and SEQ ID NO:158, respectively.

In some aspects, provided herein are antibodies or antigen-binding fragments thereof that specifically binds to human GFAP, wherein the antibody or antigen-binding fragment binds to an epitope within residues 380-391 of a GFAP protein corresponding to amino acid positions set forth in SEQ ID NO:212. In some embodiments, the antibody or antigen-binding fragment comprises (a) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:128, SEQ ID NO:145 and SEQ ID NO:160, respectively; (b) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:130, SEQ ID NO:145 and SEQ ID NO:160, respectively; or (c) a heavy chain variable region comprising CDR-H1, CDR-H2 and CDR-H3 amino acid sequences of SEQ ID NO:82, SEQ ID NO:97 and SEQ ID NO:114, respectively and/or a light chain variable region comprising CDR-L1, CDR-L2 and CDR-L3 amino acid sequences of SEQ ID NO:131, SEQ ID NO:147 and SEQ ID NO:162, respectively.

In some aspects, provided herein are antibodies or antigen-binding fragments thereof that specifically binds to human GFAP, wherein the antibody or antigen-binding fragment binds to an epitope within residues 119-130 of a GFAP protein corresponding to amino acid positions set forth in SEQ ID NO:212. In some embodiments, the antibody or antigen-binding fragment comprises (a) a heavy chain variable region comprising CDR-H1, CDR-H2 and CDR-H3 amino acid sequences of SEQ ID NO:81, SEQ ID NO:96 and SEQ ID NO:113, respectively and/or a light chain variable region comprising CDR-L1, CDR-L2 and CDR-L3 amino acid sequences of SEQ ID NO:129, SEQ ID NO:146 and SEQ ID NO:161, respectively; (b) a heavy chain variable region comprising CDR-H1, CDR-H2 and CDR-H3 amino acid sequences of SEQ ID NO:84, SEQ ID NO:99 and SEQ ID NO:116, respectively and/or a light chain variable region comprising CDR-L1, CDR-L2 and CDR-L3 amino acid sequences of SEQ ID NO:133, SEQ ID NO:149 and SEQ ID NO:164, respectively; (c) a heavy chain variable region comprising CDR-H1, CDR-H2 and CDR-H3 amino acid sequences of SEQ ID NO:85, SEQ ID NO:100 and SEQ ID NO:117, respectively and/or a light chain variable region comprising CDR-L1, CDR-L2 and CDR-L3 amino acid sequences of SEQ ID NO:134, SEQ ID NO:150 and SEQ ID NO:165, respectively; (d) a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:140, SEQ ID NO:155 and SEQ ID NO:170, respectively; or (e) a heavy chain variable region comprising CDR-H1, CDR-H2 and CDR-H3 amino acid sequences of SEQ ID NO:90, SEQ ID NO:107 and SEQ ID NO:124, respectively and/or a light chain variable region comprising CDR-L1, CDR-L2 and CDR-L3 amino acid sequences of SEQ ID NO:141, SEQ ID NO:156 and SEQ ID NO:171, respectively.

In some aspects, provided herein are antibodies or antigen-binding fragments thereof that specifically binds to human GFAP, wherein the antibody or antigen-binding fragment binds to an epitope within residues 210-221 of a GFAP protein corresponding to amino acid positions set forth in SEQ ID NO:212. In some embodiments, the antibody or antigen-binding fragment comprises (a) a heavy chain variable region comprising CDR-H1, CDR-H2 and CDR-H3 amino acid sequences of SEQ ID NO:86, SEQ ID NO:101 and SEQ ID NO:118, respectively and/or a light chain variable region comprising CDR-L1, CDR-L2 and CDR-L3 amino acid sequences of SEQ ID NO:135, SEQ ID NO:151 and SEQ ID NO:166, respectively; (b) a heavy chain variable region comprising CDR-H1, CDR-H2 and CDR-H3 amino acid sequences of SEQ ID NO:78, SEQ ID NO:102 and SEQ ID NO: 119, respectively and/or a light chain variable region comprising CDR-L1, CDR-L2 and CDR-L3 amino acid sequences of SEQ ID NO:136, SEQ ID NO:152 and SEQ ID NO:167, respectively; or (c) a heavy chain variable region comprising CDR-H1, CDR-H2 and CDR-H3 amino acid sequences of SEQ ID NO:78, SEQ ID NO:103 and SEQ ID NO:120, respectively and/or a light chain variable region comprising CDR-L1, CDR-L2 and CDR-L3 amino acid sequences of SEQ ID NO:137, SEQ ID NO:142 and SEQ ID NO:158, respectively.

In some aspects, provided herein are antibodies or antigen-binding fragments thereof that specifically binds to human GFAP, wherein the antibody or antigen-binding fragment binds to an epitope within residues 320-329 of a GFAP protein corresponding to amino acid positions set forth in SEQ ID NO:212. In some embodiments, the antibody or antigen-binding fragment comprises (a) a heavy chain variable region comprising CDR-H1, CDR-H2 and CDR-H3 amino acid sequences of SEQ ID NO:87, SEQ ID NO:104 and SEQ ID NO:121, respectively and/or a light chain variable region comprising CDR-L1, CDR-L2 and CDR-L3 amino acid sequences of SEQ ID NO:138, SEQ ID NO:153 and SEQ ID NO: 168, respectively; or (b) a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO:169, respectively.

In some aspects, provided herein are antibodies or antigen-binding fragments thereof that specifically binds to human GFAP, wherein the antibody or antigen-binding fragment binds to an epitope within residues 346-357 and/or 376-387 of a GFAP protein corresponding to amino acid positions set forth in SEQ ID NO:212. In some embodiments, the antibody or antigen-binding fragment comprises a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO: 169, respectively.

In some aspects, provided herein are antibodies or antigen-binding fragments thereof that specifically binds to human GFAP, wherein the antibody or antigen-binding fragment binds to an epitope within residues 138-149 of a GFAP protein corresponding to amino acid positions set forth in SEQ ID NO:212. In some embodiments, the antibody or antigen-binding fragment comprises a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:140, SEQ ID NO:155 and SEQ ID NO:170, respectively.

In some of any of the embodiments herein, the antibody or antigen-binding fragment does not bind to an epitope within or that is or includes residues 190-202 of a human GFAP protein corresponding to amino acid positions set forth in SEQ ID NO:212; and/or does not bind to the same or overlapping epitope as a reference antibody comprising a variable heavy chain set forth in SEQ ID NO:173 and a variable light chain set forth in SEQ ID NO:190; and/or does not compete for binding to GFAP with a reference antibody comprising a variable heavy chain set forth in SEQ ID NO:173 and a variable light chain set forth in SEQ ID NO:190.

In some of any of the embodiments herein, the GFAP (e.g., human GFAP) is recombinant GFAP (e.g., recombinant human GFAP). In some of any of the embodiments herein, the GFAP (e.g., human GFAP) is native GFAP (e.g., native human GFAP). In some further embodiments, the native GFAP is present in or obtained from serum, plasma, blood, cerebrospinal fluid (CSF), urine, sweat, or saliva.

In some of any of the embodiments herein, the antibody or antigen-binding fragment is isolated. In some of any of the embodiments herein, the antibody is a humanized antibody, a chimeric antibody or a human antibody. In some of any of the embodiments herein, the antibody is a murine antibody.

In some of any of the embodiments herein, the antibody is an antigen-binding fragment thereof. In a further embodiment, the antigen-binding fragment thereof is a Fab, Fab'-SH, Fv, scFv, or (Fab')2 fragment.

In some of any of the embodiments herein, the antibody is a full length or intact antibody.

In some of any of the embodiments herein, the antibody further comprises a heavy chain constant domain and/or a light chain constant domain. In a further embodiment, the heavy chain and/or light constant domain is murine or human. In some further embodiments, the heavy chain constant domain is IgG1, IgG2a, IgG2b or IgM.

In some of any of the embodiments herein, the antibody is a monoclonal antibody.

In some of any of the embodiments herein, the antibody is attached to a label. In a further embodiment, the label is a fluorescent dye, a fluorescent protein, a radioisotope, a chromophores, a metal ion, gold particles, silver particles, magnetic particles, a polypeptides, an enzyme, streptavidin, biotin, a luminescent compound, or an oligonucleotide.

In some aspects, provided herein is a nucleic acid encoding an antibody or antigen-binding fragment described herein. In some embodiments, provided herein is a vector encoding such a nucleic acid. In a further embodiment, the vector is an expression vector. In some embodiments, provided herein is a host cell comprising such a nucleic acid or vector.

In some aspects, provided herein is a nucleic acid encoding a heavy chain comprising a heavy variable region described herein. In some embodiments, provided herein is a vector encoding such a nucleic acid. In a further embodiment, the vector is an expression vector. In some embodiments, provided herein is a host cell comprising such a nucleic acid or vector.

In some aspects, provided herein is a nucleic acid encoding a light chain comprising a light variable region described herein. In some embodiments, provided herein is a vector encoding such a nucleic acid. In a further embodiment, the vector is an expression vector. In some embodiments, provided herein is a host cell comprising such a nucleic acid or vector.

In some aspects, provided herein is a method of producing an antibody or antigen-binding fragment thereof described herein (e.g., anti-UCH-L1 antibody or anti-GFAP antibody) comprising culturing the host cell described herein under a condition that produces the antibody or antigen-binding fragment. In a further embodiment, the method further comprises recovering the antibody or antigen-binding fragment produced by the host cell. In some embodiments, provided herein is an anti-UCH-L1 antibody or antigen-binding fragment thereof produced by such methods. In some embodiments, provided herein is an anti-GFAP antibody or antigen-binding fragment thereof produced by such methods.

In some aspects, provide herein is a composition comprising an antibody or antigen-binding fragment thereof described herein (e.g., anti-UCH-L1 antibody or anti-GFAP antibody). In some embodiments, the composition further comprises a pharmaceutically acceptable carrier.

In some aspects, provided herein is a combination of antibodies or antigen-binding fragments thereof, wherein the combination comprises two or more anti-UCH-L1 antibodies or antigen-binding fragments described herein. In some embodiments, the two or more antibodies or antigen-binding fragments comprise one or more first antibody or antigen-binding fragment thereof that binds to a first epitope or region within UCH-L1; and one or more second antibody or antigen-binding fragment thereof that binds to a second epitope or region within UCH-L1. In some further embodiments, the one or more first antibody or antigen-binding fragments thereof, and the one or more second antibody or antigen-binding fragments thereof bind to a non-overlapping epitope or region of UCH-L1 (e.g., human UCH-L1) and/or do not compete for binding to UCH-L1.

In some of any such embodiments, (i) the one or more first antibody or antigen-binding fragment thereof binds to an epitope within or that is or includes residues 28-36 of UCH-L1 protein, residues 98-106 of UCH-L1 protein, residues 138-145 of UCH-L1 protein, and/or residues 142-149 of UCH-L1 protein corresponding to amino acid positions set forth in SEQ ID NO:207; and (ii) the one or more second antibody or antigen-binding fragment thereof binds to an epitope that is not the same as or does not overlap with an epitope of (i). In some of any such embodiments, (i) the one or more first antibody or antigen-binding fragment thereof binds to an epitope within or that is or includes residues 28-36 of UCH-L1 protein and/or residues 98-106 of UCH-L1 protein corresponding to amino acid positions set forth in SEQ ID NO:207; and (ii) the one or more second antibody or antigen-binding fragment thereof binds to an epitope within or that is or includes residues 138-145 of UCH-L1 protein and/or residues 142-149 of UCH-L1 protein corresponding to amino acid positions set forth in SEQ ID NO:207.

In some embodiments, the at least one of the antibodies or antigen-binding fragments of the combination of two or more anti-UCH-L1 antibodies or antigen-binding fragments described herein, optionally the one or more first antibody or antigen-binding fragment thereof or the one or more second antibody or antigen-binding fragment thereof, is conjugated to a label. In some embodiments, the at least one of the antibodies or antigen-binding fragments, optionally the one or more first antibody or antigen-binding fragment thereof or the one or more second antibody or antigen-binding fragment thereof, is attached or immobilized to a solid support. In some embodiments, the one or more first or second antibody or antigen-binding fragment is attached or immobilized to a solid support and the other of the one or more first or second antibody or antigen-binding fragment is conjugated to a label. In some embodiments, the label is a fluorescent dye, a fluorescent protein, a radioisotope, a chromophore, a metal ion, gold particles, silver particles, magnetic particles, a polypeptide, an enzyme, streptavidin, biotin, a luminescent compound, or an oligonucleotide. In some embodiments, the solid support is a bead, a column, an array, an assay plate, a microwell, a stick, a filter, or a strip.

In some aspects, provided herein is a combination antibodies or antigen-binding fragments thereof, wherein the combination comprises two or more anti-GFAP antibodies or antigen-binding fragments described herein. In some embodiments, the two or more antibodies or antigen-binding fragments comprise one or more first antibody or antigen-binding fragment thereof that binds to a first epitope or region within GFAP; and one or more second antibody or antigen-binding fragment thereof that binds to a second epitope or region within GFAP. In some further embodiments, the one or more first antibody or antigen-binding fragments thereof, and the one or more second antibody or antigen-binding fragments thereof bind to a non-overlapping epitope or region of GFAP (e.g., human GFAP) and/or do not compete for binding to GFAP.

In some of any such embodiments, (i) the one or more first antibody or antigen-binding fragment thereof binds to an epitope within or that is or includes residues 92-106 of GFAP protein, residues 190-202 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212; and (ii) the one or more second antibody or antigen-binding fragment thereof binds to an epitope that is not the same as or does not overlap with an epitope of (i). In some of any such embodiments, (i) the one or more first antibody or antigen-binding fragment thereof binds to an epitope within or that is or includes amino acid residues 190-202 of GFAP protein corresponding to amino acid positions set forth in SEQ ID NO:212; and (ii) the one or more second antibody antigen-binding fragment thereof binds to an epitope within or that is or includes residues 92-106 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212.

In some embodiments, the at least one of the antibodies or antigen-binding fragments of the combination of two or more anti-GFAP antibodies or antigen-binding fragments described herein, optionally the one or more first antibody or antigen-binding fragment thereof or the one or more second antibody or antigen-binding fragment thereof, is conjugated to a label. In some embodiments, the at least one of the antibodies or antigen-binding fragments, optionally the one or more first antibody or antigen-binding fragment thereof or one or more second antibody or antigen-binding fragment thereof, is attached or immobilized to a solid support. In some embodiments, the one or more first or second antibody or antigen-binding fragment is attached or immobilized to a solid support and the other of the one or more first or second antibody or antigen-binding fragment is conjugated to a label. In some embodiments, the label is a fluorescent dye, a fluorescent protein, a radioisotope, a chromophore, a metal ion, gold particles, silver particles, magnetic particles, a polypeptide, an enzyme, streptavidin, biotin, a luminescent compound, or an oligonucleotide. In some embodiments, the solid support is a bead, a column, an array, an assay plate, a microwell, a stick, a filter, or a strip.

In some aspects, provided herein is a combination of antibodies or antigen-binding fragments thereof, wherein the combination comprises at least one anti-UCH-L1 antibody such as at least one anti-UCH-L1 antibody described herein or a combination of anti-UCH-L1 antibodies as set forth herein; and at least one anti-GFAP antibody such as at least one anti-GFAP antibody described herein or a combination of anti-GFAP antibodies as set forth herein.

In some aspects, provided herein is a solid support, comprising immobilized thereto an antibody or antigen-binding fragment described herein (e.g., anti-UCH-L1 antibody and/or anti-GFAP antibody). In a further embodiment, the solid support is a bead, a column, an array, an assay plate, a microwell, a stick, a filter, or a strip.

In some aspects, provided herein is a device comprising a solid support described herein. In a further embodiment, the device is a rapid detection device or a rapid diagnostic device.

In some aspects, provided herein is a kit comprising an antibody or antigen-binding fragment described herein (e.g., anti-UCH-L1 antibody and/or anti-GFAP antibody), a composition described herein or a combination of antibodies or antigen-binding fragments described herein, and optionally instructions for use. In some embodiments, the kit further comprises a solid support or a device comprising a solid support. In a further embodiment, the solid support is a bead, a column, an array, an assay plate, a microwell, a stick, a filter, or a strip. In some of the embodiments herein, the device is a rapid detection device or a rapid diagnostic device. In some of any such embodiments herein, the instructions specify an assay for detecting UCH-L1 or GFAP in a sample and/or for determining an amount of UCH-L1 or GFAP in a sample.

In some aspects, provided herein is a method of detecting UCH-L1 in a human subject, the method comprising the steps of (a) contacting a sample with one or more first antibody or antigen-binding fragment such as one or more described herein (e.g., anti-UCH-L1 antibody) under conditions to form a complex comprising the antibody or antigen-binding fragment and UCH-L1; and (b) detecting the presence or absence of the complex in the sample, thereby detecting UCH-L1 in the sample. In a further embodiment, the method of detecting comprises an immunoassay. In a further embodiment, the immunoassay is an enzyme-linked immunosorbent assay (ELISA). In a further embodiment, the ELISA is a sandwich ELISA. In some of any such embodiments, detecting the presence or absence of the complex in step (b), comprises (i) contacting the complex of step (a) with one or more second antibody or antigen-binding fragments thereof under conditions to bind UCH-L1 in the complex, the one or more second antibody or antigen-binding fragment thereof being conjugated to a label capable of producing a detectable signal; and (ii) assessing the presence or absence of the detectable signal. In a further embodiment, the one or more second antibody or antigen-binding fragment comprises one or more antibody or antigen-binding fragment described herein (e.g., anti-UCH-L1 antibody).

In some aspects, provided herein is a method of detecting human UCH-L1 in a sample from a subject, the method comprising (a) contacting a sample with one or more first antibody or antigen-binding fragments that specifically binds human UCH-L1 under conditions to form a complex comprising the antibody or antigen-binding fragment and UCH-L1; and (b) detecting the presence or absence of the complex in the sample, said detecting comprising: (i) contacting the complex of step (a) with one or more second antibody or antigen-binding fragments thereof that specifically binds UCH-L1 under conditions to bind UCH-L1 in the complex, the one or more second antibody or antigen-binding fragment thereof being conjugated to a label capable of producing a detectable signal; and (ii) assessing the presence or absence of the detectable signal, thereby detecting UCH-L1 in the sample, wherein at least one of the one or more first antibody or antigen-binding fragments and one or more of the second antibody or antigen-binding fragments comprise an antibody or antigen-binding fragment described herein (e.g., anti-UCH-L1 antibody). In a further embodiment, the one or more second antibody or antigen-binding fragment binds to an epitope of UCH-L1 that is not the same as or does not overlap with an epitope bound by the antibody or antigen-binding fragment of (a). In some of any such embodiments, (1) the one or more first antibody or antigen-binding fragment thereof binds to an epitope within or that is or includes residues 28-36 of UCH-L1 protein, residues 98-106 of UCH-L1 protein, residues 138-145 of UCH-L1 protein, and/or residues 142-149 of UCH-L1 protein corresponding to amino acid positions set forth in SEQ ID NO:207; and (2) the one or more second antibody or antigen-binding fragment thereof binds to an epitope that is not the same as or does not overlap with an epitope of (1). In some of any such embodiments, (1) the one or more first antibody or antigen-binding fragment thereof binds to an epitope within or that is or includes residues 28-36 of UCH-L1 protein and/or residues 98-106 of UCH-L1 protein corresponding to amino acid positions set forth in SEQ ID NO:207; and (2) the one or more second antibody or antigen-binding fragment thereof binds to an epitope within or that is or includes residues 138-145 of UCH-L1 protein and/or residues 142-149 of UCH-L1 protein corresponding to amino acid positions set forth in SEQ ID NO:207.

In some aspects, provided herein is a method of detecting GFAP in a human subject, the method comprising the steps of: (a) contacting a sample with one or more first antibody or antigen-binding fragment such as one or more described herein (e.g., anti-GFAP antibody) under conditions to form a complex comprising the antibody or antigen-binding fragment and GFAP; and (b) detecting the presence or absence of the complex in the sample, thereby detecting GFAP in the sample. In a further embodiment, the method of detecting comprises an immunoassay. In a further embodiment, the immunoassay is an enzyme-linked immunosorbent assay (ELISA). In a further embodiment, the ELISA is a sandwich ELISA. In some of any such embodiments, detecting the presence or absence of the complex in step (b), comprises (i) contacting the complex of step (a) with one or more second antibody or antigen-binding fragments thereof under conditions to bind GFAP in the complex, the one or more second antibody or antigen-binding fragment thereof being conjugated to a label capable of producing a detectable signal; and (ii) assessing the presence or absence of the detectable signal. In a further embodiment, the one or more second antibody or antigen-binding fragment comprises one or more antibody or antigen-binding fragment described herein (e.g., anti-GFAP antibody).

In some aspects, provided herein is a method of detecting human GFAP in a sample from a subject, the method comprising (a) contacting a sample with one or more first antibody or antigen-binding fragments that specifically binds human GFAP under conditions to form a complex comprising the antibody or antigen-binding fragment and GFAP; and (b) detecting the presence or absence of the complex in the sample, said detecting comprising: (i) contacting the complex of step (a) with one or more second antibody or antigen-binding fragments thereof that specifically binds GFAP under conditions to bind GFAP in the complex, the one or more second antibody or antigen-binding fragment thereof being conjugated to a label capable of producing a detectable signal; and (ii) assessing the presence or absence of the detectable signal, thereby detecting GFAP in the sample, wherein at least one of the one or more first antibody or antigen-binding fragments and one or more of the second antibody or antigen-binding fragments comprise an antibody or antigen-binding fragment described herein (e.g., anti-GFAP antibody). In a further embodiment, the one or more second antibody or antigen-binding fragment binds to an epitope of GFAP that is not the same as or does not overlap with an epitope bound by the antibody or antigen-binding fragment of (a). In some of any such embodiments, (1) the one or more first antibody or antigen-binding fragment thereof binds to an epitope within or that is or includes residues 92-106 of GFAP protein, residues 190-202 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212; and (2) the one or more second antibody or antigen-binding fragment thereof binds to an epitope that is not the same as or does not overlap with an epitope of (1). In some of any such embodiments, (1) the one or more first antibody or antigen-binding fragment thereof binds to an epitope within or that is or includes amino acid residues 190-202 of GFAP protein corresponding to amino acid positions set forth in SEQ ID NO:212; and (2) the one or more second antibody antigen-binding fragment thereof binds to an epitope within or that is or includes residues 92-106 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212.

In some embodiments of the method of detecting herein (e.g., detecting UCH-L1 and/or GFAP), prior to step (b) separating or washing the complex formed in step (a) from the sample not comprised in the complex. In some embodiments of the method, the one or more first antibody or antigen-binding fragment thereof is attached or immobilized to a solid support. In some embodiments of the method, prior to step (b)(ii) removing the one or more second antibody or antigen-binding fragments thereof not bound to the complex. In some of any such embodiments, the sample is isolated or obtained from the individual. In some of any such embodiments, the sample is serum, plasma, blood, cerebrospinal fluid (CSF), urine, sweat, or saliva. In some of any such embodiments, the method further comprises (c) determining the amount of UCH-L1 detected in the sample. In some of any such embodiments, the method further comprises (c) determining the amount of GFAP detected in the sample.

In some aspects, provided herein is a method of diagnosing brain injury or damage in a subject, the method comprising performing a method of detecting UCH-L1, such as a method of detecting described herein, thereby determining the amount of UCH-L1 in the sample; and (i) if the amount of UCH-L1 in the sample is greater than or equal to or about a UCH-L1 threshold level, diagnosing the subject as having a brain injury or damage or at risk of having a brain injury or damage; or (ii) if the amount of UCH-L1 in the sample is below the UCH-L1 threshold level, diagnosing the subject as not having a brain injury or damage or not being at risk of having a brain injury or damage. In some embodiments, if the subject is identified as having a brain injury or damage or of being at risk of having a brain injury or damage administering a therapeutic agent to the subject to treat the brain injury or damage. In some of any such embodiments, if the subject is identified as having a brain injury or damage or of being at risk of having a brain injury or damage, carrying out neuroimaging on the subject's brain. In any such embodiments, if the subject is identified as not having a brain injury or damage or not being at risk of having a brain injury or damage, neuroimaging of the subject's brain is not carried out.

In some aspects, provided herein is a method of diagnosing brain injury or damage in a subject, the method comprising performing a method of detecting GFAP, such as a method of detecting described herein, thereby determining the amount of GFAP in the sample; and (i) if the amount of GFAP in the sample is greater than or equal to or about a GFAP threshold level, diagnosing the subject as having a brain injury or damage or at risk of having a brain injury or damage; or (ii) if the amount of GFAP in the sample is below the GFAP threshold level, diagnosing the subject as not having a brain injury or damage or not being at risk of having a brain injury or damage. In some embodiments, if the subject is identified as having a brain injury or damage or of being at risk of having a brain injury or damage administering a therapeutic agent to the subject to treat the brain injury or damage. In some of any such embodiments, if the subject is identified as having a brain injury or damage or of being at risk of having a brain injury or damage, carrying out neuroimaging on the subject's brain. In any such embodiments, if the subject is identified as not having a brain injury or damage or not being at risk of having a brain injury or damage, neuroimaging of the subject's brain is not carried out.

In some aspects, provided herein is a method of diagnosing brain injury in a subject, the method comprising: (a) performing a method of detecting UCH-L1, such as a method of detecting described herein, thereby determining the amount of UCH-L1 in the sample; (b) performing a method of detecting GFAP, such as a method of detecting described herein, thereby determining the amount of GFAP in the sample; and (i) if the amount of UCH-L1 in the sample is greater than or equal to or about a UCH-L1 threshold level and/or if the amount of GFAP in the sample is greater than or equal to or about a GFAP threshold level, diagnosing the subject as having a brain injury or damage or at risk of having a brain injury or damage; or (ii) if the amount of UCH-L1 in the sample is below the UCH-L1 threshold level and/or if the amount of GFAP in the sample is below the GFAP threshold level, diagnosing the subject as not having a brain injury or damage or not being at risk of having a brain injury or damage. In some embodiments, if the subject is identified as having a brain injury or damage or of being at risk of having a brain injury or damage administering a therapeutic agent to the subject to treat the brain injury or damage. In some of any such embodiments, if the subject is identified as having a brain injury or damage or of being at risk of having a brain injury or damage, carrying out neuroimaging on the subject's brain. In any such embodiments, if the subject is identified as not having a brain injury or damage or not being at risk of having a brain injury or damage, neuroimaging of the subject's brain is not carried out.

In some aspects, provided herein is a method of treating a subject for a brain injury or damage, comprising: a) performing the method of diagnosing such as a method described herein; and b) if the subject is identified as having a brain injury or damage or being at risk of having a brain injury or damage administering a therapeutic agent to the subject to treat the brain injury or damage. In a further embodiment, the therapeutic agent is selected from an N-methyl-D-aspartate (NMDA) receptor antagonist, a sodium channel antagonist, a nitric oxide synthase (NOS) inhibitor, a glycine site antagonist, a potassium channel opener, an AMPA/kainate receptor antagonist, a calcium channel antagonist, a GABA-A receptor modulator, an anti-inflammatory agent or a combination thereof.

In some aspects, provided herein is a method of predicting if a subject is in need of neuroimaging for a suspected brain injury or damage, the method comprising (a) performing a method of detecting UCH-L1, such as in a method of detecting described herein, thereby determining the amount of UCH-L1 in the sample; and/or (b) performing the method of detecting GFAP, such as in a method of detecting described herein, thereby determining the amount of GFAP in the sample; and (i) if the amount of UCH-L1 in the sample is greater than or equal to or about a UCH-L1 threshold level and/or if the amount of GFAP in the sample is greater than or equal to or about a GFAP threshold level, predicting the subject is in need of neuroimaging; or (ii) if the amount of UCH-L1 in the sample is below the UCH-L1 threshold level and/or if the amount of GFAP in the sample is below the GFAP threshold level, predicting the subject is not in need of neuroimaging.

In some aspects, provided herein is a method of method of predicting if a subject is in need of neuroimaging for a suspected brain injury or damage, comprising a) performing a method of diagnosing or detecting UCH-L1 and/or GFAP, such as in a method of diagnosing or detecting described herein; and b) if the subject is identified as having a brain injury or damage or being at risk of having a brain injury or damage predicting the subject is in need of neuroimaging. In some embodiments, the method further comprises carrying out the neuroimaging on the subject's brain.

In some any such embodiments of the methods herein, the neuroimaging is by computed tomography (CT) or magnetic resonance imaging (MRI).

In some of any such embodiments of the methods herein, the UCH-L1 threshold level is or is about 30 pg/mL, is or is about 40 mg/mL, is or is about 60 pg/mL, is or is about 80 pg/mL, is or is about 100 pg/mL, is or is about 150 pg/mL, is or is about 200 pg/mL, is or is about 250 pg/mL, is or is about 300 pg/mL, is or is about 400 pg/mL or is or is about 500 pg/mL. In some embodiments, the UCH-L1 threshold level is or is about 100 pg/mL. In some embodiments, the UCH-L1 threshold level is or is about 200 pg/ml.

In some of any such embodiments of the methods herein, the GFAP threshold level is or is about 10 pg/mL, is or is about 20 pg/mL, is or is about 30 pg/mL, is or is about 40 pg/mL, is or is about 50 pg/ml, is or is about 60 pg/mL, is or is about 70 pg/mL, is or is about 80 pg/mL, is or is about 90 pg/mL, is or is about 100 pg/mL, is or is about 150 pg/mL, is or is about 200 pg/mL, is or is about 250 pg/mL or is or is about 300 pg/mL. In some embodiments, the GFAP threshold level is or is about 50 pg/ml. In some embodiments, the GFAP threshold level is or is about 70 pg/ml.

In some of any such embodiments herein, the UCH-L1 threshold level is 200 pg/mL and the GFAP threshold level is 70 pg/mL.

In some of any such embodiments of the methods herein, the brain injury or damage is associated with or caused by mechanical damage, hypoxia, infectious disease, disease affecting nerve cells, toxin damage or neurological disease or condition. In some embodiments, the mechanical damage is traumatic brain injury or chronic traumatic encephalopathy. In a further embodiment, the brain injury or damage is traumatic brain injury. In a further embodiment, the traumatic brain injury is a mild traumatic brain injury. In some embodiments, the hypoxia is associated with stroke, vasculitis, ischemia, or cardiac disease. In some embodiments, the infectious disease comprises infection with a *Mycobacterium* bacteria, *Neisseria meningitidis*, a Herpesviridiae virus, a poliovirus, mumps virus, an Enteroviridiae virus, West Nile virus, or tick-borne encephalitis virus. In some embodiments, the disease affecting nerve cells is Alzheimer's disease, Lewy body dementia, vascular dementia, diabetic dementia, Parkinson's disease, ALS, or prion disease. In some embodiments, the toxin damage is associated with exposure to nerve agents, alcoholic dementia, heavy metal poisoning, psychoactive agents, chemotherapeutic agents, biological agents, or antibiotics.

In some of any such embodiments of the methods herein, the sample is obtained from the subject no more than about 30 minutes, 1 hour, 2 hours, 4 hours, 6 hours, 8 hours, 12 hours, 24 hours or 48 hours after a brain injury or damage or a suspected brain injury or damage In some of any such embodiments of the methods herein, the sample is obtained from the subject no more than about 8 hours after a brain injury or damage or a suspected brain injury or damage.

In some of any such embodiments of the methods herein, the sample is serum.

In some of any such embodiments of the methods herein, the sample is CSF.

In some of any such embodiments of the methods herein, the method is performed in vitro.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

Provided are antibodies that bind ubiquitin c-terminal hydrolase L1 (UCH-L1), including antigen-binding fragment of such antibodies, nucleic acids encoding such antibodies and antigen-binding fragments, and cells, such as recombinant cells for expressing and production of these antibodies and antigen-binding fragments. Also provided herein are antibodies that bind glial fibrillary acidic protein (GFAP), including antigen-binding fragment of such antibodies, nucleic acids encoding such antibodies and antigen-binding fragments, and cells, such as recombinant cells for expressing and production of these antibodies and antigen-binding fragments. Also provided are methods of producing and using the antibodies and antigen-binding fragments such as in methods for detecting UCH-L1 and/or GFAP in a sample from an individual, methods of diagnosing a brain injury or neurological condition in an individual and methods of predicting the likelihood such an individual will need neuroimaging (e.g., a computed tomography scan) and/or therapeutic intervention.

All references cited herein, including patent applications, patent publications, and scientific literature and databases, are herein incorporated by reference in their entirety for all purposes to the same extent as if each individual reference were specifically and individually indicated to be incorporated by reference.

For clarity of disclosure, and not by way of limitation, the detailed description is divided into the subsections that follow. The section headings used herein are for organizational purposes only and are not to be construed as limiting the subject matter described.

I. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, "antibody" refers to immunoglobulins and immunoglobulin fragments, whether natural or partially or wholly synthetically, such as recombinantly, produced, including any fragment thereof containing at least a portion of the variable heavy chain and/or light chain region of the immunoglobulin molecule that is sufficient to form an antigen binding site and, when assembled, to specifically bind antigen. Hence, an antibody includes any protein having a binding domain that is homologous or substantially homologous to an immunoglobulin antigen-binding domain (antibody combining site). Typically, antibodies minimally include all or at least a portion of the variable heavy ($V_H$) chain and/or the variable light ($V_L$) chain. In general, the pairing of a $V_H$ and $V_L$ together form the antigen-binding site, although, in some cases, a single $V_H$ or $V_L$ domain is sufficient for antigen-binding. The antibody also can include all or a portion of the constant region. Hence, it is understood that reference to an antibody herein includes full-length antibody and antigen-binding fragments, including those that specifically bind to UCH-L1 or GFAP. The term antibody also includes antibody compositions with polyepitopic specificity, multispecific antibodies (e.g., bispecific antibodies), diabodies, and single-chain molecules. Antibodies include polyclonal antibodies or monoclonal antibodies. Antibody also includes synthetic antibodies or recombinantly produced antibodies. The term "immunoglobulin" (Ig) is used interchangeably with "antibody" herein.

Thus, the term antibody includes full-length antibodies and portions thereof including antibody fragments, wherein such contain a heavy chain or portion thereof and/or a light chain or portion thereof. An antibody can contain two heavy chains (which can be denoted H and H') and two light chains (which can be denoted L and L'). Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains (CH1, CH2 and CH3) for each of the α and γ chains and four CH domains (CH1, CH2, CH3 and CH4) for μ and ε isotypes. Each L chain has at the N-terminus, a variable domain ($V_L$) followed by a constant domain ($C_L$) at its other end. In some cases, the heavy chain can be a full-length immunoglobulin heavy chain or a portion thereof sufficient to form an antigen binding site (e.g., heavy chains include, but are not limited to, VH chains, VH-CH1 chains and VH-CH1-CH2-CH3 chains), and/or each light chain can be a full-length light chain or a portion thereof sufficient to form an antigen binding site (e.g., light chains include, but are not limited to, VL chains and VL-CL chains). For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, CT, 1994, page 71 and Chapter 6. Each heavy chain (H and H') pairs with one light chain (L and L', respectively).

The terms "full-length antibody," "intact antibody" or "whole antibody" are used interchangeably to refer to an antibody in its substantially intact form, as opposed to an antibody fragment. A full-length antibody is an antibody typically having two full-length heavy chains (e.g., VH-CH1-CH2-CH3 or VH-CH1-CH2-CH3-CH4) and two full-length light chains (VL-CL) and hinge regions, such as antibodies produced from mammalian species (e.g. human, mouse, rat, rabbit, non-human primate, etc.) by antibody secreting B cells and antibodies with the same domains that are produced synthetically. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Antibody fragments, include, but are not limited to, Fab fragments, Fab' fragments, F(ab')$_2$ fragments, Fv fragments, disulfide-linked Fvs (dsFv), Fd fragments, Fd' fragments; diabodies; linear antibodies (see U.S. Pat. No. 5,641,870, Example 2; Zapata et al., *Protein Eng.* 8(10): 1057-1062 [1995]); single-chain antibody molecules, including single-chain Fvs (scFv) or single-chain Fabs (scFab); antigen-binding fragments of any of the above and multispecific antibodies from from antibody fragments.

"Fv" is composed of one heavy- and one light-chain variable region domain linked by non-covalent association. From the folding of these two domains emanate six complementarity determining regions (CDR) (3 in each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although, in some cases, at a lower affinity than the entire binding site.

"dsFv" refers to an Fv with an engineered intermolecular disulfide bond, which stabilizes the $V_H$-$V_L$ pair.

An "Fd fragment" is a fragment of an antibody containing a variable domain ($V_H$) and one constant region domain (CH1) of an antibody heavy chain.

A "Fab fragment" is an antibody fragment that results from digestion of a full-length immunoglobulin with papain, or a fragment having the same structure that is produced synthetically, e.g., by recombinant methods. A Fab fragment contains a light chain (containing a $V_L$ and $C_L$) and another chain containing a variable domain of a heavy chain ($V_H$) and one constant region domain of the heavy chain ($C_H1$).

A "F(ab')$_2$ fragment" is an antibody fragment that results from digestion of an immunoglobulin with pepsin at pH 4.0-4.5, or a fragment having the same structure that is produced synthetically, e.g., by recombinant methods. The F(ab')$_2$ fragment essentially contains two Fab fragments where each heavy chain portion contains an additional few amino acids, including cysteine residues that form disulfide linkages joining the two fragments.

A "Fab' fragment" is a fragment containing one half (one heavy chain and one light chain) of the F(ab')$_2$ fragment.

An "Fd' fragment" is a fragment of an antibody containing one heavy chain portion of a F(ab')$_2$ fragment.

An "Fv' fragment" is a fragment containing only the $V_H$ and $V_L$ domains of an antibody molecule.

An "scFv fragment" refers to an antibody fragment that contains a variable light chain ($V_L$) and variable heavy chain ($V_H$), covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

"Diabodies" are dimeric scFv; diabodies typically have shorter peptide linkers than scFvs, and preferentially dimerize.

As used herein, a "variable domain" with reference to an antibody is a specific Ig domain of an antibody heavy or light chain that are generally the most variable parts of the antibody (relative to other antibodies of the same class). The amino-terminal domain of each light chain and each heavy chain has one variable region domain. The variable domains of the heavy chain and light chain may be referred to as "$V_H$" and "$V_L$", respectively. Each variable region contains complementarity-determining region CDRs that are part of the antigen binding site domain and framework regions (FRs). The variable domains, which contain the antigen binding sites, provide antigen specificity, and thus are responsible for antigen recognition.

The term "complementarity determining region" or "CDR" refers to sequences of amino acids within antibody variable regions, which interact with cognate antigen and confer antigen specificity and/or binding affinity. The CDRs are or are found within a "hypervariable region" or "HVR" of an antibody, which are hypervariable in sequence and/or form structurally defined loops ("hypervariable loops"). In some cases, CDRs are also referred to as a hypervariable region or hypervariable loop. In general, there are three CDRs in each heavy chain variable region (CDR-H1, CDR-H2, CDR-H3) and three CDRs in each light chain variable region (CDR-L1, CDR-L2, CDR-L3).

"Framework regions" and "FR" refer to those variable domain residues of the variable regions of the heavy and light chains other than the CDR residues as herein defined. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

It is within the level of a skilled artisan to identify the amino acid sequence boundaries of a given CDR or FR using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme) and Martin et al., "Modeling antibody hypervariable loops: a combined algorithm," PNAS, 1989, 86(23):9268-9272, ("AbM" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1 provides exemplary numbering schemes known to a skilled artisan for identifying CDRs and FRs in antibodies. The Kabat designation is based on structural alignments and sequence variability and is the most commonly used (Kabat et al., *Sequences of Proteins of Immunological Interest*, 5$^{th}$ Ed. Public Health Service, National Institute of Health, Bethesda, MD (1991)). The Chothia designation is based on structural information relating to the location of the structural loops (Chothia and Lesk *J. Mol. Biol.* 196:901-917 (1987)). The "contact" designation is based on an analysis of the available complex crystal structures. The AbM designation is another standard for describing CDRs and is used by Oxford's Molecular's AbM antibody modeling software.

TABLE 1

| CDR | Kabat | AbM | Chothia | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H35B | H26--H32 . . . 34 | H30--H35B |
| CDR-H1 (Chothia Numbering[2]) | H31--H35 | H26--H35 | H26--H32 | H30--H35 |
| CDR-H2 | H50--H65 | H50--H58 | H52--H56 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273,927-948

Unless otherwise indicated, the variable-domain residues (CDR residues and framework region residues) are numbered according to Kabat et al., supra. It is within the level of a skilled artisan to readily determine CDR and FR variable domain residues in accord with any of the other well-known numbering schemes and designations. It is understood that embodiments described with respect to Kabat CDRs are also provided herein based on any other alternative known standard or scheme for describing or classifying a CDR or hypervariable loop of an antibody.

The expression "variable-domain residue-numbering as in Kabat" or "amino-acid-position numbering as in Kabat" or "numbering according to Kabat" and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

As used herein, a constant region domain is a domain in an antibody heavy or light chain that contains a sequence of amino acids that is comparatively more conserved among antibodies than the variable region domain. Each light chain has a single light chain constant region (CL) domain, which is either of the kappa or lambda type. Each heavy chain contains one or more heavy chain constant region (CH) domains that can be assigned to different classes or isotypes. There are five classes of immunoglobulins: IgA, IgD, IgE, IgG and IgM, having heavy chains designated α, δ, ε, γ and µ, respectively. Full-length IgA, IgD and IgG isotypes contain CH1, CH2, CH3 and a hinge region, while IgE and IgM contain CH1, CH2, CH3 and CH4. The γ and α classes are further divided into subclasses on the basis of relatively minor differences in the CH sequence and function, e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable. An antibody constant region can include an Fc portion. Although the boundaries of the Fc region of an immunoglobulin heavy chain might vary, the human IgG heavy-chain Fc region usually includes the region containing the CH2 and CH3 domains and the hinge region, such as an amino acid residue at position Cys226, or from Pro230, to the carboxyl-terminus thereof.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments truncated forms of monoclonal antibodies can be made by recombinant techniques. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies provided in accord with the present disclosure may be made by a variety of techniques, including, for example, the hybridoma method, recombinant DNA methods, phage-display technologies and other technologies known to a skilled artisan for making or producing antibodies.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). As used herein, "humanized antibody" is used as a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an CDR of the recipient are replaced by residues from an CDR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the CDRs correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. In some embodiments, the number of these amino acid substitutions in the FR are no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); *Harris, Biochem. Soc. Transactions* 23:1035-1038 (1995); Hurle and Gross, *Curr. Op. Biotech.* 5:428-433 (1994); and U.S. Pat. Nos. 6,982,321 and 7,087,409. In some embodiments, humanized antibodies are directed against a single antigenic site. In some embodiments, humanized antibodies are directed against multiple antigenic sites. An alternative humanization method is described in U.S. Pat. No. 7,981,843 and U.S. Patent Application Publication No. 2006/0134098.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An antibody that "binds to", "specifically binds to" or is "specific for" a particular a polypeptide or an epitope on a particular polypeptide is one that binds to that particular polypeptide or epitope on a particular polypeptide without substantially binding to any other polypeptide or polypeptide epitope. In some embodiments, binding of an anti-UCH-L1 antibody described herein to an unrelated, non-UCH-L1 polypeptide is less than about 10% of the antibody binding to UCH-L1 as measured by methods known in the art (e.g., enzyme-linked immunosorbent assay (ELISA)). In some embodiments, binding of an anti-GFAP antibody described herein to an unrelated, non-GFAP polypeptide is less than about 10% of the antibody binding to GFAP as measured by methods known in the art (e.g., enzyme-linked immunosorbent assay (ELISA)). Typically, an antibody that immunospecifically binds (or that specifically binds) to UCH-L1 or GFAP is one that binds thereto with a dissociation constant ($K_D$) of $1\times10^{-7}$ M or $1\times10^{-8}$ M or less (or an affinity constant $K_A$ of about or $1\times10^7$ M$^{-1}$ or $1\times10^8$ M$^{-1}$ or greater).

"Binding affinity" as used herein refers to the strength of the non-covalent interactions between a single binding site of a molecule (e.g., an antibody) and its binding partner (e.g., an antigen). In some embodiments, the affinity of an antibody for a UCH-L1 or a GFAP can generally be represented by a dissociation constant ($K_D$). Affinity can be measured by common methods known in the art, including those described herein.

The term "UCH-L1" as used herein refers to a human UCH-L1 protein or isoforms or variants thereof, including naturally occurring variants of human UCH-L1, such as splice variants or allelic variants. The amino acid sequence of an exemplary human UCH-L1 is shown in SEQ ID NO:207. The amino acid sequence of another exemplary human UCH-L1 is shown in SEQ ID NO:208. The amino acid sequence of yet another exemplary human UCH-L1 is shown in SEQ ID NO:209. The amino acid sequence of an exemplary human UCH-L1 is shown in SEQ ID NO:210. The amino acid sequence of another exemplary human UCH-L1 is shown in SEQ ID NO:211. In some embodiments, human UCH-L1 can refer to a variant, such as an allelic variant or splice variant, that exhibits at least or at least about 85%, 86%, 87%, 88%, 89%, 90%, 91%, 92%, 93%, 94%, 95%, 96%, 97%, 98%, or 99% sequence identity to any of SEQ ID NOS: 207, 208, 209, 210 or 211. In some embodiments, it is understood that the provided antibodies or antigen-binding fragments may exhibit cross-reactive binding to another mammalian UCH-L1 protein, such as a murine UCH-L1 or a primate UCH-L1.

```
Human UCH-L1 isoform 1 amino acid sequence
                              (SEQ ID NO: 207)
MQLKPMEINPEMLNKVLSRLGVAGQWRFVDVLGLEEESLGSVP

APACALLLLFPLTAQHENFRKKQIEELKGQEVSPKVYFMKQTI

GNSCGTIGLIHAVANNQDKLGFEDGSVLKQFLSETEKMSPEDR

AKCFEKNEAIQAAHDAVAQEGQCRVDDKVNFHFILFNNVDGHL

YELDGRMPFPVNHGASSEDTLLKDAAKVCREFTEREQGEVRFS

AVALCKAA

Human UCH-L1 isoform 2 amino acid sequence
                              (SEQ ID NO: 208)
MQLKPMEINPEMLNKVLSRLGVAGQWRFVDVLGLEEESLGSVP

APACALLLLFPLTAQHENFRKKQIEELKGQEVSPKVYFMKQTI

GNSCGTIGLIHAVANNQDKLGFEDGSVLKQFLSETEKMSPEDR

AKCFEKNEAIQAAHDAVAQEGQCRVDDKVNFHFILFNNVDGHL

YELDGRMPFPVNHGASSEDTLLKDAAKALKHKQSAQLSTGPLW

CELQMVKHSPQCMSCIRYLTL

Human UCH-L1 isoform 3 amino acid sequence
                              (SEQ ID NO: 209)
MQLKPMEINPEMLNKVLSRLGVAGQWRFVDVLGLEEESLGSVP

APACALLLLFPLTAQHENFRKKQIEELKGQEVSPKVYFMKQTI

GNSCGTIGLIHAVANNQDKLGFEDGSVLKQFLSETEKMSPEDR

AKCFEKNEAIQAAHDAVAQEGQCRVDDKMDECLFR

Human UCH-L1 isoform 4 amino acid sequence
                              (SEQ ID NO: 210)
MQLKPMEINPEMLNKVLSRLGVAGQWRFVDVLGLEEESLGSVP

APACALLLLFPLTAQHENFRKKQIEELKGQEVSPKVYFMKQTI

GNSCGTIGLIHAVANNQDKLGFEDGSVLKQFLSETEKMSPEDR

AKCFEKNEAIQAAHDAVAQEGQCRVDDKTLPRSAENSPSVSKE

KSASLPWLSARQPNALWEGLC

Human UCH-L1 isoform 5 amino acid sequence
                              (SEQ ID NO: 211)
MQLKPMEINPEMLNKVLSRLGVAGQWRFVDVLGLEEESLGSVP

APACALLLLFPLTAQHENFRKKQIEELKGQEVSPKVYFMKQTI

GNSCGTIGLIHAVANNQDKLGFEDGSVLKQFLSETEKMSPEDR

AKCFEKNEAIQAAHDAVAQEGQCRVDDKTLPRHLSTSRVHSCP

LGHCGVSFRW
```

The term "glial fibrillary acidic protein" or "GFAP" as used herein refers to a human GFAP protein or isoforms, fragments or variants thereof, including naturally occurring variants of human GFAP, such as splice variants or allelic variants. The amino acid sequence of an exemplary human GFAP is shown in SEQ ID NO:212. The amino acid sequence of another exemplary human GFAP is shown in SEQ ID NO:213. The amino acid sequence of yet another exemplary human GFAP is shown in SEQ ID NO:214. In some embodiments, human GFAP can refer to a variant, such as an allelic variant or splice variant, that exhibits at least or at least about 85%, 86%, 87%, 88%, 89%, 90%, 91%, 92%, 93%, 94%, 95%, 96%, 97%, 98%, or 99% sequence identity to any of SEQ ID NOS: 212, 213 or 214. In some embodiments, it is understood that the provided antibodies or antigen-binding fragments may exhibit cross-reactive binding to another mammalian GFAP protein, such as a murine GFAP or a primate GFAP.

```
Human GFAP isoform 1 amino acid sequence
                              (SEQ ID NO: 212)
MERRRITSAARRSYVSSGEMMVGGLAPGRRLGPGTRLSLARMP

PPLPTRVDFSLAGALNAGFKETRASERAEMMELNDRFASYIEK

VRFLEQQNKALAAELNQLRAKEPTKLADVYQAELRELRLRLDQ

LTANSARLEVERDNLAQDLATVRQKLQDETNLRLEAENNLAAY

RQEADEATLARLDLERKIESLEEEIRFLRKIHEEEVRELQEQL

ARQQVHVELDVAKPDLTAALKEIRTQYEAMASSNMHEAEEWYR

SKFADLTDAAARNAELLRQAKHEANDYRRQLQSLTCDLESLRG

TNESLERQMREQEERHVREAASYQEALARLEEEGQSLKDEMAR

HLQEYQDLLNVKLALDIEIATYRKLLEGEENRITIPVQTFSNL

QIRETSLDTKSVSEGHLKRNIVVKTVEMRDGEVIKESKQEHKD

VM.

Human GFAP isoform 2 amino acid sequence
                              (SEQ ID NO: 213)
MERRRITSAARRSYVSSGEMMVGGLAPGRRLGPGTRLSLARMP

PPLPTRVDFSLAGALNAGFKETRASERAEMMELNDRFASYIEK

VRFLEQQNKALAAELNQLRAKEPTKLADVYQAELRELRLRLDQ

LTANSARLEVERDNLAQDLATVRQKLQDETNLRLEAENNLAAY

RQEADEATLARLDLERKIESLEEEIRFLRKIHEEEVRELQEQL

ARQQVHVELDVAKPDLTAALKEIRTQYEAMASSNMHEAEEWYR

SKFADLTDAAARNAELLRQAKHEANDYRRQLQSLTCDLESLRG

TNESLERQMREQEERHVREAASYQEALARLEEEGQSLKDEMAR

HLQEYQDLLNVKLALDIEIATYRKLLEGEENRITIPVQTFSNL

QIRGGKSTKDGENHKVTRYLKSLTIRVIPIQAHQIVNGTPPAR

G.
```

```
Human GFAP isoform 3 amino acid sequence
                                   (SEQ ID NO: 214)
MERRRITSAARRSYVSSGEMMVGGLAPGRRLGPGTRLSLARMP

PPLPTRVDFSLAGALNAGFKETRASERAEMMELNDRFASYIEK

VRFLEQQNKALAAELNQLRAKEPTKLADVYQAELRELRLRLDQ

LTANSARLEVERDNLAQDLATVRQKLQDETNLRLEAENNLAAY

RQEADEATLARLDLERKIESLEEEIRFLRKIHEEEVRELQEQL

ARQQVHVELDVAKPDLTAALKEIRTQYEAMASSNMHEAEEWYR

SKFADLTDAAARNAELLRQAKHEANDYRRQLQSLTCDLESLRG

TNESLERQMREQEERHVREAASYQEALARLEEEGQSLKDEMAR

HLQEYQDLLNVKLALDIEIATYRKLLEGEENRITIPVQTFSNL

QIRGQYSRASWEGHWSPAPSSRACRLLQTGTEDQGKGIQLSLG

AFVTLQRS.
```

As used herein, "corresponding" with reference to a sequence of amino acids or "at a position corresponding to" or recitation that amino acid positions "correspond to" amino acid positions in a disclosed sequence, such as set forth in the Sequence Listing, refers to amino acid positions identified upon alignment with the disclosed sequence to maximize identity using a standard alignment algorithm. In some embodiments, exemplary corresponding residues of a UCH-L1 can be identified by alignment of a sequence with an exemplary UCH-L1 sequence set forth in SEQ ID NO:207. In some embodiments, exemplary corresponding residues of a GFAP protein can be identified by alignment of a sequence with an exemplary GFAP sequence set forth in SEQ ID NO:212. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New. Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

An "isolated" nucleic acid molecule encoding an antibody or antibody chain (L or H chain) herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "naked antibody" refers to an antibody that is not conjugated to a moiety or label.

As used herein, "antibody conjugate" refers to an antibody that is attached to a moiety or label via a covalent or noncovalent interaction.

As used herein, the phrase "conjugated to an antibody," "linked to an antibody" or "attached to an antibody" or other variations thereof, when referring to the attachment of a moiety to an antibody or antigen-binding fragment thereof, such as a label or other moiety, means that the moiety is attached to the antibody or antigen-binding fragment thereof by any known means for linking molecules, including via covalent or non-covalent interaction. Conjugation can employ any of a variety of linking agents to effect conjugation, including, but not limited to, peptide or compound linkers or chemical cross-linking agents. In some embodiments, the attachment is by any known means for linking peptides, such as, for example, by production of fusion protein by recombinant means or post-translationally by chemical means.

As used herein, detection includes methods that permit visualization (by eye or equipment) of a protein. A protein can be visualized using an antibody specific to the protein. Detection of a protein can also be facilitated by fusion of a protein with a tag including an epitope tag or label.

The term "label" means any moiety which can be attached or linked, directly or indirectly, to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

As used herein, a "solid phase binding assay" refers to an in vitro assay in which an antigen is contacted with a ligand, where one of the antigen or ligand are bound to a solid support. Upon antigen-ligand interaction, the unwanted or non-specific components can be removed (e.g. by washing) and the antigen-ligand complex detected.

By "solid support" is meant a non-aqueous matrix to which an antibody according to the provided disclosure can adhere or attach. For example, solid supports include, but are not limited to, a microtiter plate, a membrane (e.g., nitrocellulose), a bead, a dipstick, a thin-layer chromatographic plate, or other solid medium.

The term "composition" refers to any mixture of two or more products, substances, or compounds, including antibodies. It may be a solution, a suspension, liquid, powder, a paste, aqueous, non-aqueous or any combination thereof. The preparation is generally in such form as to permit the biological activity of the active ingredient (e.g. antibody) to be effective.

"Carriers" as used herein include pharmaceutically acceptable carriers, excipients, or stabilizers that are non-toxic to the cell or mammal being exposed thereto at the dosages and concentrations employed. Acceptable carriers, excipients, or stabilizers that are compatible for use in a diagnostic assay or detection assay are also included. Often the acceptable carrier is an aqueous pH buffered solution. Examples of acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional reagents and instructions for use of the combination or elements thereof, for a purpose including, but not limited to, detection, diagnosis, and/or assessment of a biological activity or property.

As used herein, an "article of manufacture" is a product that is made and sold. As used throughout this application, the term is intended to encompass any of the antibodies provided herein, including compositions and combinations thereof, contained in articles of packaging.

As used herein, an individual "at risk" of developing a disorder may or may not have detectable disease or symptoms of disease, and may or may not have displayed detectable disease or symptoms of disease. "At risk" denotes that an individual has one or more risk factors that correlate with development of a brain damage or injury, such as traumatic brain injury or other neurological injury or condition as known in the art. Non-limiting examples of such risk factors include, for example, a bolt or jolt to the head, a penetrating head injury, a change in mental status or consciousness (either brief or for an extended period), memory loss, or other similar symptom or outcome that may indicate a brain injury. An individual having one or more of these risk factors has a higher probability of developing the disorder than an individual without one or more of these risk factors.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disorder (e.g., an eosinophil-mediated disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at the earlier stage of disease, the prophylactically effective amount can be less than the therapeutically effective amount.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is human.

II. Anti-UCH-L1 Antibodies and Anti-GFAP Antibodies

Provided herein are anti-GFAP antibodies and anti-UCH-L1 antibodies. In some embodiments, the provided antibodies detect GFAP and UCH-L1, respectively, such as in a sample from an individual, such as a human patient. In some embodiments, the sample is from an individual having or suspecting of having brain damage, such as due to a neurodegenerative disorder, stroke or damage or injury, such as mild, moderate or severe traumatic brain injury, as described herein.

In some embodiments, GFAP and UCH-L1 have been shown to be associated with neurological damage or brain injury (see e.g., US2011/0143375). Cells in the brain, including neuronal cells and non-neuronal cells (e.g., glial cells), may be harmed directly and/or indirectly due to injury or disease. Several proteins, including GFAP and UCH-L1, can be released from harmed brain cells or from unharmed brain cells that are associated with the harmed brain cells. For example, a brain cell that is directly harmed may release a protein indicative of direct damage. Alternatively or concurrently, an unharmed brain cell, may respond to harm of surrounding brain cells and release a protein indicative of damage in the area.

GFAP, a member of the cytoskeletal protein family, is the principal 8-9 nanometer intermediate filament of glial cells such as mature astrocytes of the central nervous system (CNS). GFAP is a monomeric molecule with a molecular mass between 35 or 40 and 53 kDa and an isoelectric point between 5.7 and 5.8. GFAP is highly brain specific protein that, normally, is not found outside the CNS in appreciable amounts. GFAP can be released into the body, such as the blood and cerebrospinal fluid (CSF), soon after brain injury. For example, in some cases, following injury, either as a result of trauma, disease, genetic disorders, or chemical insult, astrocytes in the CNS can become reactive in a way that is characterized by rapid synthesis of GFAP by a process termed astrogliosis or gliosis. In some embodiments, GFAP can be susceptible to proteolytic modifications, which, in some cases, can result in breakdown products of GFAP (see e.g. Papa et al. (2012) Ann Emerg. Med., 59:10 McMahon et al. (2015) J. Neurotrauma, 32:527-533). In some cases, calpain over-activation at the site of damage or injury can lead to the release of GFAP breakdown products. In some cases, existing methods for detecting GFAP in a bodily fluid have not been optimal.

UCH-L1 is present in neurons and is elevated upon damage to neurons. It is commonly used as a biomarker in studies of the mammalian CNS. Several isoforms of UCH-L1 exist with the prototype UCH-L1 known to be about 25 kDa in size. Although UCH-L1 appears to be a good candidate as a biomarker for detecting brain damage, elevated levels of UCH-L1 are difficult to detect reliably partly due to the complex structure of UCH-L1. This is a result of the knotted tertiary structure folding upon itself and obscuring the binding sites from detection antibodies raised against UCH-L1. In some cases, existing methods for detecting UCH-L1 in bodily fluids have not been optimal.

The provided antibodies overcome these problems. Exemplary anti-GFAP or anti-UCH-L1 antibodies are described in the following subsections. In some embodiments, one or more of the provided anti-UCH-L1 antibodies and/or one or more of the provided anti-GFAP antibodies can be used, alone or together, in methods of detection or diagnosis of brain damage, such as due to a neurological condition or other condition associated with a brain injury and/or in methods to predict whether a subject is in need of, e.g. does or does not need, a CT scan.

A. Anti-UCH-L1 Antibodies

In one aspect, provided are antibodies that bind to a human UCH-L1, including a fragment, isoform or variant of a human UCH-L1 protein. In some embodiments, the human UCH-L1 protein is one released from damaged cells or tissue and/or present in a bodily fluid (e.g. serum, cerebrospinal fluid or other bodily fluid as described) as a result of brain damage or injury. In some embodiments, the anti-UCH-L1 antibody binds to a human UCH-L1 protein comprising the amino acid sequence selected from any of SEQ ID NOs:207-211 or a variant thereof having an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from SEQ ID NOs: 207-211.

In some embodiments, the UCH-L1 variant is a UCH-L1 having at least about 80% amino acid sequence identity with a UCH-L1 amino acid sequence which is a: (i) full-length native human UCH-L1 amino acid sequence, e.g. set forth in any of SEQ ID NOS: 207-211; (ii) full-length recombinant human UCH-L1 amino acid sequence, e.g. set forth in any of SEQ ID NOS: 207-211; (iii) a UCH-L1 amino acid sequence of (i) or (ii) lacking the signal peptide; (iv) or any other fragment of a full-length UCH-L1 amino acid sequence of (i) or (ii), such as those encoded by a nucleic acid that represents only a portion of the complete coding sequence for a full-length UCH-L1 protein. Such UCH-L1 variants include, for instance, polypeptides wherein one or more amino acid residues are added, or deleted, at the N- or C-terminus of the full-length native amino acid sequence or full-length recombinant amino acid sequence. Ordinarily, a UCH-L1 variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native UCH-L1 amino acid sequence (e.g. set forth in SEQ ID NO:207-211), a full-length recombinant UCH-L1 amino acid sequence (e.g. set forth in SEQ ID NOS:207-211), or an UCH-L1 amino acid sequence thereof lacking the signal peptide or any other fragment of such full-length UCH-L1 amino acid sequence. In some embodiments, UCH-L1 variants, including fragments of a full length sequence, are at least about 10 amino acids in length, alternatively at least about 20, 30, 40, 50, 60, 70, 80, 90, 100, 110, 120, 130, 140, 150, 160, 170, 180, 190, 200, 210, 220 amino acids in length, or more. In some embodiments, UCH-L1 variants will have no more than one conservative amino acid substitution as compared to the native UCH-L1 amino acid sequence or recombinant UCH-L1 amino acid sequence, alternatively no more than 2, 3, 4, 5, 6, 7, 8, 9, or 10 conservative amino acid substitutions as compared to the native UCH-L1 amino acid sequence or recombinant UCH-L1 amino acid sequence.

In some embodiments, the anti-UCH-L1 antibody binds an epitope or region corresponding to an epitope or region contained in a human UCH-L1 protein set forth in SEQ ID NO:207 or the same epitope or region in an isoform or fragment or variant of the UCH-L1 protein set forth in SEQ ID NO:207.

In some embodiments, the UCH-L1 protein (e.g., human UCH-L1 protein) is a recombinant UCH-L1 protein such as a recombinant UCH-L1 protein produced in a bacterial host cell (e.g., E. coli cell) or mammalian host cell (e.g., CHO cell). In some embodiments, the UCH-L1 protein (e.g., human UCH-L1 protein) is a native UCH-L1 protein such a native-UCH-L1 protein present or obtained from serum, plasma, blood (e.g., whole blood), cerebrospinal fluid, urine, sweat, saliva or any other biological fluid present or obtained from an individual (e.g., human). In some embodiments, the anti-UCH-L1 antibody binds to a glycosylated UCH-L1.

In some embodiments, the anti-UCH-L1 antibody described herein binds to a linear epitope of UCH-L1 (e.g., human UCH-L1). In some embodiments, the anti-UCH-L1 antibody described herein binds to a conformational epitope of UCH-L1 (e.g., human UCH-L1).

In some embodiments, the anti-UCH-L1 antibodies bind to a particular epitope or region of UCH-L1. In some embodiments, the anti-UCH-L1 antibody binds to an epitope containing one or more amino acids that is, includes or is within (or is entirely within) a portion of UCH-L1 corresponding to positions 98-106 of the human UCH-L1 set forth in SEQ ID NO:207. In some embodiments, the anti-UCH-L1 antibody binds to an epitope containing one or more amino acids that is, includes or is within (or is entirely within) a portion of UCH-L1 corresponding to positions 28-36 of the human UCH-L1 set forth in SEQ ID NO:207. In some embodiments, the anti-UCH-L1 antibody binds to an epitope containing one or more amino acids that is, includes or is within (or is entirely within) a portion of UCH-L1 corresponding to positions 138-145 of human UCH-L1 set forth in SEQ ID NO:207. In some embodiments, the anti-UCH-L1 antibody binds to an epitope containing one or more amino acids that is, includes or is within (or is entirely within) a portion of UCH-L1 corresponding to positions 142-149 of human UCH-L1 set forth in SEQ ID NO:207. For example, in some embodiments, the anti-UCH-L1 antibody binds to an epitope that is, includes or is within (or is entirely within) a portion of UCH-L1 corresponding to positions 98-106 of human UCH-L1 set forth in SEQ ID NO:207.

In some embodiments, among the provided antibodies are antibodies that bind to the same or overlapping epitope as one or more of the other provided antibodies and/or compete for binding to UCH-L1 with one or more of the other provided antibodies. In some embodiments, among the provided antibodies are antibodies that bind to a different or distinct epitope as compared to one or more of the other provided antibodies and/or do not compete for binding to UCH-L1 with one or more of the other provided antibodies. For example, in some embodiments provided are antibodies that bind to a distinct epitope and/or do not compete for binding to UCH-L1 as compared to the antibodies designated UCH-L1-1 and UCH-L1-2 as described herein. In some embodiments, provided are antibodies that bind to a distinct epitope and/or do not compete for binding to UCH-L1 as compared to the antibody designated UCH-L1-5 as described herein.

In some embodiments, the antibodies bind to an epitope of UCH-L1 that is conserved among UCH-L1 from different species. In some embodiments, the antibodies bind to an epitope of UCH-L1 that is present in human UCH-L1 or an isoform or variant thereof but that is not present in one or more other non-human species.

In some embodiments, provided herein is an anti-UCH-L1 antibody comprising a heavy chain variable region and a light chain variable region, wherein the heavy chain variable region comprises a CDR-H3 comprising an amino acid sequence selected from SEQ ID NOs:20-27. In some embodiments, the heavy chain variable region further comprises a CDR-H1 comprising an amino acid sequence selected from SEQ ID NOs:1-8 and/or a CDR-H2 comprising an amino acid sequence selected from SEQ ID NOs:9-19.

In some embodiments, provided herein is an anti-UCH-L1 antibody comprising a heavy chain variable region and a light chain variable region, wherein the light chain variable region comprises a CDR-L3 comprising an amino acid sequence selected from SEQ ID NOs:45-50. In some embodiments, the light chain variable region further comprises a CDR-L1 comprising an amino acid sequence selected from SEQ ID NOs:28-36 and/or a CDR-L2 comprising an amino acid sequence selected from SEQ ID NOs:37-44.

In some embodiments, the heavy chain CDR sequences comprise the following:
a) a CDR-H1 set forth in SEQ ID NO:1 or SEQ ID NO:2;
b) a CDR-H2 set forth in SEQ ID NO:9 or SEQ ID NO:10; and/or
c) a CDR-H3 set forth in SEQ ID NO:20 or SEQ ID NO:21.

In some embodiments, the heavy chain CDR sequences comprise the following:
a) a CDR-H1 set forth in SEQ ID NO:3; SEQ ID NO:4; SEQ ID NO:5; SEQ ID NO:6; SEQ ID NO:7 or SEQ ID NO:8;
b) a CDR-H2 set forth in SEQ ID NO: 11; SEQ ID NO:12; SEQ ID NO:13; SEQ ID NO:14; SEQ ID NO:15; SEQ ID NO:16; SEQ ID NO: 17 or SEQ ID NO:18; and/or
c) a CDR-H3 set forth in SEQ ID NO:20; SEQ ID NO:22; SEQ ID NO:23; SEQ ID NO:24; SEQ ID NO:25; SEQ ID NO:26; or SEQ ID NO:27.

In some embodiments, the heavy chain CDR sequences comprise the following:
a) a CDR-H1 set forth in SEQ ID NO: 1;
b) a CDR-H2 set forth in SEQ ID NO: 19; and/or
c) a CDR-H3 set forth in SEQ ID NO:20.

In some embodiments, the light chain CDR sequences comprise the following:
a) a CDR-L1 set forth in SEQ ID NO:28 or SEQ ID NO:29;
b) a CDR-L2 set forth in SEQ ID NO:37 or SEQ ID NO:38; and/or
c) a CDR-L3 set forth in SEQ ID NO:45 or SEQ ID NO:46.

In some embodiments, the light chain CDR sequences comprise the following:
a) a CDR-L1 set forth in SEQ ID NO:30; SEQ ID NO:31; SEQ ID NO:32; SEQ ID NO:33; SEQ ID NO:34; SEQ ID NO:35; or SEQ ID NO:36;
b) a CDR-L2 set forth in SEQ ID NO:37, SEQ ID NO:39; SEQ ID NO:40; SEQ ID NO:41; SEQ ID NO:42; SEQ ID NO:43; or SEQ ID NO:44; and/or
c) a CDR-L3 set forth in SEQ ID NO:45; SEQ ID NO:47; or SEQ ID NO:49.

In some embodiments, the light chain CDR sequences comprise the following:
a) a CDR-L1 set forth in SEQ ID NO:28;
b) a CDR-L2 set forth in SEQ ID NO:37; and/or
c) a CDR-L3 set forth in SEQ ID NO:50.

Also provided are antibodies comprising a CDR-H1, CDR-H2, CDR-H3, CDR-L1, CDR-L2 and/or CDR-L3 sequence that is at least at or about at least 85%, 86%, 87%, 88%, 89%, 90%, 91%, 92%, 93%, 94%, 95%, 96%, 97%, 98%, or 99% identical to any of the above CDR-H1, CDR-H2, CDR-H3, CDR-L1, CDR-L2 and/or CDR-L3 sequences, respectively.

In one aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:1, (ii) CDR-H2 comprising the amino acid sequence of SEQ ID NO:9, and (iii) CDR-H3 comprising the amino acid sequence of SEQ ID NO:20; and/or wherein the light chain variable region comprises (i) CDR-L1 comprising the amino acid sequence of SEQ ID NO:28, (ii) CDR-L2 comprising the amino acid sequence of SEQ ID NO:37, and (iii) CDR-L3 comprising the amino acid sequence of SEQ ID NO:45. In some embodiments, the antibody described herein binds to an epitope corresponding to an epitope within, that is, or includes residues 98-106 of human UCH-L1 set forth in SEQ ID NO:207.

In one aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:2, (ii) CDR-H2 comprising the amino acid sequence of SEQ ID NO:10, and (iii) CDR-H3 comprising the amino acid sequence of SEQ ID NO:21; and/or wherein the light chain variable region comprises (i) CDR-L1 comprising the amino acid sequence of SEQ ID NO:29, (ii) CDR-L2 comprising the amino acid sequence of SEQ ID NO:38, and (iii) CDR-L3 comprising the amino acid sequence of SEQ ID NO:46. In some embodiments, the antibody described herein binds to an epitope corresponding to an epitope within, that is, or includes residues 28-36 of human UCH-L1 set forth in SEQ ID NO:207.

In one aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:3, (ii) CDR-H2 comprising the amino acid sequence of SEQ ID NO:11, and (iii) CDR-H3 comprising the amino acid sequence of SEQ ID NO:20; and/or wherein the light chain variable region comprises (i) CDR-L1 comprising the amino acid sequence of SEQ ID NO:30, (ii) CDR-L2 comprising the amino acid sequence of SEQ ID NO:37, and (iii) CDR-L3 comprising the amino acid sequence of SEQ ID NO:45. In some embodiments, the antibody described herein binds to an epitope corresponding to an epitope within, that is, or includes residues 98-106 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:4, (ii) CDR-H2 comprising the amino acid sequence of SEQ ID NO:12, and (iii) CDR-H3 comprising the amino acid sequence of SEQ ID NO:22; and/or wherein the light chain variable region comprises (i) CDR-L1 comprising the amino acid sequence of SEQ ID NO:31, (ii) CDR-L2 comprising the amino acid sequence of SEQ ID NO:39, and (iii) CDR-L3 comprising the amino acid sequence of SEQ ID NO:47. In some embodiments, the antibody described herein binds to an epitope corresponding to an epitope within, that is, or includes residues 138-145 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:5, (ii) CDR-H2 comprising the amino acid sequence of SEQ ID NO:13, and (iii) CDR-H3 comprising the amino acid sequence of SEQ ID NO:23; and/or a light chain variable region comprising (i) CDR-L1 comprising the amino acid sequence of SEQ ID NO:32, (ii) CDR-L2 comprising the amino acid sequence of SEQ ID NO:39, and (iii) CDR-L3 comprising the amino acid sequence of SEQ ID NO:47. In some embodiments, the antibody described herein binds to an epitope corresponding to an epitope within, that is, or includes residues 142-149 of human UCH-L1 set forth in SEQ ID NO:207

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:6, (ii) CDR-H2 comprising the amino acid sequence of SEQ ID NO:14, and (iii) CDR-H3 comprising the amino acid sequence of SEQ ID NO:24; and/or a light chain variable region comprising (i) CDR-L1 comprising the amino acid sequence of SEQ ID NO:33, (ii) CDR-L2 comprising the amino acid sequence of SEQ ID NO:40, and (iii) CDR-L3 comprising the amino acid sequence of SEQ ID NO:48. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:6, (ii) CDR-H2 comprising the amino acid sequence of SEQ ID NO:14, and (iii) CDR-H3 comprising the amino acid sequence of SEQ ID NO:24; and/or a light chain variable region comprising (i) CDR-L1 comprising the amino acid sequence of SEQ ID NO:34, (ii) CDR-L2 comprising the amino acid sequence of SEQ ID NO:41, and (iii) CDR-L3 comprising the amino acid sequence of SEQ ID NO:48. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:6, (ii) CDR-H2 comprising the amino acid sequence of SEQ ID NO:15, and (iii) CDR-H3 comprising the amino acid sequence of SEQ ID NO:24; and/or a light chain variable region comprising (i) CDR-L1 comprising the amino acid sequence of SEQ ID NO:34, (ii) CDR-L2 comprising the amino acid sequence of SEQ ID NO:42, and (iii) CDR-L3 comprising the amino acid sequence of SEQ ID NO:48. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:6, (ii) CDR-H2 comprising the amino acid sequence of SEQ ID NO:14, and (iii) CDR-H3 comprising the amino acid sequence of SEQ ID NO:24; and/or a light chain variable region comprising (i) CDR-L1 comprising the amino acid sequence of SEQ ID NO:35, (ii) CDR-L2 comprising the amino acid sequence of SEQ ID NO:41, and (iii) CDR-L3 comprising the amino acid sequence of SEQ ID NO:48. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:6, (ii) CDR-H2 comprising the amino acid sequence of SEQ ID NO:16, and (iii) CDR-H3 comprising the amino acid sequence of SEQ ID NO:25; and/or a light chain variable region comprising (i) CDR-L1 comprising the amino acid sequence of SEQ ID NO:34, (ii) CDR-L2 comprising the amino acid sequence of SEQ ID NO:42, and (iii) CDR-L3 comprising the amino acid sequence of SEQ ID NO:48. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:7, (ii) CDR-H2 comprising the amino acid sequence of SEQ ID NO:17, and (iii) CDR-H3 comprising the amino acid sequence of SEQ ID NO:26; and/or a light chain variable region comprising (i) CDR-L1 comprising the amino acid sequence of SEQ ID NO:36, (ii) CDR-L2 comprising the amino acid sequence of SEQ ID NO:43, and (iii) CDR-L3 comprising the amino acid sequence of SEQ ID NO:49. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:8, (ii) CDR-H2 comprising the amino acid sequence of SEQ ID NO:18, and (iii) CDR-H3 comprising the amino acid sequence of SEQ ID NO:27; and/or a light chain variable region comprising (i) CDR-L1 comprising the amino acid sequence of SEQ ID NO:36, (ii) CDR-L2 comprising the amino acid sequence of SEQ ID NO:44, and (iii) CDR-L3 comprising the amino acid sequence of SEQ ID NO:49. In some embodiments, the antibody described herein binds to an epitope corresponding to an epitope within, that is, or includes residues 28-36 of human UCH-L1 set forth in SEQ ID NO:207.

In another aspect, provided herein is an anti-UCH-L1 antibody comprising a heavy chain variable region and a light chain variable region, wherein the heavy chain variable region comprises (i) CDR-H1 comprising the amino acid sequence of SEQ ID NO:1, (ii) CDR-H2 comprising the amino acid sequence of SEQ ID NO:19, and (iii) CDR-H3 comprising the amino acid sequence of SEQ ID NO:20; and/or a light chain variable region comprising (i) CDR-L1 comprising the amino acid sequence of SEQ ID NO:28, (ii) CDR-L2 comprising the amino acid sequence of SEQ ID NO:37, and (iii) CDR-L3 comprising the amino acid sequence of SEQ ID NO:50. In some embodiments, the antibody described herein binds to an epitope corresponding to an epitope within, that is, or includes residues 98-106 of human UCH-L1 set forth in SEQ ID NO:207.

In some embodiments, the anti-UCH-L1 comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:51-63. In some embodiments, the anti-UCH-L1 comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:51 or 52. In some embodiments, the anti-UCH-L1 comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:53-62. In some embodiments, the anti-UCH-L1 comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NO:63.

In some embodiments, the anti-UCH-L1 comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:64-76. In some embodiments, the anti-UCH-L1 comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:64 or 65. In some embodiments, the anti-UCH-L1 comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:66-75. In some embodiments, the anti-UCH-L1 comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:76.

An anti-UCH-L1 antibody described herein may comprise any suitable framework variable domain sequence, provided that the antibody retains the ability to bind UCH-L1 (e.g., human UCH-L1). As used herein, heavy chain framework regions are designated "HC-FR1-FR4," and light chain framework regions are designated "LC-FR1-FR4."

In some embodiments, provided herein is an anti-UCH-L1 antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs:51-63. In some embodiments, provided herein is an anti-UCH-L1 antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs:51 or 52. In some embodiments, provided herein is an anti-UCH-L1 antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs:53-62. In some embodiments, provided herein is an anti-UCH-L1 antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence selected from SEQ ID NO:63. In some embodiments, an amino acid sequence having at least 85%, 86%, 87%, 88%, 89%, 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to UCH-L1 (e.g., human UCH-L1). In some embodiments, the substitutions, insertions, or deletions (e.g., 1, 2, 3, 4, or 5 amino acids) occur in regions outside the CDRs (i.e., in the FRs).

In some embodiments, an anti-UCH-L1 antibody comprises a heavy chain variable domain comprising an amino acid sequence selected from SEQ ID NO:51-63. In some embodiments, an anti-UCH-L1 antibody comprises a heavy chain variable domain comprising an amino acid sequence of SEQ ID NO:51. In some embodiments, an anti-UCH-L1 antibody comprises a heavy chain variable domain comprising an amino acid sequence of SEQ ID NO:52. In some embodiments, an anti-UCH-L1 antibody comprises a heavy chain variable domain comprising an amino acid sequence of SEQ ID NO:53. In some embodiments, an anti-UCH-L1 antibody comprises a heavy chain variable domain comprising an amino acid sequence of SEQ ID NO:54. In some embodiments, an anti-UCH-L1 antibody comprises a heavy chain variable domain comprising an amino acid sequence of SEQ ID NO:55. In some embodiments, an anti-UCH-L1 antibody comprises a heavy chain variable domain comprising an amino acid sequence of SEQ ID NO:56. In some embodiments, an anti-UCH-L1 antibody comprises a heavy chain variable domain comprising an amino acid sequence of SEQ ID NO:57. In some embodiments, an anti-UCH-L1 antibody comprises a heavy chain variable domain comprising an amino acid sequence of SEQ ID NO:58. In some embodiments, an anti-UCH-L1 antibody comprises a heavy chain variable domain comprising an amino acid sequence of SEQ ID NO:59. In some embodiments, an anti-UCH-L1 antibody comprises a heavy chain variable domain comprising an amino acid sequence of SEQ ID NO:60. In some embodiments, an anti-UCH-L1 antibody comprises a heavy chain variable domain comprising an amino acid sequence of SEQ ID NO:61. In some embodiments, an anti-UCH-L1 antibody comprises a heavy chain variable domain comprising an amino acid sequence of SEQ ID NO:62. In some embodiments, an anti-UCH-L1 antibody comprises a heavy chain variable domain comprising an amino acid sequence of SEQ ID NO:63.

In some embodiments, provided herein is an anti-UCH-L1 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs:64-76. In some embodiments, provided herein is an anti-UCH-L1 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs:64 or 65. In some embodiments, provided herein is an anti-UCH-L1 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs:66-75. In some embodiments, provided herein is an anti-UCH-L1 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NO:76. In some embodiments, an amino acid sequence having at least 85%, 86%, 87%, 88%, 89%, 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to UCH-L1 (e.g., human UCH-L1). In some embodiments, the substitutions, insertions, or deletions (e.g., 1, 2, 3, 4, or 5 amino acids) occur in regions outside the CDRs (i.e., in the FRs).

In some embodiments, an anti-UCH-L1 antibody comprises a light chain variable domain comprising an amino acid sequence selected from SEQ ID NO:64-76. In some embodiments, an anti-UCH-L1 antibody comprises a light chain variable domain comprising an amino acid sequence of SEQ ID NO:64. In some embodiments, an anti-UCH-L1 antibody comprises a light chain variable domain comprising an amino acid sequence of SEQ ID NO:65. In some embodiments, an anti-UCH-L1 antibody comprises a light chain variable domain comprising an amino acid sequence of SEQ ID NO:66. In some embodiments, an anti-UCH-L1 antibody comprises a light chain variable domain comprising an amino acid sequence of SEQ ID NO:67. In some embodiments, an anti-UCH-L1 antibody comprises a light chain variable domain comprising an amino acid sequence of SEQ ID NO:68. In some embodiments, an anti-UCH-L1 antibody comprises a light chain variable domain comprising an amino acid sequence of SEQ ID NO:69. In some embodiments, an anti-UCH-L1 antibody comprises a light chain variable domain comprising an amino acid sequence of SEQ ID NO:70. In some embodiments, an anti-UCH-L1 antibody comprises a light chain variable domain comprising an amino acid sequence of SEQ ID NO:71. In some embodiments, an anti-UCH-L1 antibody comprises a light chain variable domain comprising an amino acid sequence of SEQ ID NO:72. In some embodiments, an anti-UCH-L1 antibody comprises a light chain variable domain comprising an amino acid sequence of SEQ ID NO:73. In some embodiments, an anti-UCH-L1 antibody comprises a light chain variable domain comprising an amino acid sequence of SEQ ID NO:74. In some embodiments, an anti-UCH-L1 antibody comprises a light chain variable domain comprising an amino acid sequence of SEQ ID NO:75. In some embodiments, an anti-UCH-L1 antibody comprises a light chain variable domain comprising an amino acid sequence of SEQ ID NO:76.

In one aspect, provided herein is an anti-UCH-L1 antibody comprising a heavy chain variable domain comprising an amino acid sequence selected from SEQ ID NOs:51-63 and/or comprising a light chain variable domain comprising an amino acid sequence selected from SEQ ID NOs:64-76. In some embodiments, the anti-UCH-L1 antibody comprises a heavy chain variable domain comprising an amino acid sequence selected from SEQ ID NOs:51 or 52 and/or comprises a light chain variable domain comprising an amino acid sequence selected from SEQ ID NOs:64 or 65. In some embodiments, the anti-UCH-L1 antibody comprises a heavy chain variable domain comprising an amino acid sequence selected from SEQ ID NOs:53-62 and/or comprises a light chain variable domain comprising an amino acid sequence selected from SEQ ID NOs:66-75. In some embodiments, the anti-UCH-L1 antibody comprises a heavy chain variable domain comprising an amino acid sequence selected from SEQ ID NO:63 and/or comprises a light chain variable domain comprising an amino acid sequence selected from SEQ ID NO:76. Also provided are antibodies comprising a heavy chain variable domain and/or a light chain variable domain sequence that is at least at or about at least 85%, 86%, 87%, 88%, 89%, 90%, 91%, 92%, 93%, 94%, 95%, 96%, 97%, 98%, or 99% identical to any of the above heavy chain variable domain and/or light chain variable domain sequences, respectively.

In some embodiments, provided herein is an anti-UCH-L1 antibody comprising a heavy chain variable domain and/or a light chain variable domain of an antibody shown in Table 6, for example, UCH-L1-1, UCH-L1-2, etc.

In some embodiments, the anti-UCH-L1 antibody comprises a heavy chain variable domain comprising an amino acid sequence of SEQ ID NO:51 and/or comprises a light chain variable domain comprising an amino acid sequence of SEQ ID NO:64. In some embodiments, the anti-UCH-L1 antibody comprises a heavy chain variable domain comprising an amino acid sequence of SEQ ID NO:52 and/or comprises a light chain variable domain comprising an amino acid sequence of SEQ ID NO:65. In some embodiments, the anti-UCH-L1 antibody comprises a heavy chain variable domain comprising an amino acid sequence of SEQ ID NO:53 and/or comprises a light chain variable domain comprising an amino acid sequence of SEQ ID NO:66. In some embodiments, the anti-UCH-L1 antibody comprises a heavy chain variable domain comprising an amino acid sequence of SEQ ID NO:54 and/or comprises a light chain variable domain comprising an amino acid sequence of SEQ ID NO:67. In some embodiments, the anti-UCH-L1 antibody comprises a heavy chain variable domain comprising an amino acid sequence of SEQ ID NO:55 and/or comprises a light chain variable domain comprising an amino acid sequence of SEQ ID NO:68. In some embodiments, the anti-UCH-L1 antibody comprises a heavy chain variable domain comprising an amino acid sequence of SEQ ID NO:56 and/or comprises a light chain variable domain comprising an amino acid sequence of SEQ ID NO:69. In some embodiments, the anti-UCH-L1 antibody comprises a heavy chain variable domain comprising an amino acid sequence of SEQ ID NO:57 and/or comprises a light chain variable domain comprising an amino acid sequence of SEQ ID NO:70. In some embodiments, the anti-UCH-L1 antibody comprises a heavy chain variable domain comprising an amino acid sequence of SEQ ID NO:58 and/or comprises a light chain variable domain comprising an amino acid sequence of SEQ ID NO:71. In some embodiments, the anti-UCH-L1 antibody comprises a heavy chain variable domain comprising an amino acid sequence of SEQ ID NO:59 and/or comprises a light chain variable domain comprising an amino acid sequence of SEQ ID NO:72. In some embodiments, the anti-UCH-L1 antibody comprises a heavy chain variable domain comprising an amino acid sequence of SEQ ID NO:60 and/or comprises a light chain variable domain comprising an amino acid sequence of SEQ ID NO: 73. In some embodiments, the anti-UCH-L1 antibody comprises a heavy chain variable domain comprising an amino acid sequence of SEQ ID NO:61 and/or comprises a light chain variable domain comprising an amino acid sequence of SEQ ID NO:74. In some embodiments, the anti-UCH-L1 antibody comprises a heavy chain variable domain comprising an amino acid sequence of SEQ ID NO:62 and/or comprises a light chain variable domain comprising an amino acid sequence of SEQ ID NO:75. In some embodiments, the anti-UCH-L1 antibody comprises a heavy chain variable domain comprising an amino acid sequence of SEQ ID NO:73 and/or comprises a light chain variable domain comprising an amino acid sequence of SEQ ID NO:76.

In one aspect, an anti-UCH-L1 antibody described herein is an antibody fragment (including antigen-binding fragment), e.g., a Fab, Fab'-SH, Fv, scFv, or (Fab')$_2$ fragment.

In any of the embodiments herein, the antibody may comprise a heavy chain constant domain. In some embodiments, the heavy chain constant domain is non-human mammalian. In some embodiments, the heavy chain constant domain is non-human primate. In some embodiments, the heavy chain constant domain is non-human primate. In some embodiments, the heavy chain constant domain is murine (e.g., mouse or rat). In some embodiments, the murine heavy chain constant domain is IgG1, IgG2a, IgG2b or IgM. In some embodiments, the murine heavy chain constant domain is murine IgG1. In some embodiments, the murine IgG1 comprises the amino acid sequence of SEQ ID NO:215 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:215. In some embodiments, the murine heavy chain constant domain is murine IgG2a. In some embodiments, the murine IgG2a comprises the amino acid sequence of SEQ ID NO:216 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:216. In some embodiments, the murine heavy chain constant domain is murine IgG2b. In some embodiments, the murine IgG2b comprises the amino acid sequence of SEQ ID NO:217 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:217. In some embodiments, the murine heavy chain constant domain is murine IgM. In some embodiments, the murine IgM comprises the amino acid sequence of SEQ ID NO:223 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:223. In some embodiments, the heavy chain constant domain is human. In some embodiments, the human heavy chain constant domain is human IgG1. In some embodiments, the human IgG1 comprises the amino acid sequence of SEQ ID NO:218 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:218. In some embodiments, the human heavy chain constant domain is human IgM. In some embodiments, the human IgM comprises the amino acid sequence of SEQ ID NO:224 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:224.

There are two types of light chains, kappa and lambda, based on the amino acid sequences of their constant domains. In any of the embodiments herein, an antibody provided herein may comprise a light chain constant domain. In some embodiments, the light chain constant domain is non-human mammalian. In some embodiments, the light chain constant domain is non-human primate. In some embodiments, the light chain constant domain is non-human primate. In some embodiments, the light chain constant domain is murine (e.g., mouse or rat). In some embodiments, the murine light chain constant domain is murine kappa or murine lambda. In some embodiments, the murine kappa comprises the amino acid sequence of SEQ ID NO:219 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:219. In some embodiments, the murine lambda comprises the amino acid sequence of SEQ ID NO:220 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:220. In some embodiments, the light chain constant domain is human. In some embodiments, the human light chain constant domain is human kappa or human lambda. In some embodiments, the human kappa comprises the amino acid sequence of SEQ ID NO:221 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:221. In some embodiments, the human lambda comprises the amino acid sequence of SEQ ID NO:222 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:222.

In one aspect, an anti-UCH-L1 antibody described herein is a monoclonal antibody. In one aspect, an anti-UCH-L1 antibody described herein is a humanized antibody, a chimeric antibody or a human antibody. In one aspect, an anti-UCH-L1 antibody described herein is a mouse antibody, a rabbit antibody, a rat antibody, or a non-human primate antibody. In some embodiments, any of the anti-UCH-L1 antibodies are recombinant. In one aspect, any of the anti-UCH-L1 antibodies described herein are isolated or purified.

In some embodiments, an anti-UCH-L1 antibody provided herein has a binding affinity with a dissociation constant ($K_D$) of $10^{-8}$ M or less, e.g. from $10^{-1}$ M to $10^{-13}$ M, e.g., from $10^{-9}$ M to $10^{-13}$ M, e.g., from $10^{-10}$ M to $10^{-12}$ M. In some embodiments, an anti-UCH-L1 antibody provided herein has a dissociation constant ($K_D$) of less than or equal to 1 μM, less than or equal to 150 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM. In some embodiments, an anti-UCH-L1 antibody provided herein has a dissociation constant ($K_D$) of less than or less than about $1.0 \times 10^{-10}$ M, $2.0 \times 10^{-10}$ M, $3.0 \times 10^{-10}$ M, $4.0 \times 10^{-10}$ M, $5.0 \times 10^{-10}$ M, $6.0 \times 10^{-10}$ M, $7.0 \times 10^{-10}$ M, $8.0 \times 10^{-10}$ M, $9.0 \times 10^{-10}$ M, $1.0 \times 10^{-11}$ M, $2.0 \times 10^{-11}$ M, $3.0 \times 10^{-11}$ M, $4.0 \times 10^{-11}$ M, $5.0 \times 10^{-11}$ M, $6.0 \times 10^{-11}$ M, $7.0 \times 10^{-11}$ M, $8.0 \times 10^{-11}$ M, $9.0 \times 10^{-11}$ M, or $1.0 \times 10^{-12}$ M.

In some embodiments, an anti-UCH-L1 antibody provided herein has a binding affinity with a dissociation constant ($K_D$) of from or from about $2.0 \times 10^{-10}$ M to $5.0 \times 10^{-12}$ M, such as from or from about $2.0 \times 10^{-10}$ M to $1.0 \times 10^{-12}$ M, $2.0 \times 10^{-10}$ M to $5.0 \times 10^{-11}$ M, $2.0 \times 10^{-10}$ M to $1.0 \times 10^{-11}$ M, $2.0 \times 10^{-10}$ M to $5.0 \times 10^{-10}$ M, $5.0 \times 10^{-10}$ M to $1.0 \times 10^{-12}$ M, $5.0 \times 10^{-10}$ M to $5.0 \times 10^{-11}$ M, $5.0 \times 10^{-10}$ M to $1.0 \times 10^{-11}$ M, $1.0 \times 10^{-11}$ M to $1.0 \times 10^{-12}$ M, $1.0 \times 10^{-11}$ M to $5.0 \times 10^{-11}$ M or $5.0 \times 10^{-11}$ M to $1.0 \times 10^{-12}$ M. In some embodiments, an anti-UCH-L1 antibody provided herein has a dissociation constant ($K_D$) from or from about $2 \times 10^{-10}$ M to about $1 \times 10^{-12}$ M. In some embodiments, an anti-UCH-L1 antibody provided herein has a dissociation constant ($K_D$) from or from about $2.0 \times 10^{-10}$ M to $4.0 \times 10^{-10}$ M, $1.0 \times 10^{-11}$ M to $9.0 \times 10^{-11}$ M, or $1.0 \times 10^{-12}$ M to $5.0 \times 10^{-12}$ M. In some embodiments, an anti-UCH-L1 antibody provided herein has a dissociation constant ($K_D$) of an antibody shown in Table 4, for example, UCH-L1-1, UCH-L1-2, etc.

In one aspect, nucleic acids encoding anti-UCH-L1 antibodies are provided. In some embodiments, a nucleic acid may encode an anti-UCH-L1 antibody or antigen-binding fragment provided herein. In some embodiments, a nucleic acid may encode a heavy chain comprising a heavy chain variable region of an anti-UCH-L1 antibody or antigen-binding fragment provided herein. In some embodiments, a nucleic acid may encode a light chain comprising a light chain variable region of an anti-UCH-L1 antibody or antigen-binding fragment provided herein.

In certain embodiments, vectors, such as an expression vector, comprising nucleic acids encoding anti-UCH-L1 antibodies are provided. In certain embodiments, host cells comprising such nucleic acids and/or vectors are provided. For example, a host cell provided herein can comprise a vector comprising a nucleic acid encoding a heavy chain of an anti-UCH-L1 antibody or antigen-binding fragment provided herein. Such a host cell, in some embodiments, can further comprise a vector comprising a nucleic acid encoding a light chain of an anti-UCH-L1 antibody or antigen-binding fragment provided herein.

In another aspect of the invention, compositions comprising anti-UCH-L1 antibodies or nucleic acids encoding anti-UCH-L1 antibodies are provided. In certain embodiments, a composition provided herein can be used for the detection of UCH-L1, diagnosis of brain damage or injury (e.g. due to a neurological condition, stroke or traumatic brain injury) in an individual having or suspected of having the brain damage or injury and/or in predicting whether a subject needs a CT scan, such as those methods enumerated herein. In some embodiments, the provided anti-UCH-L1 antibodies can be used in the methods in combination with any one or more of the anti-GFAP antibodies provided herein.

B. Anti-GFAP Antibodies

In one aspect, provided herein are antibodies that bind to a human GFAP protein, including a fragment, isoform or variant of a human GFAP protein. In some embodiments, the human GFAP protein is one released from damaged cells or tissue and/or present in a bodily fluid (e.g. serum, cerebrospinal fluid or other bodily fluid as described) as a result of brain damage or injury. In some embodiments, the anti-GFAP antibody binds to a human GFAP protein comprising the amino acid sequence selected from any of SEQ ID NOs:212-214 or a variant thereof having an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from SEQ ID NOs:212-214.

In some embodiments, a GFAP variant is a GFAP having at least about 80% amino acid sequence identity with a GFAP amino acid sequence which is a: (i) full-length native GFAP amino acid sequence, e.g. set forth in any of SEQ ID NOS:212-214; (ii) full-length recombinant GFAP amino acid sequence, e.g. set forth in any of SEQ ID NOS:212-214; (iii) a GFAP amino acid sequence of (i) or (ii) lacking the signal peptide; (iv) or any other fragment of a full-length GFAP amino acid sequence of (i) or (ii), such as those encoded by a nucleic acid that represents only a portion of the complete coding sequence for a full-length GFAP protein. Such GFAP variants include, for instance, polypeptides wherein one or more amino acid residues are added, or deleted, at the N- or C-terminus of the full-length native amino acid sequence or full-length recombinant amino acid sequence. Ordinarily, a GFAP variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native GFAP amino acid sequence (e.g. set forth in SEQ ID NO:212-214), a full-length recombinant GFAP amino acid sequence (e.g. set forth in SEQ ID NO:212-214), or an GFAP amino acid sequence thereof lacking the signal peptide or any other fragment of a full-length GFAP amino acid sequence. In some embodiments, GFAP variants, including fragments of a full length sequence, are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430 amino acids in length, or more. In some embodiments, GFAP variants will have no more than one conservative amino acid substitution as compared to the native GFAP amino acid sequence or recombinant GFAP amino acid sequence, alternatively no more than 2, 3, 4, 5, 6, 7, 8, 9, or 10 conservative amino acid substitution as compared to the native GFAP amino acid sequence or recombinant GFAP amino acid sequence.

In some embodiments, the anti-GFAP antibody binds an epitope or region corresponding to an epitope or region contained in a human GFAP protein set forth in SEQ ID NO:212 or the same epitope or region in an isoform or fragment or variant of the GFAP protein set forth in SEQ ID NO:212.

In some embodiments, the GFAP protein (e.g., human GFAP protein) is a recombinant GFAP protein such as a recombinant GFAP protein produced in a bacterial host cell (e.g., *E. coli* cell) or mammalian host cell (e.g., CHO cell). In some embodiments, the GFAP protein ((e.g., human GFAP protein) is a native GFAP protein such a native-GFAP protein present or obtained from serum, plasma, blood (e.g., whole blood), cerebrospinal fluid, urine, sweat, saliva or any other biological fluid present or obtained from an individual (e.g., human). In some embodiments, the anti-GFAP antibody binds to a GFAP modified by citrullination, glycosylation, phosphorylation, or other modifications.

In some embodiments, the anti-GFAP antibody described herein binds to a linear epitope of GFAP (e.g., human GFAP). In some embodiments, the anti-GFAP antibody described herein binds to a conformational epitope of GFAP (e.g., human GFAP).

In some embodiments, the anti-GFAP antibodies bind to a particular epitope or region of GFAP. In some embodiments, the anti-GFAP antibody binds to an epitope containing one or more amino acids that is, includes or is within (or is entirely within) a portion of GFAP corresponding to positions 92-106 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 190-202 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 16-35 and/or 380 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 119 and/or 190 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 380-391 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 119-130 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 210-221 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 320-329, 346-357 and/or 376-387 of human GFAP protein set forth in SEQ ID NO:212. In some embodiments, the anti-GFAP antibody binds to an epitope containing one or more amino acids that is, includes or is within (or is entirely within) a portion of GFAP corresponding to positions 138-149 of human GFAP protein set forth in SEQ ID NO:212.

In some embodiments, among the provided antibodies are antibodies that bind to the same or overlapping epitope as one or more of the other provided antibodies and/or compete for binding to GFAP with one or more of the other provided antibodies. In some embodiments, among the provided antibodies are antibodies that bind to a different or distinct epitope as compared to one or more of the other provided antibodies and/or do not compete for binding to GFAP with one or more of the other provided antibodies. For example, in some embodiments provided are antibodies that bind to a distinct epitope and/or do not compete for binding to GFAP as compared to the antibody designated GFAP-2 as described herein. In some embodiments, provided are antibodies that bind to a distinct epitope and/or do not compete for binding to GFAP as compared to the antibody designated GFAP-6 as described herein.

In some embodiments, the antibodies bind to an epitope of GFAP that is conserved among GFAP from different species. In some embodiments, the antibodies bind to an epitope of GFAP that is present in human GFAP or an isoform or variant thereof but that is not present in one or more other non-human species.

In one aspect, provided herein is an anti-GFAP antibody comprising a heavy chain variable region and a light chain variable region, wherein the heavy chain variable region comprises a CDR-H3 comprising an amino acid sequence selected from SEQ ID NOs:108-124. In some embodiments, the heavy chain variable region further comprises a CDR-H1 comprising an amino acid sequence selected from SEQ ID NOs:77-90 and/or a CDR-H2 comprising an amino acid sequence selected from SEQ ID NOs:91-107.

In one aspect, provided herein is an anti-GFAP antibody comprising a heavy chain variable region and a light chain variable region, wherein the light chain variable region comprises a CDR-L3 comprising an amino acid sequence selected from SEQ ID NOs:157-171. In some embodiments, the heavy chain variable region further comprises a CDR-L1 comprising an amino acid sequence selected from SEQ ID NOs:125-141 and/or a CDR-L2 comprising an amino acid sequence selected from SEQ ID NOs:142-156.

In some embodiments, the heavy chain CDR sequences comprise the following:
  a) a CDR-H1 set forth in SEQ ID NO:77; SEQ ID NO:78; SEQ ID NO:79; SEQ ID NO:80; SEQ ID NO:81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO:89 or SEQ ID NO:90;
  b) a CDR-H2 set forth in SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101, SEQ ID NO:102; SEQ ID NO:103; SEQ ID NO:104; SEQ ID NO:105; SEQ ID NO:106 or SEQ ID NO: 107; and
  c) a CDR-H3 set forth in SEQ ID NO:108; SEQ ID NO:109; SEQ ID NO:110; SEQ ID NO:111; SEQ ID NO:112; SEQ ID NO: 113; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO:121; SEQ ID NO:122; SEQ ID NO:123 or SEQ ID NO:124.

In some embodiments, the heavy chain CDR sequences comprise the following:
  a) a CDR-H1 set forth in SEQ ID NO:77; SEQ ID NO:78; SEQ ID NO:79; SEQ ID NO:80; SEQ ID NO:81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO:89 or SEQ ID NO:90;
  b) a CDR-H2 set forth in SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101, SEQ ID NO: 102; SEQ ID NO: 103; SEQ ID NO: 104; SEQ ID NO: 105; SEQ ID NO:106 or SEQ ID NO:107; and
  c) a CDR-H3 set forth in SEQ ID NO:110; SEQ ID NO:111; SEQ ID NO: 112; SEQ ID NO:113; SEQ ID NO:114; SEQ ID NO: 115; SEQ ID NO: 116; SEQ ID NO: 117; SEQ ID NO: 118; SEQ ID NO: 119; SEQ ID NO: 120; SEQ ID NO:121; SEQ ID NO: 122; SEQ ID NO:123 or SEQ ID NO:124.

In some embodiments, the heavy chain CDR sequences comprise the following:
  a) a CDR-H1 set forth in SEQ ID NO:77;
  b) a CDR-H2 set forth in SEQ ID NO:91; and
  c) a CDR-H3 set forth in SEQ ID NO: 108.

In some embodiments, the heavy chain CDR sequences comprise the following:
  a) a CDR-H1 set forth in SEQ ID NO:78;
  b) a CDR-H2 set forth in SEQ ID NO: 92; and
  c) a CDR-H3 set forth in SEQ ID NO: 109.

In some embodiments, the light chain CDR sequences comprise the following:
  a) a CDR-L1 set forth in SEQ ID NO:125; SEQ ID NO:126; SEQ ID NO:127; SEQ ID NO:128; SEQ ID NO:129; SEQ ID NO: 130; SEQ ID NO:131; SEQ ID NO: 132; SEQ ID NO: 133; SEQ ID NO: 134; SEQ ID NO: 135; SEQ ID NO: 136; SEQ ID NO: 137; SEQ ID NO: 138; SEQ ID NO: 139; SEQ ID NO: 140 or SEQ ID NO: 141;
  b) a CDR-L2 set forth in SEQ ID NO:142; SEQ ID NO:143; SEQ ID NO:144; SEQ ID NO: 145; SEQ ID NO: 146; SEQ ID NO: 147; SEQ ID NO: 148; SEQ ID NO: 149; SEQ ID NO: 150; SEQ ID NO:151; SEQ ID NO: 152; SEQ ID NO: 153; SEQ ID NO: 154; SEQ ID NO:155 or SEQ ID NO:156; and c) a CDR-L3 set forth in SEQ ID NO:157; SEQ ID NO:158; SEQ ID NO:159; SEQ ID NO:160; SEQ ID NO:161; SEQ ID NO: 162; SEQ ID NO: 163; SEQ ID NO: 164; SEQ ID NO: 165; SEQ ID NO: 166; SEQ ID NO: 167; SEQ ID NO: 168; SEQ ID NO: 169; SEQ ID NO:170 or SEQ ID NO:171.

In some embodiments, the light chain CDR sequences comprise the following:

a) a CDR-L1 set forth in SEQ ID NO:126; SEQ ID NO:127; SEQ ID NO: 128; SEQ ID NO:129; SEQ ID NO:130; SEQ ID NO:131; SEQ ID NO: 132; SEQ ID NO: 133; SEQ ID NO: 134; SEQ ID NO:135; SEQ ID NO: 136; SEQ ID NO: 137; SEQ ID NO: 138; SEQ ID NO: 139; SEQ ID NO:140 or SEQ ID NO: 141;

b) a CDR-L2 set forth in SEQ ID NO: 142; SEQ ID NO: 144; SEQ ID NO: 145; SEQ ID NO:146; SEQ ID NO:147; SEQ ID NO: 148; SEQ ID NO: 149; SEQ ID NO: 150; SEQ ID NO:151; SEQ ID NO: 152; SEQ ID NO: 153; SEQ ID NO: 154; SEQ ID NO:155 or SEQ ID NO: 156; and c) a CDR-L3 set forth in SEQ ID NO: 158; SEQ ID NO: 159; SEQ ID NO: 160; SEQ ID NO:161; SEQ ID NO:162; SEQ ID NO: 163; SEQ ID NO: 164; SEQ ID NO: 165; SEQ ID NO: 166; SEQ ID NO: 167; SEQ ID NO: 168; SEQ ID NO: 169; SEQ ID NO:170 or SEQ ID NO:171.

In some embodiments, the light chain CDR sequences comprise the following:

a) a CDR-L1 set forth in SEQ ID NO: 125;
b) a CDR-L2 set forth in SEQ ID NO: 142; and
c) a CDR-L3 set forth in SEQ ID NO: 157.

In some embodiments, the light chain CDR sequences comprise the following:

a) a CDR-L1 set forth in SEQ ID NO: 126;
b) a CDR-L2 set forth in SEQ ID NO: 143; and
c) a CDR-L3 set forth in SEQ ID NO: 158.

Also provided are antibodies comprising a CDR-H1, CDR-H2, CDR-H3, CDR-L1, CDR-L2 and/or CDR-L3 sequence that is at least at or about at least 85%, 86%, 87%, 88%, 89%, 90%, 91%, 92%, 93%, 94%, 95%, 96%, 97%, 98%, or 99% identical to any of the above CDR-H1, CDR-H2, CDR-H3, CDR-L1, CDR-L2 and/or CDR-L3 sequences, respectively.

In one aspect, provided herein is an anti-GFAP antibody comprising a heavy chain variable region and a light chain variable region, wherein the heavy chain variable region comprises (i) CDR-H1 comprising the amino acid sequence of SEQ ID NO:77, (ii) CDR-H2 comprising the amino acid sequence of SEQ ID NO:91, and (iii) CDR-H3 comprising the amino acid sequence of SEQ ID NO:108; and/or wherein the light chain variable region comprises (i) CDR-L1 comprising the amino acid sequence of SEQ ID NO:125, (ii) CDR-L2 comprising the amino acid sequence of SEQ ID NO:142, and (iii) CDR-L3 comprising the amino acid sequence of SEQ ID NO:157. In some embodiments, the antibody described herein binds to an epitope corresponding to an epitope within, that is, or includes residues 92-106 of human GFAP set forth in SEQ ID NO:212.

In one aspect, provided herein is an anti-GFAP antibody comprising a heavy chain variable region and a light chain variable region, wherein the heavy chain variable region comprises (i) CDR-H1 comprising the amino acid sequence of SEQ ID NO:78, (ii) CDR-H2 comprising the amino acid sequence of SEQ ID NO:92, and (iii) CDR-H3 comprising the amino acid sequence of SEQ ID NO:109; and/or wherein the light chain variable region comprises (i) CDR-L1 comprising the amino acid sequence of SEQ ID NO:126, (ii) CDR-L2 comprising the amino acid sequence of SEQ ID NO:143, and (iii) CDR-L3 comprising the amino acid sequence of SEQ ID NO:158. In some embodiments, the antibody described herein binds to an epitope corresponding to an epitope within, that is, or includes residues 190-202 of human GFAP set forth in SEQ ID NO:212.

In one aspect, provided herein is an anti-GFAP antibody comprising a heavy chain variable region and a light chain variable region, wherein the heavy chain variable region comprises (i) CDR-H1 comprising the amino acid sequence of SEQ ID NO:79, (ii) CDR-H2 comprising the amino acid sequence of SEQ ID NO:93, and (iii) CDR-H3 comprising the amino acid sequence of SEQ ID NO:110; and/or wherein the light chain variable region comprises (i) CDR-L1 comprising the amino acid sequence of SEQ ID NO:127, (ii) CDR-L2 comprising the amino acid sequence of SEQ ID NO:144, and (iii) CDR-L3 comprising the amino acid sequence of SEQ ID NO:159 In some embodiments, the antibody described herein binds to an epitope corresponding to an epitope within, that is, or includes residues 16-35 and/or 380 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:77, (ii) CDR-H2 comprising the amino acid sequence of SEQ ID NO:94, and (iii) CDR-H3 comprising the amino acid sequence of SEQ ID NO:111; and/or wherein the light chain variable region comprises (i) CDR-L1 comprising the amino acid sequence of SEQ ID NO:128, (ii) CDR-L2 comprising the amino acid sequence of SEQ ID NO:145, and (iii) CDR-L3 comprising the amino acid sequence of SEQ ID NO:160. In some embodiments, the antibody described herein binds to an epitope corresponding to an epitope within, that is, or includes residues 119 and/or 190 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:80, (ii) CDR-H2 comprising the amino acid sequence of SEQ ID NO:95, and (iii) CDR-H3 comprising the amino acid sequence of SEQ ID NO:112; and/or a light chain variable region comprising (i) CDR-L1 comprising the amino acid sequence of SEQ ID NO:126, (ii) CDR-L2 comprising the amino acid sequence of SEQ ID NO:142, and (iii) CDR-L3 comprising the amino acid sequence of SEQ ID NO:158. In some embodiments, the antibody described herein binds to an epitope corresponding to an epitope within, that is, or includes residues 119-130 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:81, (ii) CDR-H2 comprising the amino acid sequence of SEQ ID NO:96, and (iii) CDR-H3 comprising the amino acid sequence of SEQ ID NO:113; and/or a light chain variable region comprising (i) CDR-L1 comprising the amino acid sequence of SEQ ID NO:129, (ii) CDR-L2 comprising the amino acid sequence of SEQ ID NO:146, and (iii) CDR-L3 comprising the amino acid sequence of SEQ ID NO:161. In some embodiments, the antibody described herein binds to an epitope corresponding to an epitope within, that is, or includes residues 380-391 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:77, (ii) CDR-H2 comprising the amino acid sequence of SEQ ID NO:94, and (iii) CDR-H3 comprising the amino acid sequence of SEQ ID NO:111; and/or a light chain variable region comprising (i) CDR-L1 comprising the amino acid sequence of SEQ ID NO:130 (ii) CDR-L2 comprising the amino acid sequence of SEQ ID NO:145, and (iii) CDR-L3 comprising the amino acid sequence of SEQ ID NO:160. In some embodiments, the antibody described herein binds to an epitope corresponding to an epitope within, that is, or includes residues 380-391 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:82, (ii) CDR-H2 comprising the amino acid sequence of SEQ ID NO:97, and (iii) CDR-H3 comprising the amino acid sequence of SEQ ID NO:114; and/or a light chain variable region comprising (i) CDR-L1 comprising the amino acid sequence of SEQ ID NO:131, (ii) CDR-L2 comprising the amino acid sequence of SEQ ID NO:147, and (iii) CDR-L3 comprising the amino acid sequence of SEQ ID NO:162. In some embodiments, the antibody described herein binds to an epitope corresponding to an epitope within, that is, or includes residues 380-391 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:83, (ii) CDR-H2 comprising the amino acid sequence of SEQ ID NO:98, and (iii) CDR-H3 comprising the amino acid sequence of SEQ ID NO:115; and/or a light chain variable region comprising (i) CDR-L1 comprising the amino acid sequence of SEQ ID NO:132, (ii) CDR-L2 comprising the amino acid sequence of SEQ ID NO:148, and (iii) CDR-L3 comprising the amino acid sequence of SEQ ID NO:163.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:84, (ii) CDR-H2 comprising the amino acid sequence of SEQ ID NO:99, and (iii) CDR-H3 comprising the amino acid sequence of SEQ ID NO:116; and/or a light chain variable region comprising (i) CDR-L1 comprising the amino acid sequence of SEQ ID NO:133, (ii) CDR-L2 comprising the amino acid sequence of SEQ ID NO:149, and (iii) CDR-L3 comprising the amino acid sequence of SEQ ID NO:164. In some embodiments, the antibody described herein binds to an epitope corresponding to an epitope within, that is, or includes residues 119-130 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:85, (ii) CDR-H2 comprising the amino acid sequence of SEQ ID NO:100, and (iii) CDR-H3 comprising the amino acid sequence of SEQ ID NO:117; and/or a light chain variable region comprising (i) CDR-L1 comprising the amino acid sequence of SEQ ID NO:134, (ii) CDR-L2 comprising the amino acid sequence of SEQ ID NO:150, and (iii) CDR-L3 comprising the amino acid sequence of SEQ ID NO: 165. In some embodiments, the antibody described herein binds to an epitope corresponding to an epitope within, that is, or includes residues 119-130 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:86, (ii) CDR-H2 comprising the amino acid sequence of SEQ ID NO:101, and (iii) CDR-H3 comprising the amino acid sequence of SEQ ID NO:118; and/or a light chain variable region comprising (i) CDR-L1 comprising the amino acid sequence of SEQ ID NO:135, (ii) CDR-L2 comprising the amino acid sequence of SEQ ID NO:151, and (iii) CDR-L3 comprising the amino acid sequence of SEQ ID NO:166. In some embodiments, the antibody described herein binds to an epitope corresponding to an epitope within, that is, or includes residues 210-221 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:78, (ii) CDR-H2 comprising the amino acid sequence of SEQ ID NO:102, and (iii) CDR-H3 comprising the amino acid sequence of SEQ ID NO:119; and/or a light chain variable region comprising (i) CDR-L1 comprising the amino acid sequence of SEQ ID NO:136, (ii) CDR-L2 comprising the amino acid sequence of SEQ ID NO:152, and (iii) CDR-L3 comprising the amino acid sequence of SEQ ID NO:167. In some embodiments, the antibody described herein binds to an epitope corresponding to an epitope within, that is, or includes residues 210-221 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:78, (ii) CDR-H2 comprising the amino acid sequence of SEQ ID NO:103, and (iii) CDR-H3 comprising the amino acid sequence of SEQ ID NO:120; and/or a light chain variable region comprising (i) CDR-L1 comprising the amino acid sequence of SEQ ID NO:137, (ii) CDR-L2 comprising the amino acid sequence of SEQ ID NO:142, and (iii) CDR-L3 comprising the amino acid sequence of SEQ ID NO:158. In some embodiments, the antibody described herein binds to an epitope corresponding to an epitope within, that is, or includes residues 210-221 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:87, (ii) CDR-H2 comprising the amino acid sequence of SEQ ID NO:104, and (iii) CDR-H3 comprising the amino acid sequence of SEQ ID NO:121; and/or a light chain variable region comprising (i) CDR-L1 comprising the amino acid sequence of SEQ ID NO:138, (ii) CDR-L2 comprising the amino acid sequence of SEQ ID NO:153, and (iii) CDR-L3 comprising the amino acid sequence of SEQ ID NO:168. In some embodiments, the antibody described herein binds to an epitope corresponding to an epitope within, that is, or includes residues 320-329 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:88, (ii) CDR-H2 comprising the amino acid sequence of SEQ ID NO:105, and (iii) CDR-H3 comprising the amino acid sequence of SEQ ID NO:122; and/or a light chain variable region comprising (i) CDR-L1 comprising the amino acid sequence of SEQ ID NO:139, (ii) CDR-L2 comprising the amino acid sequence of SEQ ID NO:154, and (iii) CDR-L3 comprising the amino acid sequence of SEQ ID NO:169. In some embodiments, the antibody described herein binds to an epitope corresponding to an epitope within, that is, or includes residues 320-329, 346-357 and/or 376-387 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:89, (ii) CDR-H2 comprising the amino acid sequence of SEQ ID NO:106, and (iii) CDR-H3 comprising the amino acid sequence of SEQ ID NO:123; and/or a light chain variable region comprising (i) CDR-L1 comprising the amino acid sequence of SEQ ID NO:140, (ii) CDR-L2 comprising the amino acid sequence of SEQ ID NO:155, and (iii) CDR-L3 comprising the amino acid sequence of SEQ ID NO: 170. In some embodiments, the antibody described herein binds to an epitope corresponding to an epitope within, that is, or includes residues 119-130 and/or 138-149 of human GFAP set forth in SEQ ID NO:212.

In another aspect, provided herein is an anti-GFAP antibody comprising a heavy chain variable region and a light chain variable region, wherein the heavy chain variable region comprises (i) CDR-H1 comprising the amino acid sequence of SEQ ID NO:90, (ii) CDR-H2 comprising the amino acid sequence of SEQ ID NO:107, and (iii) CDR-H3 comprising the amino acid sequence of SEQ ID NO:124; and/or a light chain variable region comprising (i) CDR-L1 comprising the amino acid sequence of SEQ ID NO:141, (ii) CDR-L2 comprising the amino acid sequence of SEQ ID NO:156, and (iii) CDR-L3 comprising the amino acid sequence of SEQ ID NO:171. In some embodiments, the antibody described herein binds to an epitope corresponding to an epitope within, that is, or includes residues 119-130 of human GFAP set forth in SEQ ID NO:212.

In some embodiments, the anti-GFAP comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs: 172-188. In some embodiments, the anti-GFAP comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs: 174-188. In some embodiments, the anti-GFAP comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid sequence of SEQ ID NO: 172. In some embodiments, the anti-GFAP comprises a heavy chain variable region comprising a CDR-H1, a CDR-H2, and a CDR-H3, respectively, comprising the amino acid sequence of a CDR-H1, a CDR-H2, and a CDR-H3 contained within the heavy chain variable region amino acid of SEQ ID NO:173.

In some embodiments, the anti-GFAP comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs: 189-206. In some embodiments, the anti-GFAP comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs: 191-206. In some embodiments, the anti-GFAP comprises a CDR-L1, a CDR-L2, and a CDR-L3, respectively, comprising the amino acid sequence of a CDR-L1, a CDR-L2, and a CDR-L3 contained within the light chain variable region amino acid sequence of SEQ ID NO:189. In some embodiments, the anti-GFAP comprises a CDR-L1, a CDR-L2, and a CDR-L3, respectively, comprising the amino acid sequence of a CDR-L1, a CDR-L2, and a CDR-L3 contained within the light chain variable region amino acid sequence of SEQ ID NO:190.

An anti-GFAP antibody described herein may comprise any suitable framework variable domain sequence, provided that the antibody retains the ability to bind GFAP (e.g., human GFAP). As used herein, heavy chain framework regions are designated "HC-FR1-FR4," and light chain framework regions are designated "LC-FR1-FR4."

In some embodiments, provided herein is an anti-GFAP antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs: 172-188. In some embodiments, provided herein is an anti-GFAP antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs: 174-188. In some embodiments, provided herein is an anti-GFAP antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence of SEQ ID NO: 172. In some embodiments, provided herein is an anti-GFAP antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence of SEQ ID NO:173. In some embodiments, an amino acid sequence having at least 85%, 86%, 87%, 88%, 89%, 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to GFAP (e.g., human GFAP). In some embodiments, the substitutions, insertions, or deletions (e.g., 1, 2, 3, 4, or 5 amino acids) occur in regions outside the CDRs (i.e., in the FRs).

In some embodiments, an anti-GFAP antibody comprises a heavy chain variable domain comprising an amino acid sequence selected from SEQ ID NO:172-188. In some embodiments, an anti-GFAP antibody comprises a heavy chain variable domain comprising an amino acid sequence of SEQ ID NO:172. In some embodiments, an anti-GFAP antibody comprises a heavy chain variable domain comprising an amino acid sequence selected from SEQ ID NO:173. In some embodiments, an anti-GFAP antibody comprises a heavy chain variable domain comprising an amino acid sequence of SEQ ID NO:174. In some embodiments, an anti-GFAP antibody comprises a heavy chain variable domain comprising an amino acid sequence of SEQ ID NO:175. In some embodiments, an anti-GFAP antibody comprises a heavy chain variable domain comprising an amino acid sequence of SEQ ID NO:176. In some embodiments, an anti-GFAP antibody comprises a heavy chain variable domain comprising an amino acid sequence of SEQ ID NO:177. In some embodiments, an anti-GFAP antibody comprises a heavy chain variable domain comprising an amino acid sequence of SEQ ID NO: 178. In some embodiments, an anti-GFAP antibody comprises a heavy chain variable domain comprising an amino acid sequence of SEQ ID NO:179. In some embodiments, an anti-GFAP antibody comprises a heavy chain variable domain comprising an amino acid sequence of SEQ ID NO:180. In some embodiments, an anti-GFAP antibody comprises a heavy chain variable domain comprising an amino acid sequence of SEQ ID NO:181. In some embodiments, an anti-GFAP antibody comprises a heavy chain variable domain comprising an amino acid sequence of SEQ ID NO:182. In some embodiments, an anti-GFAP antibody comprises a heavy chain variable domain comprising an amino acid sequence of SEQ ID NO:183. In some embodiments, an anti-GFAP antibody comprises a heavy chain variable domain comprising an amino acid sequence of SEQ ID NO:184. In some embodiments, an anti-GFAP antibody comprises a heavy chain variable domain comprising an amino acid sequence of SEQ ID NO:185. In some embodiments, an anti-GFAP antibody comprises a heavy chain variable domain comprising an amino acid sequence of SEQ ID NO:186. In some embodiments, an anti-GFAP antibody comprises a heavy chain variable domain comprising an amino acid sequence of SEQ ID NO:187. In some embodiments, an anti-GFAP antibody comprises a heavy chain variable domain comprising an amino acid sequence of SEQ ID NO:188.

In some embodiments, provided herein is an anti-GFAP antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs: 189-206. In some embodiments, provided herein is an anti-GFAP antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence selected from SEQ ID NOs: 191-206. In some embodiments, provided herein is an anti-GFAP antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence of SEQ ID NO:189. In some embodiments, provided herein is an anti-GFAP antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to an amino acid sequence of SEQ ID NO:190. In some embodiments, an amino acid sequence having at least 85%, 86%, 87%, 88%, 89%, 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to GFAP (e.g., human GFAP). In some embodiments, the substitutions, insertions, or deletions (e.g., 1, 2, 3, 4, or 5 amino acids) occur in regions outside the CDRs (i.e., in the FRs).

In some embodiments, an anti-GFAP antibody comprises a light chain variable domain comprising an amino acid sequence selected from SEQ ID NO:189-206. In some embodiments, an anti-GFAP antibody comprises a light chain variable domain comprising an amino acid sequence of SEQ ID NO:189. In some embodiments, an anti-GFAP antibody comprises a light chain variable domain comprising an amino acid sequence of SEQ ID NO:190.

In some embodiments, an anti-GFAP antibody comprises a light chain variable domain comprising an amino acid sequence of SEQ ID NO:191. In some embodiments, an anti-GFAP antibody comprises a light chain variable domain comprising an amino acid sequence of SEQ ID NO:192. In some embodiments, an anti-GFAP antibody comprises a light chain variable domain comprising an amino acid sequence of SEQ ID NO:193. In some embodiments, an anti-GFAP antibody comprises a light chain variable domain comprising an amino acid sequence of SEQ ID NO:194. In some embodiments, an anti-GFAP antibody comprises a light chain variable domain comprising an amino acid sequence of SEQ ID NO:195. In some embodiments, an anti-GFAP antibody comprises a light chain variable domain comprising an amino acid sequence of SEQ ID NO:196. In some embodiments, an anti-GFAP antibody comprises a light chain variable domain comprising an amino acid sequence of SEQ ID NO:197. In some embodiments, an anti-GFAP antibody comprises a light chain variable domain comprising an amino acid sequence of SEQ ID NO:198. In some embodiments, an anti-GFAP antibody comprises a light chain variable domain comprising an amino acid sequence of SEQ ID NO:199. In some embodiments, an anti-GFAP antibody comprises a light chain variable domain comprising an amino acid sequence of SEQ ID NO:200. In some embodiments, an anti-GFAP antibody comprises a light chain variable domain comprising an amino acid sequence of SEQ ID NO:201. In some embodiments, an anti-GFAP antibody comprises a light chain variable domain comprising an amino acid sequence of SEQ ID NO:202. In some embodiments, an anti-GFAP antibody comprises a light chain variable domain comprising an amino acid sequence of SEQ ID NO:203. In some embodiments, an anti-GFAP antibody comprises a light chain variable domain comprising an amino acid sequence of SEQ ID NO:204. In some embodiments, an anti-GFAP antibody comprises a light chain variable domain comprising an amino acid sequence of SEQ ID NO:205. In some embodiments, an anti-GFAP antibody comprises a light chain variable domain comprising an amino acid sequence of SEQ ID NO:206.

In one aspect, provided herein is an anti-GFAP antibody comprising a heavy chain variable domain comprising an amino acid sequence selected from SEQ ID NOs:172-188 and/or comprising a light chain variable domain comprising an amino acid sequence selected from SEQ ID NOs:189-206. In some embodiments, the anti-GFAP antibody comprises a heavy chain variable domain comprising an amino acid sequence selected from SEQ ID NOs:174-188 and/or comprises a light chain variable domain comprising an amino acid sequence selected from SEQ ID NOs:191-206. In some embodiments, the anti-GFAP antibody comprises a heavy chain variable domain comprising an amino acid sequence selected from SEQ ID NO:172 and/or comprises a light chain variable domain comprising an amino acid sequence selected from SEQ ID NO:189. In some embodiments, the anti-GFAP antibody comprises a heavy chain variable domain comprising an amino acid sequence selected from SEQ ID NO:173 and/or comprises a light chain variable domain comprising an amino acid sequence selected from SEQ ID NO:190. Also provided are antibodies comprising a heavy chain variable domain and/or a light chain variable domain sequence that is at least at or about at least 85%, 86%, 87%, 88%, 89%, 90%, 91%, 92%, 93%, 94%, 95%, 96%, 97%, 98%, or 99% identical to any of the above heavy chain variable domain and/or light chain variable domain sequences, respectively.

In some embodiments, provided herein is an anti-GFAP antibody comprising a heavy chain variable domain and/or a light chain variable domain of an antibody shown in Table 10, for example, GFAP-2, GFAP-6, etc.

In some embodiments, the anti-GFAP antibody comprises a heavy chain variable domain comprising an amino acid sequence of SEQ ID NO: 172 and/or comprises a light chain variable domain comprising an amino acid sequence of SEQ ID NO:189. In some embodiments, the anti-GFAP antibody comprises a heavy chain variable domain comprising an amino acid sequence of SEQ ID NO: 173 and/or comprises a light chain variable domain comprising an amino acid sequence of SEQ ID NO:190. In some embodiments, the anti-GFAP antibody comprises a heavy chain variable domain comprising an amino acid sequence of SEQ ID NO:174 and/or comprises a light chain variable domain comprising an amino acid sequence of SEQ ID NO:191. In some embodiments, the anti-GFAP antibody comprises a heavy chain variable domain comprising an amino acid sequence of SEQ ID NO: 175 and/or comprises a light chain variable domain comprising an amino acid sequence of SEQ ID NO:192. In some embodiments, the anti-GFAP antibody comprises a heavy chain variable domain comprising an amino acid sequence of SEQ ID NO:176 and/or comprises a light chain variable domain comprising an amino acid sequence of SEQ ID NO:193. In some embodiments, the anti-GFAP antibody comprises a heavy chain variable domain comprising an amino acid sequence of SEQ ID NO:177 and/or comprises a light chain variable domain comprising an amino acid sequence of SEQ ID NO:194. In some embodiments, the anti-GFAP antibody comprises a heavy chain variable domain comprising an amino acid sequence of SEQ ID NO: 175 and/or comprises a light chain variable domain comprising an amino acid sequence of SEQ ID NO:195. In some embodiments, the anti-GFAP antibody comprises a heavy chain variable domain comprising an amino acid sequence of SEQ ID NO:178 and/or comprises a light chain variable domain comprising an amino acid sequence of SEQ ID NO:196. In some embodiments, the anti-GFAP antibody comprises a heavy chain variable domain comprising an amino acid sequence of SEQ ID NO:179 and/or comprises a light chain variable domain comprising an amino acid sequence of SEQ ID NO:197. In some embodiments, the anti-GFAP antibody comprises a heavy chain variable domain comprising an amino acid sequence of SEQ ID NO: 180 and/or comprises a light chain variable domain comprising an amino acid sequence of SEQ ID NO:198. In some embodiments, the anti-GFAP antibody comprises a heavy chain variable domain comprising an amino acid sequence of SEQ ID NO:181 and/or comprises a light chain variable domain comprising an amino acid sequence of SEQ ID NO:199. In some embodiments, the anti-GFAP antibody comprises a heavy chain variable domain comprising an amino acid sequence of SEQ ID NO:182 and/or comprises a light chain variable domain comprising an amino acid sequence of SEQ ID NO:200. In some embodiments, the anti-GFAP antibody comprises a heavy chain variable domain comprising an amino acid sequence of SEQ ID NO: 183 and/or comprises a light chain variable domain comprising an amino acid sequence of SEQ ID NO:201. In some embodiments, the anti-GFAP antibody comprises a heavy chain variable domain comprising an amino acid sequence of SEQ ID NO:184 and/or comprises a light chain variable domain comprising an amino acid sequence of SEQ ID NO:202. In some embodiments, the anti-GFAP antibody comprises a heavy chain variable domain comprising an amino acid sequence of SEQ ID NO:185 and/or comprises a light chain variable domain comprising an amino acid sequence of SEQ ID NO:203. In some embodiments, the anti-GFAP antibody comprises a heavy chain variable domain comprising an amino acid sequence of SEQ ID NO: 186 and/or comprises a light chain variable domain comprising an amino acid sequence of SEQ ID NO:204. In some embodiments, the anti-GFAP antibody comprises a heavy chain variable domain comprising an amino acid sequence of SEQ ID NO:187 and/or comprises a light chain variable domain comprising an amino acid sequence of SEQ ID NO:205. In some embodiments, the anti-GFAP antibody comprises a heavy chain variable domain comprising an amino acid sequence of SEQ ID NO:188 and/or comprises a light chain variable domain comprising an amino acid sequence of SEQ ID NO:206.

In some embodiments, the anti-GFAP antibody does not comprise a variable heavy chain comprising the CDR-H1, CDR-H2 and CDR-H3 set forth in SEQ ID NOS: 78, 92 and 109, respectively, and a variable light chain comprising the CDR-L1, CDR-L2 and CDR-L3 set forth in SEQ ID NOS: 126, 143 and 158, respectively. In some embodiments, the anti-GFAP antibody does not comprise a variable heavy chain set forth in SEQ ID NO:173 and a variable light chain set forth in SEQ ID NO:190. In some embodiments, the anti-GFAP antibody is not the antibody designated GFAP-2.

In one aspect, an anti-GFAP antibody described herein is a monoclonal antibody. In one aspect, an anti-GFAP antibody described herein is an antibody fragment (including antigen-binding fragment), e.g., a Fab, Fab'-SH, Fv, scFv, or (Fab')$_2$ fragment.

In any of the embodiments herein, the antibody may comprise a heavy chain constant domain. In some embodiments, the heavy chain constant domain is non-human mammalian. In some embodiments, the heavy chain constant domain is non-human primate. In some embodiments, the heavy chain constant domain is non-human primate. In some embodiments, the heavy chain constant domain is murine (e.g., mouse or rat). In some embodiments, the murine heavy chain constant domain is IgG1, IgG2a or IgG2b. In some embodiments, the murine heavy chain constant domain is murine IgG1. In some embodiments, the murine IgG1 comprises the amino acid sequence of SEQ ID NO:215 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:215. In some embodiments, the murine heavy chain constant domain is murine IgG2a. In some embodiments, the murine IgG2a comprises the amino acid sequence of SEQ ID NO:216 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:216. In some embodiments, the murine heavy chain constant domain is murine IgG2b. In some embodiments, the murine IgG2b comprises the amino acid sequence of SEQ ID NO:217 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:217. In some embodiments, the heavy chain constant domain is human. In some embodiments, the human heavy chain constant domain is human IgG1. In some embodiments, the human IgG1 comprises the amino acid sequence of SEQ ID NO:218 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:218.

There are two types of light chains, kappa and lambda, based on the amino acid sequences of their constant domains. In any of the embodiments herein, an antibody provided herein may comprise a light chain constant domain. In any of the embodiments herein, an antibody provided herein may comprise a light chain constant domain. In some embodiments, the light chain constant domain is non-human mammalian. In some embodiments, the light chain constant domain is non-human primate. In some embodiments, the light chain constant domain is non-human primate. In some embodiments, the light chain constant domain is murine (e.g., mouse or rat). In some embodiments, the murine light chain constant domain is kappa or lambda. In some embodiments, the murine kappa comprises the amino acid sequence of SEQ ID NO:219 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:219. In some embodiments, the murine lambda comprises the amino acid sequence of SEQ ID NO:220 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:220. In some embodiments, the light chain constant domain is human. In some embodiments, the human light chain constant domain is kappa or lambda. In some embodiments, the human kappa comprises the amino acid sequence of SEQ ID NO:221 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:221. In some embodiments, the human lambda comprises the amino acid sequence of SEQ ID NO:222 or an isoform or variant thereof that has at least 85%, 86%, 87%, 88%, 89%, 90%, 91%, 92%, 93%, 94%, 95%, 96%, 97%, 98%, or 99% sequence identity to SEQ ID NO:222.

In one aspect, an anti-GFAP antibody described herein is a monoclonal antibody. In one aspect, an anti-GFAP antibody described herein is a humanized antibody, a chimeric antibody or a human antibody. In one aspect, an anti-GFAP antibody described herein is a mouse antibody, a rabbit antibody, a rat antibody, or a non-human primate antibody. In some embodiments, any of the anti-GFAP antibodies are recombinant. In one aspect, any of the anti-GFAP antibodies described herein are isolated or purified.

In some embodiments, an anti-GFAP antibody provided herein has a binding affinity with a dissociation constant ($K_D$) of $10^{-8}$ M or less, e.g. from $10^{-1}$ M to $10^{-13}$ M, e.g., from $10^{-1}$ M to $10^{-12}$ M, e.g., from $10^{-9}$ M to $10^{-13}$ M. In some embodiments, an anti-GFAP antibody provided herein has a dissociation constant ($K_D$) of less than or equal to 1 μM, less than or equal to 150 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM. In some embodiments, an anti-GFAP antibody provided herein has a dissociation constant ($K_D$) of less than or less than about $1.0\times10^{-8}$ M, $2.0\times10^{-8}$ M, $3.0\times10^{-8}$ M, $4.0\times10^{-8}$ M, $5.0\times10^{-8}$ M, $6.0\times10^{-8}$ M, $7.0\times10^{-8}$ M, $8.0\times10^{-8}$ M, $9.0\times10^{-8}$ M, $1.0\times10^{-9}$ M, $2.0\times10^{-9}$ M, $3.0\times10^{-9}$ M, $4.0\times10^{-9}$ M, $5.0\times10^{-9}$ M, $6.0\times10^{-9}$ M, $7.0\times10^{-9}$ M, $8.0\times10^{-9}$ M, $9.0\times10^{-9}$ M, $1.0\times10^{-10}$ M, $2.0\times10^{-10}$ M, $3.0\times10^{-10}$ M, $4.0\times10^{-10}$ M, $5.0\times10^{-10}$ M, $6.0\times10^{-10}$ M, $7.0\times10^{-10}$ M, $8.0\times10^{-10}$ M, $9.0\times10^{-10}$ M, $1.0\times10^{-11}$ M, $2.0\times10^{-11}$ M, $3.0\times10^{-11}$ M, $4.0\times10^{-11}$ M, $5.0\times10^{-11}$ M, $6.0\times10^{-11}$ M, $7.0\times10^{-11}$ M, $8.0\times10^{-11}$ M, $9.0\times10^{-11}$ M, or $1.0\times10^{-12}$ M.

In some embodiments, an anti-GFRAP antibody provided herein has a dissociation constant ($K_D$) from or from about $1.0\times10^{-8}$ M to $5.0\times10^{-12}$ M, $1.0\times10^{-8}$ M to $1.0\times10^{-12}$ M, $1.0\times10^{-8}$ M to $1.0\times10^{-11}$ M, $1.0\times10^{-8}$ M to $1.0\times10^{-11}$ M, $1.0\times10^{-8}$ M to $1.0\times10^{-10}$ M, $1.0\times10^{-10}$ M to $1.0\times10^{-12}$ M, $1.0\times10^{-10}$ M to $1.0\times10^{-11}$ M, $1.0\times10^{-11}$ M to $1.0\times10^{-12}$ M. In some embodiments, an anti-GFAP antibody provided herein has a dissociation constant ($K_D$) from or from about $1.0\times10^{-8}$ M to $1.0\times10^{-12}$ M. In some embodiments, an anti-GFAP antibody provided herein has a dissociation constant ($K_D$) from or from about $1.0\times10^{-8}$ M to $2.0\times10^{-8}$ M, $1.0\times10^{-9}$ M to $6.0\times10^{-9}$ M, $2.0\times10^{-10}$ M to $9.0\times10^{-10}$ M, $1.0\times10^{-11}$ M to $8.0\times10^{-11}$ M, or $1.0\times10^{-12}$ M to $5.0\times10^{-12}$ M. In some embodiments, an anti-GFAP antibody provided herein has a dissociation constant ($K_D$) of an antibody shown in Table 8, for example, GFAP-1, GFAP-2, etc.

In one aspect, nucleic acids encoding anti-GFAP antibodies are provided. In some embodiments, a nucleic acid may encode an anti-GFAP antibody or antigen-binding fragment provided herein. In some embodiments, a nucleic acid may encode a heavy chain comprising a heavy chain variable region of an anti-GFAP antibody or antigen-binding fragment provided herein. In some embodiments, a nucleic acid may encode a light chain comprising a light chain variable region of an anti-GFAP antibody or antigen-binding fragment provided herein.

In certain embodiments, vectors, such as an expression vector, comprising nucleic acids encoding anti-GFAP antibodies are provided. In certain embodiments, host cells comprising such nucleic acids and/or vectors are provided. For example, a host cell provided herein can comprise a vector comprising a nucleic acid encoding a heavy chain of an anti-GFAP antibody or antigen-binding fragment provided herein. Such a host cell, in some embodiments, can further comprise a vector comprising a nucleic acid encoding a light chain of an anti-GFAP antibody or antigen-binding fragment provided herein.

In another aspect of the invention, compositions comprising anti-GFAP antibodies or nucleic acids encoding anti-GFAP antibodies are provided. In certain embodiments, a composition provided herein can be used for the detection of GFAP, diagnosis of brain damage or injury (e.g. due to a neurological condition, stroke or traumatic brain injury) in an individual having or suspected of having the brain damage or injury and/or in predicting whether a subject needs a CT scan, such as those methods enumerated herein. In some embodiments, the provided anti-GFAP antibodies can be used in the methods in combination with any one or more of the anti-UCH-L1 antibodies provided herein.

C. Methods to Assess Exemplary Features

The provided antibodies exhibit one or more exemplary features as described. It is within the level of one of skill in the art to assess features of the antibodies in accord with the provided description. This section provides description of exemplary methods that can be used to assess affinity, epitope specificity and one or more other features of the provided antibodies.

In some embodiments, the provided antibodies or fragments thereof can be assessed for binding to UCH-L1 or GFAP or to variants or isoforms thereof, including fragments of UCH-L1 or GFAP. The binding can be assessed in vitro (e.g. in an immunoassay) or ex vivo or in vivo. In some embodiments, the binding is assessed using an immunoassay. Immunoassays include competitive and non-competitive assay systems using techniques such as, but not limited to, western blots or immunoblots, such as quantitative western blots; radioimmunoassays; ELISA (enzyme linked immunosorbent assay); Meso Scale Discovery (MSD, Gaithersburg, Maryland); "sandwich" immunoassays; immunoprecipitation assays; ELISPOT; precipitin reactions; gel diffusion precipitin reactions; immunodiffusion assays; agglutination assays; complement-fixation assays; immunoradiometric assays; fluorescent immunoassays; protein A immunoassays; immunohistochemistry; immuno-electron microscopy or liposome immunoassays (LIA). Such assays are routine and well known in the art (see, e.g., Ausubel et al., Eds, 1994, Current Protocols in Molecular Biology, Vol. 1, John Wiley & Sons, Inc., New York).

In some cases, depending on the quantitative assay selected to measure antibody binding, absolute binding can be represented, for example, in terms of optical density (OD), such as from densitometry or spectrophotometry measurements; arbitrary fluorescent units (AFU), such as from fluorescence measurements; or lumens, such as from chemiluminescence measurements. In some examples, the specific activity is calculated by dividing the absolute binding signal by the antibody protein concentration. In some embodiments, binding activity can be normalized to a reference antibody.

In some embodiments, binding activity also can be measured in terms of binding affinity, which can be determined in terms of binding kinetics, such as measuring rates of association ($k_a$ or $k_{on}$) and/or dissociation ($k_d$ or $k_{off}$), half maximal effective concentration ($EC_{50}$) values, and/or thermodynamic data (e.g., Gibbs free energy ($\Delta G$), enthalpy ($\Delta H$), entropy ($-T\Delta S$), and/or calculating association ($K_A$) or dissociation ($K_D$) constants. Typically, determination of binding kinetics requires known antibody and antigen or substrate protein concentrations. Rates of association ($k_a$) and association constants ($K_A$) are positively correlated with binding affinity. In contrast, rates of dissociation ($k_d$), dissociation constants ($K_D$) and $EC_{50}$ values are negatively correlated with binding affinity. Thus, higher binding affinity is represented by lower $k_d$, $K_D$ and $EC_{50}$ values.

Assays for determining the binding affinity of an antibody are well known in the art (see Chen, Y., et al., (1999) J. Mol. Biol. 293:865-881 and Scatchard, G., Ann. N.Y. Acad. Sci. 51:660 (1947)). Affinity constants are expressed in units of reciprocal molarity (i.e. $M^{-1}$) and can be calculated from the rate constant for the association-dissociation reaction as measured by standard kinetic methodology for antibody reactions (e.g., immunoassays, surface plasmon resonance, biolayer interferometry or other kinetic interaction assays known in the art). The binding affinity of an antibody also can be expressed as a dissociation constant, or $K_D$. The dissociation constant is the reciprocal of the association constant, $K_D = 1/K_A$. Hence, an affinity constant also can be represented by the $K_D$. Affinity constants can be determined by standard kinetic methodology for antibody reactions, for example, immunoassays, surface plasmon resonance (SPR) (Rich and Myszka (2000) Curr. Opin. Biotechnol 11:54; Englebienne (1998) Analyst. 123:1599), isothermal titration calorimetry (ITC), biolayer interferometry (Tobias et al., Biomolecular Binding Kinetic Assays in the Octet Platform, Application Note 14, ForteBio, Div. of Pall Life Sciences, 2013) or other kinetic interaction assays known in the art (see, e.g., Paul, ed., Fundamental Immunology, 2nd ed., Raven Press, New York, pages 332-336 (1989); see also U.S. Pat. No. 7,229,619 for a description of exemplary SPR and ITC methods for calculating the binding affinity of antibodies). Instrumentation and methods for real time detection and monitoring of binding rates are known and are commercially available (e.g., BIAcore 2000, BIAcore AB, Upsala, Sweden and GE Healthcare Life Sciences; Malmqvist (2000) Biochem. Soc. Trans. 27:335; Octet QK$^e$, ForteBio).

In one embodiment, the binding affinity of an anti-UCH-L1 antibody or anti-GFAP antibody can be determined by a biolayer interferometry assay. For example, UCH-L1-His tagged protein is immobilized onto capture sensors (ForteBio), and incubated with increasing concentrations of an anti-UCH-L1 antibody or anti-UCH-L1 Fab to obtain affinity measurements using an instrument such as, for example, the Octet QK$^e$ System (ForteBio).

In some embodiments, the provided anti-UCH-L1 or anti-GFAP antibodies bind to particular epitopes in UCH-L1 or GFAP, respectively, such as an epitope that is or is within or includes a region of UCH-L1 or GFAP as described. Assays for mapping epitopes bound by the antibodies and reference antibodies also may be used and are known. In some embodiments, the epitope can be a linear epitope. In some embodiments, the epitope can be a conformational epitope.

In an exemplary epitope mapping assay, a protein antigen, such as recombinant human UCH-L1 or recombinant human GFAP of particular fragments thereof, is added to a microplate and incubated so that the protein coats the wells on the plate. In some embodiments, one or more various truncations of the protein can be assessed, each representing or differing from one or more other truncated protein by the presence or absence of a particular region or sequence of amino acids. In some embodiments, a plurality of overlapping truncated proteins can be generated that each lack up to 10, 20, 30, 40, 50, 60, 70, 80, 90, 100, 150, 200, 250 or more N- or C-terminal amino acid residues. As a comparison, binding to the full-length protein also can be compared. Each of the truncated fragments or full-length protein can be contacted with the particular test antibody and binding can be assessed or determined using known techniques.

In some embodiments, a provided antibody (e.g. first antibody) binds to a distinct or non-overlapping epitope compared to the reference antibody (e.g. second antibody). In some embodiments, two antibodies specifically bind to a different or non-overlapping epitope if all or essentially all amino acid mutations in the antigen that reduce or eliminate binding of one antibody do not reduce or eliminate binding of the other antibody. In some embodiments, two antibodies specifically do not bind to an overlapping epitope if at least some of the amino acid mutations in the antigen that reduce binding or eliminate binding to the antigen by one antibody do not reduce or eliminate binding to the antigen by the other antibody.

In some embodiments, whether an antibody "competes for binding" to a particular antigen or substrate (e.g. UCH-L1 or GFAP) can be assessed using a competition assay. An antibody "competes for binding" to an antigen (e.g. UCH-L1 or GFAP) with a reference antibody if it competitively inhibits binding of the reference antibody to the antigen, and/or if the reference antibody competitively inhibits binding of the antibody to the antigen. An antibody competitively inhibits binding of a reference antibody to an antigen if the presence of the antibody in excess detectably inhibits (blocks) binding of the other antibody to its antigen. A particular degree of inhibition may be specified. In some embodiments, addition of the provided antibody in excess, e.g., 1-, 2-, 5-, 10-, 50- or 100-fold excess, as compared to the amount or concentration of the reference antibody, can be used to assess if either inhibit binding to the antigen by the other. In some embodiments, an antibody competes for binding if inhibition of binding is by at least 50%, and in some embodiments by at least 75%, 90% or 99%. In some embodiments, an antibody does not compete for binding if inhibition of binding is by less than 50%, such as in some embodiments by less than 40%, 30%, 20%, 10% or less. In some aspects, the competitive inhibition is as measured in a competitive binding assay (see, e.g., Junghans et al., Cancer Res. 1990:50:1495-1502).

In some embodiments, among the provided antibodies are antibodies that do not compete for binding with one or more other reference antibody. In some embodiments, antibodies that bind to the same antigen (e.g. UCH-L1 or GFAP) but do not compete for binding thereto can be used as paired antibodies in an assay (e.g. sandwich ELISA) for detecting or measuring UCH-L1 or GFAP in a sample as described.

In some embodiments, to determine among the anti-UCH-L1 antibodies which can be used as pairs, each of the provided anti-UCH-L1 antibodies as described above can be labeled with a detectable label (e.g. HRP) and tested in a sandwich format individually with each of the other provided anti-UCH-L1 antibodies.

In some embodiments, to determine among the anti-GFAP antibodies which can be used as pairs, each of the provided anti-GFAP antibodies as described above can be labeled with a detectable label (e.g. HRP) and tested in a sandwich format individually with each of the other provided anti-GFAP antibodies.

III. Antibody Production and Preparation

In some embodiments, the provided antibodies or fragments thereof are prepared using techniques available in the art for generating antibodies, exemplary methods of which are described in more detail in the following sections.

A. Antibody Formats and Modifications

1. Antibody Fragments

Among the provided antibodies are antibody fragments. Antibody fragments may be generated by traditional means, such as enzymatic digestion, or by recombinant techniques. In certain circumstances there are advantages of using antibody fragments, rather than whole antibodies. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10: 163-167 (1992)). According to another approach, F(ab')2 fragments can be isolated directly from recombinant host cell culture. Fab and F(ab')2 fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

Among the provided antibodies are humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent (e.g., mouse) antibody is screened against the entire library of known human variable-domain sequences. The human sequence which is closest to that of the rodent is then accepted as the human framework for the humanized antibody (Sims et al. (1993) J Immunol. 151: 2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those, skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Hunan Antibodies

Among the provided antibodies are human antibodies. Human anti-UCH-L1 antibodies and/or human anti-GFAP antibodies can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boemer et al., J. Immunol., 147: 86 (1991).

Gene shuffling can also be used to derive human antibodies from non-human (e.g., rodent) antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e., the epitope governs the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

In some embodiments, provided herein are bispecific antibodies, which are monoclonal antibodies that have binding specificities for at least two different antigens. In certain embodiments, bispecific antibodies are human or humanized antibodies. In certain embodiments, one of the binding specificities is for UCH-L1 and the other is for any other antigen (e.g., GFAP). In certain embodiments, one of the binding specificities is for GFAP and the other is for any other antigen (e.g., UCH-L1). In certain embodiments, bispecific antibodies may bind to two different epitopes of UCH-L1. In certain embodiments, bispecific antibodies may bind to two different epitopes of GFAP. Bispecific antibodies may also be used to localize cytotoxic agents to cells which express UCH-L1 and/or GFAP. Bispecific antibodies can be prepared as full length antibodies or antibody fragments (e.g. F(ab')2 bispecific antibodies).

Methods for making bispecific antibodies are known in the art. See Milstein and Cuello, Nature, 305: 537 (1983), WO 93/08829 published May 13, 1993, and Traunecker et al., EMBO J., 10: 3655 (1991). For further details of generating bispecific antibodies see, for example, Suresh et al., Methods in Enzymology, 121:210 (1986). Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking method. Suitable cross-linking agents are well known in the art, and are disclosed in U.S. Pat. No. 4,676,980, along with a number of cross-linking techniques.

5. Single-Domain Antibodies

In some embodiments, an antibody according to the provided disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

6. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 2 under the heading of "preferred substitutions." If such substitutions result in a desirable change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):
  (1) non-polar: Ala (A), Val (V), Leu (L), Ile (I), Pro (P), Phe (F), Trp (W), Met (M)
  (2) uncharged polar: Gly (G), Ser (S), Thr (T), Cys (C), Tyr (Y), Asn (N), Gln (Q)
  (3) acidic: Asp (D), Glu (E)
  (4) basic: Lys (K), Arg (R), His (H)

Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g., a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g., binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in a constant domain of the antibodies of the invention, thereby generating a constant domain variant. The constant domain variant may comprise a human constant domain sequence (e.g., a human IgG1, IgG2, IgG3 or IgG4 constant domain) or a murine constant domain sequence (e.g., a murine IgG1, IgG2a, IgG2b, IgG2c, and IgG3 constant domain) comprising an amino acid modification (e.g. a substitution) at one or more amino acid positions including that of a hinge cysteine.

B. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used.

Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species (e.g., mouse, non-human primate, etc.).

1. Generating Antibodies Using Prokaryotic Host Cells:

a) Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-lactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include lysogeny broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing an ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli*, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose. Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

c) Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephacryl 5-200.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

2. Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NSO, CHOK1, CHOK1SV or derivatives, including cell lines deficient in glutamine synthetase (GS). Methods for the use of GS as a selectable marker for mammalian cells are described in U.S. Pat. Nos. 5,122,464 and 5,891,693.

d) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous sarcoma virus long terminal repeat can be used as the promoter.

e) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the mouse cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF (phenylmethylsulfonyl fluoride) may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:1567-1575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, performed at low salt concentrations (e.g., from about 0-0.25M salt).

C. Labeled Antibodies

The anti-UCH-L1 antibodies and/or anti-GFAP antibodies provided herein may be attached directly or indirectly to a label. For example, the antibody may be conjugated, coupled or linked to the label. Labels are well known by one of skill in the art. Labels contemplated herein include, but are not limited to, fluorescent dyes, fluorescent proteins, radioisotopes, chromophores, metal ions, gold particles (e.g., colloidal gold particles), silver particles, particles with strong light scattering properties, magnetic particles (e.g., magnetic bead particles such as Dynabeads® magnetic beads), polypeptides (e.g., FLAG™ tag, human influenza hemagglutinin (HA) tag, etc.), enzymes such as peroxidase (e.g., horseradish peroxidase) or a phosphatase (e.g., alkaline phosphatase), streptavidin, biotin, luminescent compounds (e.g., chemiluminescent substrates), oligonucleotides, members of a specific binding pair (e.g., a ligands and its receptor) and other labels well known in the art that are used for visualizing or detecting an antibody when directly or indirectly attached to said antibody.

In some embodiments, the label is useful for qualitatively and/or quantitatively determining the location of the target antigen (e.g., UCH-L1 or GFAP) bound by the antibody (e.g., anti-UCH-L1 antibody or anti-GFAP antibody). In some embodiments, the label is useful for qualitatively and/or quantitatively determining the amount of target antigen (e.g., UCH-L1 or GFAP) bound by the antibody (e.g., anti-UCH-L1 antibody or anti-GFAP antibody).

In some embodiments, the label is a detectable label (e.g., a fluorescent dye label). In some embodiments, the label is an affinity label (e.g., a biotin label).

Methods for directly or indirectly attaching label to an antibody are well known in the art. Labels and labeling kits are commercially available such as from Invitrogen Corp, Carlsbad, Calif.

In some embodiments, the label is compatible for use in a detection assay. In some embodiments, the label is compatible for use in a diagnostic assay. For example, an anti-UCH-L1 antibody directly or indirectly attached to a horseradish peroxidase can be used in a detection assay or diagnostic assay provided herein. The horseradish peroxidase labeled anti-UCH-L1 antibody can bind to a UCH-L1 protein (e.g., human UCH-L1 protein) in a sample. Anti-UCH-L1 antibodies that are bound to UCH-L1 protein can be detecting by adding an appropriate substrate that produces a color change in the presence of horseradish peroxidase. In another example, an anti-GFAP antibody directly or indirectly attached to colloidal gold particles can be used in a detection assay or diagnostic assay provided herein. The colloidal gold particle labeled anti-GFAP antibody can bind to a GFAP protein (e.g., human GFAP protein) in a sample. Anti-GFAP antibodies that are bound to GFAP protein can be detecting by detecting a color change in the solution due to aggregation of the gold particles. Other methods for detecting gold particle labeled antibodies are well known in the art (see Dykman et al. (2011) Acta Naturae. 3(2):34-55).

In some embodiments, the anti-UCH-L1 antibodies and/or anti-GFAP antibodies provided herein do not need to be attached to a label in order to allow detection of its binding to a target antigen (e.g., UCH-L1 or GFAP). For example, detection of binding between an anti-UCH-L1 and a UCH-L1 protein can be achieved through use of a secondary antibody that is directly or indirectly attached to a label. In some embodiments, a system comprising a primary antibody and secondary antibody may be used to detect the target antigen (e.g., UCH-L1 or GFAP) bound by the anti-UCH-L1 antibody or anti-GFAP antibody. Such systems are well known to those skilled in the art. For example, a primary antibody (e.g., a mouse anti-UCH-L1 antibody) that specifically recognizes a target protein is exposed to a sample that may contain the target protein of interest (e.g., human UCH-L1). A secondary antibody with an appropriate label, such as a label described herein (e.g., colloidal gold particles), that recognizes the species or isotype of the primary antibody (e.g., an anti-mouse antibody) is then contacted with the sample such that specific detection of the target protein in the sample is achieved. In some embodiments, the primary antibody is an anti-UCH-L1 antibody. In some embodiments, the primary anti-UCH-L1 antibody is a naked primary anti-UCH-L1 antibody. In some embodiments, the primary anti-UCH-L1 antibody is a labeled primary anti-UCH-L1 antibody. In some embodiments, the primary antibody is an anti-GFAP antibody. In some embodiments, the primary anti-GFAP antibody is a naked primary anti-GFAP antibody. In some embodiments, the primary anti-GFAP antibody is a labeled primary anti-GFAP antibody. Secondary antibodies contemplated herein can be polyclonal or monoclonal. In some embodiments, secondary antibodies contemplated herein can be of any immunoglobulin class including IgG, IgM, IgE, IgA, IgD and any subclass thereof. In some embodiments, secondary antibody can be reactive against, but not limited to, mouse antibodies, human antibodies, rat antibodies, non-human primate antibodies, horse antibodies, rabbit antibodies, chicken antibodies and goat antibodies. In some embodiments, the secondary antibody is an antigen-binding fragment.

D. Attachment of Antibodies to a Solid Support

The anti-UCH-L1 antibodies and/or anti-GFAP antibodies provided herein may be attached directly or indirectly to a solid support. For example, the antibody may be conjugated, coupled or linked to the solid support. Examples of solid supports encompassed herein include, but are not limited to, those formed partially or entirely of glass (e.g., controlled pore glass), polysaccharides (e.g., agarose), polyacrylamides, polystyrene, polyvinyl alcohol, nitrocellulose, cellulose, nylon, silicones and other material well known in the art that is used in a solid support for direct or indirect attachment of an antibody. Further examples of a solid support include, but are not limited to, a bead, column (e.g., chromatography column, etc.), an array (e.g., microarray, nanoarray, etc.), an assay plate, a cartridge, a stick, a filter, or a strip. In some embodiments, the solid support can comprise the well of an assay plate. In some embodiments, the solid support is a microarray. In some embodiments, the solid support can comprise a bead or is a bead. In some embodiments, the solid support is a chromatography column (e.g., an affinity chromatography column). In some embodiments, a solid support is a discontinuous solid phase of discrete particles, such as those described in U.S. Pat. No. 4,275,149.

Methods for directly or indirectly attaching an antibody to a solid support are well known in the art. Methods of attachment generally include non-specific adsorption of the antibody to the solid support or covalent attachment of the antibody, typically through a free amine group, to a chemically reactive group on the solid support, such as an activated carboxyl, hydroxyl, or aldehyde group. Methods of attachment also include indirect attachment of the antibodies to the solid support such as by coating the solid support with a capture reagent, such as streptavidin, and adding affinity labeled antibodies, such as biotin-labeled antibodies, to the solid support so that the interaction between the affinity label (e.g., biotin) and capture reagent (e.g., streptavidin) link the antibodies to the solid support. In some embodiments, the solid support comprises one or more antibodies that are not anti-UCH-L1 antibodies or ant-GFAP antibodies. For example, the solid support may comprise one or more antibodies that bind to other proteins or molecules associated with neurological damage and/or a neurological condition or one or more antibodies that serve as control antibodies.

In some instances, the solid support is part of a device or is compatible or configured for use with a device, such as a diagnostic device. For example, a solid support described herein may be a bead, column, an array, an assay plate, microwell, a cartridge, a stick, a filter, or a strip that is inserted into a device or attached to a device and is used as part of the device in order for the device to be operable. In some embodiments, the solid support is the device. In some embodiments, the device is a portable device such as a handheld device. In some embodiments, the device is a stationary device. The device may be manually operated or automatically operated. In some embodiments, the device is an electronic device. Any suitable device for use with the solid supports provided herein or use in the methods provided herein may be used. Non-limiting examples of suitable devices are described below and include commercially available devices such as, but not limited to, i-STAT® handheld (Abbott), Minicare 1-20 (Phillips) and similar handheld devices.

In some embodiments, a device provided herein (e.g., a device comprising a solid support described herein) is useful for qualitatively and/or quantitatively determining the amount of target antigen (e.g., UCH-L1 or GFAP) bound by the antibody (e.g., anti-UCH-L1 antibody or anti-GFAP antibody). In some embodiments, the amount of UCH-L1 qualitatively and/or quantitatively determined is from about 80 pg/mL to about 2560 pg/mL. In some embodiments, the amount of GFAP qualitatively and/or quantitatively determined is from about 10 pg/mL to about 320 pg/mL.

In some embodiments, the solid support is compatible for use in a detection assay. In some embodiments, the solid support is compatible for use in a diagnostic assay. In some embodiments, a sample, e.g. a bodily fluid or other sample as described herein, is contacted with the solid support. In some embodiments, the solid support is useful for qualitatively and/or quantitatively determining the location of the target antigen (e.g., UCH-L1 or GFAP) bound by the antibody (e.g., anti-UCH-L1 antibody or anti-GFAP antibody). In some embodiments, the solid support is useful for qualitatively and/or quantitatively determining the amount of target antigen (e.g., UCH-L1 or GFAP) bound by the antibody (e.g., anti-UCH-L1 antibody or anti-GFAP antibody).

In some embodiments, the amount of UCH-L1 qualitatively and/or quantitatively determined by a solid support described herein, such as for use in a detection assay and/or a diagnostic assay, is from about 80 pg/mL to about 2560 pg/mL. In some embodiments, the amount of GFAP qualitatively and/or quantitatively determined by a solid support described herein, such as for use in a detection assay and/or a diagnostic assay, is from about 10 pg/mL to about 320 pg/mL.

In general, various methodologies for preparing antibodies for use in research, testing, and clinical use are well-established in the art, consistent with the above-described methodologies and/or as deemed appropriate by one skilled in the art for a particular antibody of interest.

IV. Compositions and Combinations

Provided herein are compositions of any of the provided antibodies. Any of the antibody reagents (e.g. anti-UCH-L1 or anti-GFAP antibody), including compositions thereof, can be used alone or in combination in a detection or diagnostic method in accord with the present disclosure. Also provided are combinations of any of the provided antibodies or compositions thereof with one or more other antibodies. The combinations, which can be provided as kits, can be used together in a detection or diagnostic method in accord with the present disclosure.

A. Compositions

In some aspects, also provided herein are compositions (e.g., pharmaceutical composition) comprising any one or more of the anti-UCH-L1 antibodies and/or anti-GFAP antibodies described herein. The compositions can be used in the methods provided herein such as in methods for detecting UCH-L1 and/or GFAP in a sample and methods of diagnosing an individual with brain damage or injury or neurological condition.

Compositions are prepared for storage by mixing the active ingredient having the desired degree of purity with optional acceptable carriers, excipients or stabilizers such as pharmaceutically acceptable carriers, excipients or stabilizers (Remington: The Science and Practice of Pharmacy, 20th Ed., Lippincott Williams & Wiklins, Pub., Gennaro Ed., Philadelphia, Pa. 2000). In some embodiments, acceptable carriers, excipients, or stabilizers are nontoxic to recipients at the dosages and concentrations employed. In some embodiments, acceptable carriers, excipients, or stabilizers do not substantially alter the activity of the antibody such as when the antibody is used in a diagnostic assay. In some embodiments, acceptable carriers, excipients, or stabilizers are compatible for use in a diagnostic assay or detection assay. Acceptable carriers, excipients, or stabilizers include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers can be used to control the pH in a range which optimizes effectiveness or activity of the antibody, especially if stability is pH dependent. Buffers can be present at concentrations ranging from about 50 mM to about 250 mi. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present invention include azide, methylisothiazolinone (MIT), octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight or between about 1 to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the antibody as well as to protect the antibody against agitation-induced aggregation, which also permits the composition to be exposed to shear surface stress without causing denaturation of the active antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In some embodiments, the compositions are sterile. The composition may be rendered sterile by filtration through sterile filtration membranes. In some embodiments, the compositions herein are placed into a container having a sterile access port, for example, an intravenous solution bag or vial having a stopper pierceable by a hypodermic injection needle.

B. Combinations

Provided herein are combinations containing more than one antibody (e.g., one, two, three, four, or more antibodies) for binding or detecting UCH-L1 and/or GFAP. In some embodiments, the particular combination can be chosen based on the application, such as use in a detection or diagnostic assay as provided herein. For example, typically antibody combinations are chosen with complementary activities such that the antibodies do not adversely affect each other, e.g. do not compete for binding with each other. Such antibodies are suitably present in combination in amounts that are effective for the purpose intended. In some embodiments, the combinations are provided as part of a kit, article of manufacture or system as described elsewhere herein.

In some embodiments, provided herein is a combination of two or more anti-UCH-L1 antibodies, or composition thereof, that bind to UCH-L1 (e.g. human UCH-L1). In some embodiments, the combination comprises a pair of antibodies and/or antibody sets that are compatible and can simultaneously bind UCH-L1. In some embodiments, the antibody pair comprises a first antibody or first set of antibodies and a second antibody or second set of antibodies, wherein the first antibody or each of the antibodies of the first set of antibodies binds to a distinct or non-overlapping epitope compared to the second antibody or each of the antibodies of the second set of antibodies and/or does not compete for binding to UCH-L1 with the second antibody or set. When provided as a set, the antibodies in a first set of antibodies typically each bind to the same or overlapping epitope or region of UCH-L1 and/or do not compete for binding to UCH-L1 with one or more other antibodies in the first set of antibodies and/or the antibodies in the second set of antibodies each bind to the same or overlapping epitope or region of UCH-L1 and/or do not compete for binding to UCH-L1 with one or more other antibodies in the second set of antibodies. In some embodiments, the first antibody or set of antibodies is for capture of UCH-L1 and the second antibody or set of antibodies is for detection of bound UCH-L1 or vice versa. In some embodiments, at least one of the antibodies of the pair is attached to a label (e.g. detectable label) such as a label described herein. In some embodiments, at least one of the antibodies of the pair is attached to a solid support or capable of being attached to a solid support, such as a solid support described herein. In some embodiments, the combination is provided as a kit or as part of a system as described elsewhere herein for use in connection with an immunoassay (e.g. sandwich ELISA or competitive ELISA).

In one aspect, the first (or in some cases the second) anti-UCHL1 antibody or set of antibodies binds to an epitope of UCH-L1 that is, includes or is within (or entirely within) a region corresponding to amino acid positions 98-106 of human UCH-L1 set forth in SEQ ID NO:207 (e.g. any as described, such as the antibody designated UCH-L1-1, UCH-L1-3, or UCH-L1-13 or an antibody comprising the same CDRs as present in the variable heavy chain and variable light chain of the antibody designated UCH-L1-1, UCH-L1-3, or UCH-L1-13 or an antibody comprising a variable heavy chain and a variable light chain comprising the sequence of the variable heavy chain and the variable light chain, respectively, of the antibody designated UCH-L1-1, UCH-L1-3, or UCH-L1-13) and the other of the first or second antibody or set binds to a distinct or non-overlapping region and/or does not compete for binding to an epitope within the region corresponding to amino acid positions 98-106 of human UCH-L1 set forth in SEQ ID NO:207. In some embodiments, the other antibody or set, which can be the other of the first or second antibody, binds to an epitope of UCH-L1 that is, or includes or is within (or entirely within) a region corresponding to amino acid positions 28-36 of human UCH-L1 set forth in SEQ ID NO:207 (e.g. any as described, such as the antibody designated UCH-L1-2, UCH-L1-6, UCH-L1-7, UCH-L1-8, UCH-L1-9, UCH-L1-10, UCH-L1-11 or UCH-L1-12 or an antibody comprising the same CDRs present in the variable heavy chain and the variable light chain as the antibody designated UCH-L1-2, UCH-L1-6, UCH-L1-7, UCH-L1-8, UCH-L1-9, UCH-L1-10, UCH-L1-11 or UCH-L1-12 or an antibody comprising a variable heavy chain and a variable light chain comprising the sequence of the variable heavy chain and the variable light chain, respectively, of the antibody designated UCH-L1-2, UCH-L1-6, UCH-L1-7, UCH-L1-8, UCH-L1-9, UCH-L1-10, UCH-L1-11 or UCH-L1-12). In other embodiments, the other antibody or set, which can be the first or second antibody, binds to an epitope of UCH-L1 that is or includes or is within (or entirely within) a region corresponding to amino acid positions 138-145 of human UCH-L1 set forth in SEQ ID NO:207 (e.g. any as described, such as the antibody designated UCH-L1-4 or an antibody comprising the same CDRs a present in the variable heavy chain and variable light chain as the antibody designated UCH-L1-4 or an antibody comprising a variable heavy chain and a variable light chain comprising the sequence of the variable heavy chain and variable light chain of the antibody designated UCH-L1-4). In other embodiments, the other antibody or set, which can be the first or second antibody, binds to an epitope of UCH-L1 that is, includes or is within (or entirely within) a region corresponding to amino acid positions 142-149 of human UCH-L1 set forth in SEQ ID NO:207 (e.g. any as described, such as the antibody designated UCH-L1-5 or an antibody comprising the same CDRs a present in the variable heavy chain and variable light chain as the antibody designated UCH-L1-5 or an antibody comprising a variable heavy chain and a variable light chain comprising the sequence of the variable heavy chain and variable light chain of the antibody designated UCH-L1-5).

In some embodiments, the first (or in some cases the second) anti-UCHL1 antibody or set of antibodies is the antibody designated UCH-L1-1 or UCH-L1-2 or an antibody comprising the same CDRs as present in the variable heavy chain and variable light chain of the antibody designated UCH-L1-1 or UCH-L1-2 or an antibody comprising a variable heavy chain and a variable light chain comprising the sequence of the variable heavy chain and the variable light chain, respectively, of the antibody designated UCH-L1-1 or UCH-L1-2; and the other antibody, which can be the first or second antibody, is the antibody designated UCH-L1-5 or an antibody comprising the same CDRs as present in the variable heavy chain and variable light chain of the antibody designated UCH-L1-5 or an antibody comprising a variable heavy chain and a variable light chain comprising the sequence of the variable heavy chain and the variable light chain, respectively, of the antibody designated UCH-L1-5.

In some embodiments, the combination or kit comprises a first antibody that is an anti-UCH-L1 antibody comprising a heavy chain variable domain comprising the amino acid sequence of SEQ ID NO:51 and a light chain variable domain comprising the amino acid sequence of SEQ ID NO:64, and/or is an anti-UCH-L1 antibody comprising a heavy chain variable domain comprising the amino acid sequence of SEQ ID NO:52 and a light chain variable domain comprising the amino acid sequence of SEQ ID NO:65. In some embodiments, the combination comprises a first antibody set comprising an anti-UCH-L1 antibody comprising a heavy chain variable domain comprising the amino acid sequence of SEQ ID NO:51 and a light chain variable domain comprising the amino acid sequence of SEQ ID NO:64, and an anti-UCH-L1 antibody comprising a heavy chain variable domain comprising the amino acid sequence of SEQ ID NO:52 and a light chain variable domain comprising the amino acid sequence of SEQ ID NO:65. In some embodiments, the combination or kit comprises a second antibody that is an anti-UCH-L1 antibody comprising a heavy chain variable region comprising the amino acid sequence of SEQ ID NO:55 and a light chain variable domain comprising the amino acid sequence of SEQ ID NO:68.

In some embodiments, provided herein is a combination of two or more anti-GFAP antibodies, or composition thereof, that bind to GFAP (e.g. human GFAP). In some embodiments, the combination comprises a pair of antibodies and/or antibody sets that are compatible and can simultaneously bind GFAP. In some embodiments, the antibody pair comprises a first antibody or set of antibodies and a second antibody or set of antibodies, wherein the first antibody or each of the antibodies of the first set of antibodies binds to a distinct or non-overlapping epitope compared to the second antibody or second set of antibodies and/or does not compete for binding to GFAP with the second antibody or set. When provided as a set, the antibodies in a first set of antibodies each bind to the same or overlapping epitope or region of GFAP and/or do not compete for binding to GFAP with one or more other antibodies in the first set of antibodies and/or the antibodies in the second set of antibodies each bind to the same or overlapping epitope or region of GFAP and/or do not compete for binding to GFAP with one or more other antibodies in the second set of antibodies. In some embodiments, the first antibody or first set of antibodies is used for capture of GFAP and the second antibody or second set of antibodies is used for detection of bound GFAP or vice versa. In some embodiments, at least one of the antibodies of the pair is attached to a label (e.g. detectable label) such as a label described herein. In some embodiments, at least one of the antibodies of the pair is attached to a solid support or capable of being attached to a solid support, such as a solid support described herein. In some embodiments, the combination is provided as a kit or as part of a system as described elsewhere herein for use in connection with a sandwich immunoassay (e.g. sandwich ELISA) or a competitive immunoassay (e.g. competitive ELISA).

In one aspect, the first (or in some cases the second) anti-GFAP antibody or set of antibodies binds to an epitope of GFAP that is, includes or is within (or entirely within) a region corresponding to amino acid positions 92-106 of human GFAP set forth in SEQ ID NO:212 (e.g. any as described, such as the antibody designated GFAP-1 or an antibody comprising the same CDRs as present in the variable heavy chain and variable light chain of the antibody designated GFAP-1 or an antibody comprising a variable heavy chain and a variable light chain comprising the sequence of the variable heavy chain and the variable light chain, respectively, of the antibody designated GFAP-1) and the other of the first or second antibody or set binds to a distinct or non-overlapping region and/or does not compete for binding to an epitope within the region corresponding to amino acid positions 92-106 of human GFAP set forth in SEQ ID NO:212. In some embodiments, the other antibody or set, which can be the other of the first or second antibody, binds to an epitope of GFAP that is, includes or is within (or entirely within), a region corresponding to amino acid positions 190-202 of human GFAP set forth in SEQ ID NO:212 (e.g. any as described, such as the antibody designated GFAP-2 or an antibody comprising the same CDRs present in the variable heavy chain and the variable light chain as the antibody designated GFAP-2 or an antibody comprising a variable heavy chain and a variable light chain comprising the sequence of the variable heavy chain and the variable light chain, respectively, of the antibody designated GFAP-2). In other embodiments, the other antibody or set, which can be the other of the first or second antibody, binds to an epitope of GFAP that is, includes or is within (or entirely within) a region corresponding to amino acid positions 16-35 and/or 380 of human GFAP set forth in SEQ ID NO:212 (e.g. any as described, such as the antibody designated GFAP-3 or an antibody comprising the same CDRs present in the variable heavy chain and the variable light chain as the antibody designated GFAP-3 or an antibody comprising a variable heavy chain and a variable light chain comprising the sequence of the variable heavy chain and the variable light chain, respectively, of the antibody designated GFAP-3). In further embodiments, the other antibody or set, which can be the other of the first or second antibody, binds to an epitope of GFAP that is, includes or is within (or entirely within) a region corresponding to amino acid positions 119 and/or 190 of human GFAP set forth in SEQ ID NO:212 (e.g. any as described, such as the antibody designated GFAP-5 or an antibody comprising the same CDRs present in the variable heavy chain and the variable light chain as the antibody designated GFAP-5 or an antibody comprising a variable heavy chain and a variable light chain comprising the sequence of the variable heavy chain and the variable light chain, respectively, of the antibody designated GFAP-5). In additional embodiments, the other antibody or set, which can be the other of the first or second antibody, binds to an epitope of GFAP that is, includes or is within (or entirely within) a region corresponding to amino acid positions 380-391 of human GFAP set forth in SEQ ID NO:212 (e.g. any as described, such as the antibody designated GFAP-4, GFAP-7, GFAP-8, or GFAP-9 or an antibody comprising the same CDRs present in the variable heavy chain and the variable light chain as the antibody designated GFAP-4, GFAP-7, GFAP-8, or GFAP-9 or an antibody comprising a variable heavy chain and a variable light chain comprising the sequence of the variable heavy chain and the variable light chain, respectively, of the antibody designated GFAP-4, GFAP-7, GFAP-8, or GFAP-9).

In one aspect, the first (or in some cases the second) anti-GFAP antibody or set of antibodies binds to an epitope of GFAP that is, includes or is within (or entirely within) a region corresponding to amino acid positions 119-130 of human GFAP set forth in SEQ ID NO:212 (e.g. any as described, such as the antibody GFAP-6, GFAP-11, GFAP-12, GFAP-18 or GFAP-19 or an antibody comprising the same CDRs present in the variable heavy chain and the variable light chain as the antibody designated GFAP-6, GFAP-11, GFAP-12, GFAP-18 or GFAP-19 or an antibody comprising a variable heavy chain and a variable light chain comprising the sequence of the variable heavy chain and the variable light chain, respectively, of the antibody designated GFAP-6, GFAP-11, GFAP-12, GFAP-18 or GFAP-19) and the other of the first or second antibody or set binds to a distinct or non-overlapping region and/or does not compete for binding to an epitope within the region corresponding to amino acid positions 119-130 of human GFAP set forth in SEQ ID NO:212. In some embodiments, the other antibody or set, which can be the other of the first or second antibody, binds to an epitope of GFAP that is, includes or is within (or entirely within) a region corresponding to amino acid positions 210-221 of human GFAP set forth in SEQ ID NO:212 (e.g. any as described, such as the antibody designated GFAP-13, GFAP-14, or GFAP-15 or an antibody comprising the same CDRs present in the variable heavy chain and the variable light chain as the antibody designated GFAP-13, GFAP-14, or GFAP-15 or an antibody comprising a variable heavy chain and a variable light chain comprising the sequence of the variable heavy chain and the variable light chain, respectively, of the antibody designated GFAP-13, GFAP-14, or GFAP-15) and the other of the first or second antibody or set binds to a distinct or non-overlapping region and/or does not compete for binding to an epitope within the region corresponding to amino acid positions 210-221 of human GFAP set forth in SEQ ID NO:212. In other embodiments, the other antibody or set, which can be the other of the first or second antibody, binds to an epitope of GFAP that is, includes or is within (or entirely within) a region corresponding to amino acid positions 320-390 of human GFAP set forth in SEQ ID NO:212 (e.g. any as described, such as the antibody designated GFAP-16 or GFAP-17 or an antibody comprising the same CDRs present in the variable heavy chain and the variable light chain as the antibody designated GFAP-16 or GFAP-17 or an antibody comprising a variable heavy chain and a variable light chain comprising the sequence of the variable heavy chain and the variable light chain, respectively, of the antibody designated GFAP-16 or GFAP-17) and the other of the first or second antibody or set binds to a distinct or non-overlapping region and/or does not compete for binding to an epitope within the region corresponding to amino acid positions 320-390 of human GFAP set forth in SEQ ID NO:212. In further embodiments, the other antibody or set, which can be the other of the first or second antibody, binds to an epitope of GFAP that is, includes or is within (or entirely within) a region corresponding to amino acid positions 346-357 and/or 376-387 of human GFAP set forth in SEQ ID NO:212 (e.g. any as described, such as the antibody designated GFAP-17 or an antibody comprising the same CDRs present in the variable heavy chain and the variable light chain as the antibody designated GFAP-17 or an antibody comprising a variable heavy chain and a variable light chain comprising the sequence of the variable heavy chain and the variable light chain, respectively, of the antibody designated GFAP-17) and the other of the first or second antibody or set binds to a distinct or non-overlapping region and/or does not compete for binding to an epitope within the region corresponding to amino acid positions 346-357 and/or 376-387 of human GFAP set forth in SEQ ID NO:212. In further embodiments, the other antibody or set, which can be the other of the first or second antibody, binds to an epitope of GFAP that is, includes or is within (or entirely within), a region corresponding to amino acid positions 138-149 of human GFAP set forth in SEQ ID NO:212 (e.g. any as described, such as the antibody designated GFAP-18 or an antibody comprising the same CDRs present in the variable heavy chain and the variable light chain as the antibody designated GFAP-18 or an antibody comprising a variable heavy chain and a variable light chain comprising the sequence of the variable heavy chain and the variable light chain, respectively, of the antibody designated GFAP-18) and the other of the first or second antibody or set binds to a distinct or non-overlapping region and/or does not compete for binding to an epitope within the region corresponding to amino acid positions 138-149 of human GFAP set forth in SEQ ID NO:212.

In some embodiments, the first (or in some cases the second) anti-GFAP antibody or set of antibodies is the antibody designated GFAP-2 or an antibody comprising the same CDRs as present in the variable heavy chain and variable light chain of the antibody designated GFAP-2 or an antibody comprising a variable heavy chain and a variable light chain comprising the sequence of the variable heavy chain and the variable light chain, respectively, of the antibody designated GFAP-2; and the other antibody, which can be the first or second antibody, is the antibody designated GFAP-6 or an antibody comprising the same CDRs as present in the variable heavy chain and variable light chain of the antibody designated GFAP-6 or an antibody comprising a variable heavy chain and a variable light chain comprising the sequence of the variable heavy chain and the variable light chain, respectively, of the antibody designated GFAP-6.

In some embodiments, the combination or kit comprises a first antibody that is an anti-GFAP antibody comprising a heavy chain variable domain comprising the amino acid sequence of SEQ ID NO:173 and a light chain variable domain comprising the amino acid sequence of SEQ ID NO:190, and a second antibody that is an anti-GFAP antibody comprising a heavy chain variable domain comprising the amino acid sequence of SEQ ID NO:177 and a light chain variable domain comprising the amino acid sequence of SEQ ID NO:194.

In some embodiments, provided herein is a combination comprising at least one anti-UCH-L1 antibody described herein or composition thereof and at least one anti-GFAP antibody described herein or composition thereof. In some embodiments, the combination comprises a pair or set of anti-UCH-L1 antibodies such as any as described and a pair or set of anti-GFAP antibodies such as any as described. In some embodiments, the combination comprises at least two, three, four, five, six, seven, eight, nine but no more than ten antibodies.

V. Methods of Detecting UCH-L1 and/or GFAP and Diagnosis or Predicting Outcomes In some aspects, provided herein are methods for detecting UCH-L1 and/or GFAP in a sample from a subject or individual. In some embodiments, the provided methods involve immunoaffinity-based detection of UCH-L1 and/or GFAP using any of the antibodies provided herein. In some embodiments, the methods are performed in vitro. In some embodiments, the sample is obtained or isolated from the subject or individual. In some embodiments, the subject or individual is a human.

In some embodiments, provided are methods of detecting UCH-L1 and/or GFAP in a sample from a subject in which the method comprises the steps of (a) contacting a sample from the subject with one or more anti-UCH-L1 antibody provided herein and/or one or more GFAP antibody provided herein, such as combination or pair of antibodies as described herein; and (b) detecting the presence or absence of UCH-L1 and/or GFAP in the sample based on binding between a UCH-L1 and/or GFAP in the sample with the one or more anti-UCH-L1 antibody or anti-GFAP antibody, respectively. In some embodiments, the contacted is carried out under conditions to form a complex comprising the antibody or antigen-binding fragment and its antigen (e.g. UCH-L1 and/or GFAP). In some embodiments, detection of binding can be achieved by detection techniques commonly known in the art for detecting the binding between a protein target and binding agent (e.g. an antibody) such as, but not limited to, spectrophotometry, high performance liquid chromatography (HPLC), immunoassays such as enzyme-linked immunosorbent assay (ELISA), western blot, automated imaging, immunohistochemistry, flow cytometry, high-throughput screening of an array such as a microarray or nanoarray and surface plasmon resonance. In some embodiments, the antibodies provided herein can detect UCH-L1 or GFAP using any binding assay or immunoassay known to one of skill in the art including, but not limited to, enzyme linked immunosorbent assay (ELISA) or other similar immunoassay, including a sandwich ELISA or competitive ELISA; immunohistochemistry (IHC); flow cytometry, or western blot.

In some embodiments, a sample for use in the methods herein is obtained from subjects or individuals known to have or had, or are likely or suspected to have or have had, a brain damage or injury (e.g. due to a neurological damage and/or a neurological condition, such as a traumatic brain injury or other damage or injury as described). In some embodiments, the sample is obtained from the individual no more than about 30 minutes, 1 hour, 2 hours, 4 hours, 6 hours, 8 hours, 12 hours, 24 hours or 48 hours after an injury (e.g., a direct or indirect physical injury to the brain). In some embodiments, the sample is obtained from the individual no more than 8 hours after the injury. For example, the sample is obtained from the individual within or about within 5 minutes, 15 minutes, 30 minutes, 45 minutes, 1 hour, 2 hours, 3 hours, 4 hours, 5 hours, 6 hours, 7 hours but more than about 8 hours after the injury.

In some embodiments, the sample is serum, plasma, blood (e.g., whole blood), cerebrospinal fluid (CSF), urine, sweat, saliva or any other biological fluid present or obtained from an individual (e.g., human). In some embodiments, the sample is serum. In other embodiments, the sample is CSF. The sample can be used directly in the methods provided herein after obtaining it from an individual or it can be processed before use in the methods provided herein. For example, a CSF sample can be obtained from an individual and directly used in the methods herein by contacting the sample with one or more of the anti-UCH-L1 and/or anti-GFAP antibodies provided herein. Alternatively, the CSF sample can obtained from an individual and be processed prior to contacting the sample with one or more of the anti-UCH-L1 and/or anti-GFAP antibodies provided herein. Processing of the sample includes techniques commonly used in the art to purify and/or concentrate a protein sample such as washing in a buffer, incubation, centrifugation, filtration, immunoprecipitation, adsorption and/or addition of agents that remove contaminants that can interfere with detecting the binding between UCH-L1-1 and/or GFAP and an antibody.

In some embodiments, the method is a sandwich or competitive immunoassay (e.g. sandwich ELISA or a competitive ELISA assay) and the method comprises (a) contacting a sample from the subject with at least one first anti-UCH-L1 antibody to capture or bind UCH-L1 in the sample (e.g., under conditions to form a complex comprising the antibody or antigen-binding fragment and UCH-L1) and/or contacting a sample from the subject with at least one first anti-GFAP antibody to capture or bind GFAP in the sample (e.g., under conditions to form a complex comprising the antibody or antigen-binding fragment and GFAP); and (b) detecting the bound UCH-L1 in the sample by adding at least one second anti-UCH-L1 antibody to detect the presence or absence of UCH-L1 in the sample or associated with the complex and/or detecting the bound GFAP in the sample by adding at least one second anti-GFAP antibody to detect the presence or absence of GFAP in the sample or associated with the complex. In some embodiments, at least one second antibody is directly or indirectly labeled for detection or is capable of detection.

In some embodiments, the method comprises detecting or measuring only UCH-L1 in the sample. In some embodiments, the method comprises detecting or measuring only GFAP in the sample. In some embodiments, the method comprises detecting or measuring both UCH-L1 and GFAP in a sample from the subject, in which case the sample in which UCH-L1 and GFAP is measured or detected is the same sample, a portion of the same sample or a different sample form the same subject. In some embodiments of any of the provided methods, one or more other biomarker, such as associated with a brain injury or damage, can be detected or measured in a sample from the subject.

Any of the provided antibodies can be used alone or in combination in the provided methods. For example, in a sandwich ELISA or competitive ELISA, two or more anti-UCH-L1 antibody (e.g. pair of anti-UCH-L1 antibodies) and/or two or more anti-GFAP antibody (e.g. pair of anti-GFAP antibody) can be used. In some embodiments, the antibodies provided herein can be conjugated directly or indirectly to a moiety that is capable of detection. In some examples, one or more of the antibodies are modified to permit detection of binding. For example, antibodies can be conjugated to a detectable molecule that permits either direct detection or detection via secondary agents. In some embodiments, antibodies are directly labeled as described herein above. In some examples, the antibodies can be detected using a secondary reagent, such as by a secondary antibody reagent that binds to the primary antibodies as provided herein and that is coupled to a detectable protein, such as a fluorescent probe or detectable enzyme, such as horseradish peroxidase.

In some of the embodiments herein, the one or more antibody is one or more capture antibody that captures UCH-L1 and/or GFAP in the sample. In some of the embodiments herein, the one or more antibody is one or more detection antibody that binds UCH-L1 and/or GFAP in the sample and is detectable (e.g., is attached to a label). For example, the one or more antibody can be one or more capture antibody (e.g., capture anti-UCH-L1 antibody) and one or more detection antibody (e.g., detection anti-UCH-L1 antibody).

In some embodiments, the sample from the subject can be assessed for the presence, absence or amount of UCH-L1 and/or GFAP using a solid-phase binding assay. Solid-phase binding assays can detect a substrate (e.g. UCH-L1 or GFAP) in a fluid sample by binding of the substrate to a binding agent (e.g. a first anti-UCH-L1 antibody or anti-GFAP antibody, such as a capture antibody) that is fixed or immobilized to a solid surface. In some embodiments, the contacting in step a) of the methods herein comprises adding the sample (e.g., sample obtained from an individual) to a solid support or a device comprising a solid support, wherein the solid support comprises one or more antibody described herein (e.g., an anti-UCH-L1 antibody and/or an anti-GFAP antibody). In some embodiments, the contacting in step a) of the methods herein comprises mixing the sample (e.g., sample obtained from an individual) and one or more antibody described herein (e.g., an anti-UCH-L1 antibody and/or an anti-GFAP antibody) under conditions to form a complex comprising the antibody or antigen-binding fragment and the antigen or substrate (e.g. UCH-L1 or GFAP). In some embodiments, the sample is mixed with the one or more antibody in the presence of or on or in a solid support or a device comprising a solid support. In some embodiments, the sample is mixed with the one or more antibody to produce a mixture and the mixture is subsequently applied to a solid support or a device comprising a solid support. In some of the embodiments herein, the one or more antibody is directly or indirectly attached to the solid support. In some embodiments, the contacting in step a) further comprises one or more incubation of the sample and the one or more antibody. The one or more incubations can be for a time that is suitable to allow the sample to contact the one or more antibody such as for at least or at least about 30 seconds, 1 minute, 5 minutes, 10 minutes, 15 minutes, 20 minutes, 30 minutes, 45 minutes, 1 hour, 2 hours, 3 hours, 6 hours, or 12 hours or more but no more than about 24 hours after contacting a sample with the one or more antibody as described herein. In some embodiments, the contacting occurs at a temperature of from or from about 0° C. to about 50° C., such as typically 2° C. to 8° C. or 23° C. to 28° C. or 37° C. to 42° C. In some embodiments, the contacting in step a) further comprises one or more washing under conditions to retain bound UCH-L1 and/or GFAP on the solid support and/or to separate the complex away from portions of the sample not part of the complex.

In some embodiments, the detecting in step b) of the methods herein comprises detecting the binding between UCH-L1 and/or GFAP with a second substrate specific antibody (e.g. a second anti-UCH-L1 antibody or anti-GFAP antibody, such as a detection antibody) that is capable of detection of the substrate (e.g. UCH-L1 or GFAP). In some embodiments, the second antibody is a naked (unlabeled) antibody (e.g., naked anti-UCH-L1 antibody or naked anti-GFAP antibody) and detection is indirect by adding a labeled secondary antibody that binds to the naked antibody. In some embodiments, the second antibody is a labeled antibody (e.g., labeled anti-UCH-L1 antibody or labeled anti-GFAP antibody) and detection is direct. In some embodiments, the second antibody is a labeled antibody but it not capable of direct detection. For example, the label can be an enzyme and detection can be effected by addition of a substrate that produces a signal, e.g. a colorimetric signal. In some embodiments, the second antibody (detection antibody) is applied or contacted with the bound UCH-L1 and/or GFAP in the complex and allowed to incubate under conditions to allow binding to the bound substrate (e.g. UCH-L1 or GFAP) in the complex. In some embodiments, the incubations can be for a time that is suitable to allow the second antibody (detection antibody) to contact the bound UCH-L1 or GFAP, such as for at least or at least about 30 seconds, 1 minute, 5 minutes, 10 minutes, 15 minutes, 20 minutes, 30 minutes, 45 minutes, 1 hour, 2 hours, 3 hours, 6 hours or 12 hours or more but no more than about 24 hours after contacting a sample with the second antibody as described herein. In some embodiments, the contacting occurs at a temperature of from or from about 0° C. to about 30° C., such as typically 2° C. to 8° C. or 23° C. to 28° C. In some embodiments, the contacting in step b) further comprises one or more washing steps under conditions to retain binding of the second antibody to the bound substrate or complex and to remove any unbound second antibody.

In some embodiments, the presence, such as signal, of the second antibody is then detected. Detection methods include, but are not limited to, colorimetric, fluorescent, luminescent or radioactive methods. The choice of detection method is dependent on the detectable label used. In some examples, a colorimetric reaction is used in which the antibody is coupled to an enzyme, such as horseradish peroxidase (HRP), alkaline phosphatase or other detectable enzyme.

In some embodiments, the method further includes determining or quantitating the amount of UCH-L1 or GFAP in the sample. In some such aspects, the amount of substrate present in the sample is proportional to the amount of signal, e.g. color, produced. Methods for quantification of signals are well known in the art such as through use of a luminometer, spectrophotometer, or a digital imaging instrument. In some embodiments, a substrate standard is generally employed to quantitate or determine the amount of substrate (e.g. UCH-L1 or GFAP) in the sample. In some embodiments, the standard comprises known concentrations (e.g. serial dilutions) of a recombinant or native form of the protein. In some embodiments, the concentration of substrate (e.g. UCH-L1 or GFAP) in a sample can be calculated by interpolating the data to the standard curve. In some embodiments, the amount of UCH-L1 or GFAP can be expressed as a concentration of fluid sample.

In some embodiments, provided are methods of detecting UCH-L1 in a sample from a subject in which the method comprises the steps of (a) contacting a sample from the subject with one or more anti-UCH-L1 antibody provided herein, such as combination or pair of antibodies as described herein, under conditions to form one or more complexes comprising the antibody or antigen-binding fragment and UCH-L1; and (b) detecting the presence or absence of UCH-L1 in the sample based on binding between a UCH-L1 in the sample and the one or more anti-UCH-L1 antibody, which, in some cases, can be by detecting the presence or absence of the complex containing bound UCH-L1. In some embodiments, two or more antibodies are contacted with the sample, or a component of the sample, either simultaneously or sequentially. In some embodiments, the method is a sandwich or competitive immunoassay (e.g. sandwich ELISA or a competitive ELISA assay) and the method comprises (a) contacting a sample from the subject with at least one first antibody or first antibody set to capture or bind the UCH-L1 in the sample, such as under conditions to form a complex comprising the antibody or antigen-binding fragment and UCH-L1; and (b) subsequently, such as after one or more optional washing steps, contacting the bound UCH-L1, such as a complex containing the UCH-L1, with at least one second antibody or second antibody set to detect the presence or absence of UCH-L1 in the sample or complex. In some embodiments, one or more first antibody is used to capture or bind the UCH-L1, which can be the same or different. In some embodiments, the first antibody (or each of the first antibodies) is the same as the second antibody and/or competes for binding to UCH-L1 with the second antibody. In some embodiments, the first antibody (or each of the first antibodies) is different than the second antibody, such as binds to a distinct or non-overlapping epitope compared to the second antibody and/or does not compete for binding to UCH-L1 with the second antibody. In some embodiments, at least one second antibody is directly or indirectly labeled for detection. In some embodiments, the first and second antibody can be part of an antibody pair for use in detecting UCH-L1 as described elsewhere herein.

In some embodiments, the method can be used to determine the amount of UCH-L1 in the sample. Thus, also provided is a method of determining or quantifying the amount of UCH-L1 in a sample. In some embodiments, after steps (a) and (b) above, the method further comprises (c) determining or quantifying the amount of UCH-L1 in the sample by determining or quantifying the amount of UCH-L1 bound by the one or more anti-UCH-L1 antibody. In some embodiments, the amount of UCH-L1 is determined by comparison of the detectable signal to a standard curve, such as a standard curve comprising a series of known concentrations of a recombinant or native UCH-L1.

In an exemplary method, one or more first anti-UCH-L1 antibody that is generally unlabeled is first immobilized to a solid support (e.g. coated to wells of a microtiter plate), followed by incubation with a fluid sample containing or potentially containing UCH-L1 (e.g. serum or plasma or cerebrospinal fluid) to capture any UCH-L1 in the sample, for example, under conditions to form a complex of the first antibody or antibodies and UCH-L1. After washing the fluid sample with an appropriate buffer, the complex containing bound UCH-L1 can be contacted with one or more second anti-UCH-L1 antibody or antibodies as described that is labeled (e.g. HRP-conjugated anti-UCH-L1 antibody or biotin-conjugated anti-UCH-L1 antibody) to bind to the UCH-L1 bound as a complex on the solid support. Following removal of the unbound labeled second antibody or sets of antibodies, the bound labeled antibody or antibodies is detected directly or by using a detection reagent. For example, in one non-limiting example, the HRP label of the second antibody can be detected by the addition of a detection substrate, such as ABTS (2,2'-Azinobis [3-ethylbenzothiazoline-6-sulfonic acid]-diammonium salt), OPD (o-phenylenediamine dihydrochloride) or TMB (3,3',5,5'-tetramethylbenzidine) detection substrate. Other detection reagents suitable for use with particular detectable labels are well known to a skilled artisan. In some embodiments, the amount of UCH-L1 in the test sample can be determine or quantified by comparison to the standard curve.

In some embodiments, provided are methods of detecting GFAP in a sample from a subject in which the method comprises the steps of (a) contacting a sample from the subject with one or more anti-GFAP antibody provided herein, such as combination of antibodies as described herein, under conditions to form one or more complexes comprising the antibody or antigen-binding fragment and GFAP; and (b) detecting the presence, absence or amount of GFAP in the sample based on binding between a GFAP in the sample and the one or more anti-GFAP antibody, which, in some cases, can be detecting the presence or absence of the complex containing bound GFAP. In some embodiments, two or more antibodies are contacted with the sample, or a component of the sample, either simultaneously or sequentially. In some embodiments, the method is a sandwich or competitive immunoassay (e.g. sandwich ELISA or a competitive ELISA assay) and the method comprises (a) contacting a sample from the subject with at least one first antibody to capture or bind the GFAP in the sample, such as under conditions to form a complex comprising the antibody or antigen-binding fragment and GFAP; and (b) subsequently, such as after one or more optional washing steps, contacting the bound GFAP, such as a complex containing the GFAP, with at least one second antibody to detect or determine the presence, absence or amount of GFAP in the sample. In some embodiments, the one or more first antibody is used to capture or bind the GFAP, which can be the same or different. In some embodiments, the first antibody (or each of the first antibodies) is the same as the second antibody and/or competes for binding to GFAP with the second antibody. In some embodiments, the first antibody (or each of the first antibodies) is different than the second antibody, such as binds to a distinct or non-overlapping epitope compared to the second antibody and/or does not compete for binding to GFAP with the second antibody. In some embodiments, the at least one second antibody is directly or indirectly labeled for detection. In some embodiments, the first and second antibody can be part of an antibody pair for use in detecting GFAP as described elsewhere herein.

In some embodiments, the method can be used to determine the amount of GFAP in the sample. Thus, also provided is a method of determining or quantifying the amount of GFAP in a sample. In some embodiments, after steps (a) and (b) above, the method further comprises (c) determining or quantifying the amount of GFAP in the sample by determining or quantifying the amount of GFAP bound by the one or more anti-GFAP antibody. In some embodiments, the amount of GFAP is determined by comparison of the detectable signal to a standard curve, such as a standard curve comprising a series of known concentrations of a recombinant or native GFAP.

In an exemplary method, one or more first anti-GFAP antibody that is generally unlabeled is first immobilized to a solid support (e.g. coated to wells of a microtiter plate), followed by incubation with a fluid sample containing or potentially containing GFAP (e.g. serum or plasma or cerebrospinal fluid) to capture any GFAP in the sample, for example, under conditions to form a complex of the first antibody or antibodies and GFAP. After washing the fluid sample with an appropriate buffer, the bound GFAP can be contacted with one or more second anti-GFAP antibody or antibodies as described that is labeled (e.g. HRP-conjugated anti-GFAP antibody or biotin-conjugated anti-GFAP antibody) to bind to the GFAP bound as a complex on the solid support. Following removal of the unbound labeled second antibody or sets of antibodies, the bound labeled antibody or antibodies is detected directly or by using a detection reagent. For example, in one non-limiting example, the HRP label of the second antibody can be detected by the addition of a detection substrate, such as ABTS (2,2'-Azinobis [3-ethylbenzothiazoline-6-sulfonic acid]-diammonium salt), OPD (o-phenylenediamine dihydrochloride) or TMB (3,3',5,5'-tetramethylbenzidine) detection substrate. Other detection reagents suitable for use with particular detectable labels are well known to a skill artisan. In some embodiments, the amount of GFAP in the test sample can be determine or quantified by comparison to the standard curve.

In some embodiments, provided are methods of detecting UCH-L1 or determining the amount of UCH-L1 in a first sample from a subject as described above and detecting GFAP or determining the amount of GFAP in a second sample from the subject as described above, which methods can be performed simultaneously or sequentially in any order. In some embodiments, the first sample and the second sample are the same or are derived from the same test sample (e.g. each represent a portion or part of a sample). In some embodiments, methods of detecting or determining the amount of UCH-L1 and GFAP in the sample can be performed simultaneously. In some embodiments, to aid in detection of bound UCH-L1 versus bound GFAP one or more distinct detectable labels can be employed. In some embodiments, detecting UCH-L1 or determining the amount of UCH-L1 and detecting GFAP or determining the amount of GFAP are performed separately, such as sequentially.

In some embodiments, the provided methods can be used to detect, diagnose or monitor brain injury or damage or likelihood of brain injury or damage, to predict the need for an alternative diagnostic or assessment (e.g. imaging, such as a CT scan or MRI), to select a patient for treatment of brain injury or damage, and/or can be used as part of a treatment protocol in subjects that are being treated for or are candidates for being treated for brain (e.g. neural) injury or damage. In some of any such embodiments of the methods herein, the individual has neurological or brain damage or is suspected of having neurological or brain damage. In some embodiments, any disease, condition or trauma that causes or potentially causes damage to brain cells (glial or neuronal) is contemplated. In some embodiments, the brain injury or damage can be external, such as due to an infectious disease or trauma. In some embodiments, the neurological or brain damage is due to a physical injury. In some embodiments, the neurological or brain damage is due to a disease or disorder. In some embodiments, the brain injury or damage can be internal, such as due to a genetic disease (insufficiency or an excess of a protein encoded by a gene). In some embodiments, the brain or neurological damage or injury is associated with a neurological condition. In some embodiments, the brain or neurological damage or injury leads to the development or progression of a neurological condition.

Neurological damage can result from direct or indirect injury to brain cells. In some instances, neurological damage can progress in an individual and lead to a neurological condition. In some instances, a neurological condition can result in neurological damage that progressively worsens with time. In some embodiments, the injury may be physical such as a fall or brunt force hit that directly damages the brain cells or it can be due a disease or disorder that can lead to neurological damage or is associated with neurological damage. The disease or disorder can be due to an external agent such as an infectious disease or environmental toxin. The disease or disorder can be due to a condition of the body such as a genetic disease or a vitamin or mineral or protein insufficiency. In some embodiments, the disease or disorder is associated with a dysfunction of sensory-motor coordination. In some embodiments, the disease or disorder is associated with a dysfunction of sensory-motor coordination. In some embodiments, the disease or disorder is associated with peripheral nervous system dysfunction and/or central nervous system dysfunction. In some embodiments, the individual has neurological damage and/or a neurological condition due to mechanical damage, hypoxia, infectious disease, disease affecting nerve cells, or toxin damage. The mechanical damage can be, but is not limited to, traumatic brain injury or chronic traumatic encephalopathy (CTE). In some embodiments, the brain injury or damage is a traumatic brain injury, including a mild or moderate traumatic brain injury.

Traumatic brain injury (TBI) is the leading cause of death and disability in persons under 45 years of age in industrialized countries (McAllister, T. W. (1992). Neuropsychiatric sequelae of head injuries. The Psychiatric clinics of North America. 15, 395-413). Of the 1.5 million head traumas estimated to occur each year in the United States, 500,000 are likely to require hospitalization, and 80,000 result in some form of chronic disability (Langlois et al., (2006). Traumatic Brain Injury in the United States: Emergency Department Visits, Hospitalization, and Deaths, vol. Atlanta (Ga.) Centers for Disease Control and Prevention, National Center for Injury Prevention and Control). The Center for Disease Control (CDC) estimates that at least 5.3 million Americans, or about 2% of the population, currently have a long-term requirement for assistance with daily living activities as a result of TBI. Furthermore, total health costs for TBI amount to roughly $35 billion annually.

Traumatic brain injury can vary in severity from mild, moderate to severe. In some embodiments, traumatic brain injury is divided into two levels, mild traumatic brain injury (MBTI) and traumatic brain injury (TBI). An intermediate level of moderate TBI also can be employed to classify the injury. The spectrum between MTBI and extending through moderate TBI is also referred to "mild to moderate TBI" or by the abbreviation MMTBI. TBI is defined as an injury that correlates with greater than a two-fold increase or greater than a two-fold decrease in molecular marker levels or activities. MTBI is defined as an injury that correlates with less than a two-fold increase or less than a two-fold decrease in molecular marker levels or activities.

In some cases, physicians commonly attempt to distinguish between mild traumatic brain injury (MTBI) and TBI. MTBI is commonly defined by clinical symptoms including "[a]ny period of observed or self-reported transient confusion, disorientation, or impaired consciousness; [a]ny period of observed or self-reported dysfunction of memory (amnesia) around the time of injury; [o]bserved signs of other neurological or neuropsychological dysfunction, such as— seizures acutely following head injury; [a]mong infants and very young children: irritability, lethargy, or vomiting following head injury; [s]ymptoms among older children and adults such as headache, dizziness, irritability, fatigue, or poor concentration, when identified soon after injury, can be used to support the diagnosis of mild TBI, but cannot be used to make the diagnosis in the absence of loss of consciousness or altered consciousness. Any period of observed or self-reported loss of consciousness lasting 30 minutes or less." (National Center for Injury Prevention and Control. *Report to Congress on Mild Traumatic Brain Injury in the United States: Steps to Prevent a Serious Public Health Problem*. Atlanta, Ga.: Centers for Disease Control and Prevention; 2003.). Symptoms traditionally encompassing TBI include unconsciousness for more than 30 minutes; post traumatic amnesia lasting more than 24 hours; and penetrating cranial cerebral injury. In some embodiments, the methods provided herein allow for the detection of UCH-L1 and/or GFAP in an individual having or suspected of having TBI such as MTBI. In some embodiments, the methods provided herein allow for the diagnosis of TBI such as MTBI in an individual.

In some embodiments, the methods provided herein allow for the prediction of the likelihood an individual that has or is suspected of having MTBI will require neuroimaging such as a CT scan or MRI.

In some embodiments, the provided methods are for detecting, diagnosing, or monitoring the progression of traumatic brain injury or the likelihood of traumatic brain injury, to predict the need for an alternative diagnostic or assessment of a traumatic brain injury or likelihood of traumatic brain injury, to select a patient for treatment of a traumatic brain injury and/or can be used in association with treating a subject having or suspected of having traumatic brain injury. In some embodiments, the traumatic brain injury is a mild, a moderate or a severe traumatic brain injury. In some embodiments, the traumatic brain injury is a concussion, such as caused by a blow or jolt to the head. In some embodiments, a subject at risk for or suspected of having a concussion can be assessed by the provided methods to detect, diagnose or monitor the brain injury, to predict the need for an alternative diagnostic or assessment of the brain injury, to select a patient for treatment of the concussive brain injury and/or can be used in association with treating a subject having or likely to have or develop a concussive brain injury. In some embodiments, the subject who has or is suspected of having a traumatic brain injury (e.g. concussion) may be one that is need of urgent or emergency care, has or is suspected of having a sports-related head injury or other head injury, or has suffered a fall or traffic accident.

In some embodiments, the brain injury or damage is due to hypoxia. In some embodiments, an individual that has neurological damage and/or a neurological condition due to hypoxia has or had a stroke, vasculitis, ischemia and/or cardiac disease. In some embodiments, the ischemia is a generalized ischemia, such as resulting from cardiac disease, a heart attack or a stay in an intensive care unit. In some cases, hypoxia may be considered as a pathological condition in which the entire body or an area of the body is deprived of adequate oxygen supply. In some aspects, when the body as a whole is deprived of adequate oxygen supply, it may be referred to as generalized hypoxia. In other aspects, when a certain region of the body is deprived of adequate oxygen supply, it may be referred to as tissue or local hypoxia. In some cases, hypoxia can lead to tissue damage (e.g. brain damage) and even cell death. For example, a stroke caused by reduced blood flow due to a blocked artery is called an ischemic stroke because it can result in deficient blood supply and death of tissues in areas of the brain. The most common ischemic strokes include thrombotic stroke and embolic stroke. Thrombotic stroke occurs when a blood clot forms in one of the arteries that supply blood to your brain. A clot may be caused by fatty deposits (e.g., plaque) that build up in arteries and cause reduced blood flow (e.g., atherosclerosis) or other artery conditions. An embolic stroke occurs when a blood clot or other debris forms away from your brain, such as in your heart, and is swept through the bloodstream to lodge in narrower brain arteries.

In some embodiments, the provided methods can be used for detecting, diagnosing or monitoring a hypoxic brain injury or likelihood of a hypoxic brain injury, predicting the need for an alternative diagnostic or assessment of the hypoxic brain injury or potential for hypoxic brain injury, selecting a subject for treatment of a hypoxic brain injury or damage and/or can be used in association with methods of treating a subject having or suspected of having a hypoxic brain injury. In some embodiments, the provided methods can be used for detecting, diagnosing or monitoring brain damage or injury, or likelihood of brain damage or injury, associated with stroke, vasculitis or an ischemia; predicting the need for an alternative diagnostic or assessment of brain damage or injury, or likelihood of brain damage or injury, associated with stroke, vasculitis or an ischemia; selecting a subject for treatment of a stroke, vasculitis or an ischemia; and/or can be used in association with methods of treating a subject having or suspected of having a stroke, vasculitis or an ischemia.

In some embodiments, the brain injury or damage is due to an infectious disease. In some cases, an infectious disease can directly damage brain cells or may cause inflammation (e.g. encephalitis) that causes damage to nearby cells, and the individual has or had an infection resulting in or associated with in infectious disease. In some embodiments, a subject has or potentially has brain injury or damage due to infection with a virus, bacteria, fungus, parasite or prion. Infection with an infectious disease can result in acute or chronic inflammation such as in the central nervous system. For example, infection with a virus can result in viral encephalitis (e.g., HIV encephalitis) and infection with bacteria can result in meningitis or abscess formation in the brain. In some embodiments, the virus is a West Nile virus, a herpes simplex virus (e.g. HSV-1, HSV-2, HSV-3, HSV-4 or HSV-5), tick borne encephalitis virus, HIV, or a pox virus. In some embodiments, the bacteria are gram-negative bacteria or gram-positive bacteria. In some embodiments, the gram-positive bacteria are mycobacteria (e.g. *Mycobacterium tuberculosis*). Disease due to infection with a virus, bacteria, fungus, parasite or prion may directly damage cells or cause inflammation which results in injury to nearby cells such as cells in the brain or of the nervous system. In some embodiments, the provided methods can be used for detecting, diagnosing or monitoring brain injury or damage, or likelihood of brain damage or injury, associated with or caused by any such infectious diseases; predicting the need for an alternative diagnostic or assessment of brain damage or injury, or likelihood of brain damage or injury, associated with such infectious diseases; selecting a subject for treatment of an infectious disease; or can be used in association with treating a subject having or suspected of having an infectious disease.

In some embodiments, the brain injury of damage is due to a disease process or condition affecting nerve cells and the individual has or had a disease affecting nerve cells. I Diseases affecting nerve cells contemplated herein include, but are not limited to, ischemic stroke, hemorrhagic stroke, subarachnoid hemorrhage, intra cranial hemorrhage, transient ischemic attack, vascular dementia, corticobasal ganglionic degeneration, encephalitis, epilepsy, Landau-Kleffner syndrome, hydrocephalus, pseudotumor cerebri, thalamic diseases, meningitis, myelitis, movement disorders, essential tremor, spinal cord diseases, syringomyelia, Alzheimer's disease (e.g., early onset Alzheimer's disease or late onset Alzheimer's disease), multi-infarct dementia, Pick's disease, Huntington's disease, Parkinson's disease, Parkinson syndromes, frontotemporal dementia, corticobasal degeneration, multiple system atrophy, progressive supranuclear palsy, Lewy body disease, vascular dementia, diabetic dementia, amyotrophic lateral sclerosis (ALS), prion disease (e.g., Creutzfeldt-Jakob disease (CJD)), Dandy-Walker syndrome, Friedreich ataxia, Machado-Joseph disease, migraine, schizophrenia, mood disorders and depression. In some embodiments, the disease affecting nerve cells is Alzheimer's disease, Lewy body disease, vascular dementia, diabetic dementia, Parkinson's disease, amyotrophic lateral sclerosis (ALS), and/or prion disease. In some embodiments, the provided methods can be used for detecting, diagnosing or monitoring the progression of brain injury or damage in a subject having or having had a disease or condition affecting nerve cells, such as any described above; predicting the need for an alternative diagnostic or assessment of brain damage or injury, or likelihood of brain damage or injury, associated with such a disease or condition; selecting a subject for treatment of such a disease or condition; or can be used in association with treating a subject having or suspected of having such as disease or condition.

In some embodiments, the brain injury or damage is due to damage by a toxin, either acute or chronic, and the individual has or had exposure to one or more toxins. Exposure to toxins by the individual may be through any route such as by consumption, inhalation, injection or physical contact with a toxin. The exposure may have happened once or multiple times over the time period of up to or up to about one day, about two days, about three days about four days, about five days, about six days or about seven days. In some embodiments, the exposure may have happened once or multiple times over the time period of up to or up to about 1 week, about 2 weeks, about 3 weeks or about 4 weeks. In some embodiments, the exposure may have happened once or multiple times over the time period of up to or up to about 1 month, about 2 months, about 3 months, about 4 months, about 5 months, about 6 months, about 7 months, about 8 months, about 9 months, about 10 months, about 11 months or about 12 months. In some embodiments, the exposure may have happened one or multiple times over the time period of up to or up to about 1, 2, 3, 4, 5, 6, 7, 8, 9, or 10 years or more. Toxins contemplated herein include, but are not limited to, nerve agents (e.g., fluorophosphates), pesticides, alcohol, heavy metals (e.g., lead), psychoactive agent (e.g., 3,4-methylenedioxymethamphetamine (MDMA)), chemotherapeutic agents, antibiotics (e.g., streptomycin, cephalosporin, etc.), cosmetic agent (e.g., BOTOX®) or other biological agents such as those derived from a bacteria, virus, prion, fungus, or parasite (e.g., botulinum toxin). In some embodiments, the provided methods can be used for detecting, diagnosing or monitoring brain injury or damage, or likelihood of brain damage or injury, in a subject having a disease or condition associated with toxin damage, such as due to due to or associated with a toxin agent including any as described above; predicting the need for an alternative diagnostic or assessment of brain damage or injury, or likelihood of brain damage or injury, associated with such a disease or condition; selecting a subject for treatment of such a disease or condition; or can be used in association with treating a subject having or suspected of having such as disease or condition or damage.

In some embodiments, the brain injury or damage is due to other causes that may damage or affect nerve cells. In some embodiments, nerve cell damage can be associated with Multiple sclerosis, autoimmune inflammation or direct damage such as resulting in subjects with Myasthenia gravis or Guillain-Barre syndrome or due to seizure (e.g. subjects with epilepsy). In some embodiments, the provided methods can be used for detecting, diagnosing or monitoring the progression of brain injury or damage in a subject having or suspected of having nerve cell damage, such as in a subject with Multiple sclerosis, Myasthenia gravis, Guillain-Barre syndrome or other autoimmune disorder or epilepsy or otherwise suffering from or susceptible to seizure; predicting the need for an alternative diagnostic or assessment of brain damage or injury, or likelihood of brain damage or injury, associated with such a disease or condition; selecting a subject for treatment of such a disease or condition; or can be used in association with treating a subject having or suspected of having such a disease or condition or damage.

Thus, individuals or subjects who benefit from the provided methods are those suspected of having or at risk for brain injury or damage, including those having or at risk of developing abnormal neurological conditions, such as victims of brain injury caused by traumatic insults (e.g., gunshot wounds, automobile accidents, sports accidents or related injuries, concussive injuries, shaken baby syndrome), ischemic events (e.g., stroke, cerebral hemorrhage, cardiac arrest), neurodegenerative disorders (such as Alzheimer's, Huntington's, and Parkinson's diseases; prion-related disease; other forms of dementia), epilepsy, substance abuse (e.g., from amphetamines, Ecstasy/MDMA, or ethanol), and peripheral nervous system pathologies such as diabetic neuropathy, chemotherapy-induced neuropathy and neuropathic pain. For example, the provided methods can be used to detect, diagnose, or monitor brain damage, or likelihood of brain damage, associated with certain diseases or conditions; to predict the need for an alternative diagnostic or assessment of the brain damage, or likelihood of brain damage, associated with such certain diseases or conditions, selecting a subject for treatment of a certain disease or condition, and/or can be used in association with treating a subject that has or is suspected of having a disease or condition, wherein such diseases and conditions include, but are not limited to, traumatic brain injury, stroke, Alzheimer's disease, epilepsy, hypoxic ischemic encephalopathy (HIE), chronic traumatic encephalopathy (CTE), autoimmune disease (e.g., myasthenia gravis, Guillain-Barre syndrome, etc.), multiple sclerosis, seizures, epilepsy, neural disorders, brain damage, neural damage due to drug or alcohol addiction, or other diseases and disorders associated with the brain or nervous system, such as the central nervous system or peripheral nervous system.

In some embodiments, among the provided methods are methods of diagnosing or determining if a subject has, or is predicted as being likely to have or develop, a brain injury or damage (e.g. due to a neurological damage and/or a neurological condition, such as a traumatic brain injury or other damage or injury as described), which includes steps (a)-(c) as described above and further comprise, after determining the amount of UCH-L1 and/or GFAP in a sample, comparing the amount of UCH-L1 and/or GFAP to a respective threshold level or value, such as a predetermined threshold level. In some embodiments, the threshold level is a level that is at or about or above (e.g. a level at or about or greater than or greater than about 1.2-fold, 1.5-fold, 2-fold, 3-fold, 4-fold, 5-fold above) the amount of UCH-L1 and/or GFAP, respectively, found in the sample on average in a group of healthy or normal subjects or subjects that are not suspected of having the brain damage or injury. It is within the level of one of skill in the art to determine the threshold level for diagnosis of a brain injury or damage depending on the particular assay being used for detection and/or the particular antibody reagent or reagents being used. In some embodiments, the subject is diagnosed or determined to have, or is likely to have or develop, a brain injury or damage (e.g. traumatic brain injury or other damage or injury as described) if the amount of UCH-L1 in the sample is above the threshold level. In some embodiments, the subject is diagnosed or determined to have, or is likely to have or develop, a brain injury or damage (e.g. traumatic brain injury or other damage or injury as described) if the amount of GFAP in the sample is above the threshold level. In some embodiments, the subject is diagnosed or determined to have, or is likely to have or develop, a brain injury or damage (e.g. traumatic brain injury or other damage or injury as described) if the amount of UCH-L1 and GFAP in the sample is above the threshold level.

In some embodiments, among the provided methods are methods of identifying a subject in need of treatment and/or selecting or not selecting a therapy for a subject determined to have, or likely to have or develop, a brain injury or damage (e.g. due to a neurological damage and/or a neurological condition, such as a traumatic brain injury or other damage or injury as described), which includes steps (a)-(c) as described above and further comprises identifying the subject as in need of treatment and/or selecting a therapy for the subject if the determined amount of UCH-L1 and/or GFAP is above a threshold value for the amount of UCH-L1 and/or GFAP in the sample or identifying the subject as not in need of treatment and/or not selecting a therapy for the subject if a determined amount of UCH-L1 and/or GFAP is at or below a threshold level for the amount of UCH-L1 and/or GFAP in the sample. In some embodiments, the threshold level is a level that is at or about or above (e.g. no more than 1.2-fold, 1.5-fold or 2-fold above) the amount of UCH-L1 and/or GFAP, respectively, found in the sample on average in a group of healthy or normal subjects or subjects that are not suspected of having the brain damage or injury. It is within the level of one of skill in the art to determine the threshold level for identifying or not identifying a subject in need of treatment and/or selecting or not selecting a therapy for a subject having or suspected of having or developing a brain injury or damage depending on factors such as the particular therapy, the particular assay being used for detection and/or the particular antibody reagent or reagents being used and other factors within the level of a skilled artisan. In some embodiments, the subject is identified as in need of treatment and/or selected for therapy for a brain injury or damage (e.g. traumatic brain injury or other damage or injury as described) if the amount of UCH-L1 in the sample is above the threshold level or is identified as not in need of treatment and/or not selected for therapy if the amount of UCH-L1 in the sample is at or below the threshold level. In some embodiments, the subject is identified as in need of treatment and/or selected for therapy for a brain injury or damage (e.g. traumatic brain injury or other damage or injury as described) if the amount of GFAP in the sample is above the threshold level or the subject is identified as not in need of treatment and/or is not selected for therapy if the amount of GFAP in the sample is at or below the threshold level. In some embodiments, the subject is identified as in need of treatment and/or selected for therapy for a brain injury or damage (e.g. traumatic brain injury or other damage or injury as described) if the amount of UCH-L1 and GFAP in the sample is above each of the respective threshold level or the subject is identified as not in need of treatment and/or is not selected for therapy if the amount of UCH-L1 and GFAP in the sample is at or below each of the respective threshold level.

In some embodiments, such methods can further include monitoring the progression of the disease or condition over time. In some embodiments, the above methods of determining if a subject has, or is predicted as being likely to have or develop, a brain injury or damage (e.g. due to a neurological damage and/or a neurological condition, such as a traumatic brain injury or other damage or injury as described), can be repeated periodically after the first test on a sample from a subject obtained after the initial injury or damage or likelihood or potential of the initial injury or damage. In some embodiments, the method is repeated from a sample collected within 24 hours after the first test or previous test, within 48 hours of the first test or previous test, within 72 hours of the first test or previous test, within 96 hours of the first test or previous test, within one week of the first test or previous test, within 2 weeks of the first test or previous test, within 3 weeks of the first test or previous test, within one month of the first test or previous test, within 6 months of the first test or previous test or within 1 year of the first test or previous test. In some embodiments, after the one or more subsequent tests the subject is diagnosed or determined to have a brain injury or damage. In some embodiments, after the one or more subsequent tests, the subject is diagnosed or determined to no longer be at risk of a brain injury or damage. In some embodiments, after the one or more subsequent tests the subject is selected as in need of treatment or is selected for therapy of the brain injury or damage. In some embodiments, after the one or more subsequent tests, the subjected is identified as no longer being in need of treatment or therapy for the brain injury or damage.

In some embodiments, any of the above methods further comprises a step of administering a therapeutically effective amount of one or more therapeutic agent to a subject to treat the brain damage or injury (e.g. traumatic brain injury or other damage or injury as described). For example, in some embodiments, if a subject is selected as in need of treatment or is selected for therapy of the brain damage or injury (e.g. due to a neurological damage and/or a neurological condition, such as a traumatic brain injury or other damage or injury as described), the method further comprises treating the subject for the brain injury or damage. Thus, also provided are methods for treating neurological damage and/or a neurological condition in a subject which includes steps (a)-(c) above and further comprises administering a therapeutically effective amount of one or more therapeutic agent to treat the brain damage or injury (e.g. due to a neurological damage and/or a neurological condition, such as a traumatic brain injury or other damage or injury as described).

In some embodiments, the therapeutic agent can be selected based on the diagnosis of the neurological damage and/or neurological condition. In some embodiments, the therapeutic agent is an N-methyl-D-aspartate (NMDA) receptor antagonist, a sodium channel antagonist, a nitric oxide synthase (NOS) inhibitor, a glycine site antagonist, a potassium channel opener, an AMPA/kainate receptor antagonist, a calcium channel antagonist, a GABA-A receptor modulator, an anti-inflammatory agent or a combination thereof.

In some aspects, among the provided methods are methods of predicting the likelihood of an individual needing or not needing a neuroimaging diagnostic test, such as a CT (CAT) scan or MRI, for assessing the presence or severity of a brain injury or damage (e.g. due to a neurological damage and/or a neurological condition, such as a traumatic brain injury or other damage or injury as described). In some embodiments, it is found that the provided methods correlate to or are in agreement with more complex methods, such as CT scans, for assessing or determining whether a subject has or is likely to have or develop a brain injury. However, abnormal CT scans in general are useful for detecting severe brain damage or injury (e.g. severe traumatic brain injury), but are not always suitable or reliable for detecting mild or moderate brain injury (e.g. mild or moderate traumatic brain injury). Further, in some aspects, neuroimaging methods, such as CT scans, are complex, expensive and not readily available at the time or near the time of damage or injury. Many neuroimaging methods, including CT scans, have the potential of causing ionizing radiation exposure, which can be a problem if overused. Thus, compared to these other methods, the provided methods are quantitative, obtained more rapidly, safer and are readily available and accessible to subjects including outside of urgent care or an emergency room and are less expensive. Consequently, the provided methods can avoid the need for the more complex and expensive diagnostic methods when such methods are predicted not to be necessary.

In some embodiments, the provided methods of predicting the likelihood of an individual needing or not needing a neuroimaging diagnostic test includes steps (a)-(c) as described above and further comprises, after determining the amount of UCH-L1 and/or GFAP in a sample, predicting or determining the subject needs a neuroimaging diagnostic test (e.g. a CT scan) if the determined amount of UCH-L1 and/or GFAP is above a threshold value or predicting or determining the subject does not need a neuroimaging diagnostic test (e.g. CT scan) if the determined amount of UCH-L1 and/or GFAP is at or below a threshold value. In some embodiments, the subject is predicted or determined to need a neuroimaging diagnostic test (e.g. CT scan) if the determined amount of UCH-L1 is above a threshold level or is predicted or determined not to need a neuroimaging diagnostic test (e.g. CT scan) if the determined amount of UCH-L1 is at or below a threshold level. In some embodiments, the subject is predicted or determined to need a neuroimaging diagnostic test (e.g. CT scan) if the determined amount of GFAP is above a threshold level or is predicted or determined not to need a neuroimaging diagnostic test (e.g. CT scan) if the determined amount of GFAP is at or below a threshold level. In some embodiments, the subject is predicted or determined to need a neuroimaging diagnostic test (e.g. CT scan) if the determined amount of UCH-L1 and GFAP is each above a respective threshold level or is predicted or determined not to need a neuroimaging diagnostic test (e.g. CT scan) if the determined amount of UCH-L1 and GFAP is each at or below a respective threshold level.

Neuroimaging techniques are well known in the art and such techniques are contemplated for use in the methods herein. Neuroimaging techniques contemplated herein include, but are not limited to, computed tomography (CT), diffuse optical imaging (DOI), event-related optical signal (EROS) imaging, magnetic resonance imaging (MRI), functional magnetic resonance imaging (fMRI), magnetoencephalography (MEG), positron emission tomography (PET), single-photon emission computed tomography (SPECT), and cranial ultrasound. In some embodiments of the methods herein, the neuroimaging is by computed tomography (CT). In some embodiments of the methods herein, the neuroimaging is by magnetic resonance imaging (MRI).

In some embodiments, for each of the above methods, the threshold level or value is one that is a cut-off at which there is a good predictive value (e.g. accuracy, sensitivity, specificity and/or AUC) of the outcome, e.g. that brain damage has or is likely to occur, that the subject is in need of or likely in need of further neuroimaging (e.g. CT scan) and/or that the subject is in need of or likely in need of a therapeutic intervention. In some cases, such threshold level or value can be or is predetermined or known prior to performing the method, such as from a plurality of subjects previously assessed for the correlation of the biomarker or, individually, each of the UCH-L1 and GFAP biomarkers, to the presence of a brain damage or injury (e.g. the presence of traumatic brain injury, such as mild or moderate traumatic brain damage or injury), the need for neuroimaging and/or the need for a therapeutic intervention.

In some embodiments, the threshold level or value is based on a receiver operating characteristic (ROC) curve of the biomarker or each biomarker (UCH-L1 and/or GFAP) in a population of subjects having or suspected of having a brain injury or damage. In some aspects, the threshold value is an amount or concentration of the biomarker being assessed, detected or measured in the subject. In some cases, the threshold value is determined by the Youden Index, which, in some cases, is the value in which sensitivity and specificity are maximal. In some embodiments, other methods known to a skilled artisan for determining a threshold or cut-off at which there is a good predictive value (e.g. accuracy, sensitivity, specificity and/or AUC) also can be used for determining or setting the threshold value.

In some embodiments, the threshold level of GFAP or UCH-L1, or the combination of threshold values of GFAP and UCH-L1, in any of the above methods is based on a value or values that has been predetermined or selected to or does provide a sensitivity or net sensitivity of greater than 0.50, greater than 0.60, greater than 0.70, greater than 0.80, greater than 0.90 or greater than 0.95. In some cases, the threshold level of GFAP or UCH-L1, or the combination of threshold values of GFAP and UCH-L1, in any of the above methods is based on a value or values that has been predetermined or selected to or does provide a specificity or net specificity of greater than 0.25, greater than 0.30, greater than 0.40, greater than 0.50, greater than 0.60, greater than 0.70, greater than 0.80, greater than 0.90 or greater than 0.95. In some aspects, the threshold value, or the combination of the threshold values for each biomarker, has been selected to or does provide an area under the curve (AUC), such as in a ROC analysis, of greater than or greater than about 0.65, greater than or greater than about 0.70, greater than or greater than about 0.75, 0.80, greater than or greater than about 0.85, greater than or greater than about 0.90 or greater than or greater than about 0.95.

In some aspects of any of the above methods, the threshold level or amount of GFAP is or is about 10 pg/mL, is or is about 20 pg/mL, is or is about 30 pg/mL, is or is about 40 pg/mL, is or is about 50 pg/ml, is or is about 60 pg/mL, is or is about 70 pg/mL, is or is about 80 pg/mL, is or is about 90 pg/mL, is or is about 100 pg/mL, is or is about 150 pg/mL, is or is about 200 pg/mL, is or is about 250 pg/mL or is or is about 300 pg/mL.

In some aspects of any of the above methods, the threshold level or amount of UCH-L1 is or is about 30 pg/mL, is or is about 40 mg/mL, is or is about 60 pg/mL, is or is about 80 pg/mL, is or is about 100 pg/mL, is or is about 150 pg/mL, is or is about 200 pg/mL, is or is about 250 pg/mL, is or is about 300 pg/mL, is or is about 400 pg/mL or is or is about 500 pg/mL.

In some aspects of any of the above methods, the threshold level or amount of GFAP is or is about 0.2-fold, 0.5-fold, 1-fold, 1.2-fold, 1.5-fold, 2-fold, 2.5-fold, 3.0-fold, 3.5-fold, 4.0-fold, 4.5-fold, 5.0-fold, 6.0-fold, 7.0-fold, 8.0-fold, 9.0-fold or 10.0-fold at or above the amount of GFAP found in a reference sample. In some embodiments, the reference sample is from a healthy or normal subject that is not suspected of having the brain damage or injury. In some embodiments, the reference sample is an average of samples from a group of healthy or normal subjects that are not suspected of having the brain damage or injury.

In some aspects of any of the above methods, the threshold level or amount of UCH-L1 is or is about 0.2-fold, 0.5-fold, 1-fold, 1.2-fold, 1.5-fold, 2-fold, 2.5-fold, 3.0-fold, 3.5-fold, 4.0-fold, 4.5-fold, 5.0-fold, 6.0-fold, 7.0-fold, 8.0-fold, 9.0-fold or 10.0-fold at or above the amount of UCH-L1 found in a reference sample. In some embodiments, the reference sample is from a healthy or normal subject that is not suspected of having the brain damage or injury. In some embodiments, the reference sample is an average of samples from a group of healthy or normal subjects that are not suspected of having the brain damage or injury.

In some aspects of any of the above methods, the threshold level or amount of GFAP is or is about 5%, is or is about 10%, is or is about 20%, is or is about 30%, is or is about 40%, is or is about 50%, is or is about 60%, is or is about 70%, is or is about 80%, is or is about 90%, or is or is about 95% at or above the amount of GFAP found in a reference sample. In some embodiments, the reference sample is from a healthy or normal subject that is not suspected of having the brain damage or injury. In some embodiments, the reference sample is an average of samples from a group of healthy or normal subjects that are not suspected of having the brain damage or injury.

In some aspects of any of the above methods, the threshold level or amount of UCH-L1 is or is about 5%, is or is about 10%, is or is about 20%, is or is about 30%, is or is about 40%, is or is about 50%, is or is about 60%, is or is about 70%, is or is about 80%, is or is about 90%, or is or is about 95% at or above the amount of UCH-L1 found in a reference sample. In some embodiments, the reference sample is from a healthy or normal subject that is not suspected of having the brain damage or injury. In some embodiments, the reference sample is an average of samples from a group of healthy or normal subjects that are not suspected of having the brain damage or injury.

The particular threshold value for a particular brain injury or damage can be empirically determined by a skilled artisan. In some embodiments, the amount of UCH-L1 in the sample of about 200 pg/ml or less and/or the amount of GFAP in the sample of about 70 pg/ml or less indicates the individual does not require neuroimaging (e.g. CT scan). In some embodiments, the amount of UCH-L1 in the sample of about 201 pg/ml or more and/or the amount of GFAP in the sample of about 71 pg/ml or more indicates the individual requires neuroimaging (e.g. CT scan).

In some embodiments, among the provided methods are methods of monitoring the success of a therapy in a subject treated for a brain injury or damage or likelihood of a brain injury (e.g. due to a neurological damage and/or a neurological condition, such as a traumatic brain injury or other damage or injury as described). In some embodiments, the provided methods include, after treating a subject for a brain injury or damage or likelihood of brain injury or damage, repeating steps (a)-(c) as described above. In some embodiments, the methods of monitoring the success of therapy further comprises comparing the amount of UCH-L1 and/or GFAP in the sample to the amount of UCH-L1 and/or GFAP in a sample after the first test or after the previous test and if the amount of UCH-L1 and/or GFAP is the same or greater than the amount in the sample from the first test or previous test the therapy or treatment is not effective or if the amount of UCH-L1 and/or GFAP is less than the amount in the sample from the first test or previous test the therapy or treatment is effective. In some embodiments, the methods of monitoring the success of therapy further comprises comparing the amount of UCH-L1 in the sample to the amount of UCH-L1 in a sample after the first test or after the previous test and if the amount of UCH-L1 is the same or greater than the amount in the sample from the first test or previous test the therapy or treatment is not effective or if the amount of UCH-L1 is less than the amount in the sample from the first test or previous test the therapy or treatment is effective. In some embodiments, the methods of monitoring the success of therapy further comprises comparing the amount of GFAP in the sample to the amount of GFAP in a sample after the first test or after the previous test and if the amount of GFAP is the same or greater than the amount in the sample from the first test or previous test the therapy or treatment is not effective or if the amount of GFAP is less than the amount in the sample from the first test or previous test the therapy or treatment is effective. In some embodiments, the methods of monitoring the success of therapy further comprises comparing the amount of UCH-L1 and GFAP in the sample to the amount of UCH-L1 and GFAP in a sample after the first test or after the previous test and if the amount of UCH-L1 and GFAP is the same or greater than the amount in the sample from the first test or previous test the therapy or treatment is not effective or if the amount of UCH-L1 and GFAP is less than the amount in the sample from the first test or previous test the therapy or treatment is effective.

In some embodiments, if the method of treating the subject is determined to not be effective, the method can further comprise altering the treatment of the brain damage or injury (e.g. due to a neurological damage and/or a neurological condition, such as a traumatic brain injury or other damage or injury as described). In some embodiments, the method comprises increasing the amount (e.g. dose and/or frequency) of one or more of a therapeutic agent that is administered to the subject, maintaining the amount (e.g. dose and/or frequency) of one or more of a therapeutic agent that is administered to the subject, or altering the treatment of therapy for threating the brain damage or injury (e.g. due to a neurological damage and/or a neurological condition, such as a traumatic brain injury or other damage or injury as described).

In some embodiments, if the method of treating the subject is determined to be effective, the method can further comprise altering the treatment of the brain damage or injury (e.g. due to a neurological damage and/or a neurological condition, such as a traumatic brain injury or other damage or injury as described). In some embodiments, the method comprises decreasing the amount (e.g. dose and/or frequency) of one or more of a therapeutic agent that is administered to the subject, discontinuing treatment with the particular therapeutic agent or altering the treatment of therapy for threating the brain damage or injury (e.g. due to a neurological damage and/or a neurological condition, such as a traumatic brain injury or other damage or injury as described).

VI. Kits, Articles of Manufacture and Systems

Provided herein are articles of manufacture or kits that comprise an anti-UCH-L1 antibody, an anti-GFAP antibody or a combination of one or more anti-UCH-L1 and/or anti-GFAP antibodies such as those described herein. In some embodiments, the kits are compatible for operation in connection with a system or a device for detecting UCH-L1 and/or GFAP in one or more samples in accord with any of the provided methods. In some embodiments, the kit further includes the device. In some embodiments, the kit can be compatible with a device or system, or include a device or system, for detecting or assessing GFAP and/or UCH-L1, for example, for assessing a neurological or brain damage or injury and/or a neurological condition in an individual, such as in accord with any of the provided methods.

In some embodiments, in addition to containing one or more anti-UCH-L1 and/or anti-GFAP antibody as described, the kits further contain reagents for performing the methods. Kits can optionally include one or more components such as instructions for use, devices and additional reagents (e.g., sterilized water or saline solutions for dilution of the compositions and/or reconstitution of lyophilized protein), and components, such as tubes, containers and syringes for practice of the methods. In some embodiments, the kits can further contain reagents for collection of samples, preparation and processing of samples, and/or reagents for quantitating the amount of UCH-L1 or GFAP in a sample, such as, but not limited to, detection reagents, such as antibodies, buffers, substrates for enzymatic staining, chromagens or other materials, such as slides, containers, microtiter plates, and optionally, instructions for performing the methods. Those of skill in the art will recognize many other possible containers and plates and reagents that can be used in accord with the provided methods.

In some embodiments, the kit or article of manufacturer comprises reagents or components for carrying out any of the provided methods. In some embodiments, the article of manufacture or kit comprises a solid support, including a solid support formed of glass (e.g., controlled pore glass), polysaccharides (e.g., agarose), polyacrylamides, polystyrene, polyvinyl alcohol, nitrocellulose, cellulose, nylon, silicones and other material well known in the art that is used in a solid support for direct or indirect attachment of an antibody. Solid supports included in the articles of manufacture or kits provided herein include, but are not limited to, a bead, column (e.g., chromatography column, etc.), an array (e.g., microarray, nanoarray, etc.), an assay plate, a cartridge, a stick, a filter, a strip or any other solid support described herein. In some embodiments, the article of manufacture or kit comprises instructions for attaching one or more anti-UCH-L1 antibodies and/or one or more anti-GFAP antibodies to the solid support. In some embodiments, the article of manufacture or kit comprises one or more anti-UCH-L1 antibodies and/or one or more anti-GFAP antibodies attached directly or indirectly to the solid support.

In some embodiments, the article of manufacture or kit comprises one or more reagent or other materials desirable from a commercial, therapeutic, and user standpoint including secondary antibodies, affinity labels, capture reagents, buffers, diluents, signal detection agents, filters, needles, syringes, capillary tubes, and package inserts with instructions for use.

In some embodiments, kits also can contain control samples representing a standard or reference for measuring UCH-L1 and/or GFAP, such as for determining or quantitating the amount of protein in a test samples. In some embodiments, the standard or reference can be a recombinant UCH-L1 or GFAP protein or an isolated or purified native UCH-L1 or GFAP protein or composition obtained from a tissue or other sample. In some examples, the kit contains a pair of two or more anti-UCH-L1 antibodies and a UCH-L1 standard or reference and/or a pair of two or more anti-GFAP antibodies and a GFAP standard or reference.

In some embodiments, the kit provides for qualitative and/or quantitative determination of the amount of UCH-L1 in a sample (e.g., human serum). In some embodiments, the amount of UCH-L1 qualitatively and/or quantitatively that is determined is from about 80 pg/mL to about 2560 pg/mL. In some embodiments, the kit provides for qualitative and/or quantitative determination of the amount of GFAP in a sample (e.g., human serum). In some embodiments, the amount of GFAP qualitatively and/or quantitatively that is determined is from about 10 pg/mL to about 320 pg/mL.

In some embodiments, the kits can be provided as articles of manufacture that include packing materials for the packaging of the antibodies or compositions thereof or the one or more additional reagents or components. For example, the kits can contain containers, bottles, tubes, vial and any packaging material suitable for separating or organizing the components of the kit.

In some embodiments, the kit includes one or more containers. Suitable containers include, for example, bottles, vials (e.g., dual chamber vials), syringes (such as single or dual chamber syringes) and test tubes. The one or more containers may be formed from a variety of materials such as glass or plastic. The one or more containers hold a composition comprising an antibody or other reagents for use in the methods. The article of manufacture or kit herein may comprise the antibodies or reagents in separate containers or in the same container. In one example, the article of manufacture or kit may comprise a container comprising a composition comprising a set of two or more anti-UCH-L1 antibodies. In other examples, if two or more antibodies or reagents are provided in the same container, each component or reagent is separated from one or more other component in the container, such as by a divider. As another example, the article of manufacture or kit may comprise a first container comprising a composition comprising a first anti-UCH-L1 antibody or set of antibodies and a second container comprising a composition comprising a second anti-UCH-L1 antibody or set of antibodies. In some embodiments, the article of manufacture or kit may comprise a first container comprising a composition comprising a first anti-GFAP antibody or set of antibodies and a second container comprising a composition comprising a second anti-GFAP antibody or set of antibodies. In some embodiments, the article of manufacture or kit may comprise any multitude of containers comprising any combination of anti-UCH-L1 antibodies and/or anti-GFAP antibodies, such as the combinations described herein (e.g., combinations of compositions). In some embodiments, the one or more containers holding the composition may be a single-use vial or a multi-use vial, which, in some cases, may allow for repeat use of the reconstituted composition.

In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

In some embodiments, the kit can, optionally, include instructions. Instructions typically include a tangible expression describing the antibodies and, optionally, other components included in the kit, and methods for using the antibodies to detect UCH-L1 and/or GFAP in a sample. In some embodiments, the instructions are provided as a label or a package insert, which is on or associated with the container. In some embodiments, the instructions may indicate directions for reconstitution and/or use of the composition. In some embodiments, the instructions provide directions for use of the one or more anti-UCH-L1 antibody in methods of in vitro detection of UCH-L1 in an individual. In some embodiments, the article of manufacture or kit comprises instructions for the use of the one or more anti-GFAP antibody in methods of in vitro detection of GFAP in an individual. In some embodiments, the article of manufacture or kit comprises instructions for the use of a combination of antibodies described herein such as one or more anti-UCH-L1 antibody and/or one or more anti-GFAP antibody in methods of in vitro detection of UCH-L1 and/or GFAP in an individual. In some embodiments, the instructions specify that the individual is human. In some embodiments, the instructions specify that the individual has or is suspected of having a neurological or brain damage or injury, such as any described above. In some embodiments, the instructions specify the individual has, is suspected of having or is predicted to have a neurological condition. In some embodiments, the neurological condition is mild traumatic brain injury (MTBI). In some embodiments, the instructions, such as the label or package insert, may further indicate that the composition is useful or intended for in vitro methods of detection of UCH-L1 and/or GFAP, such as in connection with any of the methods described herein.

In some embodiments, the kit or article of manufacture is suitable for use or is for use with a device (also called an instrument) for detecting the bound antibodies in accord with the provided methods. In some embodiments, the device is one that can be used in association with the provided antibodies and reagents to permit protein detection using one or more techniques well known in the art such as, but not limited to, spectrophotometry, high performance liquid chromatography (HPLC), immunoassays such as enzyme-linked immunosorbent assay (ELISA), western blot, automated imaging, immunohistochemistry, flow cytometry, high-throughput screening of an array such as a microarray or nanoarray and surface plasmon resonance. In some embodiments, the device comprises a system for reading an assay output, such as comprises an automated cellular imaging system (ACIS), fluorometer, luminometer, or spectrophotometer for assay detection. In some embodiments, the kit or article of manufacture includes the device.

In some embodiments, the device comprises a solid support such as a solid support described herein. In some embodiments, a solid support may be or comprise a bead, column, an array, a microwell, an assay plate, a cartridge, a stick, a filter, or a strip. In some embodiments, the solid support is inserted into the device, attached to the device and/or held by the device, for example, when the device is operating for detection of one or more protein biomarkers (e.g. UCH-L1 and/or GFAP) in a sample. In some embodiments, the solid support, e.g. one or more microwells, may contain at least an immobilized binding agent, for example a capture reagent, such as an antibody, e.g. a first antibody as described herein for capturing the protein. In some embodiments, the solid support is configured in the device to receive a sample loaded into the device. In some embodiments, the sample is added to the solid support prior to its insertion or attachment of the solid support with or into the device. In some embodiments, the device is further configured to add solution from a dispenser into the solid support and/or remove solution from the solid support. In some embodiments, the solution is or comprises a binding agent, for example a detection reagent, such as an antibody, e.g. a second antibody as described herein for detecting the protein. In some embodiments, the solution is or comprises a wash solution. In some embodiments, the solution is or comprises a substrate or stop solution. In some embodiments, the device is configured to hold one or more of the above solutions and to individually dispense each solution at an appropriate time into the solid support held or inserted in the device.

In some embodiments, a device provided herein (e.g., a device comprising a solid support described herein) is useful for qualitatively and/or quantitatively determining the amount of target antigen (e.g., UCH-L1 or GFAP) bound by the antibody (e.g., anti-UCH-L1 antibody or anti-GFAP antibody). In some embodiments, the amount of UCH-L1 qualitatively and/or quantitatively determined is from about 80 pg/mL to about 2560 pg/mL. In some embodiments, the amount of GFAP qualitatively and/or quantitatively determined is from about 10 pg/mL to about 320 pg/mL.

In some embodiments, the device automates or partially automates an assay method that detects a particular biomarker or biomarkers, such as UCH-L1 and/or GFAP. In some embodiments, actions that may be automated by the instrument include, but are not limited to, mixing or agitation of a sample during an incubation phase, dispensing or adding one or more solutions, washing of a sample, controlling incubation times, optical illumination and/or reading of an assay, and calculation of a biomarker (e.g. UCH-L1 and/or GFAP) amount in the sample. In some embodiments, the timing of any of the above automated steps can be preset or predetermined, such as to assay specific guidelines.

In some embodiments, the device is a portable device such as a handheld device. In some embodiments, the device is a stationary device. In some embodiments, the device may be the size of a desktop printer, or smaller, and may be suitable for use in a physician's office, hospital lab, or residential dwelling. The device may be manually operated or automatically operated. In some embodiments, the device is an electronic device.

In some embodiments, the device comprises a computing system or processor. In some embodiments, the computing system comprises one or more computer executable logic (e.g., one or more computer program) that is recorded on a computer readable medium. For example, the computing system or processor is configured to execute some or all of the following functions: (i) processing a signal representative of the detected protein, (ii) comparing data as detected from the sample with a reference standard (iii) calculating an amount or concentration of the protein biomarker in the sample; and/or (iv) displaying or outputting a value representative of the calculated amount or concentration of the protein. The computing system can be configured to perform any one of the methods described herein.

In some embodiments, the calculated amount can be used to determine a neurological condition and/or neurological damage outcome, e.g. presence, absence or likelihood of having or developing a brain damage or injury as described. In some embodiments, the determining the presence, absence or likelihood of having or developing a brain injury or damage comprises comparing the amount or concentration of protein to a threshold or cutoff value as described herein. In some embodiments, the comparison to the threshold is performed by a computer. In some embodiments, the comparison to a threshold or cutoff is performed by an individual.

The computer executable logic can work in any computer that may be any of a variety of types of general-purpose computers such as a personal computer, network server, workstation, handheld device or other computer platform now or later developed. In some embodiments, a computing system is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

In some embodiments, the system is a device such as a rapid detection device or rapid diagnostic device. In some embodiments, the device is configured or automated to determine the amount of a protein in a sample within or within about 1 minutes, within or within about 2 minutes, within or within about 4 minutes, within or within about 8 minutes, within or within about 15 minutes, within or within about 30 minutes, within or within about 1 hour or within or within about 2 hours of the sample being loaded, applied or added into the device. Non-limiting examples of a rapid detection device include those adapted or based on a device described in WO2011077333; WO2015143387; US20100198142; US20120178186; US20120168305; US20140370583; U.S. Pat. Nos. 7,291,497; 7,419,821; 7,682,833; 7,723,099; 7,910,352; 8,017,382; 8,168,439; 8,309,364; and 9,023,651. Suitable devices for use in the articles of manufacture or kits provided herein include commercially available devices such as, but not limited to, i-STAT® handheld (Abbott), Minicare 1-20 (Phillips) and similar handheld devices.

VII. Exemplary Embodiments

Among the embodiments provided herein are:
1. An antibody or antigen-binding fragment thereof that specifically binds to a human ubiquitin c-terminal hydrolase L1 (UCH-L1), wherein the antibody or antigen-binding fragment comprises a heavy chain variable region comprising an amino acid sequence having at least 85% identity to an amino acid sequence selected from any one of SEQ ID NOs:51-63; and/or a light chain variable region comprising an amino acid sequence having at least 85% identity to an amino acid sequence selected from any one of SEQ ID NOs:64-76.
2. The antibody or antigen-binding fragment of embodiment 1, wherein the heavy chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs:51-63; or has the amino acid sequence selected from any one of SEQ ID NOs: 51-63.
3. The antibody or antigen-binding fragment of embodiment 1 or embodiment 2, wherein the light chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from SEQ ID NOs:64-76 or has the amino acid sequence selected from any one of SEQ ID NOs: 64-76.
4. The antibody or antigen-binding fragment of any one of embodiments 1-3, wherein:
    the heavy chain variable region comprises: (i) a CDR-H1 comprising the amino acid sequence selected from SEQ ID NOs:1-8; (ii) a CDR-H2 comprising the amino acid sequence selected from SEQ ID NOs:9-19; and (iii) a CDR-H3 comprising the amino acid sequence selected from SEQ ID NOs:20-27; and/or the light chain variable region comprises: (i) a CDR-L1 comprising the amino acid sequence selected from SEQ ID NOs:28-36; (ii) a CDR-L2 comprising the amino acid sequence selected from SEQ ID NOs:37-44; and (iii) a CDR-L3 comprising the amino acid sequence selected from SEQ ID NOs:45-50.

5. The antibody or antigen-binding fragment of any one of embodiments 1-4, wherein:
   the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:51-63; and/or
   the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:64-76.

6. An antibody or antigen-binding fragment that specifically binds to a human ubiquitin c-terminal hydrolase L1 (UCH-L1), wherein the heavy chain variable region comprises an amino acid sequence having at least 85% identity to an amino acid sequence selected from any one of SEQ ID NOs:53-62; and/or a light chain variable region comprising an amino acid sequence having at least 85% identity to an amino acid sequence selected from any one of SEQ ID NOs:66-75.

7. The antibody or antigen-binding fragment of embodiment 6, wherein:
   the heavy chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs: 53-62 or comprises the amino acid sequence set forth in any of SEQ ID NOs: 53-62; and/or
   the light chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs: 66-75 or comprises the light chain variable region comprises the amino acid sequence set forth in any one of SEQ ID NOs: 66-75.

8. The antibody or antigen-binding fragment of embodiment 6 or embodiment 7, wherein:
   (1) the heavy chain variable region comprises: (i) a CDR-H1 comprising the amino acid sequence selected from SEQ ID NOs:3-8; (ii) a CDR-H2 comprising the amino acid sequence selected from SEQ ID NOs:11-18; and (iii) a CDR-H3 comprising the amino acid sequence selected from SEQ ID NOs:20-27; and/or the light chain variable region comprises: (i) a CDR-L1 comprising the amino acid sequence selected from SEQ ID NOs:30-36; (ii) a CDR-L2 comprising the amino acid sequence selected from SEQ ID NOs:37-44; and (iii) a CDR-L3 comprising the amino acid sequence selected from SEQ ID NOs:45-49; or (2) the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:53-62 and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:66-75.

9. An antibody or antigen-binding fragment thereof that specifically binds to a human ubiquitin c-terminal hydrolase L1 (UCH-L1), wherein the antibody or antigen-binding fragment comprises a heavy chain variable region and a light chain variable region, wherein:
   the heavy chain variable region comprises: (i) a CDR-H1 comprising the amino acid sequence selected from SEQ ID NOs:1-8; (ii) a CDR-H2 comprising the amino acid sequence selected from SEQ ID NOs:9-18; and (iii) a CDR-H3 comprising the amino acid sequence selected from SEQ ID NOs:20-27; and/or
   wherein the light chain variable region comprises: (i) a CDR-L1 comprising the amino acid sequence selected from SEQ ID NOs:28-36; (ii) a CDR-L2 comprising the amino acid sequence selected from SEQ ID NOs:37-44; and (iii) a CDR-L3 comprising the amino acid sequence selected from SEQ ID NOs:45-49.

10. The antibody or antigen-binding fragment of any one of embodiments 1-5 and 9, wherein the antibody or antigen-binding fragment comprises:
    (a) a heavy chain variable region comprising CDR-H1, CDR-H2 and CDR-H3 amino acid sequences of SEQ ID NO:1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively;
    (b) a heavy chain variable region comprising CDR-H1, CDR-H2 and CDR-H3 amino acid sequences of SEQ ID NO:2, SEQ ID NO:10, SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively;
    (c) a heavy chain variable region comprising CDR-H1, CDR-H2 and CDR-H3 amino acid sequences of SEQ ID NO:3, SEQ ID NO: 11 and SEQ ID NO:20, respectively and/or a light chain variable region comprising CDR-L1, CDR-L2 and CDR-L3 amino acid sequences of SEQ ID NO:30, SEQ ID NO:37 and SEQ ID NO:45, respectively;
    (d) a heavy chain variable region comprising CDR-H1, CDR-H2 and CDR-H3 amino acid sequences of SEQ ID NO:4, SEQ ID NO: 12 and SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively;
    (e) a heavy chain variable region comprising CDR-H1, CDR-H2 and CDR-H3 amino acid sequences of SEQ ID NO:5, SEQ ID NO:13 and SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively;
(f) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:33, SEQ ID NO:40, SEQ ID NO:48, respectively;
(g) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:34, SEQ ID NO:41 and SEQ ID NO:48, respectively;
(h) a heavy chain variable region comprising CDR-H1, CDR-H2 and CDR-H3 amino acid sequences of SEQ ID NO:6, SEQ ID NO:15 and SEQ ID NO:24, respectively and/or a light chain variable region comprising CDR-L1, CDR-L2 and CDR-L3 amino acid sequences of SEQ ID NO:34, SEQ ID NO:42 and SEQ ID NO:48, respectively;
(i) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:35, SEQ ID NO:41 and SEQ ID NO:48, respectively;
(j) a heavy chain variable region comprising CDR-H1, CDR-H2 and CDR-H3 amino acid sequences of SEQ ID NO:6, SEQ ID NO:16 and SEQ ID NO:25, respectively and/or a light chain variable region comprising CDR-L1, CDR-L2 and CDR-L3 amino acid sequences of SEQ ID NO:34, SEQ ID NO:42 and SEQ ID NO:48, respectively;
(k) a heavy chain variable region comprising CDR-H1, CDR-H2 and CDR-H3 amino acid sequences of SEQ ID NO:7, SEQ ID NO:17 and SEQ ID NO:26, respectively and/or a light chain variable region comprising CDR-L1, CDR-L2 and CDR-L3 amino acid sequences of SEQ ID NO:36, SEQ ID NO:43 and SEQ ID NO:49, respectively;
(l) a heavy chain variable region comprising CDR-H1, CDR-H2 and CDR-H3 amino acid sequences of SEQ ID NO:8, SEQ ID NO:18 and SEQ ID NO:27, respectively and/or a light chain variable region comprising CDR-L1, CDR-L2 and CDR-L3 amino acid sequences of SEQ ID NO:36, SEQ ID NO:44 and SEQ ID NO:49, respectively; or
(m) a heavy chain variable region comprising CDR-H1, CDR-H2 and CDR-H3 amino acid sequences of SEQ ID NO:1, SEQ ID NO:19 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:50, respectively.

11. The antibody or antigen-binding fragment of any one of embodiments 1-5, 9 and 10, wherein the antibody or antigen-binding fragment comprises:
(a) a heavy chain variable region comprising the amino acid sequence of SEQ ID NO:51 or an amino acid sequence having at least 90% identity to an amino acid sequence of SEQ ID NO:51; and/or a light chain variable region comprising the amino acid sequence of SEQ ID NO:64 or an amino acid sequence having at least 90% identity to the amino acid sequence of SEQ ID NO:64;
(b) a heavy chain variable region comprising the amino acid sequence of SEQ ID NO:52 or an amino acid sequence having at least 90% identity to an amino acid sequence of SEQ ID NO:52; and/or a light chain variable region comprising the amino acid sequence of SEQ ID NO: 65 or an amino acid sequence having at least 90% identity to an amino acid sequence of SEQ ID NO:65;
(c) a heavy chain variable region comprising the amino acid sequence of SEQ ID NO: 53 or an amino acid sequence having at least 90% identity to an amino acid sequence of SEQ ID NO:53; and/or a light chain variable region comprising the amino acid sequence of SEQ ID NO: 66 or an amino acid sequence having at least 90% identity to an amino acid sequence of SEQ ID NO:66;
(d) a heavy chain variable region comprising the amino acid sequence of SEQ ID NO: 54 or an amino acid sequence having at least 90% identity to an amino acid sequence of SEQ ID NO:54; and/or a light chain variable region comprising the amino acid sequence of SEQ ID NO: 67 or an amino acid sequence having at least 90% identity to an amino acid sequence of SEQ ID NO:67;
(e) a heavy chain variable region comprising the amino acid sequence of SEQ ID NO: 55 or an amino acid sequence having at least 90% identity to an amino acid sequence of SEQ ID NO:55; and/or a light chain variable region comprising the amino acid sequence of SEQ ID NO: 68 or an amino acid sequence having at least 90% identity to an amino acid sequence of SEQ ID NO:68;
(f) a heavy chain variable region comprising the amino acid sequence of SEQ ID NO: 56 or an amino acid sequence having at least 90% identity to an amino acid sequence of SEQ ID NO:56; and/or a light chain variable region comprising the amino acid sequence of SEQ ID NO: 69 or an amino acid sequence having at least 90% identity to an amino acid sequence of SEQ ID NO:69;
(g) a heavy chain variable region comprising the amino acid sequence of SEQ ID NO: 57 or an amino acid sequence having at least 90% identity to an amino acid sequence of SEQ ID NO:57; and/or a light chain variable region comprising the amino acid sequence of SEQ ID NO: 70 or an amino acid sequence having at least 90% identity to an amino acid sequence of SEQ ID NO:70;
(h) a heavy chain variable region comprising the amino acid sequence of SEQ ID NO: 58 or an amino acid sequence having at least 90% identity to an amino acid sequence of SEQ ID NO:58; and/or a light chain variable region the amino acid sequence of SEQ ID NO: 71 or comprising an amino acid sequence having at least 90% identity to an amino acid sequence of SEQ ID NO:71;
(i) a heavy chain variable region comprising the amino acid sequence of SEQ ID NO: 59 or an amino acid sequence having at least 90% identity to an amino acid sequence of SEQ ID NO:59; and/or a light chain variable region comprising the amino acid sequence of SEQ ID NO: 72 or an amino acid sequence having at least 90% identity to an amino acid sequence of SEQ ID NO:72;

(j) a heavy chain variable region comprising the amino acid sequence of SEQ ID NO: 60 or an amino acid sequence having at least 90% identity to an amino acid sequence of SEQ ID NO:60; and/or a light chain variable region comprising the amino acid sequence of SEQ ID NO: 73 or an amino acid sequence having at least 90% identity to an amino acid sequence of SEQ ID NO:73;

(k) a heavy chain variable region comprising the amino acid sequence of SEQ ID NO: 61 or an amino acid sequence having at least 90% identity to an amino acid sequence of SEQ ID NO:61; and/or a light chain variable region comprising the amino acid sequence of SEQ ID NO: 74 or an amino acid sequence having at least 90% identity to an amino acid sequence of SEQ ID NO:74;

(l) a heavy chain variable region comprising the amino acid sequence of SEQ ID NO: 62 or an amino acid sequence having at least 90% identity to an amino acid sequence of SEQ ID NO:62; and/or a light chain variable region comprising the amino acid sequence of SEQ ID NO: 75 or an amino acid sequence having at least 90% identity to an amino acid sequence of SEQ ID NO:75; or (m) a heavy chain variable region comprising the amino acid sequence of SEQ ID NO: 63 or an amino acid sequence having at least 90% identity to an amino acid sequence of SEQ ID NO:63; and/or a light chain variable region comprising the amino acid sequence of SEQ ID NO: 76 or an amino acid sequence having at least 90% identity to an amino acid sequence of SEQ ID NO:76.

12. The antibody or antigen-binding fragment of any one of embodiments 1-5 and 9-11, wherein the antibody or antigen-binding fragment comprises:
(a) a heavy chain variable region comprising CDR-H1, CDR-H2 and CDR-H3 amino acid sequences of SEQ ID NO:1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively;
(b) a heavy chain variable region comprising CDR-H1, CDR-H2 and CDR-H3 amino acid sequences of SEQ ID NO:2, SEQ ID NO:10, SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively;
(c) a heavy chain variable region comprising CDR-H1, CDR-H2 and CDR-H3 amino acid sequences of SEQ ID NO:4, SEQ ID NO:12, SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively;
(d) a heavy chain variable region comprising CDR-H1, CDR-H2 and CDR-H3 amino acid sequences of SEQ ID NO:6, SEQ ID NO:14, SEQ ID NO:24, respectively and/or a light chain variable region comprising CDR-L1, CDR-L2 and CDR-L3 amino acid sequences of SEQ ID NO:33, SEQ ID NO:40 and SEQ ID NO:48, respectively; or
(e) a heavy chain variable region comprising CDR-H1, CDR-H2 and CDR-H3 amino acid sequences of SEQ ID NO:5, SEQ ID NO:13, SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively.

13. The antibody or antigen-binding fragment of any one of embodiments 1-5 and 9-12, wherein the antibody or antigen-binding fragment comprises:
(a) a heavy chain variable region comprising CDR-H1, CDR-H2 and CDR-H3 amino acid sequences of SEQ ID NO:1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively; or
(b) a heavy chain variable region comprising CDR-H1, CDR-H2 and CDR-H3 amino acid sequences of SEQ ID NO:2, SEQ ID NO:10, SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively.

14. The antibody or antigen-binding fragment of any one of embodiments 1-5, and 9-13, wherein the antibody or antigen-binding fragment comprises:
(a) a heavy chain variable region comprising the amino acid sequence of SEQ ID NO:51 or an amino acid sequence having at least 90% identity to an amino acid sequence of SEQ ID NO: 51; and/or a light chain variable region comprising the amino acid sequence of SEQ ID NO:64 or an amino acid sequence having at least 90% identity to the amino acid sequence of SEQ ID NO:64;
(b) a heavy chain variable region comprising the amino acid sequence of SEQ ID NO:52 or an amino acid sequence having at least 90% identity to an amino acid sequence of SEQ ID NO: 52; and/or a light chain variable region comprising the amino acid sequence of SEQ ID NO:65 or an amino acid sequence having at least 90% identity to an amino acid sequence of SEQ ID NO:65;
(c) a heavy chain variable region comprising the amino acid sequence of SEQ ID NO:54 or an amino acid sequence having at least 90% identity to an amino acid sequence of SEQ ID NO:54; and/or a light chain variable region comprising the amino acid sequence of SEQ ID NO:67 or an amino acid sequence having at least 90% identity to an amino acid sequence of SEQ ID NO:67;
(d) a heavy chain variable region comprising the amino acid sequence of SEQ ID NO:56 or an amino acid sequence having at least 90% identity to an amino acid sequence of SEQ ID NO:56; and/or a light chain variable region comprising the amino acid sequence of SEQ ID NO:69 or an amino acid sequence having at least 90% identity to an amino acid sequence of SEQ ID NO:69; or
(e) a heavy chain variable region comprising the amino acid sequence of SEQ ID NO:55 or an amino acid sequence having at least 90% identity to an amino acid sequence of SEQ ID NO:55; and/or a light chain variable region comprising the amino acid sequence of SEQ ID NO:68 or an amino acid sequence having at least 90% identity to an amino acid sequence of SEQ ID NO:68.

15. The antibody or antigen-binding fragment of any one of embodiments 1-5, and 9-14, wherein the antibody or antigen-binding fragment comprises:

(a) a heavy chain variable region comprising the amino acid sequence of SEQ ID NO:51 or an amino acid sequence having at least 90% identity to an amino acid sequence of SEQ ID NO:51; and/or a light chain variable region comprising the amino acid sequence of SEQ ID NO:64 or an amino acid sequence having at least 90% identity to the amino acid sequence of SEQ ID NO:64; or (b) a heavy chain variable region comprising the amino acid sequence of SEQ ID NO:52 or an amino acid sequence having at least 90% identity to an amino acid sequence of SEQ ID NO:52; and/or a light chain variable region comprising the amino acid sequence of SEQ ID NO: 65 or an amino acid sequence having at least 90% identity to an amino acid sequence of SEQ ID NO:65.

16. The antibody or antigen-binding fragment of any one of embodiments 1-5 and 10-14, wherein the antibody or antigen-binding fragment comprises a heavy chain variable region comprising CDR-H1, CDR-H2 and CDR-H3 amino acid sequences of SEQ ID NO: 1, SEQ ID NO:19 and SEQ ID NO:20 and/or a light chain variable region comprising CDR-L1, CDR-L2 and CDR-L3 amino acid sequences of SEQ ID NO:28, SEQ ID NO:37 and SEQ ID NO:50, respectively.

17. The antibody or antigen-binding fragment of any one of embodiments 1-5, 10-14 and 16, wherein the antibody or antigen-binding fragment comprises a heavy chain variable region comprising the amino acid sequence of SEQ ID NO: 63 or an amino acid sequence having at least 90% identity to an amino acid sequence of SEQ ID NO:63; and/or a light chain variable region comprising the amino acid sequence of SEQ ID NO: 76 or an amino acid sequence having at least 90% identity to an amino acid sequence of SEQ ID NO:76.

18. The antibody or antigen-binding fragment of any one of embodiments 1-11, wherein the antibody or antigen-binding fragment comprises:

(a) a heavy chain variable region comprising CDR-H1, CDR-H2 and CDR-H3 amino acid sequences of SEQ ID NO:3, SEQ ID NO:11 and SEQ ID NO:20, respectively and/or a light chain variable region comprising CDR-L1, CDR-L2 and CDR-L3 amino acid sequences of SEQ ID NO:30, SEQ ID NO:37 and SEQ ID NO:45, respectively;

(b) a heavy chain variable region comprising CDR-H1, CDR-H2 and CDR-H3 amino acid sequences of SEQ ID NO:4, SEQ ID NO: 12 and SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively;

(c) a heavy chain variable region comprising CDR-H1, CDR-H2 and CDR-H3 amino acid sequences of SEQ ID NO:5, SEQ ID NO:13 and SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively;

(d) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:33, SEQ ID NO:40, SEQ ID NO:48, respectively;

(e) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:34, SEQ ID NO:41 and SEQ ID NO:48, respectively;

(f) a heavy chain variable region comprising CDR-H1, CDR-H2 and CDR-H3 amino acid sequences of SEQ ID NO:6, SEQ ID NO:15 and SEQ ID NO:24, respectively and/or a light chain variable region comprising CDR-L1, CDR-L2 and CDR-L3 amino acid sequences of SEQ ID NO:34, SEQ ID NO:42 and SEQ ID NO:48, respectively;

(g) a heavy chain variable region comprising CDR-H1, CDR-H2 and CDR-H3 amino acid sequences of SEQ ID NO:6, SEQ ID NO:14 and SEQ ID NO:24, respectively and/or a light chain variable region comprising CDR-L1, CDR-L2 and CDR-L3 amino acid sequences of SEQ ID NO:35, SEQ ID NO:41 and SEQ ID NO:48, respectively;

(h) a heavy chain variable region comprising CDR-H1, CDR-H2 and CDR-H3 amino acid sequences of SEQ ID NO:6, SEQ ID NO:16 and SEQ ID NO:25, respectively and/or a light chain variable region comprising CDR-L1, CDR-L2 and CDR-L3 amino acid sequences of SEQ ID NO:34, SEQ ID NO:42 and SEQ ID NO:48, respectively;

(i) a heavy chain variable region comprising CDR-H1, CDR-H2 and CDR-H3 amino acid sequences of SEQ ID NO:7, SEQ ID NO:17 and SEQ ID NO:26, respectively and/or a light chain variable region comprising CDR-L1, CDR-L2 and CDR-L3 amino acid sequences of SEQ ID NO:36, SEQ ID NO:43 and SEQ ID NO:49, respectively; or (k) a heavy chain variable region comprising CDR-H1, CDR-H2 and CDR-H3 amino acid sequences of SEQ ID NO:8, SEQ ID NO:18 and SEQ ID NO:27, respectively and/or a light chain variable region comprising CDR-L1, CDR-L2 and CDR-L3 amino acid sequences of SEQ ID NO:36, SEQ ID NO:44 and SEQ ID NO:49, respectively.

19. The antibody or antigen-binding fragment of any one of embodiments 1-11 and 18, wherein the antibody or antigen-binding fragment comprises:

(a) a heavy chain variable region comprising the amino acid sequence of SEQ ID NO: 53 or an amino acid sequence having at least 90% identity to an amino acid sequence of SEQ ID NO:53; and/or a light chain variable region comprising the amino acid sequence of SEQ ID NO: 66 or an amino acid sequence having at least 90% identity to an amino acid sequence of SEQ ID NO:66;

(b) a heavy chain variable region comprising the amino acid sequence of SEQ ID NO: 54 or an amino acid sequence having at least 90% identity to an amino acid sequence of SEQ ID NO:54; and/or a light chain variable region comprising the amino acid sequence of SEQ ID NO: 67 or an amino acid sequence having at least 90% identity to an amino acid sequence of SEQ ID NO:67;

(c) a heavy chain variable region comprising the amino acid sequence of SEQ ID NO: 55 or an amino acid sequence having at least 90% identity to an amino acid sequence of SEQ ID NO:55; and/or a light chain variable region comprising the amino acid sequence of SEQ ID NO: 68 or an amino acid sequence having at least 90% identity to an amino acid sequence of SEQ ID NO:68;

(d) a heavy chain variable region comprising the amino acid sequence of SEQ ID NO: 56 or an amino acid sequence having at least 90% identity to an amino acid sequence of SEQ ID NO:56; and/or a light chain variable region comprising the amino acid sequence of SEQ ID NO: 69 or an amino acid sequence having at least 90% identity to an amino acid sequence of SEQ ID NO:69;

(e) a heavy chain variable region comprising the amino acid sequence of SEQ ID NO: 57 or an amino acid sequence having at least 90% identity to an amino acid sequence of SEQ ID NO:57; and/or a light chain variable region comprising the amino acid sequence of SEQ ID NO: 70 or an amino acid sequence having at least 90% identity to an amino acid sequence of SEQ ID NO:70;

(f) a heavy chain variable region comprising the amino acid sequence of SEQ ID NO: 58 or an amino acid sequence having at least 90% identity to an amino acid sequence of SEQ ID NO:58; and/or a light chain variable region the amino acid sequence of SEQ ID NO: 71 or comprising an amino acid sequence having at least 90% identity to an amino acid sequence of SEQ ID NO:71;

(g) a heavy chain variable region comprising the amino acid sequence of SEQ ID NO: 59 or an amino acid sequence having at least 90% identity to an amino acid sequence of SEQ ID NO:59; and/or a light chain variable region comprising the amino acid sequence of SEQ ID NO: 72 or an amino acid sequence having at least 90% identity to an amino acid sequence of SEQ ID NO:72;

(h) a heavy chain variable region comprising the amino acid sequence of SEQ ID NO: 60 or an amino acid sequence having at least 90% identity to an amino acid sequence of SEQ ID NO:60; and/or a light chain variable region comprising the amino acid sequence of SEQ ID NO: 73 or an amino acid sequence having at least 90% identity to an amino acid sequence of SEQ ID NO:73;

(i) a heavy chain variable region comprising the amino acid sequence of SEQ ID NO: 61 or an amino acid sequence having at least 90% identity to an amino acid sequence of SEQ ID NO:61; and/or a light chain variable region comprising the amino acid sequence of SEQ ID NO: 74 or an amino acid sequence having at least 90% identity to an amino acid sequence of SEQ ID NO:74; or (j) a heavy chain variable region comprising the amino acid sequence of SEQ ID NO: 62 or an amino acid sequence having at least 90% identity to an amino acid sequence of SEQ ID NO:62; and/or a light chain variable region comprising the amino acid sequence of SEQ ID NO: 75 or an amino acid sequence having at least 90% identity to an amino acid sequence of SEQ ID NO:75.

20. The antibody or antigen-binding fragment of any one of embodiments 1-19, wherein:
the antibody or antigen-binding fragment binds UCH-L1 with a dissociation constant ($K_D$) of less than or less than about $1.0 \times 10^{-10}$ M, $2.0 \times 10^{-10}$ M, $3.0 \times 10^{-10}$ M, $4.0 \times 10^{-10}$ M, $5.0 \times 10^{-10}$ M, $6.0 \times 10^{-10}$ M, $7.0 \times 10^{-10}$ M, $8.0 \times 10^{-10}$ M, $9.0 \times 10^{-10}$ M, $1.0 \times 10^{-11}$ M, $2.0 \times 10^{-11}$ M, $3.0 \times 10^{-11}$ M, $4.0 \times 10^{-11}$ M, $5.0 \times 10^{-11}$ M, $6.0 \times 10^{-11}$ M, $7.0 \times 10^{-11}$ M, $8.0 \times 10^{-11}$ M, $9.0 \times 10^{-11}$ M, or $1.0 \times 10^{-12}$ M; or the antibody or antigen-binding fragment binds UCH-L1 with a dissociation constant ($K_D$) from or from about $2.0 \times 10^{-10}$ M to $4.0 \times 10^{-10}$ M, $1.0 \times 10^{-11}$ M to $9.0 \times 10^{-11}$ M, $1.0 \times 10^{-12}$ M to $5.0 \times 10^{-12}$ M, or $2.0 \times 10^{-10}$ M to $1.0 \times 10^{-12}$ M.

21. The antibody or antigen-binding fragment of any one of embodiments 1-20, wherein the antibody or antigen-binding fragment binds to an epitope within or that is or includes residues 28-36 of UCH-L1 protein, residues 98-106 of UCH-L1 protein, residues 138-145 of UCH-L1 protein, and/or residues 142-149 of UCH-L1 protein corresponding to amino acid positions set forth in SEQ ID NO:207.

22. An antibody or antigen-binding fragment thereof that specifically binds to a human UCH-L1, wherein the antibody or antigen-binding fragment binds to an epitope within or that is or includes residues 98-106 of UCH-L1 protein corresponding to amino acid positions set forth in SEQ ID NO:207.

23. The antibody or antigen-binding fragment of embodiment 22, wherein the antibody or antigen-binding fragment comprises:

(a) a heavy chain variable region comprising CDR-H1, CDR-H2 and CDR-H3 amino acid sequences of SEQ ID NO:1, SEQ ID NO:9 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:45, respectively;

(b) a heavy chain variable region comprising CDR-H1, CDR-H2 and CDR-H3 amino acid sequences of SEQ ID NO:3, SEQ ID NO: 11 and SEQ ID NO:20, respectively and/or a light chain variable region comprising CDR-L1, CDR-L2 and CDR-L3 amino acid sequences of SEQ ID NO:30, SEQ ID NO:37 and SEQ ID NO:45, respectively; or (c) heavy chain variable region comprising CDR-H1, CDR-H2 and CDR-H3 amino acid sequences of SEQ ID NO:1, SEQ ID NO:19 and SEQ ID NO:20, respectively and/or a light chain variable region comprising CDR-L1, CDR-L2 and CDR-L3 amino acid sequences of SEQ ID NO:28, SEQ ID NO:37 and SEQ ID NO:50, respectively.

24. An antibody or antigen-binding fragment thereof that specifically binds to a human UCH-L1, wherein the antibody or antigen-binding fragment binds to an epitope within or that is or includes residues 28-36 UCH-L1 corresponding to amino acid positions of UCH-L1 set forth in SEQ ID NO:207.

25. The antibody or antigen-binding fragment of embodiment 24, wherein the antibody or antigen-binding fragment comprises:

(a) a heavy chain variable region comprising CDR-H1, CDR-H2 and CDR-H3 amino acid sequences of SEQ ID NO:2, SEQ ID NO: 10 and SEQ ID NO:21, respectively and/or a light chain variable region comprising CDR-L1, CDR-L2 and CDR-L3 amino acid sequences of SEQ ID NO:29, SEQ ID NO:38 and SEQ ID NO:46, respectively;

(b) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:33, SEQ ID NO:40 and SEQ ID NO:48, respectively;
(c) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:34, SEQ ID NO:41 and SEQ ID NO:48, respectively;
(d) a heavy chain variable region comprising CDR-H1, CDR-H2 and CDR-H3 amino acid sequences of SEQ ID NO:6, SEQ ID NO: 15 and SEQ ID NO:24, respectively and/or a light chain variable region comprising CDR-L1, CDR-L2 and CDR-L3 amino acid sequences of SEQ ID NO:34, SEQ ID NO:42 and SEQ ID NO:48, respectively;
(e) a heavy chain variable region comprising CDR-H1, CDR-H2 and CDR-H3 amino acid sequences of SEQ ID NO:6, SEQ ID NO: 14 and SEQ ID NO:24, respectively and/or a light chain variable region comprising CDR-L1, CDR-L2 and CDR-L3 amino acid sequences of SEQ ID NO:35, SEQ ID NO:41 and SEQ ID NO:48, respectively;
(f) a heavy chain variable region comprising CDR-H1, CDR-H2 and CDR-H3 amino acid sequences of SEQ ID NO:6, SEQ ID NO: 16 and SEQ ID NO:25, respectively and/or a light chain variable region comprising CDR-L1, CDR-L2 and CDR-L3 amino acid sequences of SEQ ID NO:34, SEQ ID NO:42 and SEQ ID NO:48, respectively;
(g) a heavy chain variable region comprising CDR-H1, CDR-H2 and CDR-H3 amino acid sequences of SEQ ID NO:7, SEQ ID NO: 17 and SEQ ID NO:26, respectively and/or a light chain variable region comprising CDR-L1, CDR-L2 and CDR-L3 amino acid sequences of SEQ ID NO:36, SEQ ID NO:43 and SEQ ID NO:49, respectively; or
(h) a heavy chain variable region comprising CDR-H1, CDR-H2 and CDR-H3 amino acid sequences of SEQ ID NO:8, SEQ ID NO: 18 and SEQ ID NO:27, respectively and/or a light chain variable region comprising CDR-L1, CDR-L2 and CDR-L3 amino acid sequences of SEQ ID NO:36, SEQ ID NO:44 and SEQ ID NO:49, respectively.

26. An antibody or antigen-binding fragment thereof that specifically binds to a human UCH-L1, wherein the antibody or antigen-binding fragment binds to an epitope within or that is or includes residues 138-145 of UCH-L1 protein corresponding to amino acid positions set forth in SEQ ID NO:207.

27. The antibody or antigen-binding fragment of embodiment 26, wherein the antibody or antigen-binding fragment comprises a heavy chain variable region comprising CDR-H1, CDR-H2 and CDR-H3 amino acid sequences of SEQ ID NO:4, SEQ ID NO:12 and SEQ ID NO:22, respectively and/or a light chain variable region comprising CDR-L1, CDR-L2 and CDR-L3 amino acid sequences of SEQ ID NO:31, SEQ ID NO:39 and SEQ ID NO:47, respectively.

28. An antibody or antigen-binding fragment thereof that specifically binds to a human UCH-L1, wherein the antibody or antigen-binding fragment binds to an epitope within or that is or includes residues 142-149 of UCH-L1 protein corresponding to amino acid positions set forth in SEQ ID NO:207.

29. The antibody or antigen-binding fragment of embodiment 28, wherein the antibody or antigen-binding fragment comprises a heavy chain variable region comprising CDR-H1, CDR-H2 and CDR-H3 amino acid sequences of SEQ ID NO:5, SEQ ID NO:13 and SEQ ID NO:23, respectively and/or a light chain variable region comprising CDR-L1, CDR-L2 and CDR-L3 amino acid sequences of SEQ ID NO:32, SEQ ID NO:39 and SEQ ID NO:47, respectively.

30. The antibody or antigen-binding fragment of any one of embodiments 1-29, wherein the UCH-L1 is recombinant UCH-L1.

31. The antibody or antigen-binding fragment of any one of embodiments 1-29, wherein the UCH-L1 is native UCH-L1.

32. The antibody or antigen-binding fragment of embodiment 31, wherein the native UCH-L1 is present in or obtained from serum, plasma, blood, cerebrospinal fluid (CSF), urine, sweat, or saliva.

33. An antibody or antigen-binding fragment thereof that specifically binds to human glial fibrillary acidic protein (GFAP), wherein the antibody or antigen-binding fragment comprises a heavy chain variable region comprising an amino acid sequence having at least 85% identity to an amino acid sequence selected from any one of SEQ ID NOs:172-188; and/or a light chain variable region comprising an amino acid sequence having at least 85% identity to an amino acid sequence selected from any one of SEQ ID NOs:189-206.

34. The antibody or antigen-binding fragment of embodiment 33, wherein the heavy chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs:172-188 or has the amino acid sequence selected from any one of SEQ ID NOs:172-188.

35. The antibody or antigen-binding fragment of embodiment 33 or embodiment 34, wherein the light chain variable region comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOs:189-206 or has the amino acid sequence selected from any one of SEQ ID NOs:189-206.

36. The antibody or antigen-binding fragment of any one of embodiments 33-35, wherein:
the heavy chain variable region comprises: (i) a CDR-H1 comprising the amino acid sequence selected from SEQ ID NOs:77-90; (ii) a CDR-H2 comprising the amino acid sequence selected from SEQ ID NOs:91-107; and (iii) a CDR-H3 comprising the amino acid sequence selected from SEQ ID NOs: 108-124; and/or
wherein the light chain variable region comprises: (i) a CDR-L1 comprising the amino acid sequence selected from SEQ ID NOs:125-141; (ii) a CDR-L2 comprising the amino acid sequence selected from SEQ ID NOs:142-156; and (iii) a CDR-L3 comprising the amino acid sequence selected from SEQ ID NOs:157-171.

37. The antibody or antigen-binding fragment of any one of embodiments 33-36, wherein:
the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:172-188; and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:189-206.

38. An antibody or antigen-binding fragment that specifically binds to a human glial fibrillary acidic protein (GFAP), wherein the heavy chain variable region comprises an amino acid sequence having at least 85% identity to an amino acid sequence selected from any one of SEQ ID NOS:174-188; and/or a light chain variable region comprising an amino acid sequence having at least 85% identity to an amino acid sequence selected from any one of SEQ ID NO: 191-206.

39. The antibody or antigen-binding fragment of embodiment 38, wherein:
    the heavy chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOS: 174-188 or comprises the amino acid sequence set forth in any of SEQ ID NOS: 174-188; and/or
    the light chain variable region comprises at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to an amino acid sequence selected from any one of SEQ ID NOS: 191-206 or comprises the light chain variable region comprises the amino acid sequence set forth in any one of SEQ ID NOS:191-206.

40. The antibody or antigen-binding fragment of embodiment 38 or embodiment 39, wherein:
    the heavy chain variable region comprises: (i) a CDR-H1 comprising the amino acid sequence selected from SEQ ID NOs:79-90; (ii) a CDR-H2 comprising the amino acid sequence selected from SEQ ID NOs:93-107; and (iii) a CDR-H3 comprising the amino acid sequence selected from SEQ ID NOs: 110-124; and/or the light chain variable region comprises: (i) a CDR-L1 comprising the amino acid sequence selected from SEQ ID NOs:127-141; (ii) a CDR-L2 comprising the amino acid sequence selected from SEQ ID NOs:144-156; and (iii) a CDR-L3 comprising the amino acid sequence selected from SEQ ID NOs:159-171; or
    the heavy chain variable region comprises a CDR-H1, a CDR-H2, and a CDR-H3, respectively, comprising the amino acid sequence of a CDR-H1, a CDR-H2, and a CDR-H3 contained within the heavy chain variable region amino acid sequence selected from any one of SEQ ID NOs:174-188 and/or the light chain variable region comprises a CDR-L1, a CDR-L2, and a CDR-L3, respectively, comprising the amino acid sequence of a CDR-L1, a CDR-L2, and a CDR-L3 contained within the light chain variable region amino acid sequence selected from any one of SEQ ID NOs:191-206.

41. An antibody or antigen-binding fragment that specifically binds to glial fibrillary acidic protein (GFAP), wherein the antibody or antigen-binding fragment comprises a heavy chain variable region and a light chain variable region, wherein:
    the heavy chain variable region comprises: (i) CDR-H1 comprising the amino acid sequence selected from SEQ ID NOs:77-90; (ii) CDR-H2 comprising the amino acid sequence selected from SEQ ID NOs: 91-107; and (iii) CDR-H3 comprising the amino acid sequence selected from SEQ ID NOs:108-124; and/or
    the light chain variable region comprises: (i) CDR-L1 comprising the amino acid sequence selected from SEQ ID NOs:125-141; (ii) CDR-L2 comprising the amino acid sequence selected from SEQ ID NOs: 142-156; and (iii) CDR-L3 comprising the amino acid sequence selected from SEQ ID NOs:157-171.

42. The antibody or antigen-binding fragment of any one of embodiments 33-37 and 41, wherein the antibody or antigen-binding fragment comprises:
    (a) a heavy chain variable region comprising CDR-H1, CDR-H2 and CDR-H3 amino acid sequences of SEQ ID NO:77, SEQ ID NO:91 and SEQ ID NO:108, respectively and/or a light chain variable region comprising CDR-L1, CDR-L2 and CDR-L3 amino acid sequences of SEQ ID NO:125, SEQ ID NO:142 and SEQ ID NO:157, respectively;
    (b) a heavy chain variable region comprising CDR-H1, CDR-H2 and CDR-H3 amino acid sequences of SEQ ID NO:78, SEQ ID NO:92 and SEQ ID NO:109, respectively and/or a light chain variable region comprising CDR-L1, CDR-L2 and CDR-L3 amino acid sequences of SEQ ID NO:126, SEQ ID NO:143 and SEQ ID NO:158, respectively;
    (c) a heavy chain variable region comprising CDR-H1, CDR-H2 and CDR-H3 amino acid sequences of SEQ ID NO:79, SEQ ID NO:93 and SEQ ID NO:110, respectively and/or a light chain variable region comprising CDR-L1, CDR-L2 and CDR-L3 amino acid sequences of SEQ ID NO:127, SEQ ID NO:144 and SEQ ID NO:159, respectively;
    (d) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:128, SEQ ID NO:145 and SEQ ID NO:160, respectively;
    (e) a heavy chain variable region comprising CDR-H1, CDR-H2 and CDR-H3 amino acid sequences of SEQ ID NO:80, SEQ ID NO:95 and SEQ ID NO:112, respectively and/or a light chain variable region comprising CDR-L1, CDR-L2 and CDR-L3 amino acid sequences of SEQ ID NO:126, SEQ ID NO:142 and SEQ ID NO:158, respectively;
    (f) a heavy chain variable region comprising CDR-H1, CDR-H2 and CDR-H3 amino acid sequences of SEQ ID NO:81, SEQ ID NO:96 and SEQ ID NO:113, respectively and/or a light chain variable region comprising CDR-L1, CDR-L2 and CDR-L3 amino acid sequences of SEQ ID NO:129, SEQ ID NO:146 and SEQ ID NO:161, respectively;
    (g) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:130, SEQ ID NO:145 and SEQ ID NO:160, respectively;
(h) a heavy chain variable region comprising CDR-H1, CDR-H2 and CDR-H3 amino acid sequences of SEQ ID NO:82, SEQ ID NO:97 and SEQ ID NO:114, respectively and/or a light chain variable region comprising CDR-L1, CDR-L2 and CDR-L3 amino acid sequences of SEQ ID NO:131, SEQ ID NO:147 and SEQ ID NO:162, respectively;
(i) a heavy chain variable region comprising CDR-H1, CDR-H2 and CDR-H3 amino acid sequences of SEQ ID NO:83, SEQ ID NO:98 and SEQ ID NO:115, respectively and/or a light chain variable region comprising CDR-L1, CDR-L2 and CDR-L3 amino acid sequences of SEQ ID NO:132, SEQ ID NO:148 and SEQ ID NO:163, respectively;
(j) a heavy chain variable region comprising CDR-H1, CDR-H2 and CDR-H3 amino acid sequences of SEQ ID NO:84, SEQ ID NO:99 and SEQ ID NO:116, respectively and/or a light chain variable region comprising CDR-L1, CDR-L2 and CDR-L3 amino acid sequences of SEQ ID NO:133, SEQ ID NO:149 and SEQ ID NO:164, respectively;
(k) a heavy chain variable region comprising CDR-H1, CDR-H2 and CDR-H3 amino acid sequences of SEQ ID NO:85, SEQ ID NO:100 and SEQ ID NO:117, respectively and/or a light chain variable region comprising CDR-L1, CDR-L2 and CDR-L3 amino acid sequences of SEQ ID NO:134, SEQ ID NO:150 and SEQ ID NO:165, respectively;
(l) a heavy chain variable region comprising CDR-H1, CDR-H2 and CDR-H3 amino acid sequences of SEQ ID NO:86, SEQ ID NO:101 and SEQ ID NO:118, respectively and/or a light chain variable region comprising CDR-L1, CDR-L2 and CDR-L3 amino acid sequences of SEQ ID NO:135, SEQ ID NO:151 and SEQ ID NO:166, respectively;
(m) a heavy chain variable region comprising CDR-H1, CDR-H2 and CDR-H3 amino acid sequences of SEQ ID NO:78, SEQ ID NO:102 and SEQ ID NO:119, respectively and/or a light chain variable region comprising CDR-L1, CDR-L2 and CDR-L3 amino acid sequences of SEQ ID NO:136, SEQ ID NO:152 and SEQ ID NO:167, respectively;
(n) a heavy chain variable region comprising CDR-H1, CDR-H2 and CDR-H3 amino acid sequences of SEQ ID NO:78, SEQ ID NO:103 and SEQ ID NO:120, respectively and/or a light chain variable region comprising CDR-L1, CDR-L2 and CDR-L3 amino acid sequences of SEQ ID NO:137, SEQ ID NO:142 and SEQ ID NO:158, respectively;
(o) a heavy chain variable region comprising CDR-H1, CDR-H2 and CDR-H3 amino acid sequences of SEQ ID NO:87, SEQ ID NO:104 and SEQ ID NO:121, respectively and/or a light chain variable region comprising CDR-L1, CDR-L2 and CDR-L3 amino acid sequences of SEQ ID NO:138, SEQ ID NO:153 and SEQ ID NO:168, respectively;
(p) a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO:169, respectively;
(q) a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:140, SEQ ID NO:155 and SEQ ID NO:170, respectively; or
(r) a heavy chain variable region comprising CDR-H1, CDR-H2 and CDR-H3 amino acid sequences of SEQ ID NO:90, SEQ ID NO:107 and SEQ ID NO:124, respectively and/or a light chain variable region comprising CDR-L1, CDR-L2 and CDR-L3 amino acid sequences of SEQ ID NO:141, SEQ ID NO:156 and SEQ ID NO:171, respectively.

43. The antibody or antigen-binding fragment of any one of embodiments 33-37, 41 and 42, wherein the antibody or antigen-binding fragment comprises:
(a) a heavy chain variable region comprising the amino acid sequence of SEQ ID NO: 172 or an amino acid sequence having at least 90% identity to an amino acid sequence of SEQ ID NO:172; and/or a light chain variable region comprising the amino acid sequence of SEQ ID NO: 189 or an amino acid sequence having at least 90% identity to an amino acid sequence of SEQ ID NO:189;
(b) a heavy chain variable region comprising the amino acid sequence of SEQ ID NO: 173 or an amino acid sequence having at least 90% identity to an amino acid sequence of SEQ ID NO:173; and/or a light chain variable region comprising the amino acid sequence of SEQ ID NO: 190 or an amino acid sequence having at least 90% identity to an amino acid sequence of SEQ ID NO:190;
(c) a heavy chain variable region comprising the amino acid sequence of SEQ ID NO: 174 or an amino acid sequence having at least 90% identity to an amino acid sequence of SEQ ID NO:174; and/or a light chain variable region comprising the amino acid sequence of SEQ ID NO: 191 or an amino acid sequence having at least 90% identity to an amino acid sequence of SEQ ID NO:191;
(d) a heavy chain variable region comprising the amino acid sequence of SEQ ID NO: 175 or an amino acid sequence having at least 90% identity to an amino acid sequence of SEQ ID NO:175; and/or a light chain variable region comprising the amino acid sequence of SEQ ID NO: 192 or an amino acid sequence having at least 90% identity to an amino acid sequence of SEQ ID NO:192;
(e) a heavy chain variable region comprising the amino acid sequence of SEQ ID NO:176 or an amino acid sequence having at least 90% identity to an amino acid sequence of SEQ ID NO:176; and/or a light chain variable region comprising the amino acid sequence of SEQ ID NO: 193 or an amino acid sequence having at least 90% identity to an amino acid sequence of SEQ ID NO: 193;
(f) a heavy chain variable region comprising the amino acid sequence of SEQ ID NO: 177 or an amino acid sequence having at least 90% identity to an amino acid sequence of SEQ ID NO:177; and/or a light chain variable region comprising the amino acid sequence of SEQ ID NO: 194 or an amino acid sequence having at least 90% identity to an amino acid sequence of SEQ ID NO:194;
(g) a heavy chain variable region comprising the amino acid sequence of SEQ ID NO: 175 or an amino acid sequence having at least 90% identity to an amino acid sequence of SEQ ID NO:175; and/or a light chain variable region comprising the amino acid sequence of SEQ ID NO: 195 or an amino acid sequence having at least 90% identity to an amino acid sequence of SEQ ID NO:195;

(h) a heavy chain variable region comprising the amino acid sequence of SEQ ID NO: 178 or an amino acid sequence having at least 90% identity to an amino acid sequence of SEQ ID NO:178; and/or a light chain variable region comprising the amino acid sequence of SEQ ID NO: 196 or an amino acid sequence having at least 90% identity to an amino acid sequence of SEQ ID NO:196;

(i) a heavy chain variable region comprising the amino acid sequence of SEQ ID NO: 179 or an amino acid sequence having at least 90% identity to an amino acid sequence of SEQ ID NO:179; and/or a light chain variable region comprising the amino acid sequence of SEQ ID NO: 197 or an amino acid sequence having at least 90% identity to an amino acid sequence of SEQ ID NO:197;

(j) a heavy chain variable region comprising the amino acid sequence of SEQ ID NO: 180 or an amino acid sequence having at least 90% identity to an amino acid sequence of SEQ ID NO:180; and/or a light chain variable region comprising the amino acid sequence of SEQ ID NO: 198 or an amino acid sequence having at least 90% identity to an amino acid sequence of SEQ ID NO:198;

(k) a heavy chain variable region comprising the amino acid sequence of SEQ ID NO: 181 or an amino acid sequence having at least 90% identity to an amino acid sequence of SEQ ID NO:181; and/or a light chain variable region comprising the amino acid sequence of SEQ ID NO: 199 or an amino acid sequence having at least 90% identity to an amino acid sequence of SEQ ID NO:199;

(l) a heavy chain variable region comprising the amino acid sequence of SEQ ID NO: 182 or an amino acid sequence having at least 90% identity to an amino acid sequence of SEQ ID NO:182; and/or a light chain variable region comprising the amino acid sequence of SEQ ID NO: 200 or an amino acid sequence having at least 90% identity to an amino acid sequence of SEQ ID NO:200;

(m) a heavy chain variable region comprising the amino acid sequence of SEQ ID NO: 183 or an amino acid sequence having at least 90% identity to an amino acid sequence of SEQ ID NO:183; and/or a light chain variable region comprising the amino acid sequence of SEQ ID NO: 201 or an amino acid sequence having at least 90% identity to an amino acid sequence of SEQ ID NO:201;

(n) a heavy chain variable region comprising the amino acid sequence of SEQ ID NO: 184 or an amino acid sequence having at least 90% identity to an amino acid sequence of SEQ ID NO:184; and/or a light chain variable region comprising the amino acid sequence of SEQ ID NO: 202 or an amino acid sequence having at least 90% identity to an amino acid sequence of SEQ ID NO:202;

(o) a heavy chain variable region comprising the amino acid sequence of SEQ ID NO: 185 or an amino acid sequence having at least 90% identity to an amino acid sequence of SEQ ID NO:185; and/or a light chain variable region comprising the amino acid sequence of SEQ ID NO: 203 or an amino acid sequence having at least 90% identity to an amino acid sequence of SEQ ID NO:203;

(p) a heavy chain variable region comprising the amino acid sequence of SEQ ID NO: 186 or an amino acid sequence having at least 90% identity to an amino acid sequence of SEQ ID NO:186; and/or a light chain variable region comprising the amino acid sequence of SEQ ID NO: 204 or an amino acid sequence having at least 90% identity to an amino acid sequence of SEQ ID NO:204;

(q) a heavy chain variable region comprising the amino acid sequence of SEQ ID NO: 187 or an amino acid sequence having at least 90% identity to an amino acid sequence of SEQ ID NO:187; and/or a light chain variable region comprising the amino acid sequence of SEQ ID NO: 205 an amino acid sequence having at least 90% identity to an amino acid sequence of SEQ ID NO:205; or (r) a heavy chain variable region comprising the amino acid sequence of SEQ ID NO: 188 or an amino acid sequence having at least 90% identity to an amino acid sequence of SEQ ID NO:188; and/or a light chain variable region comprising the amino acid sequence of SEQ ID NO: 206 or an amino acid sequence having at least 90% identity to an amino acid sequence of SEQ ID NO:206.

44. The antibody or antigen-binding fragment of any one of embodiments 33-37 and 41-43, wherein the antibody or antigen-binding fragment comprises a heavy chain variable region comprising CDR-H1, CDR-H2 and CDR-H3 amino acid sequences of SEQ ID NO:77, SEQ ID NO:91 and SEQ ID NO:108, respectively and/or a light chain variable region comprising CDR-L1, CDR-L2 and CDR-L3 amino acid sequences of SEQ ID NO:125, SEQ ID NO:142 and SEQ ID NO:157, respectively.

45. The antibody or antigen-binding fragment of any one of embodiments 33-37 and 41-44, wherein the antibody or antigen-binding fragment comprises a heavy chain variable region comprising the amino acid sequence of SEQ ID NO: 172 or an amino acid sequence having at least 90% identity to an amino acid sequence of SEQ ID NO:172; and/or a light chain variable region comprising the amino acid sequence of SEQ ID NO: 189 or an amino acid sequence having at least 90% identity to an amino acid sequence of SEQ ID NO:189.

46. The antibody or antigen-binding fragment of any one of embodiments 33-37 and 41-43, wherein the antibody or antigen-binding fragment comprises a heavy chain variable region comprising CDR-H1, CDR-H2 and CDR-H3 amino acid sequences of SEQ ID NO:78, SEQ ID NO:92 and SEQ ID NO:109, respectively and/or a light chain variable region comprising CDR-L1, CDR-L2 and CDR-L3 amino acid sequences of SEQ ID NO:126, SEQ ID NO:143 and SEQ ID NO:158, respectively.

47. The antibody or antigen-binding fragment of any one of embodiments 33-37, 41-43 and 46, wherein the antibody or antigen-binding fragment comprises a heavy chain variable region comprising the amino acid sequence of SEQ ID NO: 173 or an amino acid sequence having at least 90% identity to an amino acid sequence of SEQ ID NO:173; and/or a light chain variable region comprising the amino acid sequence of SEQ ID NO: 190 or an amino acid sequence having at least 90% identity to an amino acid sequence of SEQ ID NO:190.

48. The antibody or antigen-binding fragment of any one of embodiments 33-43, wherein the antibody or antigen-binding fragment comprises:
- (a) a heavy chain variable region comprising CDR-H1, CDR-H2 and CDR-H3 amino acid sequences of SEQ ID NO:79, SEQ ID NO:93 and SEQ ID NO:110, respectively and/or a light chain variable region comprising CDR-L1, CDR-L2 and CDR-L3 amino acid sequences of SEQ ID NO:127, SEQ ID NO:144 and SEQ ID NO:159, respectively;
- (b) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:128, SEQ ID NO:145 and SEQ ID NO:160, respectively;
- (c) a heavy chain variable region comprising CDR-H1, CDR-H2 and CDR-H3 amino acid sequences of SEQ ID NO:80, SEQ ID NO:95 and SEQ ID NO:112, respectively and/or a light chain variable region comprising CDR-L1, CDR-L2 and CDR-L3 amino acid sequences of SEQ ID NO:126, SEQ ID NO:142 and SEQ ID NO:158, respectively;
- (d) a heavy chain variable region comprising CDR-H1, CDR-H2 and CDR-H3 amino acid sequences of SEQ ID NO:81, SEQ ID NO:96 and SEQ ID NO:113, respectively and/or a light chain variable region comprising CDR-L1, CDR-L2 and CDR-L3 amino acid sequences of SEQ ID NO:129, SEQ ID NO:146 and SEQ ID NO:161, respectively;
- (e) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:130, SEQ ID NO:145 and SEQ ID NO:160, respectively;
- (f) a heavy chain variable region comprising CDR-H1, CDR-H2 and CDR-H3 amino acid sequences of SEQ ID NO:82, SEQ ID NO:97 and SEQ ID NO:114, respectively and/or a light chain variable region comprising CDR-L1, CDR-L2 and CDR-L3 amino acid sequences of SEQ ID NO:131, SEQ ID NO:147 and SEQ ID NO:162, respectively;
- (g) a heavy chain variable region comprising CDR-H1, CDR-H2 and CDR-H3 amino acid sequences of SEQ ID NO:83, SEQ ID NO:98 and SEQ ID NO:115, respectively and/or a light chain variable region comprising CDR-L1, CDR-L2 and CDR-L3 amino acid sequences of SEQ ID NO:132, SEQ ID NO:148 and SEQ ID NO:163, respectively;
- (h) a heavy chain variable region comprising CDR-H1, CDR-H2 and CDR-H3 amino acid sequences of SEQ ID NO:84, SEQ ID NO:99 and SEQ ID NO:116, respectively and/or a light chain variable region comprising CDR-L1, CDR-L2 and CDR-L3 amino acid sequences of SEQ ID NO:133, SEQ ID NO:149 and SEQ ID NO:164, respectively;
- (i) a heavy chain variable region comprising CDR-H1, CDR-H2 and CDR-H3 amino acid sequences of SEQ ID NO:85, SEQ ID NO:100 and SEQ ID NO:117, respectively and/or a light chain variable region comprising CDR-L1, CDR-L2 and CDR-L3 amino acid sequences of SEQ ID NO:134, SEQ ID NO:150 and SEQ ID NO:165, respectively;
- (j) a heavy chain variable region comprising CDR-H1, CDR-H2 and CDR-H3 amino acid sequences of SEQ ID NO:86, SEQ ID NO:101 and SEQ ID NO:118, respectively and/or a light chain variable region comprising CDR-L1, CDR-L2 and CDR-L3 amino acid sequences of SEQ ID NO:135, SEQ ID NO:151 and SEQ ID NO:166, respectively;
- (k) a heavy chain variable region comprising CDR-H1, CDR-H2 and CDR-H3 amino acid sequences of SEQ ID NO:78, SEQ ID NO:102 and SEQ ID NO:119, respectively and/or a light chain variable region comprising CDR-L1, CDR-L2 and CDR-L3 amino acid sequences of SEQ ID NO:136, SEQ ID NO:152 and SEQ ID NO:167, respectively;
- (l) a heavy chain variable region comprising CDR-H1, CDR-H2 and CDR-H3 amino acid sequences of SEQ ID NO:78, SEQ ID NO:103 and SEQ ID NO:120, respectively and/or a light chain variable region comprising CDR-L1, CDR-L2 and CDR-L3 amino acid sequences of SEQ ID NO:137, SEQ ID NO:142 and SEQ ID NO:158, respectively;
- (n) a heavy chain variable region comprising CDR-H1, CDR-H2 and CDR-H3 amino acid sequences of SEQ ID NO:87, SEQ ID NO:104 and SEQ ID NO:121, respectively and/or a light chain variable region comprising CDR-L1, CDR-L2 and CDR-L3 amino acid sequences of SEQ ID NO:138, SEQ ID NO:153 and SEQ ID NO:168, respectively;
- (o) a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO:169, respectively;
- (p) a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:140, SEQ ID NO:155 and SEQ ID NO:170, respectively; or
- (q) a heavy chain variable region comprising CDR-H1, CDR-H2 and CDR-H3 amino acid sequences of SEQ ID NO:90, SEQ ID NO:107 and SEQ ID NO:124, respectively and/or a light chain variable region comprising CDR-L1, CDR-L2 and CDR-L3 amino acid sequences of SEQ ID NO:141, SEQ ID NO:156 and SEQ ID NO:171, respectively.

49. The antibody or antigen-binding fragment of any one of embodiments 33-43 and 48, wherein the antibody or antigen-binding fragment comprises:
- (a) a heavy chain variable region comprising the amino acid sequence of SEQ ID NO: 174 or an amino acid sequence having at least 90% identity to an amino acid sequence of SEQ ID NO:174; and/or a light chain variable region comprising the amino acid sequence of SEQ ID NO: 191 or an amino acid sequence having at least 90% identity to an amino acid sequence of SEQ ID NO:191;
- (b) a heavy chain variable region comprising the amino acid sequence of SEQ ID NO: 175 or an amino acid sequence having at least 90% identity to an amino acid sequence of SEQ ID NO:175; and/or a light chain variable region comprising the amino acid sequence of SEQ ID NO: 192 or an amino acid sequence having at least 90% identity to an amino acid sequence of SEQ ID NO:192;

(c) a heavy chain variable region comprising the amino acid sequence of SEQ ID NO:176 or an amino acid sequence having at least 90% identity to an amino acid sequence of SEQ ID NO:176; and/or a light chain variable region comprising the amino acid sequence of SEQ ID NO: 193 or an amino acid sequence having at least 90% identity to an amino acid sequence of SEQ ID NO:193;

(d) a heavy chain variable region comprising the amino acid sequence of SEQ ID NO: 177 or an amino acid sequence having at least 90% identity to an amino acid sequence of SEQ ID NO:177; and/or a light chain variable region comprising the amino acid sequence of SEQ ID NO: 194 or an amino acid sequence having at least 90% identity to an amino acid sequence of SEQ ID NO:194;

(e) a heavy chain variable region comprising the amino acid sequence of SEQ ID NO: 175 or an amino acid sequence having at least 90% identity to an amino acid sequence of SEQ ID NO:175; and/or a light chain variable region comprising the amino acid sequence of SEQ ID NO: 195 or an amino acid sequence having at least 90% identity to an amino acid sequence of SEQ ID NO:195;

(f) a heavy chain variable region comprising the amino acid sequence of SEQ ID NO: 178 or an amino acid sequence having at least 90% identity to an amino acid sequence of SEQ ID NO:178; and/or a light chain variable region comprising the amino acid sequence of SEQ ID NO: 196 or an amino acid sequence having at least 90% identity to an amino acid sequence of SEQ ID NO:196;

(g) a heavy chain variable region comprising the amino acid sequence of SEQ ID NO: 179 or an amino acid sequence having at least 90% identity to an amino acid sequence of SEQ ID NO:179; and/or a light chain variable region comprising the amino acid sequence of SEQ ID NO: 197 or an amino acid sequence having at least 90% identity to an amino acid sequence of SEQ ID NO:197;

(h) a heavy chain variable region comprising the amino acid sequence of SEQ ID NO: 180 or an amino acid sequence having at least 90% identity to an amino acid sequence of SEQ ID NO:180; and/or a light chain variable region comprising the amino acid sequence of SEQ ID NO: 198 or an amino acid sequence having at least 90% identity to an amino acid sequence of SEQ ID NO:198;

(i) a heavy chain variable region comprising the amino acid sequence of SEQ ID NO: 181 or an amino acid sequence having at least 90% identity to an amino acid sequence of SEQ ID NO:181; and/or a light chain variable region comprising the amino acid sequence of SEQ ID NO: 199 or an amino acid sequence having at least 90% identity to an amino acid sequence of SEQ ID NO:199;

(j) a heavy chain variable region comprising the amino acid sequence of SEQ ID NO: 182 or an amino acid sequence having at least 90% identity to an amino acid sequence of SEQ ID NO:182; and/or a light chain variable region comprising the amino acid sequence of SEQ ID NO: 200 or an amino acid sequence having at least 90% identity to an amino acid sequence of SEQ ID NO:200;

(k) a heavy chain variable region comprising the amino acid sequence of SEQ ID NO: 183 or an amino acid sequence having at least 90% identity to an amino acid sequence of SEQ ID NO:183; and/or a light chain variable region comprising the amino acid sequence of SEQ ID NO: 201 or an amino acid sequence having at least 90% identity to an amino acid sequence of SEQ ID NO:201;

(l) a heavy chain variable region comprising the amino acid sequence of SEQ ID NO: 184 or an amino acid sequence having at least 90% identity to an amino acid sequence of SEQ ID NO:184; and/or a light chain variable region comprising the amino acid sequence of SEQ ID NO: 202 or an amino acid sequence having at least 90% identity to an amino acid sequence of SEQ ID NO:202;

(n) a heavy chain variable region comprising the amino acid sequence of SEQ ID NO: 185 or an amino acid sequence having at least 90% identity to an amino acid sequence of SEQ ID NO:185; and/or a light chain variable region comprising the amino acid sequence of SEQ ID NO: 203 or an amino acid sequence having at least 90% identity to an amino acid sequence of SEQ ID NO:203;

(o) a heavy chain variable region comprising the amino acid sequence of SEQ ID NO: 186 or an amino acid sequence having at least 90% identity to an amino acid sequence of SEQ ID NO:186; and/or a light chain variable region comprising the amino acid sequence of SEQ ID NO: 204 or an amino acid sequence having at least 90% identity to an amino acid sequence of SEQ ID NO:204;

(p) a heavy chain variable region comprising the amino acid sequence of SEQ ID NO: 187 or an amino acid sequence having at least 90% identity to an amino acid sequence of SEQ ID NO:187; and/or a light chain variable region comprising the amino acid sequence of SEQ ID NO: 205 an amino acid sequence having at least 90% identity to an amino acid sequence of SEQ ID NO:205; or (q) a heavy chain variable region comprising the amino acid sequence of SEQ ID NO: 188 or an amino acid sequence having at least 90% identity to an amino acid sequence of SEQ ID NO:188; and/or a light chain variable region comprising the amino acid sequence of SEQ ID NO: 206 or an amino acid sequence having at least 90% identity to an amino acid sequence of SEQ ID NO:206.

50. The antibody or antigen-binding fragment of any one of embodiments 33-49, wherein:
the antibody or antigen-binding fragment binds GFAP with a dissociation constant ($K_D$) of less than or less than about $1.0 \times 10^{-8}$ M, $2.0 \times 10^{-8}$ M, $3.0 \times 10^{-8}$ M, $4.0 \times 10^{-8}$ M, $5.0 \times 10^{-8}$ M, $6.0 \times 10^{-8}$ M, $7.0 \times 10^{-8}$ M, $8.0 \times 10^{-8}$ M, $9.0 \times 10^{-8}$ M, $1.0 \times 10^{-9}$ M, $2.0 \times 10^{-9}$ M, $3.0 \times 10^{-9}$ M, $4.0 \times 10^{-9}$ M, $5.0 \times 10^{-9}$ M, $6.0 \times 10^{-9}$ M, $7.0 \times 10^{-9}$ M, $8.0 \times 10^{-9}$ M, $9.0 \times 10^{-9}$ M, $1.0 \times 10^{-10}$ M, $2.0 \times 10^{-10}$ M, $3.0 \times 10^{-10}$ M, $4.0 \times 10^{-10}$ M, $5.0 \times 10^{-10}$ M, $6.0 \times 10^{-10}$ M, $7.0 \times 10^{-10}$ M, $8.0 \times 10^{-10}$ M, $9.0 \times 10^{-10}$ M, $1.0 \times 10^{-11}$ M, $2.0 \times 10^{-11}$ M, $3.0 \times 10^{-11}$ M, $4.0 \times 10^{-11}$ M, $5.0 \times 10^{-11}$ M, $6.0 \times 10^{-11}$ M, $7.0 \times 10^{-11}$ M, $8.0 \times 10^{-11}$ M, $9.0 \times 10^{-11}$ M, or $1.0 \times 10^{-12}$ M; or
the antibody or antigen-binding fragment binds GFAP with a dissociation constant ($K_D$) from or from about $1.0 \times 10^{-8}$ M to $2.0 \times 10^{-8}$ M, $1.0 \times 10^{-9}$ M to $6.0 \times 10^{-9}$ M, $2.0 \times 10^{-10}$ M to $9.0 \times 10^{-10}$ M, $1.0 \times 10^{-11}$ M to $8.0 \times 10^{-11}$ M, $1.0 \times 10^{-12}$ M to $5.0 \times 10^{-12}$ M, or $1.0 \times 10^{-8}$ M to $1.0 \times 10^{-12}$ M.

51. The antibody or antigen-binding fragment of any one of embodiments 33-50, wherein the antibody or antigen-binding fragment binds to an epitope within or that is or includes residues 92-106 of GFAP protein, residues 190-202 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or within residues 138-149 of GFAP protein corresponding to amino acid positions set forth in SEQ ID NO:212.

52. An antibody or antigen-binding fragment thereof that specifically binds to human GFAP, wherein the antibody or antigen-binding fragment binds to an epitope within residues 92-106 of a GFAP protein corresponding to amino acid positions set forth in SEQ ID NO:212.

53. The antibody or antigen-binding fragment of embodiment 52, wherein the antibody or antigen-binding fragment comprises a heavy chain variable region comprising CDR-H1, CDR-H2 and CDR-H3 amino acid sequences of SEQ ID NO:77, SEQ ID NO:91 and SEQ ID NO:108, respectively and/or a light chain variable region comprising CDR-L1, CDR-L2 and CDR-L3 amino acid sequences of SEQ ID NO:125, SEQ ID NO:142 and SEQ ID NO:157, respectively.

54. An antibody or antigen-binding fragment thereof that specifically binds to human GFAP, wherein the antibody or antigen-binding fragment binds to an epitope within or that is or includes residues 190-202 of a GFAP protein corresponding to amino acid positions set forth in SEQ ID NO:212.

55. The antibody or antigen-binding fragment of embodiment 54, wherein the antibody or antigen-binding fragment comprises a heavy chain variable region comprising CDR-H1, CDR-H2 and CDR-H3 amino acid sequences of SEQ ID NO:78, SEQ ID NO:92 and SEQ ID NO:109, respectively and/or a light chain variable region comprising CDR-L1, CDR-L2 and CDR-L3 amino acid sequences of SEQ ID NO:126, SEQ ID NO:143 and SEQ ID NO:158, respectively.

56. An antibody or antigen-binding fragment thereof that specifically binds to human GFAP, wherein the antibody or antigen-binding fragment binds to an epitope within or that is or includes residues 16-35 and/or 380 of a GFAP protein corresponding to amino acid positions set forth in SEQ ID NO:212.

57. The antibody or antigen-binding fragment of embodiment 56, wherein the antibody or antigen-binding fragment comprises a heavy chain variable region comprising CDR-H1, CDR-H2 and CDR-H3 amino acid sequences of SEQ ID NO:79, SEQ ID NO:93 and SEQ ID NO:110, respectively and/or a light chain variable region comprising CDR-L1, CDR-L2 and CDR-L3 amino acid sequences of SEQ ID NO:127, SEQ ID NO:144 and SEQ ID NO:159, respectively.

58. An antibody or antigen-binding fragment thereof that specifically binds to human GFAP, wherein the antibody or antigen-binding fragment binds to an epitope that is or includes residues 119 and/or 190 of a GFAP protein corresponding to amino acid positions set forth in SEQ ID NO:212.

59. The antibody or antigen-binding fragment of embodiment 58, wherein the antibody or antigen-binding fragment comprises a heavy chain variable region comprising CDR-H1, CDR-H2 and CDR-H3 amino acid sequences of SEQ ID NO:80, SEQ ID NO:95 and SEQ ID NO:112 respectively and/or a light chain variable region comprising CDR-L1, CDR-L2 and CDR-L3 amino acid sequences of SEQ ID NO:126, SEQ ID NO:142 and SEQ ID NO:158, respectively.

60. The antibody or antigen-binding fragment thereof of any of embodiments 1-59, wherein the antibody or antigen-binding fragment:
    does not bind to an epitope within or that is or includes residues 190-202 of a human GFAP protein corresponding to amino acid positions set forth in SEQ ID NO:212; and/or
    does not bind to the same or overlapping epitope as a reference antibody comprising a variable heavy chain set forth in SEQ ID NO:173 and a variable light chain set forth in SEQ ID NO:190; and/or
    does not compete for binding to GFAP with a reference antibody comprising a variable heavy chain set forth in SEQ ID NO: 173 and a variable light chain set forth in SEQ ID NO:190.

61. An antibody or antigen-binding fragment thereof that specifically binds to human GFAP, wherein the antibody or antigen-binding fragment binds to an epitope within or that is or includes residues 380-391 of a GFAP protein corresponding to amino acid positions set forth in SEQ ID NO:212.

62. The antibody or antigen-binding fragment of embodiment 61, wherein the antibody or antigen-binding fragment comprises:
    (a) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:128, SEQ ID NO:145 and SEQ ID NO:160, respectively;
    (b) a heavy chain variable region comprising CDR-H1, CDR-H2 and CDR-H3 amino acid sequences of SEQ ID NO:77, SEQ ID NO:94 and SEQ ID NO:111, respectively and/or a light chain variable region comprising CDR-L1, CDR-L2 and CDR-L3 amino acid sequences of SEQ ID NO:130, SEQ ID NO:145 and SEQ ID NO:160, respectively; or
    (c) a heavy chain variable region comprising CDR-H1, CDR-H2 and CDR-H3 amino acid sequences of SEQ ID NO:82, SEQ ID NO:97 and SEQ ID NO:114, respectively and/or a light chain variable region comprising CDR-L1, CDR-L2 and CDR-L3 amino acid sequences of SEQ ID NO:131, SEQ ID NO:147 and SEQ ID NO:162, respectively.

63. An antibody or antigen-binding fragment thereof that specifically binds to human GFAP, wherein the antibody or antigen-binding fragment binds to an epitope within or that is or includes residues 119-130 of a GFAP protein corresponding to amino acid positions set forth in SEQ ID NO:212.

64. The antibody or antigen-binding fragment of embodiment 63, wherein the antibody or antigen-binding fragment comprises:
    (a) a heavy chain variable region comprising CDR-H1, CDR-H2 and CDR-H3 amino acid sequences of SEQ ID NO:81, SEQ ID NO:96 and SEQ ID NO:113, respectively and/or a light chain variable region comprising CDR-L1, CDR-L2 and CDR-L3 amino acid sequences of SEQ ID NO:129, SEQ ID NO:146 and SEQ ID NO:161, respectively;
(b) a heavy chain variable region comprising CDR-H1, CDR-H2 and CDR-H3 amino acid sequences of SEQ ID NO:84, SEQ ID NO:99 and SEQ ID NO:116, respectively and/or a light chain variable region comprising CDR-L1, CDR-L2 and CDR-L3 amino acid sequences of SEQ ID NO:133, SEQ ID NO:149 and SEQ ID NO:164, respectively;
(c) a heavy chain variable region comprising CDR-H1, CDR-H2 and CDR-H3 amino acid sequences of SEQ ID NO:85, SEQ ID NO:100 and SEQ ID NO:117, respectively and/or a light chain variable region comprising CDR-L1, CDR-L2 and CDR-L3 amino acid sequences of SEQ ID NO:134, SEQ ID NO:150 and SEQ ID NO:165, respectively;
(d) a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:140, SEQ ID NO:155 and SEQ ID NO:170, respectively; or
(e) a heavy chain variable region comprising CDR-H1, CDR-H2 and CDR-H3 amino acid sequences of SEQ ID NO:90, SEQ ID NO:107 and SEQ ID NO:124, respectively and/or a light chain variable region comprising CDR-L1, CDR-L2 and CDR-L3 amino acid sequences of SEQ ID NO:141, SEQ ID NO:156 and SEQ ID NO:171, respectively.

65. An antibody or antigen-binding fragment thereof that specifically binds to human GFAP, wherein the antibody or antigen-binding fragment binds to an epitope within or that is or includes residues 210-221 of a GFAP protein corresponding to amino acid positions set forth in SEQ ID NO:212.

66. The antibody or antigen-binding fragment of embodiment 65, wherein the antibody or antigen-binding fragment comprises:
(a) a heavy chain variable region comprising CDR-H1, CDR-H2 and CDR-H3 amino acid sequences of SEQ ID NO:86, SEQ ID NO:101 and SEQ ID NO:118, respectively and/or a light chain variable region comprising CDR-L1, CDR-L2 and CDR-L3 amino acid sequences of SEQ ID NO:135, SEQ ID NO:151 and SEQ ID NO:166, respectively;
(b) a heavy chain variable region comprising CDR-H1, CDR-H2 and CDR-H3 amino acid sequences of SEQ ID NO:78, SEQ ID NO:102 and SEQ ID NO:119, respectively and/or a light chain variable region comprising CDR-L1, CDR-L2 and CDR-L3 amino acid sequences of SEQ ID NO:136, SEQ ID NO:152 and SEQ ID NO:167, respectively; or
(c) a heavy chain variable region comprising CDR-H1, CDR-H2 and CDR-H3 amino acid sequences of SEQ ID NO:78, SEQ ID NO:103 and SEQ ID NO:120, respectively and/or a light chain variable region comprising CDR-L1, CDR-L2 and CDR-L3 amino acid sequences of SEQ ID NO:137, SEQ ID NO:142 and SEQ ID NO:158, respectively.

67. An antibody or antigen-binding fragment thereof that specifically binds to human GFAP, wherein the antibody or antigen-binding fragment binds to an epitope within or that is or includes residues 320-329 of a GFAP protein corresponding to amino acid positions set forth in SEQ ID NO:212.

68. The antibody or antigen-binding fragment of embodiment 67, wherein the antibody or antigen-binding fragment comprises:
(a) a heavy chain variable region comprising CDR-H1, CDR-H2 and CDR-H3 amino acid sequences of SEQ ID NO:87, SEQ ID NO:104 and SEQ ID NO:121, respectively and/or a light chain variable region comprising CDR-L1, CDR-L2 and CDR-L3 amino acid sequences of SEQ ID NO:138, SEQ ID NO:153 and SEQ ID NO:168, respectively; or
(b) a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO:169, respectively.

69. An antibody or antigen-binding fragment thereof that specifically binds to human GFAP, wherein the antibody or antigen-binding fragment binds to an epitope within or that is or includes residues 346-357 and/or 376-387 of a GFAP protein corresponding to amino acid positions set forth in SEQ ID NO:212.

70. The antibody or antigen-binding fragment of embodiment 69, wherein the antibody or antigen-binding fragment comprises a heavy chain variable region comprising CDR-H1, CDR-H2 and CDR-H3 amino acid sequences of SEQ ID NO:88, SEQ ID NO:105 and SEQ ID NO:122, respectively and/or a light chain variable region comprising CDR-L1, CDR-L2 and CDR-L3 amino acid sequences of SEQ ID NO:139, SEQ ID NO:154 and SEQ ID NO: 169, respectively.

71. An antibody or antigen-binding fragment thereof that specifically binds to human GFAP, wherein the antibody or antigen-binding fragment binds to an epitope within or that is or includes residues 138-149 of a GFAP protein corresponding to amino acid positions set forth in SEQ ID NO:212.

72. The antibody or antigen-binding fragment of embodiment 71, wherein the antibody or antigen-binding fragment comprises a heavy chain variable region comprising CDR-H1, CDR-H2 and CDR-H3 amino acid sequences of SEQ ID NO:89, SEQ ID NO:106 and SEQ ID NO:123, respectively and/or a light chain variable region comprising CDR-L1, CDR-L2 and CDR-L3 amino acid sequences of SEQ ID NO:141, SEQ ID NO:156 and SEQ ID NO: 171 or CDR-L3 amino acid sequences of SEQ ID NO:140, SEQ ID NO:155 and SEQ ID NO: 170, respectively.

73. The antibody or antigen-binding fragment of any one of embodiments 33-72, wherein the GFAP is recombinant GFAP.

74. The antibody or antigen-binding fragment of any one of embodiments 1-72, wherein the GFAP is native GFAP.

75. The antibody or antigen-binding fragment of embodiment 74, wherein the native GFAP is present in or obtained from serum, plasma, blood, cerebrospinal fluid (CSF), urine, sweat, or saliva.

76. The antibody or antigen-binding fragment of any one of embodiments 1-75, wherein the antibody or antigen-binding fragment is isolated.

77. The antibody or antigen-binding fragment of any one of embodiments 1-76, wherein the antibody is a humanized antibody, a chimeric antibody or a human antibody.

78. The antibody or antigen-binding fragment of any one of embodiments 1-76, wherein the antibody is a murine antibody.
79. The antibody or antigen-binding fragment of any one of embodiments 1-78, wherein the antibody is an antigen-binding fragment thereof.
80. The antibody or antigen-binding fragment of embodiment 79, wherein the antigen-binding fragment thereof is a Fab, Fab'-SH, Fv, scFv, or (Fab')2 fragment.
81. The antibody or antigen-binding fragment of any one of embodiments 1-78, wherein the antibody further comprises a heavy chain constant domain and/or a light chain constant domain.
82. The antibody or antigen-binding fragment of embodiment 81, wherein the heavy chain and/or light constant domain is murine or human.
83. The antibody or antigen-binding fragment of embodiment 81 or 82, wherein the heavy chain constant domain is IgG1, IgG2a, IgG2b or IgM.
84. The antibody or antigen-binding fragment of 1-78 and 81-83 that is a full length or intact antibody.
85. The antibody or antigen-binding fragment of any one of embodiments 1-84, wherein the antibody is a monoclonal antibody.
86. The antibody or antigen-binding fragment of any one of embodiments 1-85, wherein the antibody is attached to a label.
87. The antibody or antigen-binding fragment of embodiment 86, wherein the label is a fluorescent dye, a fluorescent protein, a radioisotopes, a chromophores, a metal ion, gold particles, silver particles, magnetic particles, a polypeptides, an enzyme, streptavidin, biotin, a luminescent compound, or an oligonucleotide.
88. A nucleic acid encoding the antibody or antigen-binding fragment of any one of embodiments 1-87.
89. A nucleic acid encoding a heavy chain comprising the heavy variable region of any one of embodiments 1-87.
90. A nucleic acid encoding a light chain comprising the light variable region of any one of embodiments 1-87.
91. A vector comprising the nucleic acid of any one of embodiments 88-90.
92. The vector of embodiment 91, wherein the vector is an expression vector.
93. A host cell comprising the nucleic acid of any one of embodiments 88-90 or the vector of embodiment 91 or 92.
94. A method of producing an antibody or antigen-binding fragment thereof comprising culturing the host cell of embodiment 93 under a condition that produces the antibody or antigen-binding fragment.
95. The method of embodiment 94, further comprising recovering the antibody or antigen-binding fragment produced by the host cell.
96. An anti-UCH-L1 antibody or antigen-binding fragment thereof produced by the method of embodiment 94 or embodiment 95.
97. An anti-GFAP antibody or antigen-binding fragment thereof produced by the method of embodiment 94 or embodiment 95.
98. A composition comprising the antibody or antigen-binding fragment of any one of embodiments 1-87, 96 and 97.
99. The composition of embodiment 98, further comprising a pharmaceutically acceptable carrier.
100. A combination, comprising two or more anti-UCH-L1 antibodies or antigen-binding fragments thereof of any one of embodiments 1-32, 76-87 and 96.
101. The combination of embodiment 100, wherein the two or more antibodies or antigen-binding fragments comprise:
one or more first antibody or antigen-binding fragment thereof that binds to a first epitope or region within UCH-L1; and
one or more second antibody or antigen-binding fragment thereof that binds to a second epitope or region within UCH-L1.
102. The combination of embodiment 101, wherein the one or more first antibody or antigen-binding fragments thereof, and the one or more second antibody or antigen-binding fragments thereof bind to a non-overlapping epitope or region of human UCH-L1 and/or do not compete for binding to UCH-L1.
103. The combination of any of embodiment 100-102, wherein:
(i) the one or more first antibody or antigen-binding fragment thereof binds to an epitope within or that is or includes residues 28-36 of UCH-L1 protein, residues 98-106 of UCH-L1 protein, residues 138-145 of UCH-L1 protein, and/or residues 142-149 of UCH-L1 protein corresponding to amino acid positions set forth in SEQ ID NO:207; and
(ii) the one or more second antibody or antigen-binding fragment thereof binds to an epitope that is not the same as or does not overlap with an epitope of (i).
104. The combination of any of embodiments 100-103, wherein:
(i) the one or more first antibody or antigen-binding fragment thereof binds to an epitope within or that is or includes residues 28-36 of UCH-L1 protein and/or residues 98-106 of UCH-L1 protein corresponding to amino acid positions set forth in SEQ ID NO:207; and
(ii) the one or more second antibody or antigen-binding fragment thereof binds to an epitope within or that is or includes residues 138-145 of UCH-L1 protein and/or residues 142-149 of UCH-L1 protein corresponding to amino acid positions set forth in SEQ ID NO:207.
105. A combination, comprising two or more anti-GFAP antibodies or antigen-binding fragments thereof of any one of embodiments 33-87 and 97.
106. The combination of embodiment 105, wherein the two or more antibodies comprise:
one or more first antibody or antigen-binding fragment thereof that bind to a first epitope or region within GFAP; and
one or more second antibody or antigen-binding fragment thereof that binds to a second epitope or region within GFAP.
107. The combination of embodiment 106, wherein the one or more first antibody or antigen-binding fragments thereof, and the one or more second antibody or antigen-binding fragments thereof bind to a non-overlapping epitope or region of human GFAP and/or do not compete for binding to GFAP.
108. The combination of any of embodiments 105-107, wherein:
(i) the one or more first antibody or antigen-binding fragment thereof binds to an epitope within or that is or includes residues 92-106 of GFAP protein, residues 190-202 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212; and (ii) the one or more second antibody or antigen-binding fragment thereof binds to an epitope that is not the same as or does not overlap with an epitope of (i).

109. The combination of any of embodiments 105-108, wherein:
   (i) the one or more first antibody or antigen-binding fragment thereof binds to an epitope within or that is or includes amino acid residues 190-202 of GFAP protein corresponding to amino acid positions set forth in SEQ ID NO:212; and
   (ii) the one or more second antibody or antigen-binding fragment thereof binds to an epitope within or that is or includes residues 92-106 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212.

110. The combination of any one of embodiments 100-109, wherein at least one of the antibodies or antigen-binding fragments, optionally the one or more first antibody or antigen-binding fragment thereof or the one or more second antibody or antigen-binding fragment thereof, is conjugated to a label.

111. The combination of any one of embodiments 100-110, wherein at least one of the antibodies or antigen-binding fragments, optionally the one or more first antibody or antigen-binding fragment thereof or the one or more second antibody or antigen-binding fragment thereof, is attached or immobilized to a solid support.

112. The combination of any one of embodiments 100-111, wherein the one or more first antibody or antigen binding fragment thereof or the one or more second antibody or antigen-binding fragment thereof is attached or immobilized to a solid support and the other of the one or more first antibody or antigen-binding fragment thereof or the one or more second antibody or antigen-binding fragment thereof is conjugated to a label.

113. The combination of any of embodiments 110-112, wherein the label is a fluorescent dye, a fluorescent protein, a radioisotopes, a chromophores, a metal ion, gold particles, silver particles, magnetic particles, a polypeptides, an enzyme, streptavidin, biotin, a luminescent compound, or an oligonucleotide.

114. The combination of any of embodiments 111-113, wherein the solid support is a bead, a column, an array, an assay plate, a microwell, a stick, a filter, or a strip.

115. A combination, comprising:
   at least one anti-UCH-L1 antibody of any one of embodiments 1-32, 76-87, and 96 or a combination of anti-UCH-L1 antibodies set forth in any one of embodiments 100-104 and 110-114; and
   at least one anti-GFAP antibody of any one of embodiments 33-87 and 97 or a combination of anti-GFAP antibodies set forth in any one of embodiments 105-114.

116. A solid support, comprising immobilized thereto an antibody or antigen-binding fragment of any of embodiments 1-87, 96 and 97.

117. The solid support of embodiment 116, wherein the solid support is a bead, a column, an array, an assay plate, a microwell, a stick, a filter, or a strip.

118. A device comprising the solid support of embodiment 116 or embodiment 117.

119. The device of embodiments 118, wherein the device is a rapid detection device or a rapid diagnostic device.

120. A kit comprising the antibody or antigen-binding fragment of any one of embodiments 1-87, 96 and 97, the composition of embodiment 98 or 99 or the combination of any one of embodiments 100-115, and optionally instructions for use.

121. The kit of embodiment 120, further comprising a solid support or a device comprising a solid support.

122. The kit of embodiment 121, wherein the solid support is a bead, a column, an array, an assay plate, a microwell, a stick, a filter, or a strip.

123. The kit of embodiment 121 or embodiment 122, wherein the device is a rapid detection device or a rapid diagnostic device.

124. The kit of any one of embodiments 120-123, wherein the instructions specify an assay for detecting UCH-L1 or GFAP in a sample and/or for determining an amount of UCH-L1 or GFAP in a sample.

125. A method of detecting UCH-L1 in a human subject, the method comprising the steps of
   (a) contacting a sample with one or more first antibody or antigen-binding fragment of any one of embodiments 1-32, 76-87 and 96 under conditions to form a complex comprising the antibody or antigen-binding fragment and UCH-L1; and
   (b) detecting the presence or absence of the complex in the sample, thereby detecting UCH-L1 in the sample.

126. The method of embodiment 125 that is an immunoassay.

127. The method of embodiment 126, wherein the immunoassay is an enzyme-linked immunosorbent assay (ELISA).

128. The method of embodiment 127, wherein the ELISA is a sandwich ELISA.

129. The method of any of embodiments 125-128, wherein detecting the presence or absence of the complex in step (b), comprises:
   (i) contacting the complex of step (a) with one or more second antibody or antigen-binding fragments thereof under conditions to bind UCH-L1 in the complex, the one or more second antibody or antigen-binding fragment thereof being conjugated to a label capable of producing a detectable signal; and
   (ii) assessing the presence or absence of the detectable signal.

130. The method of embodiment 129, wherein the one or more second antibody or antigen-binding fragment comprises one or more antibody or antigen-binding fragment of any one of embodiments 1-32, 76-87 and 96.

131. A method of detecting human UCH-L1 in a sample from a subject, the method comprising:
   (a) contacting a sample with one or more first antibody or antigen-binding fragments that specifically binds human UCH-L1 under conditions to form a complex comprising the antibody or antigen-binding fragment and UCH-L1; and (b) detecting the presence or absence of the complex in the sample, said detecting comprising:
  (i) contacting the complex of step (a) with one or more second antibody or antigen-binding fragments thereof that specifically binds UCH-L1 under conditions to bind UCH-L1 in the complex, the one or more second antibody or antigen-binding fragment thereof being conjugated to a label capable of producing a detectable signal; and
  (ii) assessing the presence or absence of the detectable signal, thereby detecting UCH-L1 in the sample,
  wherein at least one of the one or more first antibody or antigen-binding fragments and one or more of the second antibody or antigen-binding fragments comprise an antibody or antigen-binding fragment of any one of embodiments 1-32, 76-87 and 96.

132. The method of any of embodiments 129-131, wherein the one or more second antibody or antigen-binding fragment binds to an epitope of UCH-L1 that is not the same as or does not overlap with an epitope bound by the antibody or antigen-binding fragment of (a).

133. The method of any of embodiments 129-132, wherein:
  (1) the one or more first antibody or antigen-binding fragment thereof binds to an epitope within or that is or includes residues 28-36 of UCH-L1 protein, residues 98-106 of UCH-L1 protein, residues 138-145 of UCH-L1 protein, and/or residues 142-149 of UCH-L1 protein corresponding to amino acid positions set forth in SEQ ID NO:207; and
  (2) the one or more second antibody or antigen-binding fragment thereof binds to an epitope that is not the same as or does not overlap with an epitope of (1).

134. The method of any of embodiments 129-132, wherein:
  (1) the one or more first antibody or antigen-binding fragment thereof binds to an epitope within or that is or includes residues 28-36 of UCH-L1 protein and/or residues 98-106 of UCH-L1 protein corresponding to amino acid positions set forth in SEQ ID NO:207; and
  (2) the one or more second antibody or antigen-binding fragment thereof binds to an epitope within or that is or includes residues 138-145 of UCH-L1 protein and/or residues 142-149 of UCH-L1 protein corresponding to amino acid positions set forth in SEQ ID NO:207.

135. A method of detecting GFAP in a human subject, the method comprising the steps of:
  (a) contacting a sample with one or more first antibody or antigen-binding fragment of any one of embodiments 33-87 and 97 under conditions to form a complex comprising the antibody or antigen-binding fragment and GFAP; and
  (b) detecting the presence or absence of the complex in the sample, thereby detecting GFAP in the sample.

136. The method of embodiment 135 that is an immunoassay.

137. The method of embodiment 136, wherein the immunoassay is an enzyme-linked immunosorbent assay (ELISA).

138. The method of embodiment 137, wherein the ELISA is a sandwich ELISA.

139. The method of any of embodiments 135-138, wherein detecting the presence or absence of the complex in step (b), comprises:
  (i) contacting the complex of step (a) with one or more second antibody or antigen-binding fragments thereof under conditions to bind GFAP in the complex, the one or more second antibody or antigen-binding fragment thereof being conjugated to a label capable of producing a detectable signal; and
  (ii) assessing the presence or absence of the detectable signal.

140. The method of embodiment 139, wherein the one or more second antibody or antigen-binding fragment comprises one or more antibody or antigen-binding fragment of any one of embodiments 33-87 and 97.

141. A method of detecting human GFAP in a sample from a subject, the method comprising:
  (a) contacting a sample with one or more first antibody or antigen-binding fragments that specifically binds human GFAP under conditions to form a complex comprising the antibody or antigen-binding fragment and GFAP; and
  (b) detecting the presence or absence of the complex in the sample, said detecting comprising:
    (i) contacting the complex of step (a) with one or more second antibody or antigen-binding fragments thereof that specifically binds GFAP under conditions to bind GFAP in the complex, the one or more second antibody or antigen-binding fragment thereof being conjugated to a label capable of producing a detectable signal; and
    (ii) assessing the presence or absence of the detectable signal, thereby detecting GFAP in the sample,
  wherein at least one of the one or more first antibody or antigen-binding fragments and/or one or more of the second antibody or antigen-binding fragments comprise an antibody or antigen-binding fragment of any one of embodiments 33-87 and 97.

142. The method of any of embodiments 139-141, wherein the one or more second antibody or antigen-binding fragment binds to an epitope of GFAP that is not the same as or does not overlap with an epitope bound by the antibody or antigen-binding fragment of (a).

143. The method of any of embodiments 139-142, wherein:
  (1) the one or more first antibody or antigen-binding fragment thereof binds to an epitope within or that is or includes residues 92-106 of GFAP protein, residues 190-202 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212; and
  (2) the one or more second antibody or antigen-binding fragment thereof binds to an epitope that is not the same as or does not overlap with an epitope of (1).

144. The method of any of embodiments 139-142, wherein:
  (1) the one or more first antibody or antigen-binding fragment thereof binds to an epitope within or that is or includes amino acid residues 190-202 of GFAP protein corresponding to amino acid positions set forth in SEQ ID NO:212; and (2) the one or more second antibody antigen-binding fragment thereof binds to an epitope within or that is or includes residues 92-106 of GFAP protein, residues 16-35 and/or 380 of GFAP protein, residues 119 and/or 190 of GFAP protein, residues 380-391 of GFAP protein, residues 119-130 of GFAP protein, residues 210-221 of GFAP protein, residues 320-329 of GFAP protein, 346-357 and/or 376-387 of GFAP protein and/or residues 138-149 of GFAP protein corresponding to amino acid positions set forth in SEQ ID NO:212.

145. The method of any of embodiments 125-144, wherein prior to step (b) separating or washing the complex formed in step (a) from the sample not comprised in the complex.

146. The method of any of embodiments 125-145, wherein the one or more first antibody or antigen-binding fragment thereof is attached or immobilized to a solid support.

147. The method of any of embodiments 129-134 and 139-146, wherein prior to step (b)(ii) removing the one or more second antibody or antigen-binding fragments thereof not bound to the complex.

148. The method of any of embodiments 125-147, wherein the sample is isolated or obtained from the individual.

149. The method of any of embodiments 125-148, wherein the sample is serum, plasma, blood, cerebrospinal fluid (CSF), urine, sweat, or saliva.

150. The method of any of embodiments 125-134 and 145-149, further comprising: (c) determining the amount of UCH-L1 detected in the sample.

151. The method of any of embodiments 125-150, further comprising: (c) determining the amount of GFAP detected in the sample.

152. A method of diagnosing brain injury or damage in a subject, the method comprising performing the method of embodiment 150, thereby determining the amount of UCH-L1 in the sample; and
  (i) if the amount of UCH-L1 in the sample is greater than or equal to or about a UCH-L1 threshold level, diagnosing the subject as having a brain injury or damage or at risk of having a brain injury or damage; or
  (ii) if the amount of UCH-L1 in the sample is below the UCH-L1 threshold level, diagnosing the subject as not having a brain injury or damage or not being at risk of having a brain injury or damage.

153. A method of diagnosing brain injury or damage in a subject, the method comprising performing the method of embodiment 151, thereby determining the amount of GFAP in the sample; and
  (i) if the amount of GFAP in the sample is greater than or equal to or about a GFAP threshold level, diagnosing the subject as having a brain injury or damage or at risk of having a brain injury or damage; or
  (ii) if the amount of GFAP in the sample is below the GFAP threshold level, diagnosing the subject as not having a brain injury or damage or not being at risk of having a brain injury or damage.

154. A method of diagnosing brain injury or damage in a subject, the method comprising:
  (a) performing the method of embodiment 150, thereby determining the amount of UCH-L1 in the sample;
  (b) performing the method of embodiment 151, thereby determining the amount of GFAP in the sample; and
  (i) if the amount of UCH-L1 in the sample is greater than or equal to or about a UCH-L1 threshold level and/or if the amount of GFAP in the sample is greater than or equal to or about a GFAP threshold level, diagnosing the subject as having a brain injury or damage or at risk of having a brain injury or damage; or
  (ii) if the amount of UCH-L1 in the sample is below the UCH-L1 threshold level and/or if the amount of GFAP in the sample is below the GFAP threshold level, diagnosing the subject as not having a brain injury or damage or not being at risk of having a brain injury or damage.

155. The method of any of embodiments 152-154, wherein if the subject is identified as having a brain injury or damage or of being at risk of having a brain injury or damage administering a therapeutic agent to the subject to treat the brain injury or damage.

156. A method of treating a subject for a brain injury or damage, comprising:
  a) performing the method of any of embodiments 152-154; and
  b) if the subject is identified as having a brain injury or damage or being at risk of having a brain injury or damage administering a therapeutic agent to the subject to treat the brain injury or damage.

157. The method of embodiments 155 or embodiment 156, wherein the therapeutic agent is selected from a N-methyl-D-aspartate (NMDA) receptor antagonist, a sodium channel antagonist, a nitric oxide synthase (NOS) inhibitor, a glycine site antagonist, a potassium channel opener, an AMPA/kainate receptor antagonist, a calcium channel antagonist, a GABA-A receptor modulator, an anti-inflammatory agent or a combination thereof.

158. The method of any of embodiments 152-154, wherein if the subject is identified as having a brain injury or damage or of being at risk of having a brain injury or damage, carrying out neuroimaging on the subject's brain.

159. The method of any of embodiment 152-154, wherein if the subject is identified as not having a brain injury or damage or not being at risk of having a brain injury or damage, neuroimaging of the subject's brain is not carried out.

160. A method of predicting if a subject is in need of neuroimaging for a suspected brain injury or damage, the method comprising:
  (a) performing the method of embodiment 150, thereby determining the amount of UCH-L1 in the sample; and/or
  (b) performing the method of embodiment 151, thereby determining the amount of GFAP in the sample; and
  (i) if the amount of UCH-L1 in the sample is greater than or equal to or about a UCH-L1 threshold level and/or if the amount of GFAP in the sample is greater than or equal to or about a GFAP threshold level, predicting the subject is in need of neuroimaging; or
  (ii) if the amount of UCH-L1 in the sample is below the UCH-L1 threshold level and/or if the amount of GFAP in the sample is below the GFAP threshold level, predicting the subject is not in need of neuroimaging.

161. A method of predicting if a subject is in need of neuroimaging for a suspected brain injury or damage, comprising:
   a) performing the method of any of embodiments 152-154; and
   b) if the subject is identified as having a brain injury or damage or being at risk of having a brain injury or damage predicting the subject is in need of neuroimaging.
162. The method of embodiment 161, further comprising carrying out the neuroimaging on the subject's brain.
163. The method of any of embodiments 158, 161 or 162, wherein the neuroimaging is by computed tomography (CT) or magnetic resonance imaging (MRI).
164. The method of any of embodiments 152 and 154-163, wherein the UCH-L1 threshold level is or is about 30 pg/mL, is or is about 40 mg/mL, is or is about 60 pg/mL, is or is about 80 pg/mL, is or is about 100 pg/mL, is or is about 150 pg/mL, is or is about 200 pg/mL, is or is about 250 pg/mL, is or is about 300 pg/mL, is or is about 400 pg/mL or is or is about 500 pg/mL.
165. The method of any of embodiments 152 and 154-164, wherein the UCH-L1 threshold level is or is about 100 pg/mL.
166. The method of any of embodiments 152 and 154-164, wherein the UCH-L1 threshold level is or is about 200 pg/ml.
167. The method of any of embodiments 153-166, wherein the GFAP threshold level is or is about 10 pg/mL, is or is about 20 pg/mL, is or is about 30 pg/mL, is or is about 40 pg/mL, is or is about 50 pg/ml, is or is about 60 pg/mL, is or is about 70 pg/mL, is or is about 80 pg/mL, is or is about 90 pg/mL, is or is about 100 pg/mL, is or is about 150 pg/mL, is or is about 200 pg/mL, is or is about 250 pg/mL or is or is about 300 pg/mL.
168. The method of any of embodiments 153-167, wherein GFAP threshold level is or is about 50 pg/ml.
169. The method of any of embodiments 153-167, wherein GFAP threshold level is or is about 70 pg/ml.
170. The method of any of embodiments 154-169, wherein the UCH-L1 threshold level is 200 pg/mL and the GFAP threshold level is 70 pg/mL.
171. The method of any of embodiments 152-170, wherein the brain injury or damage is associated with or caused by mechanical damage, hypoxia, infectious disease, disease affecting nerve cells, toxin damage or neurological disease or condition.
172. The method of embodiment 171, wherein the mechanical damage is traumatic brain injury or chronic traumatic encephalopathy.
173. The method of any of embodiments 172, wherein the brain injury or damage is traumatic brain injury.
174. The method of embodiment 173, wherein the traumatic brain injury is a mild traumatic brain injury.
175. The method of embodiment 171, wherein the hypoxia is associated with stroke, vasculitis, ischemia, or cardiac disease.
176. The method of embodiment 171, wherein the infectious disease comprises infection with a *Mycobacterium* bacteria, *Neisseria meningitidis*, a Herpesviridae virus, a poliovirus, mumps virus, an Enteroviridae virus, West Nile virus, or tick-borne encephalitis virus.
177. The method of embodiment 171, wherein the disease affecting nerve cells is Alzheimer's disease, Lewy body dementia, vascular dementia, diabetic dementia, Parkinson's disease, ALS, or prion disease.
178. The method of embodiment 171, wherein the toxin damage is associated with exposure to nerve agents, alcoholic dementia, heavy metal poisoning, psychoactive agents, chemotherapeutic agents, biological agents, or antibiotics.
179. The method of any of embodiments 125-178, wherein the sample is obtained from the subject no more than about 30 minutes, 1 hour, 2 hours, 4 hours, 6 hours, 8 hours, 12 hours, 24 hours or 48 hours after a brain injury or damage or a suspected brain injury or damage.
180. The method of any of embodiments 125-179, wherein the sample is obtained from the subject no more than about 8 hours after a brain injury or damage or a suspected brain injury or damage.
181. The method of any of embodiments 125-180, wherein the sample is serum.
182. The method of any of embodiments 125-180, wherein the sample is CSF.
183. The method of any of embodiments 125-182 that is performed in vitro.

VIII. Examples

The following examples are included for illustrative purposes only and are not intended to limit the scope of the invention.

Example 1: Generation of Mouse Anti-UCH-L1 Antibodies

Antibodies were generated from immunization of mice with recombinant human UCH-L1 (full length sequence of amino acids set forth in SEQ ID NO:207) and sequenced. Several strategies were employed for the generation of mouse anti-UCH-L1 antibodies.

For generation of mouse anti-UCH-L1 antibodies designated UCH-L1-1 and UCH-L1-2, recombinant human UCH-L1 was expressed from *E. coli* and used as an immunogen. BALB/c mice or NIH Swiss mice were inoculated with the human UCH-L1 antigen to generate an immune response. Hybridoma fusions were produced and screened for antibodies that bound to UCH-L1 using indirect ELISA and sandwich ELISA with either recombinant UCH-L1 or native UCH-L1 obtained from cerebrospinal fluid (CSF).

For generation of the mouse anti-UCH-L1 antibody designated UCH-L1-13, affinity-purified recombinant human UCH-L1 mixed with Sigma Adjuvant System adjuvant (Catalog No. S6322) was used for immunization of BALB/c mice or NIH Swiss mice. Hybridoma fusions were produced and screened by western blot for antibodies that bound to recombinant human UCH-L1 or UCH-L1 from rat brain lysate as well as screened by indirect ELISA with recombinant UCH-L1.

For all other mouse anti-UCH-L1 antibodies (i.e., UCH-L1-5, UCH-L1-3, UCH-L1-11, UCH-L1-12, UCH-L1-4, UCH-L1-6, UCH-L1-7, UCH-L1-8, UCH-L1-9, and UCH-L1-10), a strategy was employed to identify antibodies that bind to an epitope that is distinct from that bound by antibody UCH-L1-1 (VH chain set forth in SEQ ID NO:51 and the VL chain set forth in SEQ ID NO:64). In this approach, 1p g of recombinant human UCH-L1 expressed from *E. coli* was mixed with 1 pg of antibody UCH-L1-1 and rotated overnight at 4° C. to form immune complexes, then conjugated to KLH (keyhole limpet hemocyanin) and mixed with Freund's adjuvant for injection in mice. For the second and third injections the process was the same except incomplete Freund's adjuvant was used. For the final boost, unconjugated recombinant human UCH-L1 was injected in the mice. Hybridoma fusions were produced and screened for antibodies that bound to UCH-L1 using indirect ELISA and sandwich ELISA with either recombinant UCH-L1 or native UCH-L1 obtained from CSF.

Antibodies that bound to human UCH-L1 protein during screening were identified and are set forth in Table 3. Epitope mapping to regions of UCH-L1 and isotype specificity experiments also were performed to further characterize the antibodies as set forth in Table 3.

Application Note 14, ForteBio, Div. of Pall Life Sciences, 2013. Polyhistidine-tagged recombinant human UCH-L1 expressed from *E. coli* was used as the antigen. The antigen was bound at a concentration of 8.3 pg/ml to an anti-Penta-HIS(HIS1K) capture biosensor containing an anti-histidine antibody (ForteBio) for use with the Octet QK$^e$ instrument. The sensor was then incubated with increasing concentrations of a tested anti-UCH-L1 antibody with concentrations ranging from about 0.006 to about 0.16 μM to obtain affinity measurements.

TABLE 3

Isotype of mouse anti-UCH-L1 antibodies

| Antibody clone | Isotype | Epitope within, that is, or includes UCH-L1 Amino Acid Sequence (corresponding to residues set forth in SEQ ID NO: 207) |
|---|---|---|
| UCH-L1-1 | IgG1 isotype | 98-106 |
| UCH-L1-2 | IgG1 isotype | 28-36 |
| UCH-L1-3 | IgG1 isotype | 98-106 |
| UCH-L1-4 | IgG1 isotype | 138-145 |
| UCH-L1-5 | IgG2b isotype | 142-149 |
| UCH-L1-6 | IgG2a isotype | 28-36 |
| UCH-L1-7 | IgG2b isotype | 28-36 |
| UCH-L1-8 | IgG2b isotype | 28-36 |
| UCH-L1-9 | IgG2b isotype | 28-36 |
| UCH-L1-10 | IgG2b isotype | 28-36 |
| UCH-L1-11 | IgG2b isotype | 28-36 |
| UCH-L1-12 | IgG2a isotype | 28-36 |
| UCH-L1-13 | IgM isotype | 98-106 |

The affinities of the antibodies that bound to human UCH-L1 protein were determined and are set forth in Table 4. The rates of association ($k_{on}$) and dissociation ($k_{off}$) of the anti-UCH-L1 antibodies were determined by bio-layer interferometry using an Octet QK$^e$ instrument according to the manufacturer's instructions (ForteBio). See Tobias et al., *Biomolecular Binding Kinetic Assays in the Octet Platform*,

TABLE 4

Affinities of mouse anti-UCH-L1 antibodies

| Antibody clone | $K_D$ (M) | Kon (1/Ms) | Kdis (1/s) | Antibody Concentration Range Tested (μM) |
|---|---|---|---|---|
| UCH-L1-1 | <1.00E-12 | 58,760 | 0.0000001 | 0.05-0.0063 |
| UCH-L1-2 | 2.07E-10 | 145,700 | 0.0000301 | 0.05-0.0063 |
| UCH-L1-3 | 3.67E-10 | 36,370 | 0.0000134 | 0.166-0.02 |
| UCH-L1-4 | 3.69E-11 | 378,500 | 0.0000140 | 0.05-0.0062 |
| UCH-L1-5 | <1.00E-12 | 459,300 | 0.0000001 | 0.05-0.0062 |
| UCH-L1-6 | <1.00E-12 | 145,400 | 0.0000001 | 0.05-0.0063 |
| UCH-L1-7 | 1.87E-11 | 132,800 | 0.0000025 | 0.05-0.0063 |
| UCH-L1-8 | 4.74E-11 | 141,000 | 0.0000067 | 0.05-0.0063 |
| UCH-L1-9 | 8.57E-11 | 117,600 | 0.0000101 | 0.05-0.0063 |
| UCH-L1-10 | 4.30E-11 | 107,400 | 0.0000046 | 0.05-0.0063 |
| UCH-L1-11 | 1.25E-11 | 199,700 | 0.0000130 | 0.05-0.0063 |
| UCH-L1-12 | 1.36E-11 | 165,800 | 0.0000206 | 0.05-0.0063 |
| UCH-L1-13 | Not determined | Not determined | Not determined | Not determined |

Exemplary antibodies were sequenced and SEQ ID NOs are set forth in Table 5 and Table 6.

TABLE 5

Amino acid sequences of CDRs from mouse anti-UCH-L1 antibodies$^a$

| Antibody | CDR-H1 | CDR-H2 | CDR-H3 |
|---|---|---|---|
| UCH-L1-1 | SYWMH SEQ ID NO: 1 | NIYPGSGSTNYDEKFKS SEQ ID NO: 9 | EDY SEQ ID NO: 20 |
| UCH-L1-2 | SHAMS SEQ ID NO: 2 | TISSGGSNTYYPDSVKG SEQ ID NO: 10 | HGEVRRGYYFDY SEQ ID NO: 21 |
| UCH-L1-3 | SYWIH SEQ ID NO: 3 | NIYPGSGITNYDEKFKT SEQ ID NO: 11 | EDY SEQ ID NO: 20 |
| UCH-L1-4 | EHFMN SEQ ID NO: 4 | IINPYTDGTNYDQKFKD SEQ ID NO: 12 | WGGDGEGY SEQ ID NO: 22 |
| UCH-L1-5 | EYYMS SEQ ID NO: 5 | FIRNRAHGYTTEYSASVKG SEQ ID NO: 13 | SYGAPFAY SEQ ID NO: 23 |
| UCH-L1-6 | EYTMH SEQ ID NO: 6 | GINPNNGRTSYNQKFKG SEQ ID NO: 14 | RLGRGFYFDY SEQ ID NO: 24 |
| UCH-L1-7 | EYTMH SEQ ID NO: 6 | GINPNNGRTSYNQKFKG SEQ ID NO: 14 | RLGRGFYFDY SEQ ID NO: 24 |
| UCH-L1-8 | EYTMH SEQ ID NO: 6 | GLNPNNGRTSYNQKFKG SEQ ID NO: 15 | RLGRGFYFDY SEQ ID NO: 24 |

TABLE 5-continued

Amino acid sequences of CDRs from mouse anti-UCH-L1 antibodies[a]

| | | | |
|---|---|---|---|
| UCH-L1-9 | EYTMH<br>SEQ ID NO: 6 | GINPNNGRTSYNQKFKG<br>SEQ ID NO: 14 | RLGRGFYFDY<br>SEQ ID NO: 24 |
| UCH-L1-10 | EYTMH<br>SEQ ID NO: 6 | GFNPNNGRTSYNQKFKG<br>SEQ ID NO: 16 | RLYRGFYFDY<br>SEQ ID NO: 25 |
| UCH-L1-11 | RYAMS<br>SEQ ID NO: 7 | TISTAGSYTYYPDSVKG<br>SEQ ID NO: 17 | QGTGTYAMDY<br>SEQ ID NO: 26 |
| UCH-L1-12 | KNAMS<br>SEQ ID NO: 8 | TISTGGTYTYYPDSVKG<br>SEQ ID NO: 18 | QRTGTYAMDH<br>SEQ ID NO: 27 |
| UCH-L1-13 | SYWMH<br>SEQ ID NO: 1 | NIYPGSGTTNYDEKFKS<br>SEQ ID NO: 19 | EDY<br>SEQ ID NO: 20 |
| Antibody | CDR-L1 | CDR-L2 | CDR-L3 |
| UCH-L1-1 | RSSQNIVHSNGNTYLE<br>SEQ ID NO: 28 | KVSNRFS<br>SEQ ID NO: 37 | FQGSHVPFT<br>SEQ ID NO: 45 |
| UCH-L1-2 | SASQGITNYLN<br>SEQ ID NO: 29 | YTSSLHS<br>SEQ ID NO: 38 | QHYSNLPWT<br>SEQ ID NO: 46 |
| UCH-L1-3 | RSSQSIVHSNGNTYLE<br>SEQ ID NO: 30 | KVSNRFS<br>SEQ ID NO: 37 | FQGSHVPFT<br>SEQ ID NO: 45 |
| UCH-L1-4 | RSSKSLLHSNGNTYLY<br>SEQ ID NO: 31 | RMSNLAS<br>SEQ ID NO: 39 | MQHLEYPLT<br>SEQ ID NO: 47 |
| UCH-L1-5 | RSSKSLLHSDGNTYLY<br>SEQ ID NO: 32 | RMSNLAS<br>SEQ ID NO: 39 | MQHLEYPLT<br>SEQ ID NO: 47 |
| UCH-L1-6 | RASESVESYGNNLIH<br>SEQ ID NO: 33 | LSSNLEP<br>SEQ ID NO: 40 | QQSNGDPYT<br>SEQ ID NO: 48 |
| UCH-L1-7 | RASESVDSYGNNLMH<br>SEQ ID NO: 34 | LSSNLES<br>SEQ ID NO: 41 | QQSNGDPYT<br>SEQ ID NO: 48 |
| UCH-L1-8 | RASESVDSYGNNLMH<br>SEQ ID NO: 34 | RASNLES<br>SEQ ID NO: 42 | QQSNGDPYT<br>SEQ ID NO: 48 |
| UCH-L1-9 | RASESVDSYGNNFMH<br>SEQ ID NO: 35 | LSSNLES<br>SEQ ID NO: 41 | QQSNGDPYT<br>SEQ ID NO: 48 |
| UCH-L1-10 | RASESVDSYGNNLMH<br>SEQ ID NO: 34 | RASNLES<br>SEQ ID NO: 42 | QQSNGDPYT<br>SEQ ID NO: 48 |
| UCH-L1-11 | RASGNIHNYLA<br>SEQ ID NO: 36 | NAKTLAD<br>SEQ ID NO: 43 | QHFWSTTWT<br>SEQ ID NO: 49 |
| UCH-L1-12 | RASGNIHNYLA<br>SEQ ID NO: 36 | NANTLAD<br>SEQ ID NO: 44 | QHFWSTTWT<br>SEQ ID NO: 49 |
| UCH-L1-13 | RSSQNIVHSNGNTYLE<br>SEQ ID NO: 28 | KVSNRFS<br>SEQ ID NO: 37 | FQGSHVPYT<br>SEQ ID NO: 50 |

[a]Amino acid sequences shown according to Kabat numbering.

TABLE 6

Amino acid sequences of variable regions of mouse anti-UCH-L1 antibodies

| Antibody Name | Variable Heavy Chain | Variable Light Chain |
|---|---|---|
| UCH-L1-1 | SEQ ID NO: 51 | SEQ ID NO: 64 |
| UCH-L1-2 | SEQ ID NO: 52 | SEQ ID NO: 65 |
| UCH-L1-3 | SEQ ID NO: 53 | SEQ ID NO: 66 |
| UCH-L1-4 | SEQ ID NO: 54 | SEQ ID NO: 67 |
| UCH-L1-5 | SEQ ID NO: 55 | SEQ ID NO: 68 |
| UCH-L1-6 | SEQ ID NO: 56 | SEQ ID NO: 69 |
| UCH-L1-7 | SEQ ID NO: 57 | SEQ ID NO: 70 |
| UCH-L1-8 | SEQ ID NO: 58 | SEQ ID NO: 71 |
| UCH-L1-9 | SEQ ID NO: 59 | SEQ ID NO: 72 |
| UCH-L1-10 | SEQ ID NO: 60 | SEQ ID NO: 73 |
| UCH-L1-11 | SEQ ID NO: 61 | SEQ ID NO: 74 |
| UCH-L1-12 | SEQ ID NO: 62 | SEQ ID NO: 75 |
| UCH-L1-13 | SEQ ID NO: 63 | SEQ ID NO: 76 |

Example 2: Generation of Mouse Anti-GFAP Antibodies

Antibodies were generated from immunization of mice with human GFAP (full length sequence of amino acids set forth in SEQ ID NO:212) and sequenced. Several strategies were employed for the generation of mouse anti-GFAP antibodies.

For generation of the mouse anti-GFAP antibodies designated GFAP-2 anti-GFAP antibody, recombinant denatured human GFAP was used as an immunogen. BALB/c mice or NIH Swiss mice were inoculated with the human GFAP antigen to generate an immune response. Hybridoma fusions were produced and screened for antibodies that bound to GFAP using indirect ELISA and sandwich ELISA with either recombinant GFAP or native GFAP obtained from cerebrospinal fluid (CSF).

For generation of the mouse anti-GFAP antibodies designated GFAP-1 anti-GFAP antibody, recombinant human GFAP mixed with Freund's complete adjuvant was used for immunization of BALB/c mice or NIH Swiss mice. Hybridoma fusions were produced and screened for antibodies that by indirect ELISA or sandwich ELISA with recombinant GFAP.

For all other anti-GFAP antibodies (i.e., GFAP-3, GFAP-4, GFAP-5, GFAP-6, GFAP-7, GFAP-8, GFAP-9, GFAP-10, GFAP-11, GFAP-12, GFAP-13, GFAP-14, GFAP-15, GFAP-16, GFAP-17, GFAP-18, and GFAP-19), 1p g of recombinant human GFAP expressed from *E. coli* was mixed with 1p g of GFAP-2 antibody (VH chain set forth in SEQ ID NO:173 and the VL chain set forth in SEQ ID NO:190) and rotated overnight at 4° C. to form immune complexes, then conjugated to KLH and mixed with Freund's adjuvant for injection in mice. For the second and third injections the process was the same except incomplete Freund's adjuvant was used. For the final boost, unconjugated recombinant human GFAP was injected in the mice. Hybridoma fusions were produced and screened for antibodies that bound to GFAP using indirect ELISA and sandwich ELISA with either recombinant GFAP or native GFAP obtained from CSF.

Antibodies that bound to human GFAP protein during screening were identified and are set forth in Table 7. Epitope mapping to regions of GFAP and isotype specificity experiments also were performed to further characterize the antibodies as set forth in Table 7.

TABLE 7

Isotype of mouse anti-GFAP antibodies

| Antibody clone | Isotype | Epitope within, that is, or includes GFAP Amino Acid Sequence (corresponding to residues set forth in SEQ ID NO: 212) |
|---|---|---|
| GFAP-1 | IgG1 isotype | 92-106 |
| GFAP-2 | IgG1 isotype | 190-202 |
| GFAP-3 | IgG2b isotype | 16-35 and/or 380 |
| GFAP-4 | IgG1 isotype | 380-391 |
| GFAP-5 | IgG2a isotype | 119 and/or 190 |
| GFAP-6 | IgG2b isotype | 119-130 |
| GFAP-7 | IgG1 isotype | 380-391 |
| GFAP-8 | IgG2b isotype | 380-391 |
| GFAP-9 | IgG2a isotype | 380-391 |
| GFAP-10 | IgG1 isotype | Not determined |
| GFAP-11 | IgG2b isotype | 119-130 |
| GFAP-12 | IgG2a isotype | 119-130 |
| GFAP-13 | IgG1 isotype | 210-221 |
| GFAP-14 | IgG2b isotype | 210-221 |
| GFAP-15 | IgG1 isotype | 210-221 |
| GFAP-16 | IgG1 isotype | 320-329 |
| GFAP-17 | IgG2a isotype | 320-329, 346-357 and/or 376-387 |
| GFAP-18 | IgG2b isotype | 119-130 and/or 138-149 |
| GFAP-19 | IgG2b isotype | 119-130 |

The affinities of the antibodies that bound to human GFAP protein were determined and are set forth in Table 8. The rates of association ($k_{on}$) and dissociation ($k_{off}$) of the anti-GFAP antibodies were determined by bio-layer interferometry using an Octet QK$^e$ instrument according to the manufacturer's instructions (ForteBio). See Tobias et al., *Biomolecular Binding Kinetic Assays in the Octet Platform*, Application Note 14, ForteBio, Div. of Pall Life Sciences, 2013. Polyhistidine-tagged recombinant human GFAP expressed from *E. coli* was used as the antigen. The antigen was bound at a concentration of 8.3 µg/ml to an anti-Penta-HIS(HIS1K) capture biosensor containing an anti-histidine antibody (ForteBio) for use with the Octet QK$^e$ instrument. The sensor was then incubated with increasing concentrations of a tested anti-GFAP antibody with concentrations ranging from about 0.006 to about 0.5 µM to obtain affinity measurements.

TABLE 8

Affinities of mouse anti-GFAP antibodies

| Antibody clone | $K_D$ (M) | Kon (1/Ms) | Kdis (1/s) | Antibody Concentration Range Tested (µM) |
|---|---|---|---|---|
| GFAP-1 | 1.07E−11 | 161,500 | 0.0000017 | 0.05-0.0063 |
| GFAP-2 | 5.57E−11 | 593,100 | 0.0000330 | 0.05-0.0063 |
| GFAP-3 | 1.20E−08 | 58,040 | 0.0006980 | 0.5-0.0185 |
| GFAP-4 | 2.93E−09 | 53,740 | 0.0001580 | 0.166-0.02 |
| GFAP-5 | 5.36E−09 | 20,010 | 0.0001070 | 0.166-0.02 |
| GFAP-6 | 8.56E−10 | 116,100 | 0.0001240 | 0.166-0.02 |
| GFAP-7 | 8.56E−10 | 67,820 | 0.0000580 | 0.166-0.02 |
| GFAP-8 | 1.11E−09 | 119,900 | 0.0001330 | 0.166-0.02 |
| GFAP-9 | 1.80E−08 | 38,960 | 0.0007010 | 0.166-0.02 |
| GFAP-10 | <1.00E−12 | 53,300 | 0.0000001 | 0.166-0.02 |
| GFAP-11 | 3.96E−10 | 314,900 | 0.0001250 | 0.05-0.0063 |
| GFAP-12 | 1.33E−08 | 17,970 | 0.0002400 | 0.166-0.02 |
| GFAP-13 | 6.00E−10 | 323,600 | 0.0001940 | 0.05-0.0063 |
| GFAP-14 | 2.80E−10 | 298,900 | 0.0000840 | 0.05-0.0063 |
| GFAP-15 | 2.02E−10 | 1,146,000 | 0.0002310 | 0.05-0.0063 |
| GFAP-16 | 2.73E−10 | 173,100 | 0.0000470 | 0.05-0.0063 |
| GFAP-17 | 2.08E−10 | 86,650 | 0.0000180 | 0.05-0.0063 |
| GFAP-18 | 7.37E−11 | 343,900 | 0.0000250 | 0.05-0.0063 |
| GFAP-19 | 4.23E−10 | 150,900 | 0.0000640 | 0.05-0.0063 |

Exemplary antibodies were sequenced and SEQ ID NOs are set forth in Table 9 and Table 10.

TABLE 9

Amino acid sequences of CDRs from mouse anti-GFAP antibodies[a]

| Antibody | CDR-H1 | CDR-H2 | CDR-H3 |
|---|---|---|---|
| GFAP-1 | SYWMH<br>SEQ ID NO: 77 | AFYPENSDTNYNQKFKG<br>SEQ ID NO: 91 | PLLFSAYFDF<br>SEQ ID NO: 108 |
| GFAP-2 | SFGMH<br>SEQ ID NO: 78 | YISSGSSIIYYADTVKG<br>SEQ ID NO: 92 | SDWGSFAY<br>SEQ ID NO: 109 |
| GFAP-3 | NYWMS<br>SEQ ID NO: 79 | QIRLKSDNYATHYAESVKG<br>SEQ ID NO: 93 | GEFLSWFAY<br>SEQ ID NO: 110 |
| GFAP-4 | SYWMH<br>SEQ ID NO: 77 | AIHPGNRDTSYNQKFKD<br>SEQ ID NO: 94 | EDY<br>SEQ ID NO: 111 |
| GFAP-5 | AYGMH<br>SEQ ID NO: 80 | YISSGSSTIYYADTVKG<br>SEQ ID NO: 95 | SYALDY<br>SEQ ID NO: 112 |
| GFAP-6 | DTDMH<br>SEQ ID NO: 81 | LIDPAIGNTKYDPKFQG<br>SEQ ID NO: 96 | SDRYLAWFAY<br>SEQ ID NO: 113 |
| GFAP-7 | SYWMH<br>SEQ ID NO: 77 | AIHPGNRDTSYNQKFKD<br>SEQ ID NO: 94 | EDY<br>SEQ ID NO: 111 |
| GFAP-8 | SYWMH<br>SEQ ID NO: 77 | AIHPGNRDTSYNQKFKD<br>SEQ ID NO: 94 | EDY<br>SEQ ID NO: 111 |
| GFAP-9 | SGFYWS<br>SEQ ID NO: 82 | YISYDGSNNYNPSLKN<br>SEQ ID NO: 97 | AYGYDGAWFAY<br>SEQ ID NO: 114 |
| GFAP-10 | YYAMS<br>SEQ ID NO: 83 | SISSGGTTYHPDSVKG<br>SEQ ID NO: 98 | GGHWYFDV<br>SEQ ID NO: 115 |
| GFAP-11 | NYGMN<br>SEQ ID NO: 84 | WINTNIGEPTYAEEFKG<br>SEQ ID NO: 99 | WKNYGYFDY<br>SEQ ID NO: 116 |
| GFAP-12 | NYWIE<br>SEQ ID NO: 85 | EILPGSGSTNYNEKFKG<br>SEQ ID NO: 100 | YYGNYAGAMDY<br>SEQ ID NO: 117 |
| GFAP-13 | NYIMH<br>SEQ ID NO: 86 | FINPYNDYTEYNEKFKG<br>SEQ ID NO: 101 | ATFAY<br>SEQ ID NO: 118 |
| GFAP-14 | SFGMH<br>SEQ ID NO: 78 | YISSDSNTVYYADTVKG<br>SEQ ID NO: 102 | YAMDY<br>SEQ ID NO: 119 |
| GFAP-15 | SFGMH<br>SEQ ID NO: 78 | YISSGSRTIFYADTVKG<br>SEQ ID NO: 103 | GGYGSSFDY<br>SEQ ID NO: 120 |
| GFAP-16 | DHTIH<br>SEQ ID NO: 87 | YIYPGDGSTKYNEKFKG<br>SEQ ID NO: 104 | PAPYWNFDV<br>SEQ ID NO: 121 |
| GFAP-17 | YYWMS<br>SEQ ID NO: 88 | EIRLKSNIYATHYAASVKG<br>SEQ ID NO: 105 | FGTGAMDY<br>SEQ ID NO: 122 |
| GFAP-18 | NFAMS<br>SEQ ID NO: 89 | SISSGGTTYYPDNVKG<br>SEQ ID NO: 106 | GGLHYFGY<br>SEQ ID NO: 123 |
| GFAP-19 | SYDMS<br>SEQ ID NO: 90 | YISSGGGSTYYPDTMKG<br>SEQ ID NO: 107 | HYGTYLYYLDY<br>SEQ ID NO: 124 |

| Antibody | CDR-L1 | CDR-L2 | CDR-L3 |
|---|---|---|---|
| GFAP-1 | RSSQSIVHSYGNTYLE<br>SEQ ID NO: 125 | KVSNRFS<br>SEQ ID NO: 142 | FQGSHVPYT<br>SEQ ID NO: 157 |
| GFAP-2 | RSSQSLVYSNGNTYLH<br>SEQ ID NO: 126 | KVSNRFF<br>SEQ ID NO: 143 | SQSTHVPYT<br>SEQ ID NO: 158 |
| GFAP-3 | KSSQSLFNSRTKNYLA<br>SEQ ID NO: 127 | WASTRES<br>SEQ ID NO: 144 | KQSYYLYT<br>SEQ ID NO: 159 |
| GFAP-4 | KSSQSLLNSNNQRNYLD<br>SEQ ID NO: 128 | FASTRES<br>SEQ ID NO: 145 | QQHYSIPLT<br>SEQ ID NO: 160 |

TABLE 9-continued

Amino acid sequences of CDRs from
mouse anti-GFAP antibodies[a]

| | | | |
|---|---|---|---|
| GFAP-5 | RSSQSLVYSNGNTYLH SEQ ID NO: 126 | KVSNRFS SEQ ID NO: 142 | SQSTHVPYT SEQ ID NO: 158 |
| GFAP-6 | RASQSISDFLH SEQ ID NO: 129 | YSSQSIS SEQ ID NO: 146 | QNGHTFPYT SEQ ID NO: 161 |
| GFAP-7 | KSSQSLLNSSNQRNYLD SEQ ID NO: 130 | FASTRES SEQ ID NO: 145 | QQHYSIPLT SEQ ID NO: 160 |
| GFAP-8 | KSSQSLLNSSNQRNYLD SEQ ID NO: 130 | FASTRES SEQ ID NO: 145 | QQHYSIPLT SEQ ID NO: 160 |
| GFAP-9 | KASQNVRTAVA SEQ ID NO: 131 | LASNRHT SEQ ID NO: 147 | LQHWNNPYT SEQ ID NO: 162 |
| GFAP-10 | SASSSVSYMH SEQ ID NO: 132 | DTSKLAS SEQ ID NO: 148 | QQWSTNPLT SEQ ID NO: 163 |
| GFAP-11 | TASSSVSSSYLH SEQ ID NO: 133 | STSNLAS SEQ ID NO: 149 | HQYHRSPYT SEQ ID NO: 164 |
| GFAP-12 | RASENIYSYLA SEQ ID NO: 134 | NAKTLAE SEQ ID NO: 150 | QLHYGTPYT SEQ ID NO: 165 |
| GFAP-13 | KSSQSLLDSAGKTYLN SEQ ID NO: 135 | LVSKLDS SEQ ID NO: 151 | WQGTHFPWT SEQ ID NO: 166 |
| GFAP-14 | SASSSVSYMY SEQ ID NO: 136 | LTSNLAS SEQ ID NO: 152 | QQWSSNPPT SEQ ID NO: 167 |
| GFAP-15 | RSSQSLVYSNGNIYLH SEQ ID NO: 137 | KVSNRFS SEQ ID NO: 142 | SQSTHVPYT SEQ ID NO: 158 |
| GFAP-16 | KASQDIKKNIA SEQ ID NO: 138 | YTSTLQP SEQ ID NO: 153 | LQYDHLRT SEQ ID NO: 168 |
| GFAP-17 | KSSQSLLYRTNQKNYLA SEQ ID NO: 139 | WASSRES SEQ ID NO: 154 | QQYYSYPWT SEQ ID NO: 169 |
| GFAP-18 | KASQDVNTAVA SEQ ID NO: 140 | SASYRYI SEQ ID NO: 155 | HQYYSTPLT SEQ ID NO: 170 |
| GFAP-19 | RASQNISDFLH SEQ ID NO: 141 | YASQSIS SEQ ID NO: 156 | QNGHSFPPT SEQ ID NO: 171 |

[a]Amino acid sequences shown according to Kabat numbering.

TABLE 10

Amino acid sequences of variable regions of mouse anti-GFAP antibodies

| Antibody Name | Variable Heavy Chain | Variable Light Chain |
|---|---|---|
| GFAP-1 | SEQ ID NO: 172 | SEQ ID NO: 189 |
| GFAP-2 | SEQ ID NO: 173 | SEQ ID NO: 190 |
| GFAP-3 | SEQ ID NO: 174 | SEQ ID NO: 191 |
| GFAP-4 | SEQ ID NO: 175 | SEQ ID NO: 192 |
| GFAP-5 | SEQ ID NO: 176 | SEQ ID NO: 193 |
| GFAP-6 | SEQ ID NO: 177 | SEQ ID NO: 194 |
| GFAP-7 | SEQ ID NO: 175 | SEQ ID NO: 195 |
| GFAP-8 | SEQ ID NO: 175 | SEQ ID NO: 195 |
| GFAP-9 | SEQ ID NO: 178 | SEQ ID NO: 196 |
| GFAP-10 | SEQ ID NO: 179 | SEQ ID NO: 197 |
| GFAP-11 | SEQ ID NO: 180 | SEQ ID NO: 198 |
| GFAP-12 | SEQ ID NO: 181 | SEQ ID NO: 199 |
| GFAP-13 | SEQ ID NO: 182 | SEQ ID NO: 200 |
| GFAP-14 | SEQ ID NO: 183 | SEQ ID NO: 201 |
| GFAP-15 | SEQ ID NO: 184 | SEQ ID NO: 202 |
| GFAP-16 | SEQ ID NO: 185 | SEQ ID NO: 203 |
| GFAP-17 | SEQ ID NO: 186 | SEQ ID NO: 204 |
| GFAP-18 | SEQ ID NO: 187 | SEQ ID NO: 205 |
| GFAP-19 | SEQ ID NO: 188 | SEQ ID NO: 206 |

Example 3: Diagnostic Detection of UCH-L1 and/or GFAP in Traumatic Brain Injury Patients The ability of exemplary generated anti-UCH-L1 antibodies and anti-GFAP antibodies to detect human UCH-L1 and human GFAP, respectively, in serum of human subjects known or suspected of having a mild or moderate concussion was assessed by ELISA. Samples from 266 lightly concussed patients were obtained. The samples were obtained from the patients no more than 8 hours after injury. Each sample was diluted with a diluent containing Tween-20, mouse IgG isotype antibody, casein and buffer.

For each assay, a sandwich ELISA was used in which a "capture antibody" was coated onto wells of a 96-well plate. The capture antibody was contacted with the protein antigen by addition of a biological sample (e.g. serum) in duplicate or standard curve in triplicate to wells under conditions to capture/concentrate/hold the antigen. Then, a labeled "detection antibody" able to bind to a distinct or non-overlapping epitope on the UCH-L1 or GFAP antigen from the capture antibody was added to detect the captured antigen. The signal was read on a luminometer and the amount of protein antigen contained in the serum was quantitated by comparison to the standard curve.

The subjects all had received a computed tomography (CT) scan for assessing the brain injury. 60 of the 266 patients tested positive for traumatic brain injury (TBI) after assessment with a CT scan while 206 of the 266 patients tested negative for TBI by CT scan. The sensitivity of detection of UCH-L1 and/or GFAP was correlated to the CT results.

A. UCH-L1

In one exemplary assay, two anti-UCH-L1 antibodies, UCH-L1-1 and UCH-L1-2, were used as capture antibodies and were adsorbed to wells in a 96-well microplate (Nunc, Maxisorp) at about 10 μg/ml per each antibody in a volume of 100 μL per well. The microplate was blocked with casein (SurModics) in preparation for incubation with a sample.

The patient samples or the antigen standard (recombinant UCH-L1) at 0-1280 μg/mL for standard curve were then added to the microplate and the microplate was incubated for 1 hour. After incubation, the microplate was washed and a horseradish peroxidase (HRP)-labeled anti-UCH-L1 detection antibody, UCH-L1-5, was added to each well of the microplate at a concentration of about 200 ng/mL+/−20%. The microplate was incubated for 1 hour. After incubation, the microplate was washed and the bound HRP was detected by addition of a luminol containing substrate (SurModics Sensitive Plus). The signal was read by placing the microplate in a luminometer. The signal emitted by the sample wells was compared to the signal emitted by control wells containing known amounts of recombinant UCH-L1 protein. The signal emitted by the control wells was used to establish a calibration curve for assessing the amount of UCH-L1 in each tested sample (see Table 11) and the amount of UCH-L1 in each sample was quantitated.

B. GFAP

In one exemplary assay, an anti-GFAP antibody, GFAP-2, was used as a capture antibody and was adsorbed to wells in a 96-well microplate (Nunc, Maxisorp) at about 2 μg/mL. The microplate was blocked with casein (SurModics) in preparation for incubation with a sample.

The patient samples or the antigen standard (GFAP purified from human brain) at 0-640 pg/mL for standard curve were then added to the microplate and the microplate was incubated for 1 hour. After incubation, the microplate was washed and a horseradish peroxidase (HRP)-labeled anti-GFAP antibody, GFAP-6, was added to each well of the microplate at a concentration of about 200 ng/mL+/−20%. The microplate was incubated for 1 hour. After incubation, the microplate was washed and the bound HRP was detected by addition of a luminol containing substrate (SurModics Sensitive Plus). The signal was read by placing the microplate on a luminometer. The signal emitted by the sample wells was compared to the signal emitted by control wells containing known amounts of native GFAP protein purified from human brain. The signal emitted by the control wells was used to establish a calibration curve for assessing the amount of GFAP in each tested sample (see Table 11) and the amount of GFAP in each sample was quantitated.

C. Results

Table 11 sets forth the results of exemplary calibration (standard) curves based on the UCH-L1 and GFAP standards used in the above assays.

TABLE 11

Calibration curves

| GFAP pg/ml | Relative Light Unit (rlu) | UCH-L1 pg/ml | Relative Light Unit (rlu) |
|---|---|---|---|
| 640 | 1,120,148 | 1280 | 2,172,896 |
| 320 | 487,043 | 640 | 921,060 |
| 160 | 208,100 | 320 | 420,539 |
| 80 | 72,745 | 160 | 168,699 |
| 40 | 22,692 | 80 | 71,298 |
| 20 | 7,424 | 40 | 28,189 |
| 10 | 3,640 | 20 | 14,039 |
| 0 | 369 | 0 | 3,969 |

The standard curves were compared to the signal from samples from the 266 lightly concussed patients and used to quantitate the amount of UCH-L1 and GFAP protein in the samples. The results are set forth in Table 12, which showed that UCH-L1 and/or GFAP were detected in patient samples. Bolded cells under column 2 (i.e., UCH-L1 pg/ml) indicate amount of UCH-L1 under a cut-off value of 200 pg/mL or less and bolded cells under column 5 (i.e., GFAP pg/ml) indicate amount of GFAP under cut-off value of 70 pg/mL or less. Bolded cells under column 7 (i.e., CT Scan Result) indicate false negative patients that were predicted to test negative for concussion by CT scan based on both GFAP and UCH-L1 measured amounts falling under their respective cut-off values but tested positive upon CT scan, as discussed further below.

TABLE 12

UCH-L1 and GFAP levels in samples from 266 concussed patients

| Subject ID | UCH-L1 pg/ml | UCH-L1 % CV | GFAP % CV | GFAP pg/mL | GFAP Result | CT Scan Result |
|---|---|---|---|---|---|---|
| 41009 | >1280 | 0% | 2% | 229 | | POS |
| 62-011 | 1215 | 1% | 2% | 456 | | POS |
| 47059 | 419 | 1% | 1% | 125 | | POS |
| 61-003 | 1160 | 0% | 38% | | invalid (high CV) | POS |
| 48037 | 348 | 3% | 1% | 359 | | POS |
| 47008 | 663 | 3% | 2% | 228 | | POS |
| 47064 | 504 | 1% | 1% | 212 | | POS |
| 48040 | 628 | 3% | 5% | 14 | | POS |
| 48038 | 385 | 0% | 2% | 28 | | POS |
| 42004 | 402 | 0% | 0% | 75 | | POS |
| 65-004 | 433 | 3% | 2% | 167 | | POS |
| 61-011 | 772 | 3% | 0% | >640 | | POS |
| 49038 | 1087 | 1% | 2% | 34 | | POS |
| 41067 | >1280 | 2% | 1% | 142 | | POS |
| 47010 | 448 | 0% | 4% | 172 | | POS |
| 61-018 | 159 | 0% | 31% | 1 | | POS |
| 47060 | >1280 | 3% | 0% | >640 | | POS |
| 47029 | >1280 | 1% | 0% | >640 | | POS |
| 47014 | 830 | 0% | 0% | 522 | | POS |
| 46041 | 1250 | 2% | 0% | >640 | | POS |
| 65-001 | 995 | 1% | 2% | 341 | | POS |
| 46020 | 214 | 0% | 3% | 11 | | POS |
| 48024 | 484 | 3% | 0% | 67 | | POS |
| 46001 | 718 | 2% | 3% | 228 | | POS |
| 47053 | 560 | 2% | 1% | 432 | | POS |
| 46045 | 484 | 2% | 0% | >640 | | POS |
| 46012 | 712 | 0% | 0% | >640 | | POS |
| 47035 | 524 | 1% | 1% | 416 | | POS |
| 47056 | 529 | 4% | 0% | >640 | | POS |
| 61-017 | 711 | 3% | 1% | 449 | | POS |
| 61-010 | 185 | 2% | 5% | 36 | | POS |
| 47054 | 336 | 3% | 7% | 566 | | POS |
| 47044 | 1029 | 1% | 0% | >640 | | POS |
| 61-006 | 998 | 4% | 0% | 227 | | POS |
| 46025 | 573 | 2% | 13% | >640 | | POS |

TABLE 12-continued

UCH-L1 and GFAP levels in samples from 266 concussed patients

| Subject ID | UCH-L1 pg/ml | UCH-L1 % CV | GFAP % CV | GFAP pg/mL | GFAP Result | CT Scan Result |
|---|---|---|---|---|---|---|
| 65-002 | >1280 | 0% | 0% | >640 | | POS |
| 47015 | 355 | 0% | 1% | 61 | | POS |
| 47001 | 940 | 2% | 0% | >640 | | POS |
| 46008 | 534 | 2% | 1% | 202 | | POS |
| 46032 | 696 | 2% | 2% | 84 | | POS |
| 64-008 | 1167 | 3% | 0% | >640 | | POS |
| 62-003 | 856 | 4% | 0% | >640 | | POS |
| 61-014 | 870 | 1% | 1% | 298 | | POS |
| 65-003 | 336 | 3% | 1% | 52 | | POS |
| 64-004 | 274 | 2% | 4% | 28 | | POS |
| 61-012 | 197 | 17% | 0% | 244 | | POS |
| 62-002 | 803 | 1% | 0% | >640 | | POS |
| 64-006 | 507 | 4% | 0% | >640 | | POS |
| 49031 | 135 | 1% | 1% | 72 | | POS |
| 47047 | 339 | 8% | 0% | >640 | | POS |
| 47038 | 430 | 2% | 0% | >640 | | POS |
| 65-005 | 802 | 0% | 0% | >640 | | POS |
| 46029 | >1280 | 0% | 0% | >640 | | POS |
| 61-015 | 583 | 0% | 0% | 162 | | POS |
| 62-013 | >1280 | 0% | 1% | 226 | | POS |
| 48002 | 406 | 2% | 3% | 579 | | POS |
| 61-016 | 113 | 4% | 0% | 71 | | POS |
| 62-008 | 440 | 2% | 1% | 499 | | POS |
| 62-001 | 153 | 7% | 1% | 43 | | IND |
| 41049 | 544 | 3% | 0% | 96 | | Neg |
| 41069 | >1280 | 0% | 7% | 24 | | Neg |
| 41028 | 774 | 1% | 7% | 4 | | Neg |
| 41005 | 837 | 1% | 1% | 193 | | Neg |
| 49012 | 125 | 1% | 2% | 27 | | Neg |
| 48018 | 126 | 25% | 4% | 4 | | Neg |
| 41046 | 619 | 2% | 3% | 78 | | Neg |
| 49037 | 1095 | 0% | 3% | 32 | | Neg |
| 41061 | 1077 | 0% | 1% | 57 | | Neg |
| 41016 | 278 | 4% | 11% | 3 | | Neg |
| 41047 | 353 | 2% | 4% | 37 | | Neg |
| 41035 | 864 | 9% | No Result | | INS | Neg |
| 48039 | >1280 | 1% | 1% | 43 | | Neg |
| 61-005 | >1280 | 2% | 0% | 271 | | NEG |
| 41024 | 507 | 4% | 1% | 59 | | Neg |
| 48001 | 381 | 2% | 0% | 0 | | Neg |
| 48041 | 407 | 1% | 1% | 42 | | Neg |
| 47020 | 564 | 1% | 1% | 69 | | Neg |
| 47025 | 607 | 5% | 1% | 197 | | Neg |
| 48012 | 510 | 8% | 1% | 244 | | Neg |
| 41014 | 758 | 5% | 15% | 30 | | Neg |
| 41022 | 592 | 1% | 1% | 41 | | Neg |
| 41066 | >1280 | 0% | 1% | 29 | | Neg |
| 41040 | 144 | 6% | 0% | 0 | | Neg |
| 48020 | 232 | 1% | 6% | 6 | | Neg |
| 48035 | 382 | 0% | 16% | 8 | | Neg |
| 47022 | 492 | 1% | 0% | 48 | | Neg |
| 41050 | 763 | 5% | 0% | 0 | | Neg |
| 41041 | 1256 | 2% | 10% | 12 | | Neg |
| 41017 | 86 | 1% | 0% | | | Neg |
| 41036 | 586 | 26% | 2% | 21 | | Neg |
| 41039 | 238 | 3% | 120% | invalid (high CV) | | Neg |
| 46002 | 266 | 2% | 0% | 26 | | Neg |
| 46006 | 335 | 3% | 18% | 5 | | Neg |
| 41058 | 466 | 1% | 50% | invalid (high CV) | | Neg |
| 46047 | 62 | 4% | 100% | 1 | | Neg |
| 48030 | 267 | 1% | 11% | 12 | | Neg |
| 47011 | 312 | 6% | 3% | 215 | | Neg |
| 46044 | 386 | 2% | 1% | 177 | | Neg |
| 46010 | 739 | 1% | 19% | 7 | | Neg |
| 48007 | 121 | 10% | 41% | 6 | | Neg |
| 47017 | 146 | 5% | 0% | 32 | | Neg |
| 49043 | 154 | 4% | 98% | 6 | | Neg |
| 46046 | 200 | 5% | 2% | 100 | | Neg |
| 41064 | 331 | 4% | 2% | 3 | | Neg |
| 49035 | 563 | 0% | 1% | 46 | | Neg |
| 49054 | 583 | 0% | 6% | 49 | | Neg |
| 62-006 | 360 | 14% | 1% | 59 | | Neg |
| 46034 | 128 | 1% | 1% | 36 | | Neg |
| 48014 | 142 | 2% | 2% | 26 | | Neg |
| 46009 | 166 | 6% | 2% | 4 | | Neg |
| 46043 | 221 | 0% | 1% | 73 | | Neg |
| 49056 | 227 | 3% | 0% | 71 | | Neg |
| 48017 | 253 | 3% | 2% | 33 | | Neg |
| 41030 | 394 | 5% | 39% | 4 | | Neg |
| 46042 | 86 | 3% | 3% | 7 | | Neg |
| 49039 | 88 | 0% | 3% | 5 | | Neg |
| 48023 | 110 | 1% | 1% | 2 | | Neg |
| 47021 | 152 | 4% | 2% | 35 | | Neg |
| 46048 | 164 | 3% | 2% | 19 | | Neg |
| 49060 | 175 | 1% | 3% | 2 | | Neg |
| 41042 | 214 | 3% | 11% | 25 | | Neg |
| 49034 | 224 | 6% | 1% | 30 | | Neg |
| 49013 | 371 | 0% | 2% | 26 | | Neg |
| 48003 | 377 | 1% | 3% | 7 | | Neg |
| 41023 | 534 | 3% | 7% | 14 | | Neg |
| 47052 | 133 | 2% | 1% | 58 | | Neg |
| 48022 | 226 | 2% | 10% | 5 | | Neg |
| 48008 | 349 | 0% | No Result | | INS | Neg |
| 41012 | >1280 | 0% | 1% | 185 | | Neg |
| 49063 | 82 | 0% | 12% | 4 | | Neg |
| 46039 | 117 | 1% | 0% | 195 | | Neg |
| 49016 | 160 | 8% | 14% | 2 | | Neg |
| 49022 | 265 | 1% | 2% | 23 | | Neg |
| 49050 | 274 | 1% | 1% | 16 | | Neg |
| 41045 | 329 | 3% | 1% | 99 | | Neg |
| 46022 | 336 | 1% | 2% | 23 | | Neg |
| 49028 | 378 | 4% | 0% | 3 | | Neg |
| 48029 | >1280 | 7% | 3% | 45 | | Neg |
| 48004 | 62 | 6% | 104% | 3 | | Neg |
| 49019 | 67 | 3% | 9% | 22 | | Neg |
| 48009 | 97 | 3% | 7% | 1 | | Neg |
| 41068 | 207 | 4% | 2% | 16 | | Neg |
| 46021 | 223 | 1% | 1% | 81 | | Neg |
| 41027 | 273 | 1% | 13% | 9 | | Neg |
| 49044 | 96 | 1% | 25% | 6 | | Neg |
| 46037 | 184 | 5% | 5% | 5 | | Neg |
| 41031 | 213 | 0% | 0% | 34 | | Neg |
| 47013 | 286 | 2% | 2% | 244 | | Neg |
| 48015 | 616 | 0% | 98% | 0 | | Neg |
| 47028 | 743 | 0% | 0% | >640 | | Neg |
| 47062 | 811 | 3% | 1% | 36 | | Neg |
| 41055 | 162 | 5% | 16% | 7 | | Neg |
| 47043 | 186 | 1% | 64% | 2 | | Neg |
| 49023 | 191 | 5% | 0% | 42 | | Neg |
| 47002 | 213 | 6% | 1% | 78 | | Neg |
| 49024 | 225 | 4% | 11% | 8 | | Neg |
| 49025 | 268 | 0% | 5% | 8 | | Neg |
| 46024 | 312 | 0% | 1% | 259 | | Neg |
| 47034 | 408 | 2% | 1% | 294 | | Neg |
| 48025 | 621 | 0% | 6% | 21 | | Neg |
| 48021 | 93 | 3% | 141% | 0 | | Neg |
| 46030 | 103 | 1% | 96% | 1 | | Neg |
| 46014 | 295 | 1% | 4% | 36 | | Neg |
| 41063 | 297 | 2% | 1% | 12 | | Neg |
| 48028 | 488 | 0% | 1% | 199 | | Neg |
| 49020 | 555 | 3% | 0% | 6 | | Neg |
| 47050 | 1044 | 4% | 2% | 50 | | Neg |
| 49027 | >1280 | 3% | 1% | 172 | | Neg |
| 46011 | 195 | 3% | 1% | 18 | | Neg |
| 49055 | 221 | 1% | 8% | 23 | | Neg |
| 47032 | 263 | 2% | 5% | 1 | | Neg |
| 49045 | 420 | 0% | 3% | 6 | | Neg |
| 47004 | >1280 | 1% | 2% | 52 | | Neg |
| 41026 | 100 | 4% | 9% | 3 | | Neg |
| 48034 | 108 | 3% | 13% | 4 | | Neg |
| 47006 | 176 | 3% | 1% | 20 | | Neg |
| 46007 | 192 | 1% | 7% | 12 | | Neg |
| 49062 | 196 | 1% | 11% | 6 | | Neg |
| 48032 | 244 | 2% | 10% | 7 | | Neg |
| 47005 | 249 | 1% | 0% | 37 | | Neg |
| 46035 | 308 | 1% | 0% | >640 | | Neg |

TABLE 12-continued

UCH-L1 and GFAP levels in samples from 266 concussed patients

| Subject ID | UCH-L1 pg/ml | UCH-L1 % CV | GFAP % CV | GFAP pg/mL | GFAP Result | CT Scan Result |
|---|---|---|---|---|---|---|
| 47018 | 377 | 0% | 1% | 79 | | Neg |
| 48042 | 380 | 4% | 0% | 7 | | Neg |
| 41021 | 590 | 1% | 75% | 1 | | Neg |
| 43004 | 711 | 2% | 0% | 15 | | Neg |
| 41053 | >1280 | 6% | 1% | 166 | | Neg |
| 49030 | >1280 | 0% | 0% | 223 | | Neg |
| 49053 | 422 | 8% | 24% | 2 | | Neg |
| 49015 | 567 | 3% | 2% | 25 | | Neg |
| 49061 | 651 | 4% | 0% | 167 | | Neg |
| 47039 | 889 | 1% | 1% | 393 | | Neg |
| 41054 | 1150 | 2% | 0% | 258 | | Neg |
| 49040 | 78 | 15% | 0% | 0 | | Neg |
| 47041 | 98 | 9% | 14% | 6 | | Neg |
| 47063 | 237 | 1% | 1% | 80 | | Neg |
| 48031 | 254 | 1% | 10% | 10 | | Neg |
| 46015 | 282 | 2% | 3% | 222 | | Neg |
| 49018 | 295 | 1% | 1% | 64 | | Neg |
| 47051 | 465 | 0% | 1% | 428 | | Neg |
| 46017 | 478 | 3% | 1% | 327 | | Neg |
| 46005 | 180 | 3% | 7% | 8 | | Neg |
| 47048 | 199 | 11% | 0% | 119 | | Neg |
| 41060 | 293 | 3% | 1% | 77 | | Neg |
| 49017 | 309 | 1% | 4% | 6 | | Neg |
| 46003 | 311 | 5% | 1% | 65 | | Neg |
| 41059 | 315 | 1% | 2% | 11 | | Neg |
| 47058 | 370 | 2% | 0% | >640 | | Neg |
| 49064 | 825 | 4% | 5% | 22 | | Neg |
| 49051 | 130 | 4% | 4% | 11 | | Neg |
| 48033 | 135 | 1% | 0% | 18 | | Neg |
| 46023 | 135 | 2% | 2% | 18 | | Neg |
| 47037 | 154 | 2% | 1% | 20 | | Neg |
| 47057 | 159 | 4% | 9% | 40 | | Neg |
| 41007 | 215 | 2% | 99% | 0 | | Neg |
| 47033 | 365 | 3% | 32% | 14 | | Neg |
| 47031 | 86 | 0% | 1% | 1 | | Neg |
| 46016 | 117 | 4% | 1% | 7 | | Neg |
| 49029 | 153 | 1% | 1% | 36 | | Neg |
| 47040 | 193 | 2% | 8% | 18 | | Neg |
| 47023 | 199 | 4% | 6% | 26 | | Neg |
| 41065 | 217 | 4% | 1% | 76 | | Neg |
| 47016 | 269 | 3% | 1% | 7 | | Neg |
| 47019 | 301 | 2% | 0% | 189 | | Neg |
| 49021 | 372 | 2% | 2% | 22 | | Neg |
| 47036 | 586 | 1% | 2% | 419 | | Neg |
| 49057 | 938 | 3% | 4% | 49 | | Neg |
| 49058 | 103 | 1% | 8% | 4 | | Neg |
| 49041 | 308 | 2% | 1% | 66 | | Neg |
| 41011 | 424 | 0% | 18% | 9 | | Neg |
| 41006 | 1026 | 3% | 2% | 71 | | Neg |
| 41010 | >1280 | 3% | 2% | 15 | | Neg |
| 46033 | 252 | 3% | 1% | 211 | | Neg |
| 41037 | 351 | 0% | 6% | 52 | | Neg |
| 48019 | 354 | 0% | 2% | 88 | | Neg |
| 49033 | 408 | 2% | 16% | 7 | | Neg |
| 49026 | 411 | 2% | 13% | 12 | | Neg |
| 49042 | 613 | 1% | 1% | 122 | | Neg |
| 46036 | 227 | 0% | 7% | 36 | | Neg |
| 46031 | 232 | 5% | 1% | 156 | | Neg |
| 47027 | 123 | 4% | 1% | 13 | | Neg |
| 41056 | >1280 | 0% | 2% | 91 | | Neg |
| 42005 | 157 | 0% | 0% | 12 | | Neg |
| 41043 | 115 | 2% | 1% | 17 | | Neg |
| 42003 | 166 | 0% | 19% | 4 | | Neg |
| 46013 | 240 | 1% | 1% | 42 | | Neg |
| 47012 | 192 | 0% | 0% | 25 | | Neg |
| 43001 | >1280 | 2% | 0% | 187 | | Neg |
| 41013 | 106 | 6% | 5% | 64 | | Neg |
| 41038 | 49 | 3% | 66% | 0 | | Neg |
| 41052 | >1280 | 1% | 1% | 149 | | Neg |
| 48006 | 677 | 7% | 0% | >640 | | Neg |
| 61-002 | 140 | 2% | 1% | 81 | | Neg |
| 41062 | 147 | 0% | 7% | 19 | | Neg |
| 41018 | 603 | 2% | 1% | 19 | | Neg |
| 42001 | 105 | 17% | 3% | 13 | | Neg |
| 41020 | 169 | 3% | 0% | 15 | | Neg |
| 41019 | 139 | 6% | 2% | 73 | | Neg |
| 41004 | 108 | 7% | 7% | 7 | | Neg |
| 41032 | 125 | 0% | 1% | 60 | | Neg |
| 43002 | 72 | 3% | 1% | 4 | | Neg |
| 43006 | 215 | 1% | 0% | 92 | | Neg |
| 41003 | 135 | 0% | 8% | 3 | | Neg |
| 62-010 | 289 | 2% | 1% | 72 | | Neg |
| 43008 | 135 | 1% | 4% | 44 | | Neg |
| 42002 | 404 | 2% | 0% | 101 | | Neg |
| 41008 | 594 | 1% | 0% | 200 | | Neg |

Pos indicates positive; Neg indicates negative; and CV indicates coefficient of variation.

The results from the ELISA were compared to the CT results. As shown in Table 13, it was found that a sensitivity criteria or cut-off based on detection of both UCH-L1 greater than or about 200 pg/mL and GFAP of greater than or about 70 pg/mL correlated with the CT results. By these criteria, 57 of the 60 patients that tested positive for TBI by a CT scan were correctly identified as patients with TBI using the assay with the anti-UCH-L1 and anti-GFAP antibodies. 66 of the 266 patients that tested negative for TBI by a CT scan were correctly identified as patients without TBI using the assay with the anti-UCH-L1 and anti-GFAP antibodies. Thus, these results demonstrated that if a subject has a UCH-L1 value less than 200 pg/mL and a GFAP value less than 70 pg/mL, the subject does not need a CAT scan. Thus, in some embodiments, the methods can identify or predict subjects who will need a CT scan.

TABLE 13

Comparison to CT Results
Cut-off: UCH-L1 200 pg/mL; GFAP 70 pg/mL

| Assay Result | CT Result | |
|---|---|---|
| | Positive | Negative |
| Positive | 57 | 140 |
| Negative | 3 | 66 |
| | 60 | 206 |
| Sensitivity | 95.0% | |
| Specificity | 32.0% | |

Example 4: Evaluation of Detection Capability for UCH-L1 and GFAP by Immunoassay The ability of exemplary generated anti-UCH-L1 antibodies and anti-GFAP antibodies to detect human UCH-L1 and human GFAP, respectively, in serum of human subjects was assessed by an immunoassay. UCH-L1 or GFAP concentrations in human serum were measured using a 96-well microplate immunochemical chemiluminescent assay. Both UCH-L1 and GFAP assays were based on the chemiluminescent sandwich immunoassay technique as described above in Example 3, which used both capture and detection antibodies that recognize different epitopes on the target analyte (i.e., UCH-L1 or GFAP).

Generally, samples (i.e., clinical specimens, controls, or standards) were pipetted into wells of a 96-well microplate that was coated with either a UCH-L1-specific mouse monoclonal antibody or GFAP-specific mouse monoclonal antibody that captured the target analyte (i.e., UCH-L1 antigen or GFAP antigen, respectively), thereby immobilizing the target analyte to the well. After washing away any unbound proteins, a second UCH-L1-specific mouse monoclonal antibody or GFAP-specific mouse monoclonal antibody, which had been conjugated to the enzyme horseradish peroxidase (HRP), was added to the well. The HRP-conjugated antibody completed the immunochemical sandwich. After washing away unbound HRP-conjugated antibody, a chemiluminescent substrate was added to the well. The HRP enzyme catalyzed a specific reaction with the chemiluminescent substrate and produced light at 300 nm to 700 nm, which was detected with a 96-well plate-based luminometer. The amount of light generated was proportional to the amount of conjugated antibody in the well. The results from the wells containing standards were used to create a dose-response curve to quantify the amount of target analyte (i.e., UCH-L1 antigen or GFAP antigen) in the sample.

A. Detection Capability for UCH-L1 by Immunoassay

Study Methodology

In one exemplary assay, the Lower Level of Quantification (LLoQ) and Upper Level of Quantification (ULoQ) was assessed by measuring a seven member panel containing UCH-L1 concentrations spanning the reportable range of the assay. Within laboratory precision was estimated by testing the seven member panel with three operators, three kit lots for five days with one run per day at one site. Each panel member was tested in four measurements per run resulting in sixty measurements for each panel member per kit lot.

Two anti-UCH-L1 antibodies, UCH-L1-1 and UCH-L1-2, were used as capture antibodies and were adsorbed to wells in a 96-well microplate (Nunc, Maxisorp) at about 10 μg/ml per each antibody in a volume of 100 μL per well. The microplate was blocked with casein (SurModics) in preparation for incubation with a sample containing the antigen standard. The antigen standard (i.e., recombinant UCH-L1) was added to the microplate at concentrations spanning the reportable range of the assay and the microplate was incubated for 1 hour. After incubation, the microplate was washed and a horseradish peroxidase (HRP)-labeled anti-UCH-L1 detection antibody, UCH-L1-5, was added to each well of the microplate at a concentration of about 200 ng/mL+/−20% adjustment. The microplate was incubated for 1 hour. After incubation, the microplate was washed and the bound HRP was detected by addition of a luminol containing substrate (SurModics Sensitive Plus). The signal was read by placing the microplate in a luminometer. The amount of UCH-L1 in each sample was quantitated.

Statistical Analysis

The analysis was performed in accordance with CLSI EP17-A2 *Evaluation of Detection Capability for Clinical Laboratory Measurement procedures: Approved Guideline-Second Edition*. Analytical precision estimates were generated for the entire Level of Quantification (LoQ) dataset. A two-factor Restricted Maximum Likelihood (REML) model was generated to obtain within-laboratory variance component estimates for the precision profile model.

Results

A summary of the two-factor nested model is found in Table 14.

TABLE 14

| | Variance Components | | | |
|---|---|---|---|---|
| | Mean Conc | | Within-Laboratory | |
| Sample | (pg/mL) | N | SD | % CV |
| Lot 1 | | | | |
| QU1 | 2964.6 | 60 | 188.0 | 6.3% |
| U3 | 2089.0 | 60 | 109.6 | 5.2% |
| U1 | 1101.8 | 60 | 52.8 | 4.8% |
| U2 | 381.8 | 60 | 20.0 | 5.2% |
| U5 | 305.0 | 60 | 17.4 | 5.7% |
| U4 | 190.9 | 60 | 13.0 | 6.8% |
| QU2 | 84.6 | 60 | 6.5 | 7.7% |
| Lot 2 | | | | |
| QU1 | 3003.1 | 60 | 175.6 | 5.8% |
| U3 | 2142.5 | 60 | 92.7 | 4.3% |
| U1 | 1152.6 | 60 | 38.8 | 3.4% |
| U2 | 396.9 | 60 | 19.4 | 4.9% |
| U5 | 288.8 | 60 | 15.4 | 5.3% |
| U4 | 196.5 | 60 | 12.2 | 6.2% |
| QU2 | 67.5 | 60 | 5.4 | 8.0% |
| Lot 3 | | | | |
| QU1 | 2882.2 | 60 | 254.3 | 8.8% |
| U3 | 2028.8 | 60 | 126.5 | 6.2% |
| U1 | 1112.4 | 60 | 49.2 | 4.4% |
| U2 | 377.9 | 60 | 20.4 | 5.4% |
| U5 | 273.9 | 60 | 17.1 | 6.2% |
| U4 | 180.2 | 60 | 16.0 | 8.9% |
| QU2 | 66 | 60 | 6.5 | 9.8% |

Precision profiles using within-laboratory precision as % CV and mean measured concentrations of the panel members were generated (Table 15).

TABLE 15

| | LoQ Precision Profile Results | | |
|---|---|---|---|
| LoQ | Concentration (pg/mL) | SD at LoQ (pg/mL) | % CV at LoQ |
| LLoQ | 79.0 | 8.1 | 10.2 |
| ULoQ | 2561.0 | 197.2 | 7.7 |

These results demonstrated that the LoQ (e.g., measurable range) spans the reportable range for the UCH-L1 assay (i.e., 80 pg/mL to 2560 pg/mL).

B. Detection Capability for GFAP by Immunoassay

Study Methodology

In one exemplary assay, the Lower Level of Quantification (LLoQ) and Upper Level of Quantification (ULoQ) was assessed by measuring a seven member panel containing GFAP concentrations spanning the reportable range of the assay. Within laboratory precision was estimated by testing the seven member panel with three operators, three kit lots for five days with one run per day at one site. Each panel member was tested in four measurements per run resulting in sixty measurements for each panel member per kit lot.

An anti-GFAP antibody, GFAP-2, was used as a capture antibody and was adsorbed to wells in a 96-well microplate (Nunc, Maxisorp) at about 2 pg/mL. The microplate was blocked with casein (SurModics) in preparation for incubation with a sample. The antigen standard (GFAP purified from human brain) was added to the microplate at concentrations spanning the reportable range of the assay. The microplate was incubated for 1 hour. After incubation, the microplate was washed and a horseradish peroxidase (HRP)-labeled anti-GFAP antibody, GFAP-6, was added to each well of the microplate at a concentration of about 200 ng/mL+/−20% adjustment. The microplate was incubated for 1 hour. After incubation, the microplate was washed and the bound HRP was detected by addition of a luminol containing substrate (SurModics Sensitive Plus). The signal was read by placing the microplate on a luminometer. The amount of GFAP in each sample was quantitated.

Statistical Analysis

The analysis was performed in accordance with CLSI EP17-A2 *Evaluation of Detection Capability for Clinical Laboratory Measurement procedures: Approved Guideline-Second Edition*. Analytical precision estimates were generated for the entire Level of Quantification (LoQ) dataset, A two-factor Restricted Maximum Likelihood (REML) model was generated to obtain within-laboratory variance component estimates for the precision profile model.

Results

A summary of the two-factor nested model is found in Table 16.

TABLE 16

Variance Components

| Sample | Mean Conc (pg/mL) | N | Within-Laboratory SD | % CV |
|---|---|---|---|---|
| Lot 1 | | | | |
| QG1 | 271.6 | 60 | 25.7 | 9.5% |
| G3 | 243.8 | 60 | 11.8 | 4.8% |
| G1 | 140.4 | 60 | 8.6 | 6.1% |
| G2 | 39.5 | 60 | 2.2 | 5.6% |
| G5 | 27.3 | 60 | 1.6 | 5.9% |
| G4 | 7.8 | 60 | 0.8 | 10.3% |
| QG2 | 6.2 | 60 | 0.5 | 8.1% |
| Lot 2 | | | | |
| QG1 | 279.8 | 60 | 9.0 | 3.2% |
| G3 | 244.3 | 60 | 8.0 | 5.7% |
| G1 | 140.0 | 60 | 6.5 | 4.6% |
| G2 | 38.9 | 60 | 2.9 | 7.5% |
| G5 | 23.4 | 60 | 1.9 | 8.1% |
| G4 | 9.2 | 60 | 1.2 | 13.0% |
| QG2 | 8.0 | 56 | 0.8 | 10.0% |
| Lot 3 | | | | |
| QG1 | 293.0 | 60 | 11.7 | 4.0% |
| G3 | 253.9 | 60 | 9.9 | 3.9% |
| G1 | 144.4 | 60 | 4.2 | 2.9% |
| G2 | 37.3 | 60 | 1.6 | 4.3% |
| G5 | 25.3 | 60 | 1.6 | 6.3% |
| G4 | 7.6 | 60 | 1.0 | 13.2% |
| QG2 | 6.0 | 56 | 0.4 | 6.7% |

Precision profiles using within-laboratory precision as % CV and mean measured concentrations of the panel members were generated (Table 17).

TABLE 17

LoQ Precision Profile Results

| LoQ | Concentration (pg/mL) | SD at LoQ (pg/mL) | % CV at LoQ |
|---|---|---|---|
| LLoQ | 9.0 | 1.0 | 11.1 |
| ULoQ | 321.0 | 19.3 | 6.0 |

These results demonstrated that the LoQ (e.g., measurable range) spans the reportable range for the GFAP assay (i.e., 10 pg/mL to 320 pg/mL).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

Amino acid sequence of mouse UCH-L1-1 heavy chain variable domain
(SEQ ID NO: 51)
QVQLQQPGSELVRPGASVKLSCKASGYTFTSYWMHWV

KQRPGQGLEWIGNIYPGSGSTNYDEKFKSKATLTVDT

SSSTAYMQLSSLTSEDSAVYYCTREDYWGQGTTLTVS

S

Amino acid sequence of mouse UCH-L1-2 heavy chain variable domain
(SEQ ID NO: 52)
EVMLVESGGGLVKPGGSLKLSCAASGFIFSSHAMSWI

RQIPEKRLEWVATISSGGSNTYYPDSVKGRFTISRDN

AKNILYLQMSSLRSEDTAIYYCTRHGEVRRGYYFDYW

GQGTTLTVSS

Amino acid sequence of mouse UCH-L1-3 heavy chain variable domain
(SEQ ID NO: 53)
QVQLQQPGSELVRPGASVKLSCRASGYTFTSYWIHWV

KQRHGQGLEWIGNIYPGSGITNYDEKFKTKGTLTVDT

SSSTVYMHLISLTSEDSAVYYCTREDYWGQGTTLTVS

S

Amino acid sequence of mouse UCH-L1-4 heavy chain variable domain
(SEQ ID NO: 54)
AVQLQQSGPELVKPGASVKISCKTSGDTFTEHFMNWV

KQSHGESLEWIGIINPYTDGTNYDQKFKDKATLTVDK

SSSTAYMELRSLTSEDSAVYYCARWGGDGEGYWGQGT

TLTVSS

Amino acid sequence of mouse UCH-L1-5 heavy chain variable domain
(SEQ ID NO: 55)
EVKLVESGGGSVQPGGSLSLSCAASGFTFTEYYMSWV

RQFPGKALEWLAFIRNRAHGYTTEYSASVKGRFTISR

DNSQSILYLQMNALRTEDSATYYCASSYGAPFAYVVG

QGTLVSVSA

Amino acid sequence of mouse UCH-L1-6 heavy chain variable domain
(SEQ ID NO: 56)
EVQLQQSGPELVKPGASVKISCKTSGYTFTEYTMHWV

KQSHGKSLDWIGGINPNNGRTSYNQKFKGKATLTVDK

| SEQUENCES | |
|---|---|
| SSSTAYMDFRSLTSEDSAVYYCARRLGRGFYFDYWGQ | |
| GTTLTVSS | |
| Amino acid sequence of mouse UCH-L1-7 heavy chain variable domain (SEQ ID NO: 57) | |
| EVQLQQSGPELVKPGASVKISCKTSGYTFTEYTMHWV | |
| KQSHGKSLDWIGGINPNNGRTSYNQKFKGKATLTVDK | |
| SSSTAYMELRSLTSEDSAVYYCARRLGRGFYFDYWGQ | |
| GTTLTVSS | |
| Amino acid sequence of mouse UCH-L1-8 heavy chain variable domain (SEQ ID NO: 58) | |
| EVQLQQSGPDLVKPGTSVKISCKTSGYTFTEYTMHWV | |
| KQSHGRSLEWIGGLNPNNGRTSYNQKFKGKATLTVDK | |
| SSSIAYMELRSLTSEDSAVYYCARRLGRGFYFDYWGQ | |
| GTTLTVSS | |
| Amino acid sequence of mouse UCH-L1-9 heavy chain variable domain (SEQ ID NO: 59) | |
| EVQLQQSGPELVKPGASVKISCKTSGYTFTEYTMHWV | |
| KQSHGKSLDWIGGINPNNGRTSYNQKFKGKATLTVDK | |
| SSSTAYMELRSLTSEDSTVYYCARRLGRGFYFDYWGQ | |
| GTTLTVSS | |
| Amino acid sequence of mouse UCH-L1-10 heavy chain variable domain (SEQ ID NO: 60) | |
| EVQLQQSGPDLVKPGTSVKISCKTSGYTFTEYTMHWV | |
| KQSHGRSLEWIGGFNPNNGRTSYNQKFKGKATLTVDK | |
| SSSTAYMELRSLTSEDSAVYYCSRRLYRGFYFDYWGQ | |
| GTTLTVSS | |
| Amino acid sequence of mouse UCH-L1-11 heavy chain variable domain (SEQ ID NO: 61) | |
| EVQLVESGGGLVKPGGSLKLSCAASGFTFSRYAMSWV | |
| RQTPEKRLEWVATISTAGSYTYYPDSVKGRFTISRDN | |
| AKNTLYLQMSSLRSEDTALYYCARQGTGTYAMDYWGQ | |
| GTSVTVSS | |
| Amino acid sequence of mouse UCH-L1-12 heavy chain variable domain (SEQ ID NO: 62) | |
| EVQLVESGGGLVKPGGSLKLSCAASGFTFSKNAMSWV | |
| RQTPEKRLEWVATISTGGTYTYYPDSVKGQFTISRDN | |
| AKNTLYLQMSSLRSEDTAMYFCARQRTGTYAMDHWGQ | |
| GTSVTVSS | |
| Amino acid sequence of mouse UCH-L1-13 heavy chain variable domain (SEQ ID NO: 63) | |
| QVQLQQPGSELVRPGASVKLSCKASGYTFTSYWMHWV | |
| KQRPGQGLEWIGNIYPGSGTTNYDEKFKSKATLTVDT | |

| SEQUENCES | |
|---|---|
| SSSTAYMQLNSLTSEDSAVYYCTREDYWGQGTTLTVS | |
| S | |
| Amino acid sequence of mouse UCH-L1-1 light chain variable domain (SEQ ID NO: 64) | |
| DVLMTQTPLSLPVSLGDQASISCRSSQNIVHSNGNTY | |
| LEWYLQKPGQSPKLLIYKVSNRFSGVPDRFSGSGSGT | |
| DFTLKISRVEAEDLGVYYCFQGSHVPFTFGSGTKLEI | |
| K | |
| Amino acid sequence of mouse UCH-L1-2 light chain variable domain (SEQ ID NO: 65) | |
| DIQMTQTPSSLSASLGDRVTISCSASQGITNYLNWYQ | |
| QKPDGTVKLLIYYTSSLHSGVPSRFSGSGSGTDYSLT | |
| ISNLEPEDFATYYCQHYSNLPWTFGGGTKLEIK | |
| Amino acid sequence of mouse UCH-L1-3 light chain variable domain (SEQ ID NO: 66) | |
| DVLMTQTPLSLPVSLGDQASISCRSSQSIVHSNGNTY | |
| LEWYLQKPGQSPKLLIYKVSNRFSGVPDRFSGSGSGT | |
| DFTLKISGVETEDLGVYYCFQGSHVPFTFGGGTKLEI | |
| K | |
| Amino acid sequence of mouse UCH-L1-4 light chain variable domain (SEQ ID NO: 67) | |
| DIVMTQAAPSVSVTPGESVSISCRSSKSLLHSNGNTY | |
| LYWFLKRPGQSPQLLIYRMSNLASGVPDRVSGSGSGT | |
| AFTLRISRVEAEDVGIYYCMQHLEYPLTFGAGTKLEL | |
| K | |
| Amino acid sequence of mouse UCH-L1-5 light chain variable domain (SEQ ID NO: 68) | |
| DIVMTQAAPSVPVTPGESVSISCRSSKSLLHSDGNTY | |
| LYWFLQRPGQSPQLLIYRMSNLASGVPDRSGSGSGT | |
| AFTLRISRVEAEDVGVYYCMQHLEYPLTFGAGTKLEL | |
| K | |
| Amino acid sequence of mouse UCH-L1-6 light chain variable domain (SEQ ID NO: 69) | |
| DIVLTQSPASLAVSLGQRATISCRASESVESYGNNLI | |
| HWYQQKLGQPPKLLIYLSSNLEPGIPARFSGRGSRTD | |
| FTLTINPVEADDVATYYCQQSNGDPYTFGGGTKLEIR | |
| Amino acid sequence of mouse UCH-L1-7 light chain variable domain (SEQ ID NO: 70) | |
| DIVLTQSPASLAVSLGQRATISCRASESVDSYGNNLM | |
| HWYQQKPGQPPKLLIYLSSNLESGIPARFSGRGSRTD | |
| FTLTINPVEADDVATYYCQQSNGDPYTFGGGTKLEIK | |

| SEQUENCES |
|---|
| Amino acid sequence of mouse UCH-L1-8 light chain variable domain<br>(SEQ ID NO: 71)<br>DIVLTQSPASLAVSLGQRATISCRASESVDSYGNNLM<br>HWYQQKPGQSPKLLIYRASNLESGIPGRFSGRGSRTD<br>FTLTINPVEADDVATYYCQQSNGDPYTFGGGTKLEIK |
| Amino acid sequence of mouse UCH-L1-9 light chain variable domain<br>(SEQ ID NO: 72)<br>DIVLTQSPASLAVSLGQRATISCRASESVDSYGNNFM<br>HWYQQKPGQPPKLLIYLSSNLESGIPARFSGRGSRTD<br>FTLTINPVEADDVATYYCQQSNGDPYTFGGGTKLEMK |
| Amino acid sequence of mouse UCH-L1-10 light chain variable domain<br>(SEQ ID NO: 73)<br>DIVLTQSPASLAVSLGQRATISCRASESVDSYGNNLM<br>HWYQQKPGQSPKLLIYRASNLESGIPGRFSGRGSRTD<br>FSLTINPVEADDVATYYCQQSNGDPYTFGGGTKLEIK |
| Amino acid sequence of mouse UCH-L1-11 light chain variable domain<br>(SEQ ID NO: 74)<br>DIQMTQSPASLSASVGETVTITCRASGNIHNYLAWYQ<br>QNQGKSPQLLVYNAKTLADGVPSRFSGSGSGTQYSLK<br>INRLQPEDFGSYYCQHFWSTTWTFGGGTKLEIK |
| Amino acid sequence of mouse UCH-L1-12 light chain variable domain<br>(SEQ ID NO: 75)<br>DIQMTQSPASLSASVGETVTITCRASGNIHNYLAWYQ<br>QKQGKSPQLLVYNANTLADGVPPRFSGSGSGTQYSLK<br>VNSLQPEDFGNYYCQHFWSTTWTFGGGTRLEIK |
| Amino acid sequence of mouse UCH-L1-13 light chain variable domain<br>(SEQ ID NO: 76)<br>DVLMTQSPLSLPVSLGDQASISCRSSQNIVHSNGNTY<br>LEWYLQKPGQSPKLLIYKVSNRFSGVPDRFSGSGSGT<br>DFTLKISRVEAEDLGVYYCFQGSHVPYTFGGGTKLEIK |
| Amino acid sequence of mouse GFAP-1 heavy chain variable domain<br>(SEQ ID NO: 172)<br>EVHLQQSGTVLARPGASVKMSCKASGYSFTSYWMHWV<br>KQRPGQGLEWIGAFYPENSDTNYNQKFKGKARLTAVT<br>SANTAYMELNSLTNEDSAVYYCTRPLLFSAYFDFWGQ<br>GTTLTVSS |
| Amino acid sequence of mouse GFAP-2 heavy chain variable domain<br>(SEQ ID NO: 173)<br>DVQLVESGGGLVQPGGSRKLSCAASGFTFSSFGMHWV<br>RQAPEKGLEWVAYISSGSSIIYYADTVKGRFTISRDN<br>PKNTLFLQMTSLRSEDTAMYYCTGSDWGSFAYWGQGT<br>LVTVSA |
| Amino acid sequence of mouse GFAP-3 heavy chain variable domain<br>(SEQ ID NO: 174)<br>EVKLEESGGGLVQPGGSMKLSCVASGFTFTNYWMSWV<br>RQSPEKGLEWVAQIRLKSDNYATHYAESVKGRFTISR<br>DDSKSSVYLQMNNLRAEDTGIYYCTGGEFLSWFAYWG<br>QGTLVTVSA |
| Amino acid sequence of mouse GFAP-4 heavy chain variable domain<br>(SEQ ID NO: 175)<br>EVQLLQSGTVLARPGASVKMSCKASGYSFTSYWMHWI<br>KQRPGQGLEWIGAIHPGNRDTSYNQKFKDKAKLTAVT<br>SASTAYMELSSLTNEDSAVYFCTREDYWGQGTTLTVS<br>S |
| Amino acid sequence of mouse GFAP-5 heavy chain variable domain<br>(SEQ ID NO: 176)<br>EVQLVESGGGLVKPGGSLKLSCAASGFTFSAYGMHWV<br>RQAPEKGLEWIAYISSGSSTIYYADTVKGRFTISRDN<br>AKNTLFLQMTSLRSEDTAMYYCASSYALDYWGQGTSV<br>TVSS |
| Amino acid sequence of mouse GFAP-6 heavy chain variable domain<br>(SEQ ID NO: 177)<br>EVQLQQSGAEFVKPGASVKLSCTASGFNIKDTDMHWV<br>RQRPEQGLESIGLIDPAIGNTKYDPKFQGKATITADT<br>SSNAAYLQLSSLTSEDTAVYYCARSDRYLAWFAYWGQ<br>GTLVTVSA |
| Amino acid sequence of mouse GFAP-7 heavy chain variable domain<br>(SEQ ID NO: 175)<br>EVQLLQSGTVLARPGASVKMSCKASGYSFTSYWMHWI<br>KQRPGQGLEWIGAIHPGNRDTSYNQKFKDKAKLTAVT<br>SASTAYMELSSLTNEDSAVYFCTREDYWGQGTTLTVS<br>S |
| Amino acid sequence of mouse GFAP-8 heavy chain variable domain<br>(SEQ ID NO: 175)<br>EVQLLQSGTVLARPGASVKMSCKASGYSFTSYWMHWI<br>KQRPGQGLEWIGAIHPGNRDTSYNQKFKDKAKLTAVT<br>SASTAYMELSSLTNEDSAVYFCTREDYWGQGTTLTVS<br>S |
| Amino acid sequence of mouse GFAP-9 heavy chain variable domain<br>(SEQ ID NO: 178)<br>DVQLQESGPGLVKPSQSLSLTCSVTGYSITSGFYWSWI<br>RQFPGNKLEWMGYISYDGSNNYNPSLKNRISITRDTSK |

| SEQUENCES |
|---|
| NQFFLKLNSVTTEDTATYYCARAYGYDGAWFAYWGQGT LVTVSA |
| Amino acid sequence of mouse GFAP-10 heavy chain variable domain (SEQ ID NO: 179) EVKLVESGGGLVKPGGSLKLSCAASGFTFSYYAMSWV RQTPEKRLEWVASISSGGTTYHPDSVKGRFTISRDNA RNILYLQMSSLRSEDTAMYYCARGGHWYFDVWGAGTT VTVSS |
| Amino acid sequence of mouse GFAP-11 heavy chain variable domain (SEQ ID NO: 180) QIQLVQSGPELKKPGETVKISCKASGYTFTNYGMNW VKQAPGEGLKWMGWINTNIGEPTYAEEFKGRFAFSL EASASTAYLQINNLKNEDTATYFCARWKNYGYFDYW GQGTTLTVSS |
| Amino acid sequence of mouse GFAP-12 heavy chain variable domain (SEQ ID NO: 181) QVQLQQSGAELMKPGASVKISCKATGYTFSNYWIEW VKQRPGHGLEWIGEILPGSGSTNYNEKFKGKATFTA DTSSNTAYMQLSSLTSEDSAVYYCAIYYGNYAGAMD YWGQGTSVTVSS |
| Amino acid sequence of mouse GFAP-13 heavy chain variable domain (SEQ ID NO: 182) EVLLQQSGPELVKPGASVKMSCKTSGYTFANYIMHW VKQTPGQGLEWIGFINPYNDYTEYNEKFKGKATLTS DKSSSTAYMEFSGLTSEDSAVYYCSTATFAYWGQGT LVTVSA |
| Amino acid sequence of mouse GFAP-14 heavy chain variable domain (SEQ ID NO: 183) DVQLVESGGGSVQPGGSRKLSCAASGFTFSSFGMHWV RQAPEKGLEWVAYISSDSNTVYYADTVKGRFTISRDN PKNTLFLQMTSLRSEDTAMYYCARYAMDYWGQGTSVT VSS |
| Amino acid sequence of mouse GFAP-15 heavy chain variable domain (SEQ ID NO: 184) DVQLVESGGGLLEPGGSRKLSCAASGFTFSSFGMHWV RQAPEKGLEWVAYISSGSRTIFYADTVKGRFTISRDN PKNTLFLQMTSLRSGDTAMYYCVRGGYGSSFDYWGQG TTLTVSS |
| Amino acid sequence of mouse GFAP-16 heavy chain variable domain (SEQ ID NO: 185) QVQLQQSDAELVKPGASVKISCKASGYTFTDHTIHWV KQRPEQGLEWIGYIYPGDGSTKYNEKFKGKATLTADK |

| SEQUENCES |
|---|
| SSSTVYMQLNSLTSEDSAVYFCARPAPYWNFDVWGAG TTVTVSS |
| Amino acid sequence of mouse GFAP-17 heavy chain variable domain (SEQ ID NO: 186) EVKLEESGGGLVQPGGSMKLSCVASGFTFSYYWMSWV RQSPEKGLEWIAEIRLKSNIYATHYAASVKGRFTISR DDSKSSVYLQMNNLRAEDTGIYFCTRFGTGAMDYWGQ GTSVTVSS |
| Amino acid sequence of mouse GFAP-18 heavy chain variable domain (SEQ ID NO: 187) EVILVESGGGLVKPGGSLKVSCAVSGFTFSNFAMSWV RQTPEKRLEWVASISSGGTTYYPDNVKGRFTISRDNA RNIMYLQMSSLRSEDTAMYFCARGGLHYFGYWGQGTT LTVSS |
| Amino acid sequence of mouse GFAP-19 heavy chain variable domain (SEQ ID NO: 188) EVQLVESGGGLVKPGGSPKLSCAASGFAFSSYDMSWV RQTPEKRLEWVAYISSGGGSTYYPDTMKGRFTISRDN AKNTLYLQMSSLKSEDTAMYYCARHYGTYLYYLDYWG QGTTLTVSS |
| Amino acid sequence of mouse GFAP-1 light chain variable domain (SEQ ID NO: 189) DVLMTQTPLSLPVSLGDQASISCRSSQSIVHSYGNTY LEWYLQKPGLSPKLLIYKVSNRFSGVPDRFSGSGSGT DFTLTISRVEAEDLGVYYCFQGSHVPYTFGGGTKLEI K |
| Amino acid sequence of mouse GFAP-2 light chain variable domain (SEQ ID NO: 190) DVVMTQTPLSLPVSLGDQASISCRSSQSLVYSNGNTY LHWYLQKPGQSPKLLIYKVSNRFFGVPDRFSGSGSGT DFTLKISRVEAEDLGVYFCSQSTHVPYTFGGGTKLEI K |
| Amino acid sequence of mouse GFAP-3 light chain variable domain (SEQ ID NO: 191) DIVMSQSPSSLAVSAGEKVTMSCKSSQSLFNSRTRKN YLAWYQQKPGQSPKLLIYWASTRESGVPDRFTGSGSG TDFTLTISSVQAEDLAVYYCKQSYYLYTFGSGTKLEI K |
| Amino acid sequence of mouse GFAP-4 light chain variable domain (SEQ ID NO: 192) DIVMTQSPSSLAMSVGQKVTMSCKSSQSLLNSNNQRN YLDWYQQKPGQSPKLLVYFASTRESGVPDRFIGSGSG |

TDFTLTISSVQAEDLADYFCQQHYSIPLTFGAGTKLELK

Amino acid sequence of mouse GFAP-5 light chain variable domain
(SEQ ID NO: 193)
DVVMTQTPLSLPVSLGDQASISCRSSQSLVYSNGNTYLHWYLQKPGQSPKLLIYKVSNRFSGVPDRFSGSGSTDFTLKISRVEAEDLGVYFCSQSTHVPYTFGSGTKLEIK Amino acid sequence of mouse GFAP-6 light chain variable domain
(SEQ ID NO: 194)
DIVMTQSPATLSVTPGDRVSLSCRASQSISDFLHWYQQKSHGSPRLLIKYSSQSISGIPSRFSGSGSGSDFTLSINSVEPEDVGVYYCQNGHTFPYTFGGGTKLEIK Amino acid sequence of mouse GFAP-7 light chain variable domain
(SEQ ID NO: 195)
DIVMTQSPSSLAMSVGQKVTMSCKSSQSLLNSSNQRNYLDWYQQKPGQSPKLLVYFASTRESGVPDRFIGSGSGTDFTLTISSVQAEDLADYFCQQHYSIPLTFGAGTKLELK Amino acid sequence of mouse GFAP-8 light chain variable domain
(SEQ ID NO: 195)
DIVMTQSPSSLAMSVGQKVTMSCKSSQSLLNSSNQRNYLDWYQQKPGQSPKLLVYFASTRESGVPDRFIGSGSGTDFTLTISSVQAEDLADYFCQQHYSIPLTFGAGTKLELK Amino acid sequence of mouse GFAP-9 light chain variable domain
(SEQ ID NO: 196)
DIVMTQSQKFMSTSVGDRVSITCKASQNVRTAVAWYQQKPGQSPKALIYLASNRHTGVPDRFTGSGSGTDFTLTISNVQSEDLADYFCLQHWNNPYTFGGGTKLEIK Amino acid sequence of mouse GFAP-10 light chain variable domain
(SEQ ID NO: 197)
QIVLTQSPAIMSASPGEKVTMTCSASSSVSYMHWYQQKSGTSPKRWIYDTSKLASGVPARFSGSGSGTSYSLTISSMEAEDAATYYCQQWSTNPLTFGAGTKLDLK Amino acid sequence of mouse GFAP-11 light chain variable domain
(SEQ ID NO: 198)
QIVLTQSPAIMSASLGERVTMTCTASSSVSSSYLHWYQQKPGSSPKLWIYSTSNLASGVPARFSGSGSGTSYSLTISSLEAEDAATYYCHQYHRSPYTFGGGTKLEIK Amino acid sequence of mouse GFAP-12 light chain variable domain
(SEQ ID NO: 199)
DIQMTQSPASLSASVGETVTITCRASENIYSYLAWYQQKQGKSPQLLVYNAKTLAEGVPSRFSGSGSGTQFSLKINSLQPEDFGSYYCQLHYGTPYTFGSGTKLEIK Amino acid sequence of mouse GFAP-13 light chain variable domain
(SEQ ID NO: 200)
DVVMTQTPLTLSVTIGQPASISCKSSQSLLDSAGKTYLNWLLQKSGQSPKRLIYLVSKLDSGVPDRFTGSGSGTDFTLKISRVEAEDLGVYYCWQGTHFPWTFGGGTKLEIK Amino acid sequence of mouse GFAP-14 light chain variable domain
(SEQ ID NO: 201)
QIVLTQSPALMSASPGEKVTMTCSASSSVSYMWYQQKPRSSPKPWIYLTSNLASGVPARFSGSGSGTSYSLTISSMEAEDAATYYCQQWSSNPPTFGAGTKLELK Amino acid sequence of mouse GFAP-15 light chain variable domain
(SEQ ID NO: 202)
DVVMTQTPLSLPVSLGDQASISCRSSQSLVYSNGNIYLHWYLQKPGQSPKLLIYKVSNRFSGVPDRFSGSGSGTDFTLKISRVEAEDLGVYFCSQSTHVPYTFGGGTKLEIK Amino acid sequence of mouse GFAP-16 light chain variable domain
(SEQ ID NO: 203)
DIQMTQSPSSLSASLGGKVTITCKASQDIKKNIAWYQHKPGKGPRLLIWYTSTLQPGIPSRFSGSGSGRDYSFSISNLEPEDIATYYCLQYDHLRTFGGGTKLEIK Amino acid sequence of mouse GFAP-17 light chain variable domain
(SEQ ID NO: 204)
DIVMSQSPSSLAVSVGEKVTMSCKSSQSLLYRTNQKNYLAWYQQKPGQSPKLLIYWASSRESGVPDRFSGSGSGTDFTLTISSVKAEDLAVYYCQQYYSYPWTFGGGTKLEIK Amino acid sequence of mouse GFAP-18 light chain variable domain
(SEQ ID NO: 205)
DIVMTQSHKFMSTSVGDRVSITCKASQDVNTAVAWYQQKPGQSLKLLIYSASYRYIGVPDRFTGSGSGTDFTFTINSVQAEDLAVYYCHQYYSTPLTFGTGTKLELK

| SEQUENCES |
|---|
| Amino acid sequence of mouse GFAP-19 light chain variable domain (SEQ ID NO: 206) |
| DIVLTQSPATLSVTPGDRVSLSCRASQNISDFLHWYQ |
| QKSHESPRLLIKYASQSISGIPSRFSGSGSGSDFTLS |
| INSVEPEDVGVYYCQNGHSFPPTFGGGTKLEIK |
| Amino acid sequence of mouse IgG1 heavy chain constant domain (SEQ ID NO: 215) |
| AKTTPPSVYPLAPGSAAQTNSMVTLGCLVKGYFPEPV |
| TVTWNSGSLSSGVHTFPAVLQSDLYTLSSSVTVPSSP |
| RPSETVTCNVAHPASSTKVDKKIVPRDCGCKPCICTV |
| PEVSSVFIFPPKPKDVLTITLTPKVTCVVVDISKDDP |
| EVQFSWFVDDVEVHTAQTQPREEQFNSTFRSVSELPI |
| MHQDWLNGKEFKCRVNSAAFPAPIEKTISKTKGRPKA |
| PQVYTIPPPKEQMAKDKVSLTCMITDFFPEDITVEWQ |
| WNGQPAENYKNTQPIMNTNGSYFVYSKLNVQKSNWEA |
| GNTFTCSVLHEGLHNHHTEKSLSHSPGK |
| Amino acid sequence of mouse IgG2a heavy chain constant domain (SEQ ID NO: 216) |
| AKTTAPSVYPLVPVCGGTTGSSVTLGCLVKGYFPEPV |
| TLTWNSGSLSSGVHTFPALLQSGLYTLSSSVTVTSNT |
| WPSQTITCNVAHPASSTKVDKKIEPRVPITQNPCPPH |
| QRVPPCAAPDLLGGPSVFIFPPKIKDVLMISLSPMVT |
| CVVVDVSEDDPDVQISWFVNNVEVHTAQTQTHREDYN |
| STLRVVSALPIQHQDWMSGKEFKCKVNNRALPSPIEK |
| TISKPRGPVRAPQVYVLPPPAEEMTKKEFSLTCMITG |
| FLPAEIAVDWTSNGRTEQNYKNTATVLDSDGSYFMYS |
| KLRVQKSTWERGSLFACSVVHEVLHNHLTTKTISRSL |
| GK |
| Amino acid sequence of mouse IgG2b heavy chain constant domain (SEQ ID NO: 217) |
| KTTPPSVYPLAPGCGDTTGSSVTLGCLVKGYFPESVT |
| VTWNSGSLSSSVHTFPALLQSGLYTMSSSVTVPSSTW |
| PSQTVTCSVAHPASSTTVDKKLEPSGPISTINPCPPC |
| KECHKCPAPNLEGGPSVFIFPPNIKDVLMISLTPKVT |
| CVVVDVSEDDPDVQISWFVNNVEVHTAQTQTHREDYN |
| STIRVVSTLPIQHQDWMSGKEFKCKVNNKDLPSPIER |
| TISKIKGLVRAPQVYILPPPAEQLSRKDVSLTCLVVG |
| FNPGDISVEWTSNGHTEENYKDTAPVLDSDGSYFIYS |
| KLNMKTSKWEKTDSFSCNVRHEGLKNYYLKKTISRSP |

| SEQUENCES |
|---|
| GLDLDDICAEAKDGELDGLWTTITIFISLFLLSVCYS |
| ASVTLFKVKWIFSSVVELKQKISPDYRNMIGQGA |
| Amino acid sequence of human IgG1 heavy chain constant domain (SEQ ID NO: 218) |
| ASTKGPSVFPLAPSSKSTSGGTAALGCLVKDYFPEPV |
| TVSWNSGALTSGVHTFPAVLQSSGLYSLSSVVTVPSS |
| SLGTQTYICNVNHKPSNTKVDKRVEPKSCDKTHTCPP |
| CPAPELLGGPSVFLFPPKPKDTLMISRTPEVTCVVVD |
| VSHEDPEVKFNWYVDGVEVHNAKTKPREEQYNSTYRV |
| VSVLTVLHQDWLNGKEYKCKVSNKALPAPIEKTISKA |
| KGQPREPQVYTLPPSREEMTKNQVSLTCLVKGFYPSD |
| IAVEWESNGQPENNYKTTPPVLDSDGSFFLYSKLTVD |
| KSRWQQGNVFSCSVMHEALHNHYTQKSLSLSPG |
| Amino acid sequence of murine kappa light chain constant domain (SEQ ID NO: 219) |
| ADAAPTVSIFPPSSEQLTSGGASVVCFLNNFYPKDI |
| NVKWKIDGSERQNGVLNSWTDQDSKDSTYSMSSTLT |
| LTKDEYERHNSYTCEATHKTSTSPIVKSFNRNEC |
| Amino acids equence of murine lambda light chain constant domain (SEQ ID NO: 220) |
| QPKSSPSVTLFPPSSEELETNKATLVCTITDFYPGV |
| VTVDWKVDGTPVTQGMETTQPSKQSNNKYMASSYLT |
| LTARAWERHSSYSCQVTHEGHTVEKSLSRADCS |
| Amino acid sequence of human kappa light chain constant domain (SEQ ID NO: 221) |
| TVAAPSVFIFPPSDEQLKSGTASVVCLLNNFYPREA |
| KVQWKVDNALQSGNSQESVTEQDSKDSTYSLSSTLT |
| LSKADYEKHKVYACEVTHQGLSSPVTKSFNRGEC |
| Amino acid sequence of human lambda light chain constant domain (SEQ ID NO: 222) |
| GQPKANPTVTLFPPSSEELQANKATLVCLISDFYPG |
| AVTVAWKADGSPVKAGVETTKPSKQSNNKYAASSYL |
| SLTPEQWKSHRSYSCQVTHEGSTVEKTVAPTECS |
| Amino acid sequence of mouse IgM heavy chain constant domain (SEQ ID NO: 223) |
| SQSFPNVFPLVSCESPLSDKNLVAMGCLARDFLPST |
| ISFTWNYQNNTEVIQGIRTFPTLRTGGKYLATSQVL |
| LSPKSILEGSDEYLVCKIHYGGKNRDLHVPIPAVAE |
| MNPNVNVFVPPRDGFSGPAPRKSKLICEATNFTPKP |
| ITVSWLKDGKLVESGFTTDPVTIENKGSTPQTYKVI |
| STLTISEIDWLNLNVYTCRVDHRGLTFLKNVSSTCA |

SEQUENCES

```
ASPSTDILTFTIPPSFADIFLSKSANLTCLVSNLAT

YETLNISWASQSGEPLETKIKIMESHPNGTFSAKGV

ASVCVEDWNNRKEFVCTVTHRDLPSPQKKFISKPNE

VHKHPPAVYLLPPAREQLNLRESATVTCLVKGFSPA

DISVQWLQRGQLLPQEKYVTSAPMPEPGAPGFYFTH

SILTVTEEEWNSGETYTCVVGHEALPHLVTERTVDK

STGKPTLYNVSLIMSDTGGTCY

Amino acid sequence of human IgM
heavy chain constant domain
                        (SEQ ID NO: 224)
GSASAPTLFPLVSCENSPSDTSSVAVGCLAQDFLPD

SITLSWKYKNNSDISSTRGFPSVLRGGKYAATSQVL

LPSKDVMQGTDEHVVCKVQHPNGNKEKNVPLPVIAE
```

SEQUENCES

```
LPPKVSVFVPPRDGFFGNPRKSKLICQATGFSPRQI

QVSWLREGKQVGSGVTTDQVQAEAKESGPTTYKVTS

TLTIKESDWLGQSMFTCRVDHRGLTFQQNASSMCVP

DQDTAIRVFAIPPSFASIFLTKSTKLTCLVTDLTTY

DSVTISWTRQNGEAVKTHTNISESHPNATFSAVGEA

SICEDDWNSGERFTCTVTHTDLPSPLKQTISRPKGV

ALHRPDVYLLPPAREQLNLRESATITCLVTGFSPAD

VFVQWMQRGQPLSPEKYVTSAPMPEPQAPGRYFAHS

ILTVSEEEWNTGETYTCVAHEALPNRVTERTVDKST

GKPTLYNVSLVMSDTAGTCY
```

What is claimed is:

1. An antibody or antigen-binding fragment thereof that specifically binds to a human ubiquitin c-terminal hydrolase L1 (UCH-L1) protein, comprising:
    a heavy chain variable region that comprises CDR-H1, CDR-H2, and CDR-H3 amino acid sequences; and
    a light chain variable region that comprises CDR-L1, CDR-L2, and CDR-L3 amino acid sequences,
    wherein:
    (1) the heavy chain variable region comprises (i) the CDR-H1 amino acid sequence comprising SEQ ID NO:2, (ii) the CDR-H2 amino acid sequence comprising SEQ ID NO:10, and (iii) the CDR-H3 amino acid sequence comprising SEQ ID NO:21; and
    the light chain variable region comprises (i) the CDR-L1 amino acid sequence comprising SEQ ID NO:29, (ii) the CDR-L2 amino acid sequence comprising SEQ ID NO:38, and (iii) the CDR-L3 amino acid sequence comprising SEQ ID NO:46; or
    (2) the heavy chain variable region comprises (i) the CDR-H1 amino acid sequence comprising SEQ ID NO:5, (ii) the CDR-H2 amino acid sequence comprising SEQ ID NO:13, and (iii) the CDR-H3 amino acid sequence comprising SEQ ID NO:23; and
    the light chain variable region comprises (i) the CDR-L1 amino acid sequence comprising SEQ ID NO:32, (ii) the CDR-L2 amino acid sequence comprising SEQ ID NO:39, and (iii) the CDR-L3 amino acid sequence comprising SEQ ID NO:47; or
    (3) the heavy chain variable region comprises (i) the CDR-H1 amino acid sequence comprising SEQ ID NO:3, (ii) the CDR-H2 amino acid sequence comprising SEQ ID NO:11, and (iii) the CDR-H3 amino acid sequence comprising SEQ ID NO:20; and
    the light chain variable region comprises (i) the CDR-L1 amino acid sequence comprising SEQ ID NO:30, (ii) the CDR-L2 amino acid sequence comprising SEQ ID NO:37, and (iii) the CDR-L3 amino acid sequence comprising SEQ ID NO:45; or
    (4) the heavy chain variable region comprises (i) the CDR-H1 amino acid sequence comprising SEQ ID NO:4, (ii) the CDR-H2 amino acid sequence comprising SEQ ID NO:12, and (iii) the CDR-H3 amino acid sequence comprising SEQ ID NO:22; and
    the light chain variable region comprises (i) the CDR-L1 amino acid sequence comprising SEQ ID NO:31, (ii) the CDR-L2 amino acid sequence comprising SEQ ID NO:39, and (iii) the CDR-L3 amino acid sequence comprising SEQ ID NO:47; or
    (5) the heavy chain variable region comprises (i) the CDR-H1 amino acid sequence comprising SEQ ID NO:6, (ii) the CDR-H2 amino acid sequence comprising SEQ ID NO:14, and (iii) the CDR-H3 amino acid sequence comprising SEQ ID NO:24; and
    the light chain variable region comprises (i) the CDR-L1 amino acid sequence comprising SEQ ID NO:33, (ii) the CDR-L2 amino acid sequence comprising SEQ ID NO:40, and (iii) the CDR-L3 amino acid sequence comprising SEQ ID NO:48; or
    (6) the heavy chain variable region comprises (i) the CDR-H1 amino acid sequence comprising SEQ ID NO:6, (ii) the CDR-H2 amino acid sequence comprising SEQ ID NO:14, and (iii) the CDR-H3 amino acid sequence comprising SEQ ID NO:24; and
    the light chain variable region comprises (i) the CDR-L1 amino acid sequence comprising SEQ ID NO:34, (ii) the CDR-L2 amino acid sequence comprising SEQ ID NO:41, and (iii) the CDR-L3 amino acid sequence comprising SEQ ID NO:48; or
    (7) the heavy chain variable region comprises (i) the CDR-H1 amino acid sequence comprising SEQ ID NO:6, (ii) the CDR-H2 amino acid sequence comprising SEQ ID NO:15, and (iii) the CDR-H3 amino acid sequence comprising SEQ ID NO:24; and
    the light chain variable region comprises (i) the CDR-L1 amino acid sequence comprising SEQ ID NO:34, (ii) the CDR-L2 amino acid sequence comprising SEQ ID NO:42, and (iii) the CDR-L3 amino acid sequence comprising SEQ ID NO:48; or
    (8) the heavy chain variable region comprises (i) the CDR-H1 amino acid sequence comprising SEQ ID NO:6, (ii) the CDR-H2 amino acid sequence comprising SEQ ID NO:14, and (iii) the CDR-H3 amino acid sequence comprising SEQ ID NO:24; and
    the light chain variable region comprises (i) the CDR-L1 amino acid sequence comprising SEQ ID NO:35, (ii) the CDR-L2 amino acid sequence comprising SEQ ID NO:41, and (iii) the CDR-L3 amino acid sequence comprising SEQ ID NO:48; or
    (9) the heavy chain variable region comprises (i) the CDR-H1 amino acid sequence comprising SEQ ID NO:6, (ii) the CDR-H2 amino acid sequence comprising SEQ ID NO:16, and (iii) the CDR-H3 amino acid sequence comprising SEQ ID NO:25; and
    the light chain variable region comprises (i) the CDR-L1 amino acid sequence comprising SEQ ID NO:34, (ii) the CDR-L2 amino acid sequence comprising SEQ ID NO:42, and (iii) the CDR-L3 amino acid sequence comprising SEQ ID NO:48; or
    (10) the heavy chain variable region comprises (i) the CDR-H1 amino acid sequence comprising SEQ ID NO:7, (ii) the CDR-H2 amino acid sequence comprising SEQ ID NO:17, and (iii) the CDR-H3 amino acid sequence comprising SEQ ID NO:26; and the light chain variable region comprises (i) the CDR-L1 amino acid sequence comprising SEQ ID NO:36, (ii) the CDR-L2 amino acid sequence comprising SEQ ID NO:43, and (iii) the CDR-L3 amino acid sequence comprising SEQ ID NO:49; or

(11) the heavy chain variable region comprises (i) the CDR-H1 amino acid sequence comprising SEQ ID NO:8, (ii) the CDR-H2 amino acid sequence comprising SEQ ID NO:18, and (iii) the CDR-H3 amino acid sequence comprising SEQ ID NO:27; and the light chain variable region comprises (i) the CDR-L1 amino acid sequence comprising SEQ ID NO:36, (ii) the CDR-L2 amino acid sequence comprising SEQ ID NO:44, and (iii) the CDR-L3 amino acid sequence comprising SEQ ID NO:49.

2. The antibody or antigen-binding fragment of claim 1, wherein:
the heavy chain variable region comprises (i) the CDR-H1 amino acid sequence comprising SEQ ID NO:2, (ii) the CDR-H2 amino acid sequence comprising SEQ ID NO:10, and (iii) the CDR-H3 amino acid sequence comprising SEQ ID NO:21; and
the light chain variable region comprises (i) the CDR-L1 amino acid sequence comprising SEQ ID NO:29, (ii) the CDR-L2 amino acid sequence comprising SEQ ID NO:38, and (iii) the CDR-L3 amino acid sequence comprising SEQ ID NO:46.

3. The antibody or antigen-binding fragment of claim 2, wherein:
the heavy chain variable region comprises SEQ ID NO:52; and
the light chain variable region comprises SEQ ID NO:65.

4. A method of detecting a human ubiquitin c-terminal hydrolase L1 (UCH-L1) protein, comprising:
obtaining a biological sample collected from a human subject;
contacting the biological sample with the antibody or antigen-binding fragment of claim 2 under conditions that form a complex comprising the antibody or antigen-binding fragment and UCH-L1; and
detecting the complex in the biological sample so as to detect UCH-L1.

5. The antibody or antigen-binding fragment of claim 1, wherein:
the heavy chain variable region comprises (i) the CDR-H1 amino acid sequence comprising SEQ ID NO:5, (ii) the CDR-H2 amino acid sequence comprising SEQ ID NO:13, and (iii) the CDR-H3 amino acid sequence comprising SEQ ID NO:23; and
the light chain variable region comprises (i) the CDR-L1 amino acid sequence comprising SEQ ID NO:32, (ii) the CDR-L2 amino acid sequence comprising SEQ ID NO:39, and (iii) the CDR-L3 amino acid sequence comprising SEQ ID NO:47.

6. The antibody or antigen-binding fragment of claim 5, wherein:
the heavy chain variable region comprises SEQ ID NO:55; and
the light chain variable region comprises SEQ ID NO:68.

7. A method of detecting a human ubiquitin c-terminal hydrolase L1 (UCH-L1) protein, comprising:
obtaining a biological sample collected from a human subject;
contacting the biological sample with the antibody or antigen-binding fragment of claim 5 under conditions that form a complex comprising the antibody or antigen-binding fragment and UCH-L1; and
detecting the complex in the biological sample so as to detect UCH-L1.

8. The antibody or antigen-binding fragment of claim 1, wherein:
the heavy chain variable region comprises (i) the CDR-H1 amino acid sequence comprising SEQ ID NO:3, (ii) the CDR-H2 amino acid sequence comprising SEQ ID NO:11, and (iii) the CDR-H3 amino acid sequence comprising SEQ ID NO:20; and
the light chain variable region comprises (i) the CDR-L1 amino acid sequence comprising SEQ ID NO:30, (ii) the CDR-L2 amino acid sequence comprising SEQ ID NO:37, and (iii) the CDR-L3 amino acid sequence comprising SEQ ID NO:45.

9. The antibody or antigen-binding fragment of claim 1, wherein:
the heavy chain variable region comprises (i) the CDR-H1 amino acid sequence comprising SEQ ID NO:4, (ii) the CDR-H2 amino acid sequence comprising SEQ ID NO:12, and (iii) the CDR-H3 amino acid sequence comprising SEQ ID NO:22; and
the light chain variable region comprises (i) the CDR-L1 amino acid sequence comprising SEQ ID NO:31, (ii) the CDR-L2 amino acid sequence comprising SEQ ID NO:39, and (iii) the CDR-L3 amino acid sequence comprising SEQ ID NO:47.

10. The antibody or antigen-binding fragment of claim 1, wherein:
the heavy chain variable region comprises (i) the CDR-H1 amino acid sequence comprising SEQ ID NO:6, (ii) the CDR-H2 amino acid sequence comprising SEQ ID NO:14, and (iii) the CDR-H3 amino acid sequence comprising SEQ ID NO:24; and
the light chain variable region comprises (i) the CDR-L1 amino acid sequence comprising SEQ ID NO:33, (ii) the CDR-L2 amino acid sequence comprising SEQ ID NO:40, and (iii) the CDR-L3 amino acid sequence comprising SEQ ID NO:48.

11. The antibody or antigen-binding fragment of claim 1, wherein:
the heavy chain variable region comprises (i) the CDR-H1 amino acid sequence comprising SEQ ID NO:6, (ii) the CDR-H2 amino acid sequence comprising SEQ ID NO:14, and (iii) the CDR-H3 amino acid sequence comprising SEQ ID NO:24; and
the light chain variable region comprises (i) the CDR-L1 amino acid sequence comprising SEQ ID NO:34, (ii) the CDR-L2 amino acid sequence comprising SEQ ID NO:41, and (iii) the CDR-L3 amino acid sequence comprising SEQ ID NO:48.

12. The antibody or antigen-binding fragment of claim 1, wherein:
the heavy chain variable region comprises (i) the CDR-H1 amino acid sequence comprising SEQ ID NO:6, (ii) the CDR-H2 amino acid sequence comprising SEQ ID NO:15, and (iii) the CDR-H3 amino acid sequence comprising SEQ ID NO:24; and
the light chain variable region comprises (i) the CDR-L1 amino acid sequence comprising SEQ ID NO:34, (ii) the CDR-L2 amino acid sequence comprising SEQ ID NO:42, and (iii) the CDR-L3 amino acid sequence comprising SEQ ID NO:48.

13. The antibody or antigen-binding fragment of claim 1, wherein:
the heavy chain variable region comprises (i) the CDR-H1 amino acid sequence comprising SEQ ID NO:6, (ii) the CDR-H2 amino acid sequence comprising SEQ ID NO:14, and (iii) the CDR-H3 amino acid sequence comprising SEQ ID NO:24; and the light chain variable region comprises (i) the CDR-L1 amino acid sequence comprising SEQ ID NO:35, (ii) the CDR-L2 amino acid sequence comprising SEQ ID NO:41, and (iii) the CDR-L3 amino acid sequence comprising SEQ ID NO:48.

14. The antibody or antigen-binding fragment of claim 1, wherein:

the heavy chain variable region comprises (i) the CDR-H1 amino acid sequence comprising SEQ ID NO:6, (ii) the CDR-H2 amino acid sequence comprising SEQ ID NO:16, and (iii) the CDR-H3 amino acid sequence comprising SEQ ID NO:25; and the light chain variable region comprises (i) the CDR-L1 amino acid sequence comprising SEQ ID NO:34, (ii) the CDR-L2 amino acid sequence comprising SEQ ID NO:42, and (iii) the CDR-L3 amino acid sequence comprising SEQ ID NO:48.

15. The antibody or antigen-binding fragment of claim 1, wherein:

the heavy chain variable region comprises (i) the CDR-H1 amino acid sequence comprising SEQ ID NO:7, (ii) the CDR-H2 amino acid sequence comprising SEQ ID NO:17, and (iii) the CDR-H3 amino acid sequence comprising SEQ ID NO:26; and the light chain variable region comprises (i) the CDR-L1 amino acid sequence comprising SEQ ID NO:36, (ii) the CDR-L2 amino acid sequence comprising SEQ ID NO:43, and (iii) the CDR-L3 amino acid sequence comprising SEQ ID NO:49.

16. The antibody or antigen-binding fragment of claim 1, wherein:

the heavy chain variable region comprises (i) the CDR-H1 amino acid sequence comprising SEQ ID NO:8, (ii) the CDR-H2 amino acid sequence comprising SEQ ID NO:18, and (iii) the CDR-H3 amino acid sequence comprising SEQ ID NO:27; and the light chain variable region comprises (i) the CDR-L1 amino acid sequence comprising SEQ ID NO:36, (ii) the CDR-L2 amino acid sequence comprising SEQ ID NO:44, and (iii) the CDR-L3 amino acid sequence comprising SEQ ID NO:49.

17. The antibody or antigen-binding fragment of claim 1, wherein the antibody or antigen-binding fragment binds UCH-L1 with a dissociation constant ($K_D$) of less than about $1.0 \times 10^{-10}$ M.

18. The antibody or antigen-binding fragment of claim 1, wherein the antibody or antigen-binding fragment binds UCH-L1 with a dissociation constant ($K_D$) of from about $2.0 \times 10^{-10}$ M to $1.0 \times 10^{-12}$ M.

19. The antibody or antigen-binding fragment of claim 1, wherein the antibody or antigen-binding fragment binds to an epitope within or that is or includes residues 28-36 of the UCH-L1 protein, residues 98-106 of the UCH-L1 protein, residues 138-145 of the UCH-L1 protein, and/or residues 142-149 of the UCH-L1 protein corresponding to amino acid positions set forth in SEQ ID NO:207.

20. An antibody or antigen-binding fragment thereof that specifically binds to a human ubiquitin c-terminal hydrolase L1 (UCH-L1) protein, comprising:

a heavy chain variable region that comprises any of SEQ ID NOs:52-62; and a light chain variable region that comprises any of SEQ ID NOs:65-75.

* * * * *

SEQUENCE LISTING

```
<160> NUMBER OF SEQ ID NOS: 224

<210> SEQ ID NO 1
<211> LENGTH: 5
<212> TYPE: PRT
<213> ORGANISM: Mus musculus
<220> FEATURE:
<223> OTHER INFORMATION: CDR-H1

<400> SEQUENCE: 1

Ser Tyr Trp Met His
1               5

<210> SEQ ID NO 2
<211> LENGTH: 5
<212> TYPE: PRT
<213> ORGANISM: Mus musculus
<220> FEATURE:
<223> OTHER INFORMATION: CDR-H1

<400> SEQUENCE: 2

Ser His Ala Met Ser
1               5

<210> SEQ ID NO 3
<211> LENGTH: 5
<212> TYPE: PRT
<213> ORGANISM: Mus musculus
<220> FEATURE:
<223> OTHER INFORMATION: CDR-H1

<400> SEQUENCE: 3

Ser Tyr Trp Ile His
1               5

<210> SEQ ID NO 4
<211> LENGTH: 5
<212> TYPE: PRT
<213> ORGANISM: Mus musculus
<220> FEATURE:
<223> OTHER INFORMATION: CDR-H1
```

```
<400> SEQUENCE: 4

Glu His Phe Met Asn
1               5

<210> SEQ ID NO 5
<211> LENGTH: 5
<212> TYPE: PRT
<213> ORGANISM: Mus musculus
<220> FEATURE:
<223> OTHER INFORMATION: CDR-H1

<400> SEQUENCE: 5

Glu Tyr Tyr Met Ser
1               5

<210> SEQ ID NO 6
<211> LENGTH: 5
<212> TYPE: PRT
<213> ORGANISM: Mus musculus
<220> FEATURE:
<223> OTHER INFORMATION: CDR-H1

<400> SEQUENCE: 6

Glu Tyr Thr Met His
1               5

<210> SEQ ID NO 7
<211> LENGTH: 5
<212> TYPE: PRT
<213> ORGANISM: Mus musculus
<220> FEATURE:
<223> OTHER INFORMATION: CDR-H1

<400> SEQUENCE: 7

Arg Tyr Ala Met Ser
1               5

<210> SEQ ID NO 8
<211> LENGTH: 5
<212> TYPE: PRT
<213> ORGANISM: Mus musculus
<220> FEATURE:
<223> OTHER INFORMATION: CDR-H1

<400> SEQUENCE: 8

Lys Asn Ala Met Ser
1               5

<210> SEQ ID NO 9
<211> LENGTH: 17
<212> TYPE: PRT
<213> ORGANISM: Mus musculus
<220> FEATURE:
<223> OTHER INFORMATION: CDR-H2

<400> SEQUENCE: 9

Asn Ile Tyr Pro Gly Ser Gly Ser Thr Asn Tyr Asp Glu Lys Phe Lys
1               5                   10                  15

Ser

<210> SEQ ID NO 10
<211> LENGTH: 17
<212> TYPE: PRT
<213> ORGANISM: Mus musculus
<220> FEATURE:
```

```
<223> OTHER INFORMATION: CDR-H2

<400> SEQUENCE: 10

Thr Ile Ser Ser Gly Gly Ser Asn Thr Tyr Tyr Pro Asp Ser Val Lys
1               5                   10                  15
Gly

<210> SEQ ID NO 11
<211> LENGTH: 17
<212> TYPE: PRT
<213> ORGANISM: Mus musculus
<220> FEATURE:
<223> OTHER INFORMATION: CDR-H2

<400> SEQUENCE: 11

Asn Ile Tyr Pro Gly Ser Gly Ile Thr Asn Tyr Asp Glu Lys Phe Lys
1               5                   10                  15
Thr

<210> SEQ ID NO 12
<211> LENGTH: 17
<212> TYPE: PRT
<213> ORGANISM: Mus musculus
<220> FEATURE:
<223> OTHER INFORMATION: CDR-H2

<400> SEQUENCE: 12

Ile Ile Asn Pro Tyr Thr Asp Gly Thr Asn Tyr Asp Gln Lys Phe Lys
1               5                   10                  15
Asp

<210> SEQ ID NO 13
<211> LENGTH: 19
<212> TYPE: PRT
<213> ORGANISM: Mus musculus
<220> FEATURE:
<223> OTHER INFORMATION: CDR-H2

<400> SEQUENCE: 13

Phe Ile Arg Asn Arg Ala His Gly Tyr Thr Thr Glu Tyr Ser Ala Ser
1               5                   10                  15
Val Lys Gly

<210> SEQ ID NO 14
<211> LENGTH: 17
<212> TYPE: PRT
<213> ORGANISM: Mus musculus
<220> FEATURE:
<223> OTHER INFORMATION: CDR-H2

<400> SEQUENCE: 14

Gly Ile Asn Pro Asn Asn Gly Arg Thr Ser Tyr Asn Gln Lys Phe Lys
1               5                   10                  15
Gly

<210> SEQ ID NO 15
<211> LENGTH: 17
<212> TYPE: PRT
<213> ORGANISM: Mus musculus
<220> FEATURE:
<223> OTHER INFORMATION: CDR-H2
```

```
<400> SEQUENCE: 15

Gly Leu Asn Pro Asn Asn Gly Arg Thr Ser Tyr Asn Gln Lys Phe Lys
1               5                   10                  15

Gly

<210> SEQ ID NO 16
<211> LENGTH: 17
<212> TYPE: PRT
<213> ORGANISM: Mus musculus
<220> FEATURE:
<223> OTHER INFORMATION: CDR-H2

<400> SEQUENCE: 16

Gly Phe Asn Pro Asn Asn Gly Arg Thr Ser Tyr Asn Gln Lys Phe Lys
1               5                   10                  15

Gly

<210> SEQ ID NO 17
<211> LENGTH: 17
<212> TYPE: PRT
<213> ORGANISM: Mus musculus
<220> FEATURE:
<223> OTHER INFORMATION: CDR-H2

<400> SEQUENCE: 17

Thr Ile Ser Thr Ala Gly Ser Tyr Thr Tyr Tyr Pro Asp Ser Val Lys
1               5                   10                  15

Gly

<210> SEQ ID NO 18
<211> LENGTH: 17
<212> TYPE: PRT
<213> ORGANISM: Mus musculus
<220> FEATURE:
<223> OTHER INFORMATION: CDR-H2

<400> SEQUENCE: 18

Thr Ile Ser Thr Gly Gly Thr Tyr Thr Tyr Tyr Pro Asp Ser Val Lys
1               5                   10                  15

Gly

<210> SEQ ID NO 19
<211> LENGTH: 17
<212> TYPE: PRT
<213> ORGANISM: Mus musculus
<220> FEATURE:
<223> OTHER INFORMATION: CDR-H2

<400> SEQUENCE: 19

Asn Ile Tyr Pro Gly Ser Gly Thr Thr Asn Tyr Asp Glu Lys Phe Lys
1               5                   10                  15

Ser

<210> SEQ ID NO 20
<211> LENGTH: 3
<212> TYPE: PRT
<213> ORGANISM: Mus musculus
<220> FEATURE:
<223> OTHER INFORMATION: CDR-H3
```

```
<400> SEQUENCE: 20

Glu Asp Tyr
1

<210> SEQ ID NO 21
<211> LENGTH: 12
<212> TYPE: PRT
<213> ORGANISM: Mus musculus
<220> FEATURE:
<223> OTHER INFORMATION: CDR-H3

<400> SEQUENCE: 21

His Gly Glu Val Arg Arg Gly Tyr Tyr Phe Asp Tyr
1               5                   10

<210> SEQ ID NO 22
<211> LENGTH: 8
<212> TYPE: PRT
<213> ORGANISM: Mus musculus
<220> FEATURE:
<223> OTHER INFORMATION: CDR-H3

<400> SEQUENCE: 22

Trp Gly Gly Asp Gly Glu Gly Tyr
1               5

<210> SEQ ID NO 23
<211> LENGTH: 8
<212> TYPE: PRT
<213> ORGANISM: Mus musculus
<220> FEATURE:
<223> OTHER INFORMATION: CDR-H3

<400> SEQUENCE: 23

Ser Tyr Gly Ala Pro Phe Ala Tyr
1               5

<210> SEQ ID NO 24
<211> LENGTH: 10
<212> TYPE: PRT
<213> ORGANISM: Mus musculus
<220> FEATURE:
<223> OTHER INFORMATION: CDR-H3

<400> SEQUENCE: 24

Arg Leu Gly Arg Gly Phe Tyr Phe Asp Tyr
1               5                   10

<210> SEQ ID NO 25
<211> LENGTH: 10
<212> TYPE: PRT
<213> ORGANISM: Mus musculus
<220> FEATURE:
<223> OTHER INFORMATION: CDR-H3

<400> SEQUENCE: 25

Arg Leu Tyr Arg Gly Phe Tyr Phe Asp Tyr
1               5                   10

<210> SEQ ID NO 26
<211> LENGTH: 10
<212> TYPE: PRT
<213> ORGANISM: Mus musculus
<220> FEATURE:
<223> OTHER INFORMATION: CDR-H3
```

<400> SEQUENCE: 26

Gln Gly Thr Gly Thr Tyr Ala Met Asp Tyr
1               5                   10

<210> SEQ ID NO 27
<211> LENGTH: 10
<212> TYPE: PRT
<213> ORGANISM: Mus musculus
<220> FEATURE:
<223> OTHER INFORMATION: CDR-H3

<400> SEQUENCE: 27

Gln Arg Thr Gly Thr Tyr Ala Met Asp His
1               5                   10

<210> SEQ ID NO 28
<211> LENGTH: 16
<212> TYPE: PRT
<213> ORGANISM: Mus musculus
<220> FEATURE:
<223> OTHER INFORMATION: CDR-L1

<400> SEQUENCE: 28

Arg Ser Ser Gln Asn Ile Val His Ser Asn Gly Asn Thr Tyr Leu Glu
1               5                   10                  15

<210> SEQ ID NO 29
<211> LENGTH: 11
<212> TYPE: PRT
<213> ORGANISM: Mus musculus
<220> FEATURE:
<223> OTHER INFORMATION: CDR-L1

<400> SEQUENCE: 29

Ser Ala Ser Gln Gly Ile Thr Asn Tyr Leu Asn
1               5                   10

<210> SEQ ID NO 30
<211> LENGTH: 16
<212> TYPE: PRT
<213> ORGANISM: Mus musculus
<220> FEATURE:
<223> OTHER INFORMATION: CDR-L1

<400> SEQUENCE: 30

Arg Ser Ser Gln Ser Ile Val His Ser Asn Gly Asn Thr Tyr Leu Glu
1               5                   10                  15

<210> SEQ ID NO 31
<211> LENGTH: 16
<212> TYPE: PRT
<213> ORGANISM: Mus musculus
<220> FEATURE:
<223> OTHER INFORMATION: CDR-L1

<400> SEQUENCE: 31

Arg Ser Ser Lys Ser Leu Leu His Ser Asn Gly Asn Thr Tyr Leu Tyr
1               5                   10                  15

<210> SEQ ID NO 32
<211> LENGTH: 16
<212> TYPE: PRT
<213> ORGANISM: Mus musculus
<220> FEATURE:
<223> OTHER INFORMATION: CDR-L1

```
<400> SEQUENCE: 32

Arg Ser Ser Lys Ser Leu Leu His Ser Asp Gly Asn Thr Tyr Leu Tyr
1               5                   10                  15

<210> SEQ ID NO 33
<211> LENGTH: 15
<212> TYPE: PRT
<213> ORGANISM: Mus musculus
<220> FEATURE:
<223> OTHER INFORMATION: CDR-L1

<400> SEQUENCE: 33

Arg Ala Ser Glu Ser Val Glu Ser Tyr Gly Asn Asn Leu Ile His
1               5                   10                  15

<210> SEQ ID NO 34
<211> LENGTH: 15
<212> TYPE: PRT
<213> ORGANISM: Mus musculus
<220> FEATURE:
<223> OTHER INFORMATION: CDR-L1

<400> SEQUENCE: 34

Arg Ala Ser Glu Ser Val Asp Ser Tyr Gly Asn Asn Leu Met His
1               5                   10                  15

<210> SEQ ID NO 35
<211> LENGTH: 15
<212> TYPE: PRT
<213> ORGANISM: Mus musculus
<220> FEATURE:
<223> OTHER INFORMATION: CDR-L1

<400> SEQUENCE: 35

Arg Ala Ser Glu Ser Val Asp Ser Tyr Gly Asn Asn Phe Met His
1               5                   10                  15

<210> SEQ ID NO 36
<211> LENGTH: 11
<212> TYPE: PRT
<213> ORGANISM: Mus musculus
<220> FEATURE:
<223> OTHER INFORMATION: CDR-L1

<400> SEQUENCE: 36

Arg Ala Ser Gly Asn Ile His Asn Tyr Leu Ala
1               5                   10

<210> SEQ ID NO 37
<211> LENGTH: 7
<212> TYPE: PRT
<213> ORGANISM: Mus musculus
<220> FEATURE:
<223> OTHER INFORMATION: CDR-L2

<400> SEQUENCE: 37

Lys Val Ser Asn Arg Phe Ser
1               5

<210> SEQ ID NO 38
<211> LENGTH: 7
<212> TYPE: PRT
<213> ORGANISM: Mus musculus
<220> FEATURE:
<223> OTHER INFORMATION: CDR-L2
```

```
<400> SEQUENCE: 38

Tyr Thr Ser Ser Leu His Ser
1               5

<210> SEQ ID NO 39
<211> LENGTH: 7
<212> TYPE: PRT
<213> ORGANISM: Mus musculus
<220> FEATURE:
<223> OTHER INFORMATION: CDR-L2

<400> SEQUENCE: 39

Arg Met Ser Asn Leu Ala Ser
1               5

<210> SEQ ID NO 40
<211> LENGTH: 7
<212> TYPE: PRT
<213> ORGANISM: Mus musculus
<220> FEATURE:
<223> OTHER INFORMATION: CDR-L2

<400> SEQUENCE: 40

Leu Ser Ser Asn Leu Glu Pro
1               5

<210> SEQ ID NO 41
<211> LENGTH: 7
<212> TYPE: PRT
<213> ORGANISM: Mus musculus
<220> FEATURE:
<223> OTHER INFORMATION: CDR-L2

<400> SEQUENCE: 41

Leu Ser Ser Asn Leu Glu Ser
1               5

<210> SEQ ID NO 42
<211> LENGTH: 7
<212> TYPE: PRT
<213> ORGANISM: Mus musculus
<220> FEATURE:
<223> OTHER INFORMATION: CDR-L2

<400> SEQUENCE: 42

Arg Ala Ser Asn Leu Glu Ser
1               5

<210> SEQ ID NO 43
<211> LENGTH: 7
<212> TYPE: PRT
<213> ORGANISM: Mus musculus
<220> FEATURE:
<223> OTHER INFORMATION: CDR-L2

<400> SEQUENCE: 43

Asn Ala Lys Thr Leu Ala Asp
1               5

<210> SEQ ID NO 44
<211> LENGTH: 7
<212> TYPE: PRT
<213> ORGANISM: Mus musculus
<220> FEATURE:
<223> OTHER INFORMATION: CDR-L2
```

```
<400> SEQUENCE: 44

Asn Ala Asn Thr Leu Ala Asp
1               5

<210> SEQ ID NO 45
<211> LENGTH: 9
<212> TYPE: PRT
<213> ORGANISM: Mus musculus
<220> FEATURE:
<223> OTHER INFORMATION: CDR-L3

<400> SEQUENCE: 45

Phe Gln Gly Ser His Val Pro Phe Thr
1               5

<210> SEQ ID NO 46
<211> LENGTH: 9
<212> TYPE: PRT
<213> ORGANISM: Mus musculus
<220> FEATURE:
<223> OTHER INFORMATION: CDR-L3

<400> SEQUENCE: 46

Gln His Tyr Ser Asn Leu Pro Trp Thr
1               5

<210> SEQ ID NO 47
<211> LENGTH: 9
<212> TYPE: PRT
<213> ORGANISM: Mus musculus
<220> FEATURE:
<223> OTHER INFORMATION: CDR-L3

<400> SEQUENCE: 47

Met Gln His Leu Glu Tyr Pro Leu Thr
1               5

<210> SEQ ID NO 48
<211> LENGTH: 9
<212> TYPE: PRT
<213> ORGANISM: Mus musculus
<220> FEATURE:
<223> OTHER INFORMATION: CDR-L3

<400> SEQUENCE: 48

Gln Gln Ser Asn Gly Asp Pro Tyr Thr
1               5

<210> SEQ ID NO 49
<211> LENGTH: 9
<212> TYPE: PRT
<213> ORGANISM: Mus musculus
<220> FEATURE:
<223> OTHER INFORMATION: CDR-L3

<400> SEQUENCE: 49

Gln His Phe Trp Ser Thr Thr Trp Thr
1               5

<210> SEQ ID NO 50
<211> LENGTH: 9
<212> TYPE: PRT
<213> ORGANISM: Mus musculus
<220> FEATURE:
<223> OTHER INFORMATION: CDR-L3
```

<400> SEQUENCE: 50

Phe Gln Gly Ser His Val Pro Tyr Thr
1               5

<210> SEQ ID NO 51
<211> LENGTH: 112
<212> TYPE: PRT
<213> ORGANISM: Mus musculus
<220> FEATURE:
<223> OTHER INFORMATION: Heavy chain variable domain

<400> SEQUENCE: 51

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Tyr Pro Gly Ser Gly Ser Thr Asn Tyr Asp Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Glu Asp Tyr Trp Gly Gln Gly Thr Thr Leu Thr Val Ser Ser
            100                 105                 110

<210> SEQ ID NO 52
<211> LENGTH: 121
<212> TYPE: PRT
<213> ORGANISM: Mus musculus
<220> FEATURE:
<223> OTHER INFORMATION: Heavy chain variable domain

<400> SEQUENCE: 52

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Ser His
            20                  25                  30

Ala Met Ser Trp Ile Arg Gln Ile Pro Glu Lys Arg Leu Glu Trp Val
        35                  40                  45

Ala Thr Ile Ser Ser Gly Gly Ser Asn Thr Tyr Tyr Pro Asp Ser Val
    50                  55                  60

Lys Gly Arg Phe Thr Ile Ser Arg Asp Asn Ala Lys Asn Ile Leu Tyr
65                  70                  75                  80

Leu Gln Met Ser Ser Leu Arg Ser Glu Asp Thr Ala Ile Tyr Tyr Cys
                85                  90                  95

Thr Arg His Gly Glu Val Arg Arg Gly Tyr Tyr Phe Asp Tyr Trp Gly
            100                 105                 110

Gln Gly Thr Thr Leu Thr Val Ser Ser
        115                 120

<210> SEQ ID NO 53
<211> LENGTH: 112
<212> TYPE: PRT
<213> ORGANISM: Mus musculus
<220> FEATURE:
<223> OTHER INFORMATION: Heavy chain variable domain

<400> SEQUENCE: 53

Gln Val Gln Leu Gln Gln Pro Gly Ser Glu Leu Val Arg Pro Gly Ala
1               5                   10                  15

Ser Val Lys Leu Ser Cys Arg Ala Ser Gly Tyr Thr Phe Thr Ser Tyr
            20                  25                  30

Trp Ile His Trp Val Lys Gln Arg His Gly Gln Gly Leu Glu Trp Ile
        35                  40                  45

Gly Asn Ile Tyr Pro Gly Ser Gly Ile Thr Asn Tyr Asp Glu Lys Phe
    50                  55                  60

Lys Thr Lys Gly Thr Leu Thr Val Asp Thr Ser Ser Ser Thr Val Tyr
65                  70                  75                  80

Met His Leu Ile Ser Leu Thr Ser Glu Asp Ser Ala Val Tyr Tyr Cys
                85                  90                  95

Thr Arg Glu Asp Tyr Trp Gly Gln Gly Thr Thr Leu Thr Val Ser Ser
            100                 105                 110

<210> SEQ ID NO 54
<211> LENGTH: 117
<212> TYPE: PRT
<213> ORGANISM: Mus musculus
<220> FEATURE:
<223> OTHER INFORMATION: Heavy chain variable domain

<400> SEQUENCE: 54

Ala Val Gln Leu Gln Gln Ser Gly Pro Glu Leu Val Lys Pro Gly Ala
1               5                   10                  15

Ser Val Lys Ile Ser Cys Lys Thr Ser Gly Asp Thr Phe Thr Glu His
            20                  25                  30

Phe Met Asn Trp Val Lys Gln Ser His Gly Glu Ser Leu Glu Trp Ile
        35                  40                  45

Gly Ile Ile Asn Pro Tyr Thr Asp Gly Thr Asn Tyr Asp Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Gly Gly Asp Gly Glu Tyr Trp Gly Gln Gly Thr Thr
            100                 105                 110

Leu Thr Val Ser Ser
        115

<210> SEQ ID NO 55
<211> LENGTH: 119
<212> TYPE: PRT
<213> ORGANISM: Mus musculus
<220> FEATURE:
<223> OTHER INFORMATION: Heavy chain variable domain

<400> SEQUENCE: 55

Glu Val Lys Leu Val Glu Ser Gly Gly Gly Ser Val Gln Pro Gly Gly
1               5                   10                  15

Ser Leu Ser Leu Ser Cys Ala Ala Ser Gly Phe Thr Phe Thr Glu Tyr
            20                  25                  30

Tyr Met Ser Trp Val Arg Gln Phe Pro Gly Lys Ala Leu Glu Trp Leu
        35                  40                  45

Ala Phe Ile Arg Asn Arg Ala His Gly Tyr Thr Thr Glu Tyr Ser Ala
    50                  55                  60

-continued

```
Ser Val Lys Gly Arg Phe Thr Ile Ser Arg Asp Asn Ser Gln Ser Ile
 65                  70                  75                  80

Leu Tyr Leu Gln Met Asn Ala Leu Arg Thr Glu Asp Ser Ala Thr Tyr
                 85                  90                  95

Tyr Cys Ala Ser Ser Tyr Gly Ala Pro Phe Ala Tyr Trp Gly Gln Gly
            100                 105                 110

Thr Leu Val Ser Val Ser Ala
        115

<210> SEQ ID NO 56
<211> LENGTH: 119
<212> TYPE: PRT
<213> ORGANISM: Mus musculus
<220> FEATURE:
<223> OTHER INFORMATION: Heavy chain variable domain

<400> SEQUENCE: 56

Glu Val Gln Leu Gln Gln Ser Gly Pro Glu Leu Val Lys Pro Gly Ala
 1                   5                  10                  15

Ser Val Lys Ile Ser Cys Lys Thr Ser Gly Tyr Thr Phe Thr Glu Tyr
                 20                  25                  30

Thr Met His Trp Val Lys Gln Ser His Gly Lys Ser Leu Asp Trp Ile
             35                  40                  45

Gly Gly Ile Asn Pro Asn Asn Gly Arg Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Asp Phe Arg Ser Leu Thr Ser Glu Asp Ser Ala Val Tyr Tyr Cys
                 85                  90                  95

Ala Arg Arg Leu Gly Arg Gly Phe Tyr Phe Asp Tyr Trp Gly Gln Gly
            100                 105                 110

Thr Thr Leu Thr Val Ser Ser
        115

<210> SEQ ID NO 57
<211> LENGTH: 119
<212> TYPE: PRT
<213> ORGANISM: Mus musculus
<220> FEATURE:
<223> OTHER INFORMATION: Heavy chain variable domain

<400> SEQUENCE: 57

Glu Val Gln Leu Gln Gln Ser Gly Pro Glu Leu Val Lys Pro Gly Ala
 1                   5                  10                  15

Ser Val Lys Ile Ser Cys Lys Thr Ser Gly Tyr Thr Phe Thr Glu Tyr
                 20                  25                  30

Thr Met His Trp Val Lys Gln Ser His Gly Lys Ser Leu Asp Trp Ile
             35                  40                  45

Gly Gly Ile Asn Pro Asn Asn Gly Arg Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Arg Leu Gly Arg Gly Phe Tyr Phe Asp Tyr Trp Gly Gln Gly
            100                 105                 110

Thr Thr Leu Thr Val Ser Ser
        115
```

<210> SEQ ID NO 58
<211> LENGTH: 119
<212> TYPE: PRT
<213> ORGANISM: Mus musculus
<220> FEATURE:
<223> OTHER INFORMATION: Heavy chain variable domain

<400> SEQUENCE: 58

Glu Val Gln Leu Gln Gln Ser Gly Pro Asp Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Arg Ser Leu Glu Trp Ile
        35                  40                  45

Gly Gly Leu Asn Pro Asn Asn Gly Arg Thr Ser Tyr Asn Gln Lys Phe
    50                  55                  60

Lys Gly Lys Ala Thr Leu Thr Val Asp Lys Ser Ser Ile Ala Tyr
65                  70                  75                  80

Met Glu Leu Arg Ser Leu Thr Ser Glu Asp Ser Ala Val Tyr Tyr Cys
                85                  90                  95

Ala Arg Arg Leu Gly Arg Gly Phe Tyr Phe Asp Tyr Trp Gly Gln Gly
            100                 105                 110

Thr Thr Leu Thr Val Ser Ser
        115

<210> SEQ ID NO 59
<211> LENGTH: 119
<212> TYPE: PRT
<213> ORGANISM: Mus musculus
<220> FEATURE:
<223> OTHER INFORMATION: Heavy chain variable domain

<400> SEQUENCE: 59

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Asp Trp Ile
        35                  40                  45

Gly Gly Ile Asn Pro Asn Asn Gly Arg Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Thr Val Tyr Tyr Cys
                85                  90                  95

Ala Arg Arg Leu Gly Arg Gly Phe Tyr Phe Asp Tyr Trp Gly Gln Gly
            100                 105                 110

Thr Thr Leu Thr Val Ser Ser
        115

<210> SEQ ID NO 60
<211> LENGTH: 119
<212> TYPE: PRT
<213> ORGANISM: Mus musculus
<220> FEATURE:
<223> OTHER INFORMATION: Heavy chain variable domain -continued

<400> SEQUENCE: 60

Glu Val Gln Leu Gln Gln Ser Gly Pro Asp Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Arg Ser Leu Glu Trp Ile
        35                  40                  45

Gly Gly Phe Asn Pro Asn Asn Gly Arg Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Arg Leu Tyr Arg Gly Phe Tyr Phe Asp Tyr Trp Gly Gln Gly
            100                 105                 110

Thr Thr Leu Thr Val Ser Ser
            115

<210> SEQ ID NO 61
<211> LENGTH: 119
<212> TYPE: PRT
<213> ORGANISM: Mus musculus
<220> FEATURE:
<223> OTHER INFORMATION: Heavy chain variable domain

<400> SEQUENCE: 61

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Ala Met Ser Trp Val Arg Gln Thr Pro Glu Lys Arg Leu Glu Trp Val
        35                  40                  45

Ala Thr Ile Ser Thr Ala Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Gly Thr Gly Thr Tyr Ala Met Asp Tyr Trp Gly Gln Gly
            100                 105                 110

Thr Ser Val Thr Val Ser Ser
            115

<210> SEQ ID NO 62
<211> LENGTH: 119
<212> TYPE: PRT
<213> ORGANISM: Mus musculus
<220> FEATURE:
<223> OTHER INFORMATION: Heavy chain variable domain

<400> SEQUENCE: 62

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Lys Asn
            20                  25                  30

Ala Met Ser Trp Val Arg Gln Thr Pro Glu Lys Arg Leu Glu Trp Val
        35                  40                  45

```
Ala Thr Ile Ser Thr Gly Gly Thr Tyr Thr Tyr Tyr Pro Asp Ser Val
        50                  55                  60

Lys Gly Gln Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Ala Arg Gln Arg Thr Gly Thr Tyr Ala Met Asp His Trp Gly Gln Gly
                100                 105                 110

Thr Ser Val Thr Val Ser Ser
            115

<210> SEQ ID NO 63
<211> LENGTH: 112
<212> TYPE: PRT
<213> ORGANISM: Mus musculus
<220> FEATURE:
<223> OTHER INFORMATION: Heavy chain variable domain

<400> SEQUENCE: 63

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Tyr Pro Gly Ser Gly Thr Thr Asn Tyr Asp Glu Lys Phe
    50                  55                  60

Lys Ser Lys Ala Thr Leu Thr Val Asp Thr Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Thr Arg Glu Asp Tyr Trp Gly Gln Gly Thr Thr Leu Thr Val Ser Ser
                100                 105                 110

<210> SEQ ID NO 64
<211> LENGTH: 112
<212> TYPE: PRT
<213> ORGANISM: Mus musculus
<220> FEATURE:
<223> OTHER INFORMATION: Light chain variable domain

<400> SEQUENCE: 64

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110
```

-continued

```
<210> SEQ ID NO 65
<211> LENGTH: 107
<212> TYPE: PRT
<213> ORGANISM: Mus musculus
<220> FEATURE:
<223> OTHER INFORMATION: Light chain variable domain

<400> SEQUENCE: 65

Asp Ile Gln Met Thr Gln Thr Pro Ser Ser Leu Ser Ala Ser Leu Gly
1               5                   10                  15

Asp Arg Val Thr Ile Ser Cys Ser Ala Ser Gln Gly Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Phe Ala Thr Tyr Tyr Cys Gln His Tyr Ser Asn Leu Pro Trp
                85                  90                  95

Thr Phe Gly Gly Gly Thr Lys Leu Glu Ile Lys
            100                 105

<210> SEQ ID NO 66
<211> LENGTH: 112
<212> TYPE: PRT
<213> ORGANISM: Mus musculus
<220> FEATURE:
<223> OTHER INFORMATION: Light chain variable domain

<400> SEQUENCE: 66

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Thr Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 67
<211> LENGTH: 112
<212> TYPE: PRT
<213> ORGANISM: Mus musculus
<220> FEATURE:
<223> OTHER INFORMATION: Light chain variable domain

<400> SEQUENCE: 67

Asp Ile Val Met Thr Gln Ala Ala Pro Ser Val Ser Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Lys Arg Pro Gly Gln Ser
        35                  40                  45
```

```
Pro Gln Leu Leu Ile Tyr Arg Met Ser Asn Leu Ala Ser Gly Val Pro
        50                  55                  60

Asp Arg Val Ser Gly Ser Gly Ser Gly Thr Ala Phe Thr Leu Arg Ile
65                  70                  75                  80

Ser Arg Val Glu Ala Glu Asp Val Gly Ile Tyr Tyr Cys Met Gln His
                85                  90                  95

Leu Glu Tyr Pro Leu Thr Phe Gly Ala Gly Thr Lys Leu Glu Leu Lys
              100                 105                 110
```

<210> SEQ ID NO 68
<211> LENGTH: 112
<212> TYPE: PRT
<213> ORGANISM: Mus musculus
<220> FEATURE:
<223> OTHER INFORMATION: Light chain variable domain

<400> SEQUENCE: 68

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asp Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
              100                 105                 110
```

<210> SEQ ID NO 69
<211> LENGTH: 111
<212> TYPE: PRT
<213> ORGANISM: Mus musculus
<220> FEATURE:
<223> OTHER INFORMATION: Light chain variable domain

<400> SEQUENCE: 69

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ser Tyr
                20                  25                  30

Gly Asn Asn Leu Ile His Trp Tyr Gln Gln Lys Leu Gly Gln Pro Pro
            35                  40                  45

Lys Leu Leu Ile Tyr Leu Ser Ser Asn Leu Glu Pro Gly Ile Pro Ala
        50                  55                  60

Arg Phe Ser Gly Arg Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Gly Asp Pro Tyr Thr Phe Gly Gly Gly Thr Lys Leu Glu Ile Arg
              100                 105                 110
```

<210> SEQ ID NO 70
<211> LENGTH: 111
<212> TYPE: PRT

<213> ORGANISM: Mus musculus
<220> FEATURE:
<223> OTHER INFORMATION: Light chain variable domain

<400> SEQUENCE: 70

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Asn Leu Met His Trp Tyr Gln Gln Lys Pro Gly Gln Pro Pro
            35                  40                  45

Lys Leu Leu Ile Tyr Leu Ser Ser Asn Leu Glu Ser Gly Ile Pro Ala
    50                  55                  60

Arg Phe Ser Gly Arg Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Gly Asp Pro Tyr Thr Phe Gly Gly Gly Thr Lys Leu Glu Ile Lys
            100                 105                 110

<210> SEQ ID NO 71
<211> LENGTH: 111
<212> TYPE: PRT
<213> ORGANISM: Mus musculus
<220> FEATURE:
<223> OTHER INFORMATION: Light chain variable domain

<400> SEQUENCE: 71

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Asn Leu Met His Trp Tyr Gln Gln Lys Pro Gly Gln Ser Pro
            35                  40                  45

Lys Leu Leu Ile Tyr Arg Ala Ser Asn Leu Glu Ser Gly Ile Pro Gly
    50                  55                  60

Arg Phe Ser Gly Arg Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Gly Asp Pro Tyr Thr Phe Gly Gly Gly Thr Lys Leu Glu Ile Lys
            100                 105                 110

<210> SEQ ID NO 72
<211> LENGTH: 111
<212> TYPE: PRT
<213> ORGANISM: Mus musculus
<220> FEATURE:
<223> OTHER INFORMATION: Light chain variable domain

<400> SEQUENCE: 72

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Asn Phe Met His Trp Tyr Gln Gln Lys Pro Gly Gln Pro Pro
            35                  40                  45

Lys Leu Leu Ile Tyr Leu Ser Ser Asn Leu Glu Ser Gly Ile Pro Ala
    50                  55                  60

Arg Phe Ser Gly Arg Gly Ser Arg Thr Asp Phe Thr Leu Thr Ile Asn
65                  70                  75                  80

Pro Val Glu Ala Asp Val Ala Thr Tyr Tyr Cys Gln Gln Ser Asn
                85                  90                  95

Gly Asp Pro Tyr Thr Phe Gly Gly Gly Thr Lys Leu Glu Met Lys
            100                 105                 110

<210> SEQ ID NO 73
<211> LENGTH: 111
<212> TYPE: PRT
<213> ORGANISM: Mus musculus
<220> FEATURE:
<223> OTHER INFORMATION: Light chain variable domain

<400> SEQUENCE: 73

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Asn Leu Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Gly
50                  55                  60

Arg Phe Ser Gly Arg Gly Ser Arg Thr Asp Phe Ser Leu Thr Ile Asn
65                  70                  75                  80

Pro Val Glu Ala Asp Val Ala Thr Tyr Tyr Cys Gln Gln Ser Asn
                85                  90                  95

Gly Asp Pro Tyr Thr Phe Gly Gly Gly Thr Lys Leu Glu Ile Lys
            100                 105                 110

<210> SEQ ID NO 74
<211> LENGTH: 107
<212> TYPE: PRT
<213> ORGANISM: Mus musculus
<220> FEATURE:
<223> OTHER INFORMATION: Light chain variable domain

<400> SEQUENCE: 74

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Asn Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Arg Leu Gln Pro
65                  70                  75                  80

Glu Asp Phe Gly Ser Tyr Tyr Cys Gln His Phe Trp Ser Thr Thr Trp
                85                  90                  95

Thr Phe Gly Gly Gly Thr Lys Leu Glu Ile Lys
            100                 105

<210> SEQ ID NO 75
<211> LENGTH: 107
<212> TYPE: PRT
<213> ORGANISM: Mus musculus
<220> FEATURE:
<223> OTHER INFORMATION: Light chain variable domain

<400> SEQUENCE: 75

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Asn Thr Leu Ala Asp Gly Val Pro Pro Arg Phe Ser Gly
    50                  55                  60

Ser Gly Ser Gly Thr Gln Tyr Ser Leu Lys Val Asn Ser Leu Gln Pro
65                  70                  75                  80

Glu Asp Phe Gly Asn Tyr Tyr Cys Gln His Phe Trp Ser Thr Thr Trp
                85                  90                  95

Thr Phe Gly Gly Gly Thr Arg Leu Glu Ile Lys
            100                 105

<210> SEQ ID NO 76
<211> LENGTH: 112
<212> TYPE: PRT
<213> ORGANISM: Mus musculus
<220> FEATURE:
<223> OTHER INFORMATION: Light chain variable domain

<400> SEQUENCE: 76

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 77
<211> LENGTH: 5
<212> TYPE: PRT
<213> ORGANISM: Mus musculus
<220> FEATURE:
<223> OTHER INFORMATION: CDR-H1

<400> SEQUENCE: 77

Ser Tyr Trp Met His
1               5

<210> SEQ ID NO 78
<211> LENGTH: 5
<212> TYPE: PRT
<213> ORGANISM: Mus musculus
<220> FEATURE:
<223> OTHER INFORMATION: CDR-H1

```
<400> SEQUENCE: 78

Ser Phe Gly Met His
1               5

<210> SEQ ID NO 79
<211> LENGTH: 5
<212> TYPE: PRT
<213> ORGANISM: Mus musculus
<220> FEATURE:
<223> OTHER INFORMATION: CDR-H1

<400> SEQUENCE: 79

Asn Tyr Trp Met Ser
1               5

<210> SEQ ID NO 80
<211> LENGTH: 5
<212> TYPE: PRT
<213> ORGANISM: Mus musculus
<220> FEATURE:
<223> OTHER INFORMATION: CDR-H1

<400> SEQUENCE: 80

Ala Tyr Gly Met His
1               5

<210> SEQ ID NO 81
<211> LENGTH: 5
<212> TYPE: PRT
<213> ORGANISM: Mus musculus
<220> FEATURE:
<223> OTHER INFORMATION: CDR-H1

<400> SEQUENCE: 81

Asp Thr Asp Met His
1               5

<210> SEQ ID NO 82
<211> LENGTH: 6
<212> TYPE: PRT
<213> ORGANISM: Mus musculus
<220> FEATURE:
<223> OTHER INFORMATION: CDR-H1

<400> SEQUENCE: 82

Ser Gly Phe Tyr Trp Ser
1               5

<210> SEQ ID NO 83
<211> LENGTH: 5
<212> TYPE: PRT
<213> ORGANISM: Mus musculus
<220> FEATURE:
<223> OTHER INFORMATION: CDR-H1

<400> SEQUENCE: 83

Tyr Tyr Ala Met Ser
1               5

<210> SEQ ID NO 84
<211> LENGTH: 5
<212> TYPE: PRT
<213> ORGANISM: Mus musculus
<220> FEATURE:
<223> OTHER INFORMATION: CDR-H1
```

```
<400> SEQUENCE: 84

Asn Tyr Gly Met Asn
1               5

<210> SEQ ID NO 85
<211> LENGTH: 5
<212> TYPE: PRT
<213> ORGANISM: Mus musculus
<220> FEATURE:
<223> OTHER INFORMATION: CDR-H1

<400> SEQUENCE: 85

Asn Tyr Trp Ile Glu
1               5

<210> SEQ ID NO 86
<211> LENGTH: 5
<212> TYPE: PRT
<213> ORGANISM: Mus musculus
<220> FEATURE:
<223> OTHER INFORMATION: CDR-H1

<400> SEQUENCE: 86

Asn Tyr Ile Met His
1               5

<210> SEQ ID NO 87
<211> LENGTH: 5
<212> TYPE: PRT
<213> ORGANISM: Mus musculus
<220> FEATURE:
<223> OTHER INFORMATION: CDR-H1

<400> SEQUENCE: 87

Asp His Thr Ile His
1               5

<210> SEQ ID NO 88
<211> LENGTH: 5
<212> TYPE: PRT
<213> ORGANISM: Mus musculus
<220> FEATURE:
<223> OTHER INFORMATION: CDR-H1

<400> SEQUENCE: 88

Tyr Tyr Trp Met Ser
1               5

<210> SEQ ID NO 89
<211> LENGTH: 5
<212> TYPE: PRT
<213> ORGANISM: Mus musculus
<220> FEATURE:
<223> OTHER INFORMATION: CDR-H1

<400> SEQUENCE: 89

Asn Phe Ala Met Ser
1               5

<210> SEQ ID NO 90
<211> LENGTH: 5
<212> TYPE: PRT
<213> ORGANISM: Mus musculus
<220> FEATURE:
<223> OTHER INFORMATION: CDR-H1
```

```
<400> SEQUENCE: 90

Ser Tyr Asp Met Ser
1               5

<210> SEQ ID NO 91
<211> LENGTH: 17
<212> TYPE: PRT
<213> ORGANISM: Mus musculus
<220> FEATURE:
<223> OTHER INFORMATION: CDR-H2

<400> SEQUENCE: 91

Ala Phe Tyr Pro Glu Asn Ser Asp Thr Asn Tyr Asn Gln Lys Phe Lys
1               5                   10                  15

Gly

<210> SEQ ID NO 92
<211> LENGTH: 17
<212> TYPE: PRT
<213> ORGANISM: Mus musculus
<220> FEATURE:
<223> OTHER INFORMATION: CDR-H2

<400> SEQUENCE: 92

Tyr Ile Ser Ser Gly Ser Ser Ile Ile Tyr Tyr Ala Asp Thr Val Lys
1               5                   10                  15

Gly

<210> SEQ ID NO 93
<211> LENGTH: 19
<212> TYPE: PRT
<213> ORGANISM: Mus musculus
<220> FEATURE:
<223> OTHER INFORMATION: CDR-H2

<400> SEQUENCE: 93

Gln Ile Arg Leu Lys Ser Asp Asn Tyr Ala Thr His Tyr Ala Glu Ser
1               5                   10                  15

Val Lys Gly

<210> SEQ ID NO 94
<211> LENGTH: 17
<212> TYPE: PRT
<213> ORGANISM: Mus musculus
<220> FEATURE:
<223> OTHER INFORMATION: CDR-H2

<400> SEQUENCE: 94

Ala Ile His Pro Gly Asn Arg Asp Thr Ser Tyr Asn Gln Lys Phe Lys
1               5                   10                  15

Asp

<210> SEQ ID NO 95
<211> LENGTH: 17
<212> TYPE: PRT
<213> ORGANISM: Mus musculus
<220> FEATURE:
<223> OTHER INFORMATION: CDR-H2
```

```
<400> SEQUENCE: 95

Tyr Ile Ser Ser Gly Ser Ser Thr Ile Tyr Tyr Ala Asp Thr Val Lys
1               5                   10                  15

Gly

<210> SEQ ID NO 96
<211> LENGTH: 17
<212> TYPE: PRT
<213> ORGANISM: Mus musculus
<220> FEATURE:
<223> OTHER INFORMATION: CDR-H2

<400> SEQUENCE: 96

Leu Ile Asp Pro Ala Ile Gly Asn Thr Lys Tyr Asp Pro Lys Phe Gln
1               5                   10                  15

Gly

<210> SEQ ID NO 97
<211> LENGTH: 16
<212> TYPE: PRT
<213> ORGANISM: Mus musculus
<220> FEATURE:
<223> OTHER INFORMATION: CDR-H2

<400> SEQUENCE: 97

Tyr Ile Ser Tyr Asp Gly Ser Asn Asn Tyr Asn Pro Ser Leu Lys Asn
1               5                   10                  15

<210> SEQ ID NO 98
<211> LENGTH: 16
<212> TYPE: PRT
<213> ORGANISM: Mus musculus
<220> FEATURE:
<223> OTHER INFORMATION: CDR-H2

<400> SEQUENCE: 98

Ser Ile Ser Ser Gly Gly Thr Thr Tyr His Pro Asp Ser Val Lys Gly
1               5                   10                  15

<210> SEQ ID NO 99
<211> LENGTH: 17
<212> TYPE: PRT
<213> ORGANISM: Mus musculus
<220> FEATURE:
<223> OTHER INFORMATION: CDR-H2

<400> SEQUENCE: 99

Trp Ile Asn Thr Asn Ile Gly Glu Pro Thr Tyr Ala Glu Glu Phe Lys
1               5                   10                  15

Gly

<210> SEQ ID NO 100
<211> LENGTH: 17
<212> TYPE: PRT
<213> ORGANISM: Mus musculus
<220> FEATURE:
<223> OTHER INFORMATION: CDR-H2

<400> SEQUENCE: 100

Glu Ile Leu Pro Gly Ser Gly Ser Thr Asn Tyr Asn Glu Lys Phe Lys
1               5                   10                  15

Gly
```

```
<210> SEQ ID NO 101
<211> LENGTH: 17
<212> TYPE: PRT
<213> ORGANISM: Mus musculus
<220> FEATURE:
<223> OTHER INFORMATION: CDR-H2

<400> SEQUENCE: 101

Phe Ile Asn Pro Tyr Asn Asp Tyr Thr Glu Tyr Asn Glu Lys Phe Lys
1               5                   10                  15
Gly

<210> SEQ ID NO 102
<211> LENGTH: 17
<212> TYPE: PRT
<213> ORGANISM: Mus musculus
<220> FEATURE:
<223> OTHER INFORMATION: CDR-H2

<400> SEQUENCE: 102

Tyr Ile Ser Ser Asp Ser Asn Thr Val Tyr Tyr Ala Asp Thr Val Lys
1               5                   10                  15
Gly

<210> SEQ ID NO 103
<211> LENGTH: 17
<212> TYPE: PRT
<213> ORGANISM: Mus musculus
<220> FEATURE:
<223> OTHER INFORMATION: CDR-H2

<400> SEQUENCE: 103

Tyr Ile Ser Ser Gly Ser Arg Thr Ile Phe Tyr Ala Asp Thr Val Lys
1               5                   10                  15
Gly

<210> SEQ ID NO 104
<211> LENGTH: 17
<212> TYPE: PRT
<213> ORGANISM: Mus musculus
<220> FEATURE:
<223> OTHER INFORMATION: CDR-H2

<400> SEQUENCE: 104

Tyr Ile Tyr Pro Gly Asp Gly Ser Thr Lys Tyr Asn Glu Lys Phe Lys
1               5                   10                  15
Gly

<210> SEQ ID NO 105
<211> LENGTH: 19
<212> TYPE: PRT
<213> ORGANISM: Mus musculus
<220> FEATURE:
<223> OTHER INFORMATION: CDR-H2

<400> SEQUENCE: 105

Glu Ile Arg Leu Lys Ser Asn Ile Tyr Ala Thr His Tyr Ala Ala Ser
1               5                   10                  15
Val Lys Gly

<210> SEQ ID NO 106
<211> LENGTH: 16
<212> TYPE: PRT
```

```
<213> ORGANISM: Mus musculus
<220> FEATURE:
<223> OTHER INFORMATION: CDR-H2

<400> SEQUENCE: 106

Ser Ile Ser Ser Gly Gly Thr Thr Tyr Pro Asp Asn Val Lys Gly
1               5                   10                  15

<210> SEQ ID NO 107
<211> LENGTH: 17
<212> TYPE: PRT
<213> ORGANISM: Mus musculus
<220> FEATURE:
<223> OTHER INFORMATION: CDR-H2

<400> SEQUENCE: 107

Tyr Ile Ser Ser Gly Gly Gly Ser Thr Tyr Tyr Pro Asp Thr Met Lys
1               5                   10                  15

Gly

<210> SEQ ID NO 108
<211> LENGTH: 10
<212> TYPE: PRT
<213> ORGANISM: Mus musculus
<220> FEATURE:
<223> OTHER INFORMATION: CDR-H3

<400> SEQUENCE: 108

Pro Leu Leu Phe Ser Ala Tyr Phe Asp Phe
1               5                   10

<210> SEQ ID NO 109
<211> LENGTH: 8
<212> TYPE: PRT
<213> ORGANISM: Mus musculus
<220> FEATURE:
<223> OTHER INFORMATION: CDR-H3

<400> SEQUENCE: 109

Ser Asp Trp Gly Ser Phe Ala Tyr
1               5

<210> SEQ ID NO 110
<211> LENGTH: 9
<212> TYPE: PRT
<213> ORGANISM: Mus musculus
<220> FEATURE:
<223> OTHER INFORMATION: CDR-H3

<400> SEQUENCE: 110

Gly Glu Phe Leu Ser Trp Phe Ala Tyr
1               5

<210> SEQ ID NO 111
<211> LENGTH: 3
<212> TYPE: PRT
<213> ORGANISM: Mus musculus
<220> FEATURE:
<223> OTHER INFORMATION: CDR-H3

<400> SEQUENCE: 111

Glu Asp Tyr
1

<210> SEQ ID NO 112
<211> LENGTH: 6
```

```
<212> TYPE: PRT
<213> ORGANISM: Mus musculus
<220> FEATURE:
<223> OTHER INFORMATION: CDR-H3

<400> SEQUENCE: 112

Ser Tyr Ala Leu Asp Tyr
1               5

<210> SEQ ID NO 113
<211> LENGTH: 10
<212> TYPE: PRT
<213> ORGANISM: Mus musculus
<220> FEATURE:
<223> OTHER INFORMATION: CDR-H3

<400> SEQUENCE: 113

Ser Asp Arg Tyr Leu Ala Trp Phe Ala Tyr
1               5                   10

<210> SEQ ID NO 114
<211> LENGTH: 11
<212> TYPE: PRT
<213> ORGANISM: Mus musculus
<220> FEATURE:
<223> OTHER INFORMATION: CDR-H3

<400> SEQUENCE: 114

Ala Tyr Gly Tyr Asp Gly Ala Trp Phe Ala Tyr
1               5                   10

<210> SEQ ID NO 115
<211> LENGTH: 8
<212> TYPE: PRT
<213> ORGANISM: Mus musculus
<220> FEATURE:
<223> OTHER INFORMATION: CDR-H3

<400> SEQUENCE: 115

Gly Gly His Trp Tyr Phe Asp Val
1               5

<210> SEQ ID NO 116
<211> LENGTH: 9
<212> TYPE: PRT
<213> ORGANISM: Mus musculus
<220> FEATURE:
<223> OTHER INFORMATION: CDR-H3

<400> SEQUENCE: 116

Trp Lys Asn Tyr Gly Tyr Phe Asp Tyr
1               5

<210> SEQ ID NO 117
<211> LENGTH: 11
<212> TYPE: PRT
<213> ORGANISM: Mus musculus
<220> FEATURE:
<223> OTHER INFORMATION: CDR-H3

<400> SEQUENCE: 117

Tyr Tyr Gly Asn Tyr Ala Gly Ala Met Asp Tyr
1               5                   10

<210> SEQ ID NO 118
<211> LENGTH: 5
<212> TYPE: PRT
```

```
<213> ORGANISM: Mus musculus
<220> FEATURE:
<223> OTHER INFORMATION: CDR-H3

<400> SEQUENCE: 118

Ala Thr Phe Ala Tyr
1               5

<210> SEQ ID NO 119
<211> LENGTH: 5
<212> TYPE: PRT
<213> ORGANISM: Mus musculus
<220> FEATURE:
<223> OTHER INFORMATION: CDR-H3

<400> SEQUENCE: 119

Tyr Ala Met Asp Tyr
1               5

<210> SEQ ID NO 120
<211> LENGTH: 9
<212> TYPE: PRT
<213> ORGANISM: Mus musculus
<220> FEATURE:
<223> OTHER INFORMATION: CDR-H3

<400> SEQUENCE: 120

Gly Gly Tyr Gly Ser Ser Phe Asp Tyr
1               5

<210> SEQ ID NO 121
<211> LENGTH: 9
<212> TYPE: PRT
<213> ORGANISM: Mus musculus
<220> FEATURE:
<223> OTHER INFORMATION: CDR-H3

<400> SEQUENCE: 121

Pro Ala Pro Tyr Trp Asn Phe Asp Val
1               5

<210> SEQ ID NO 122
<211> LENGTH: 8
<212> TYPE: PRT
<213> ORGANISM: Mus musculus
<220> FEATURE:
<223> OTHER INFORMATION: CDR-H3

<400> SEQUENCE: 122

Phe Gly Thr Gly Ala Met Asp Tyr
1               5

<210> SEQ ID NO 123
<211> LENGTH: 8
<212> TYPE: PRT
<213> ORGANISM: Mus musculus
<220> FEATURE:
<223> OTHER INFORMATION: CDR-H3

<400> SEQUENCE: 123

Gly Gly Leu His Tyr Phe Gly Tyr
1               5

<210> SEQ ID NO 124
<211> LENGTH: 11
<212> TYPE: PRT
<213> ORGANISM: Mus musculus
```

```
<220> FEATURE:
<223> OTHER INFORMATION: CDR-H3

<400> SEQUENCE: 124

His Tyr Gly Thr Tyr Leu Tyr Tyr Leu Asp Tyr
1               5                   10

<210> SEQ ID NO 125
<211> LENGTH: 16
<212> TYPE: PRT
<213> ORGANISM: Mus musculus
<220> FEATURE:
<223> OTHER INFORMATION: CDR-L1

<400> SEQUENCE: 125

Arg Ser Ser Gln Ser Ile Val His Ser Tyr Gly Asn Thr Tyr Leu Glu
1               5                   10                  15

<210> SEQ ID NO 126
<211> LENGTH: 16
<212> TYPE: PRT
<213> ORGANISM: Mus musculus
<220> FEATURE:
<223> OTHER INFORMATION: CDR-L1

<400> SEQUENCE: 126

Arg Ser Ser Gln Ser Leu Val Tyr Ser Asn Gly Asn Thr Tyr Leu His
1               5                   10                  15

<210> SEQ ID NO 127
<211> LENGTH: 17
<212> TYPE: PRT
<213> ORGANISM: Mus musculus
<220> FEATURE:
<223> OTHER INFORMATION: CDR-L1

<400> SEQUENCE: 127

Lys Ser Ser Gln Ser Leu Phe Asn Ser Arg Thr Arg Lys Asn Tyr Leu
1               5                   10                  15

Ala

<210> SEQ ID NO 128
<211> LENGTH: 17
<212> TYPE: PRT
<213> ORGANISM: Mus musculus
<220> FEATURE:
<223> OTHER INFORMATION: CDR-L1

<400> SEQUENCE: 128

Lys Ser Ser Gln Ser Leu Leu Asn Ser Asn Asn Gln Arg Asn Tyr Leu
1               5                   10                  15

Asp

<210> SEQ ID NO 129
<211> LENGTH: 11
<212> TYPE: PRT
<213> ORGANISM: Mus musculus
<220> FEATURE:
<223> OTHER INFORMATION: CDR-L1

<400> SEQUENCE: 129

Arg Ala Ser Gln Ser Ile Ser Asp Phe Leu His
1               5                   10

<210> SEQ ID NO 130
```

```
<211> LENGTH: 17
<212> TYPE: PRT
<213> ORGANISM: Mus musculus
<220> FEATURE:
<223> OTHER INFORMATION: CDR-L1

<400> SEQUENCE: 130

Lys Ser Ser Gln Ser Leu Leu Asn Ser Ser Asn Gln Arg Asn Tyr Leu
1               5                   10                  15
Asp

<210> SEQ ID NO 131
<211> LENGTH: 11
<212> TYPE: PRT
<213> ORGANISM: Mus musculus
<220> FEATURE:
<223> OTHER INFORMATION: CDR-L1

<400> SEQUENCE: 131

Lys Ala Ser Gln Asn Val Arg Thr Ala Val Ala
1               5                   10

<210> SEQ ID NO 132
<211> LENGTH: 10
<212> TYPE: PRT
<213> ORGANISM: Mus musculus
<220> FEATURE:
<223> OTHER INFORMATION: CDR-L1

<400> SEQUENCE: 132

Ser Ala Ser Ser Ser Val Ser Tyr Met His
1               5                   10

<210> SEQ ID NO 133
<211> LENGTH: 12
<212> TYPE: PRT
<213> ORGANISM: Mus musculus
<220> FEATURE:
<223> OTHER INFORMATION: CDR-L1

<400> SEQUENCE: 133

Thr Ala Ser Ser Ser Val Ser Ser Ser Tyr Leu His
1               5                   10

<210> SEQ ID NO 134
<211> LENGTH: 11
<212> TYPE: PRT
<213> ORGANISM: Mus musculus
<220> FEATURE:
<223> OTHER INFORMATION: CDR-L1

<400> SEQUENCE: 134

Arg Ala Ser Glu Asn Ile Tyr Ser Tyr Leu Ala
1               5                   10

<210> SEQ ID NO 135
<211> LENGTH: 16
<212> TYPE: PRT
<213> ORGANISM: Mus musculus
<220> FEATURE:
<223> OTHER INFORMATION: CDR-L1

<400> SEQUENCE: 135

Lys Ser Ser Gln Ser Leu Leu Asp Ser Ala Gly Lys Thr Tyr Leu Asn
1               5                   10                  15
```

```
<210> SEQ ID NO 136
<211> LENGTH: 10
<212> TYPE: PRT
<213> ORGANISM: Mus musculus
<220> FEATURE:
<223> OTHER INFORMATION: CDR-L1

<400> SEQUENCE: 136

Ser Ala Ser Ser Ser Val Ser Tyr Met Tyr
1               5                   10

<210> SEQ ID NO 137
<211> LENGTH: 16
<212> TYPE: PRT
<213> ORGANISM: Mus musculus
<220> FEATURE:
<223> OTHER INFORMATION: CDR-L1

<400> SEQUENCE: 137

Arg Ser Ser Gln Ser Leu Val Tyr Ser Asn Gly Asn Ile Tyr Leu His
1               5                   10                  15

<210> SEQ ID NO 138
<211> LENGTH: 11
<212> TYPE: PRT
<213> ORGANISM: Mus musculus
<220> FEATURE:
<223> OTHER INFORMATION: CDR-L1

<400> SEQUENCE: 138

Lys Ala Ser Gln Asp Ile Lys Lys Asn Ile Ala
1               5                   10

<210> SEQ ID NO 139
<211> LENGTH: 17
<212> TYPE: PRT
<213> ORGANISM: Mus musculus
<220> FEATURE:
<223> OTHER INFORMATION: CDR-L1

<400> SEQUENCE: 139

Lys Ser Ser Gln Ser Leu Leu Tyr Arg Thr Asn Gln Lys Asn Tyr Leu
1               5                   10                  15

Ala

<210> SEQ ID NO 140
<211> LENGTH: 11
<212> TYPE: PRT
<213> ORGANISM: Mus musculus
<220> FEATURE:
<223> OTHER INFORMATION: CDR-L1

<400> SEQUENCE: 140

Lys Ala Ser Gln Asp Val Asn Thr Ala Val Ala
1               5                   10

<210> SEQ ID NO 141
<211> LENGTH: 11
<212> TYPE: PRT
<213> ORGANISM: Mus musculus
<220> FEATURE:
<223> OTHER INFORMATION: CDR-L1

<400> SEQUENCE: 141

Arg Ala Ser Gln Asn Ile Ser Asp Phe Leu His
1               5                   10
```

<210> SEQ ID NO 142
<211> LENGTH: 7
<212> TYPE: PRT
<213> ORGANISM: Mus musculus
<220> FEATURE:
<223> OTHER INFORMATION: CDR-L2

<400> SEQUENCE: 142

Lys Val Ser Asn Arg Phe Ser
1               5

<210> SEQ ID NO 143
<211> LENGTH: 7
<212> TYPE: PRT
<213> ORGANISM: Mus musculus
<220> FEATURE:
<223> OTHER INFORMATION: CDR-L2

<400> SEQUENCE: 143

Lys Val Ser Asn Arg Phe Phe
1               5

<210> SEQ ID NO 144
<211> LENGTH: 7
<212> TYPE: PRT
<213> ORGANISM: Mus musculus
<220> FEATURE:
<223> OTHER INFORMATION: CDR-L2

<400> SEQUENCE: 144

Trp Ala Ser Thr Arg Glu Ser
1               5

<210> SEQ ID NO 145
<211> LENGTH: 7
<212> TYPE: PRT
<213> ORGANISM: Mus musculus
<220> FEATURE:
<223> OTHER INFORMATION: CDR-L2

<400> SEQUENCE: 145

Phe Ala Ser Thr Arg Glu Ser
1               5

<210> SEQ ID NO 146
<211> LENGTH: 7
<212> TYPE: PRT
<213> ORGANISM: Mus musculus
<220> FEATURE:
<223> OTHER INFORMATION: CDR-L2

<400> SEQUENCE: 146

Tyr Ser Ser Gln Ser Ile Ser
1               5

<210> SEQ ID NO 147
<211> LENGTH: 7
<212> TYPE: PRT
<213> ORGANISM: Mus musculus
<220> FEATURE:
<223> OTHER INFORMATION: CDR-L2

<400> SEQUENCE: 147

Leu Ala Ser Asn Arg His Thr
1               5

```
<210> SEQ ID NO 148
<211> LENGTH: 7
<212> TYPE: PRT
<213> ORGANISM: Mus musculus
<220> FEATURE:
<223> OTHER INFORMATION: CDR-L2

<400> SEQUENCE: 148

Asp Thr Ser Lys Leu Ala Ser
1               5

<210> SEQ ID NO 149
<211> LENGTH: 7
<212> TYPE: PRT
<213> ORGANISM: Mus musculus
<220> FEATURE:
<223> OTHER INFORMATION: CDR-L2

<400> SEQUENCE: 149

Ser Thr Ser Asn Leu Ala Ser
1               5

<210> SEQ ID NO 150
<211> LENGTH: 7
<212> TYPE: PRT
<213> ORGANISM: Mus musculus
<220> FEATURE:
<223> OTHER INFORMATION: CDR-L2

<400> SEQUENCE: 150

Asn Ala Lys Thr Leu Ala Glu
1               5

<210> SEQ ID NO 151
<211> LENGTH: 7
<212> TYPE: PRT
<213> ORGANISM: Mus musculus
<220> FEATURE:
<223> OTHER INFORMATION: CDR-L2

<400> SEQUENCE: 151

Leu Val Ser Lys Leu Asp Ser
1               5

<210> SEQ ID NO 152
<211> LENGTH: 7
<212> TYPE: PRT
<213> ORGANISM: Mus musculus
<220> FEATURE:
<223> OTHER INFORMATION: CDR-L2

<400> SEQUENCE: 152

Leu Thr Ser Asn Leu Ala Ser
1               5

<210> SEQ ID NO 153
<211> LENGTH: 7
<212> TYPE: PRT
<213> ORGANISM: Mus musculus
<220> FEATURE:
<223> OTHER INFORMATION: CDR-L2

<400> SEQUENCE: 153

Tyr Thr Ser Thr Leu Gln Pro
1               5

<210> SEQ ID NO 154
```

```
<211> LENGTH: 7
<212> TYPE: PRT
<213> ORGANISM: Mus musculus
<220> FEATURE:
<223> OTHER INFORMATION: CDR-L2

<400> SEQUENCE: 154

Trp Ala Ser Ser Arg Glu Ser
1               5

<210> SEQ ID NO 155
<211> LENGTH: 7
<212> TYPE: PRT
<213> ORGANISM: Mus musculus
<220> FEATURE:
<223> OTHER INFORMATION: CDR-L2

<400> SEQUENCE: 155

Ser Ala Ser Tyr Arg Tyr Ile
1               5

<210> SEQ ID NO 156
<211> LENGTH: 7
<212> TYPE: PRT
<213> ORGANISM: Mus musculus
<220> FEATURE:
<223> OTHER INFORMATION: CDR-L2

<400> SEQUENCE: 156

Tyr Ala Ser Gln Ser Ile Ser
1               5

<210> SEQ ID NO 157
<211> LENGTH: 9
<212> TYPE: PRT
<213> ORGANISM: Mus musculus
<220> FEATURE:
<223> OTHER INFORMATION: CDR-L3

<400> SEQUENCE: 157

Phe Gln Gly Ser His Val Pro Tyr Thr
1               5

<210> SEQ ID NO 158
<211> LENGTH: 9
<212> TYPE: PRT
<213> ORGANISM: Mus musculus
<220> FEATURE:
<223> OTHER INFORMATION: CDR-L3

<400> SEQUENCE: 158

Ser Gln Ser Thr His Val Pro Tyr Thr
1               5

<210> SEQ ID NO 159
<211> LENGTH: 8
<212> TYPE: PRT
<213> ORGANISM: Mus musculus
<220> FEATURE:
<223> OTHER INFORMATION: CDR-L3

<400> SEQUENCE: 159

Lys Gln Ser Tyr Tyr Leu Tyr Thr
1               5

<210> SEQ ID NO 160
<211> LENGTH: 9
```

<212> TYPE: PRT
<213> ORGANISM: Mus musculus
<220> FEATURE:
<223> OTHER INFORMATION: CDR-L3

<400> SEQUENCE: 160

Gln Gln His Tyr Ser Ile Pro Leu Thr
1               5

<210> SEQ ID NO 161
<211> LENGTH: 9
<212> TYPE: PRT
<213> ORGANISM: Mus musculus
<220> FEATURE:
<223> OTHER INFORMATION: CDR-L3

<400> SEQUENCE: 161

Gln Asn Gly His Thr Phe Pro Tyr Thr
1               5

<210> SEQ ID NO 162
<211> LENGTH: 9
<212> TYPE: PRT
<213> ORGANISM: Mus musculus
<220> FEATURE:
<223> OTHER INFORMATION: CDR-L3

<400> SEQUENCE: 162

Leu Gln His Trp Asn Asn Pro Tyr Thr
1               5

<210> SEQ ID NO 163
<211> LENGTH: 9
<212> TYPE: PRT
<213> ORGANISM: Mus musculus
<220> FEATURE:
<223> OTHER INFORMATION: CDR-L3

<400> SEQUENCE: 163

Gln Gln Trp Ser Thr Asn Pro Leu Thr
1               5

<210> SEQ ID NO 164
<211> LENGTH: 9
<212> TYPE: PRT
<213> ORGANISM: Mus musculus
<220> FEATURE:
<223> OTHER INFORMATION: CDR-L3

<400> SEQUENCE: 164

His Gln Tyr His Arg Ser Pro Tyr Thr
1               5

<210> SEQ ID NO 165
<211> LENGTH: 9
<212> TYPE: PRT
<213> ORGANISM: Mus musculus
<220> FEATURE:
<223> OTHER INFORMATION: CDR-L3

<400> SEQUENCE: 165

Gln Leu His Tyr Gly Thr Pro Tyr Thr
1               5

<210> SEQ ID NO 166
<211> LENGTH: 9
<212> TYPE: PRT

```
<213> ORGANISM: Mus musculus
<220> FEATURE:
<223> OTHER INFORMATION: CDR-L3

<400> SEQUENCE: 166

Trp Gln Gly Thr His Phe Pro Trp Thr
1               5

<210> SEQ ID NO 167
<211> LENGTH: 9
<212> TYPE: PRT
<213> ORGANISM: Mus musculus
<220> FEATURE:
<223> OTHER INFORMATION: CDR-L3

<400> SEQUENCE: 167

Gln Gln Trp Ser Ser Asn Pro Pro Thr
1               5

<210> SEQ ID NO 168
<211> LENGTH: 8
<212> TYPE: PRT
<213> ORGANISM: Mus musculus
<220> FEATURE:
<223> OTHER INFORMATION: CDR-L3

<400> SEQUENCE: 168

Leu Gln Tyr Asp His Leu Arg Thr
1               5

<210> SEQ ID NO 169
<211> LENGTH: 9
<212> TYPE: PRT
<213> ORGANISM: Mus musculus
<220> FEATURE:
<223> OTHER INFORMATION: CDR-L3

<400> SEQUENCE: 169

Gln Gln Tyr Tyr Ser Tyr Pro Trp Thr
1               5

<210> SEQ ID NO 170
<211> LENGTH: 9
<212> TYPE: PRT
<213> ORGANISM: Mus musculus
<220> FEATURE:
<223> OTHER INFORMATION: CDR-L3

<400> SEQUENCE: 170

His Gln Tyr Tyr Ser Thr Pro Leu Thr
1               5

<210> SEQ ID NO 171
<211> LENGTH: 9
<212> TYPE: PRT
<213> ORGANISM: Mus musculus
<220> FEATURE:
<223> OTHER INFORMATION: CDR-L3

<400> SEQUENCE: 171

Gln Asn Gly His Ser Phe Pro Pro Thr
1               5

<210> SEQ ID NO 172
<211> LENGTH: 119
<212> TYPE: PRT
<213> ORGANISM: Mus musculus
```

```
<220> FEATURE:
<223> OTHER INFORMATION: Heavy chain variable domain

<400> SEQUENCE: 172

Glu Val His Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Ala Phe Tyr Pro Glu Asn Ser Asp Thr Asn Tyr Asn Gln Lys Phe
    50                  55                  60

Lys Gly Lys Ala Arg Leu Thr Ala Val Thr Ser Ala Asn Thr Ala Tyr
65                  70                  75                  80

Met Glu Leu Asn Ser Leu Thr Asn Glu Asp Ser Ala Val Tyr Tyr Cys
                85                  90                  95

Thr Arg Pro Leu Leu Phe Ser Ala Tyr Phe Asp Phe Trp Gly Gln Gly
            100                 105                 110

Thr Thr Leu Thr Val Ser Ser
        115

<210> SEQ ID NO 173
<211> LENGTH: 117
<212> TYPE: PRT
<213> ORGANISM: Mus musculus
<220> FEATURE:
<223> OTHER INFORMATION: Heavy chain variable domain

<400> SEQUENCE: 173

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Thr Gly Ser Asp Trp Gly Ser Phe Ala Tyr Trp Gly Gln Gly Thr Leu
            100                 105                 110

Val Thr Val Ser Ala
        115

<210> SEQ ID NO 174
<211> LENGTH: 120
<212> TYPE: PRT
<213> ORGANISM: Mus musculus
<220> FEATURE:
<223> OTHER INFORMATION: Heavy chain variable domain

<400> SEQUENCE: 174

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Thr Asn Tyr
            20                  25                  30
```

```
Trp Met Ser Trp Val Arg Gln Ser Pro Glu Lys Gly Leu Glu Trp Val
         35                  40                  45

Ala Gln Ile Arg Leu Lys Ser Asp Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Gly Gly Glu Phe Leu Ser Trp Phe Ala Tyr Trp Gly Gln
                100                 105                 110

Gly Thr Leu Val Thr Val Ser Ala
        115                 120

<210> SEQ ID NO 175
<211> LENGTH: 112
<212> TYPE: PRT
<213> ORGANISM: Mus musculus
<220> FEATURE:
<223> OTHER INFORMATION: Heavy chain variable domain

<400> SEQUENCE: 175

Glu Val Gln Leu Leu Gln Ser Gly Thr Val Leu Ala Arg Pro Gly Ala
1                5                  10                  15

Ser Val Lys Met Ser Cys Lys Ala Ser Gly Tyr Ser Phe Thr Ser Tyr
                 20                  25                  30

Trp Met His Trp Ile Lys Gln Arg Pro Gly Gln Gly Leu Glu Trp Ile
         35                  40                  45

Gly Ala Ile His Pro Gly Asn Arg Asp Thr Ser Tyr Asn Gln Lys Phe
 50                  55                  60

Lys Asp Lys Ala Lys Leu Thr Ala Val Thr Ser Ala Ser Thr Ala Tyr
 65                  70                  75                  80

Met Glu Leu Ser Ser Leu Thr Asn Glu Asp Ser Ala Val Tyr Phe Cys
                 85                  90                  95

Thr Arg Glu Asp Tyr Trp Gly Gln Gly Thr Thr Leu Thr Val Ser Ser
                100                 105                 110

<210> SEQ ID NO 176
<211> LENGTH: 115
<212> TYPE: PRT
<213> ORGANISM: Mus musculus
<220> FEATURE:
<223> OTHER INFORMATION: Heavy chain variable domain

<400> SEQUENCE: 176

Glu Val Gln Leu Val Glu Ser Gly Gly Gly Leu Val Lys Pro Gly Gly
1                5                  10                  15

Ser Leu Lys Leu Ser Cys Ala Ala Ser Gly Phe Thr Phe Ser Ala Tyr
                 20                  25                  30

Gly Met His Trp Val Arg Gln Ala Pro Glu Lys Gly Leu Glu Trp Ile
         35                  40                  45

Ala Tyr Ile Ser Ser Gly Ser Ser Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Ser Ser Tyr Ala Leu Asp Tyr Trp Gly Gln Gly Thr Ser Val Thr
                100                 105                 110
```

Val Ser Ser
    115

<210> SEQ ID NO 177
<211> LENGTH: 119
<212> TYPE: PRT
<213> ORGANISM: Mus musculus
<220> FEATURE:
<223> OTHER INFORMATION: Heavy chain variable domain

<400> SEQUENCE: 177

Glu Val Gln Leu Gln Gln Ser Gly Ala Glu Phe Val Lys Pro Gly Ala
1               5                   10                  15

Ser Val Lys Leu Ser Cys Thr Ala Ser Gly Phe Asn Ile Lys Asp Thr
            20                  25                  30

Asp Met His Trp Val Arg Gln Arg Pro Glu Gln Gly Leu Glu Ser Ile
        35                  40                  45

Gly Leu Ile Asp Pro Ala Ile Gly Asn Thr Lys Tyr Asp Pro Lys Phe
    50                  55                  60

Gln Gly Lys Ala Thr Ile Thr Ala Asp Thr Ser Ser Asn Ala Ala Tyr
65                  70                  75                  80

Leu Gln Leu Ser Ser Leu Thr Ser Glu Asp Thr Ala Val Tyr Tyr Cys
                85                  90                  95

Ala Arg Ser Asp Arg Tyr Leu Ala Trp Phe Ala Tyr Trp Gly Gln Gly
            100                 105                 110

Thr Leu Val Thr Val Ser Ala
        115

<210> SEQ ID NO 178
<211> LENGTH: 120
<212> TYPE: PRT
<213> ORGANISM: Mus musculus
<220> FEATURE:
<223> OTHER INFORMATION: Heavy chain variable domain

<400> SEQUENCE: 178

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Ser Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Ala Tyr Gly Tyr Asp Gly Ala Trp Phe Ala Tyr Trp Gly Gln
            100                 105                 110

Gly Thr Leu Val Thr Val Ser Ala
        115                 120

<210> SEQ ID NO 179
<211> LENGTH: 116
<212> TYPE: PRT
<213> ORGANISM: Mus musculus
<220> FEATURE:
<223> OTHER INFORMATION: Heavy chain variable domain

<400> SEQUENCE: 179

Glu Val Lys Leu Val Glu Ser Gly Gly Leu Val Lys Pro Gly Gly
1               5                   10                  15

Ser Leu Lys Leu Ser Cys Ala Ala Ser Gly Phe Thr Phe Ser Tyr Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Thr Thr Tyr His Pro Asp Ser Val Lys
    50                  55                  60

Gly Arg Phe Thr Ile Ser Arg Asp Asn Ala Arg Asn Ile Leu Tyr Leu
65              70                  75                  80

Gln Met Ser Ser Leu Arg Ser Glu Asp Thr Ala Met Tyr Tyr Cys Ala
                85                  90                  95

Arg Gly Gly His Trp Tyr Phe Asp Val Trp Gly Ala Gly Thr Thr Val
            100                 105                 110

Thr Val Ser Ser
        115

<210> SEQ ID NO 180
<211> LENGTH: 118
<212> TYPE: PRT
<213> ORGANISM: Mus musculus
<220> FEATURE:
<223> OTHER INFORMATION: Heavy chain variable domain

<400> SEQUENCE: 180

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Glu Gly Leu Lys Trp Met
        35                  40                  45

Gly Trp Ile Asn Thr Asn Ile Gly Glu Pro Thr Tyr Ala Glu Glu Phe
    50                  55                  60

Lys Gly Arg Phe Ala Phe Ser Leu Glu Ala Ser Ala Ser Thr Ala Tyr
65              70                  75                  80

Leu Gln Ile Asn Asn Leu Lys Asn Glu Asp Thr Ala Thr Tyr Phe Cys
                85                  90                  95

Ala Arg Trp Lys Asn Tyr Gly Tyr Phe Asp Tyr Trp Gly Gln Gly Thr
            100                 105                 110

Thr Leu Thr Val Ser Ser
        115

<210> SEQ ID NO 181
<211> LENGTH: 120
<212> TYPE: PRT
<213> ORGANISM: Mus musculus
<220> FEATURE:
<223> OTHER INFORMATION: Heavy chain variable domain

<400> SEQUENCE: 181

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Ser Gly Ser Thr Asn Tyr Asn Glu Lys Phe
            50                  55                  60

Lys Gly Lys Ala Thr Phe Thr Ala Asp Thr Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Ile Tyr Tyr Gly Asn Tyr Ala Gly Ala Met Asp Tyr Trp Gly Gln
                100                 105                 110

Gly Thr Ser Val Thr Val Ser Ser
                115                 120

<210> SEQ ID NO 182
<211> LENGTH: 114
<212> TYPE: PRT
<213> ORGANISM: Mus musculus
<220> FEATURE:
<223> OTHER INFORMATION: Heavy chain variable domain

<400> SEQUENCE: 182

Glu Val Leu Leu Gln Gln Ser Gly Pro Glu Leu Val Lys Pro Gly Ala
 1               5                  10                  15

Ser Val Lys Met Ser Cys Lys Thr Ser Gly Tyr Thr Phe Ala Asn Tyr
                 20                  25                  30

Ile Met His Trp Val Lys Gln Thr Pro Gly Gln Gly Leu Glu Trp Ile
             35                  40                  45

Gly Phe Ile Asn Pro Tyr Asn Asp Tyr Thr Gly Tyr Asn Glu Lys Phe
         50                  55                  60

Lys Gly Lys Ala Thr Leu Thr Ser Asp Lys Ser Ser Ser Thr Ala Tyr
 65                  70                  75                  80

Met Glu Phe Ser Gly Leu Thr Ser Glu Asp Ser Ala Val Tyr Tyr Cys
                 85                  90                  95

Ser Thr Ala Thr Phe Ala Tyr Trp Gly Gln Gly Thr Leu Val Thr Val
                100                 105                 110

Ser Ala

<210> SEQ ID NO 183
<211> LENGTH: 114
<212> TYPE: PRT
<213> ORGANISM: Mus musculus
<220> FEATURE:
<223> OTHER INFORMATION: Heavy chain variable domain

<400> SEQUENCE: 183

Asp Val Gln Leu Val Glu Ser Gly Gly Gly Ser Val Gln Pro Gly Gly
 1               5                  10                  15

Ser Arg Lys Leu Ser Cys Ala Ala Ser Gly Phe Thr Phe Ser Ser Phe
                 20                  25                  30

Gly Met His Trp Val Arg Gln Ala Pro Glu Lys Gly Leu Glu Trp Val
             35                  40                  45

Ala Tyr Ile Ser Ser Asp Ser Asn Thr Val Tyr Tyr Ala Asp Thr Val
         50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Tyr Ala Met Asp Tyr Trp Gly Gln Gly Thr Val Thr Val
            100                 105                 110

Ser Ser

<210> SEQ ID NO 184
<211> LENGTH: 118
<212> TYPE: PRT
<213> ORGANISM: Mus musculus
<220> FEATURE:
<223> OTHER INFORMATION: Heavy chain variable domain

<400> SEQUENCE: 184

Asp Val Gln Leu Val Glu Ser Gly Gly Gly Leu Leu Glu Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
            35                  40                  45

Ala Tyr Ile Ser Ser Gly Ser Arg Thr Ile Phe Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Gly Asp Thr Ala Met Tyr Tyr Cys
                85                  90                  95

Val Arg Gly Gly Tyr Gly Ser Ser Phe Asp Tyr Trp Gly Gln Gly Thr
            100                 105                 110

Thr Leu Thr Val Ser Ser
        115

<210> SEQ ID NO 185
<211> LENGTH: 118
<212> TYPE: PRT
<213> ORGANISM: Mus musculus
<220> FEATURE:
<223> OTHER INFORMATION: Heavy chain variable domain

<400> SEQUENCE: 185

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Thr Ile His Trp Val Lys Gln Arg Pro Glu Gln Gly Leu Glu Trp Ile
            35                  40                  45

Gly Tyr Ile Tyr Pro Gly Asp Gly Ser Thr Lys Tyr Asn Glu Lys Phe
        50                  55                  60

Lys Gly Lys Ala Thr Leu Thr Ala Asp Lys Ser Ser Ser Thr Val Tyr
65                  70                  75                  80

Met Gln Leu Asn Ser Leu Thr Ser Glu Asp Ser Ala Val Tyr Phe Cys
                85                  90                  95

Ala Arg Pro Ala Pro Tyr Trp Asn Phe Asp Val Trp Gly Ala Gly Thr
            100                 105                 110

Thr Val Thr Val Ser Ser
        115

<210> SEQ ID NO 186
<211> LENGTH: 119
<212> TYPE: PRT
<213> ORGANISM: Mus musculus
<220> FEATURE:
<223> OTHER INFORMATION: Heavy chain variable domain

<400> SEQUENCE: 186

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Ser Trp Val Arg Gln Ser Pro Glu Lys Gly Leu Glu Trp Ile
        35                  40                  45

Ala Glu Ile Arg Leu Lys Ser Asn Ile Tyr Ala Thr His Tyr Ala Ala
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Phe Cys Thr Arg Phe Gly Thr Gly Ala Met Asp Tyr Trp Gly Gln Gly
            100                 105                 110

Thr Ser Val Thr Val Ser Ser
        115

<210> SEQ ID NO 187
<211> LENGTH: 116
<212> TYPE: PRT
<213> ORGANISM: Mus musculus
<220> FEATURE:
<223> OTHER INFORMATION: Heavy chain variable domain

<400> SEQUENCE: 187

Glu Val Ile Leu Val Glu Ser Gly Gly Gly Leu Val Lys Pro Gly Gly
1               5                   10                  15

Ser Leu Lys Val Ser Cys Ala Val Ser Gly Phe Thr Phe Ser Asn Phe
            20                  25                  30

Ala Met Ser Trp Val Arg Gln Thr Pro Glu Lys Arg Leu Glu Trp Val
        35                  40                  45

Ala Ser Ile Ser Ser Gly Gly Thr Thr Tyr Tyr Pro Asp Asn Val Lys
    50                  55                  60

Gly Arg Phe Thr Ile Ser Arg Asp Asn Ala Arg Asn Ile Met Tyr Leu
65                  70                  75                  80

Gln Met Ser Ser Leu Arg Ser Glu Asp Thr Ala Met Tyr Phe Cys Ala
                85                  90                  95

Arg Gly Gly Leu His Tyr Phe Asp Tyr Trp Gly Gln Gly Thr Thr Leu
            100                 105                 110

Thr Val Ser Ser
        115

<210> SEQ ID NO 188
<211> LENGTH: 120
<212> TYPE: PRT
<213> ORGANISM: Mus musculus
<220> FEATURE:
<223> OTHER INFORMATION: Heavy chain variable domain

<400> SEQUENCE: 188

Glu Val Gln Leu Val Glu Ser Gly Gly Gly Leu Val Lys Pro Gly Gly
1               5                   10                  15

Ser Pro Lys Leu Ser Cys Ala Ala Ser Gly Phe Ala Phe Ser Ser Tyr
            20                  25                  30

```
Asp Met Ser Trp Val Arg Gln Thr Pro Glu Lys Arg Leu Glu Trp Val
            35                  40                  45

Ala Tyr Ile Ser Ser Gly Gly Ser Thr Tyr Tyr Pro Asp Thr Met
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Tyr Gly Thr Tyr Leu Tyr Tyr Leu Asp Tyr Trp Gly Gln
            100                 105                 110

Gly Thr Thr Leu Thr Val Ser Ser
            115                 120
```

<210> SEQ ID NO 189
<211> LENGTH: 112
<212> TYPE: PRT
<213> ORGANISM: Mus musculus
<220> FEATURE:
<223> OTHER INFORMATION: Light chain variable domain

<400> SEQUENCE: 189

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Tyr Gly Asn Thr Tyr Leu Glu Trp Tyr Leu Gln Lys Pro Gly Leu Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110
```

<210> SEQ ID NO 190
<211> LENGTH: 112
<212> TYPE: PRT
<213> ORGANISM: Mus musculus
<220> FEATURE:
<223> OTHER INFORMATION: Light chain variable domain

<400> SEQUENCE: 190

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Phe Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Lys Leu Glu Ile Lys
            100                 105                 110
```

<210> SEQ ID NO 191
<211> LENGTH: 112
<212> TYPE: PRT
<213> ORGANISM: Mus musculus
<220> FEATURE:
<223> OTHER INFORMATION: Light chain variable domain

<400> SEQUENCE: 191

Asp Ile Val Met Ser Gln Ser Pro Ser Ser Leu Ala Val Ser Ala Gly
1               5                   10                  15

Glu Lys Val Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Tyr Thr Phe Gly Ser Gly Thr Lys Leu Glu Ile Lys
            100                 105                 110

<210> SEQ ID NO 192
<211> LENGTH: 113
<212> TYPE: PRT
<213> ORGANISM: Mus musculus
<220> FEATURE:
<223> OTHER INFORMATION: Light chain variable domain

<400> SEQUENCE: 192

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Asn Asn Gln Arg Asn Tyr Leu Asp Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys

<210> SEQ ID NO 193
<211> LENGTH: 112
<212> TYPE: PRT
<213> ORGANISM: Mus musculus
<220> FEATURE:
<223> OTHER INFORMATION: Light chain variable domain

<400> SEQUENCE: 193

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val Tyr Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Ser Gly Thr Lys Leu Glu Ile Lys
            100                 105                 110

<210> SEQ ID NO 194
<211> LENGTH: 107
<212> TYPE: PRT
<213> ORGANISM: Mus musculus
<220> FEATURE:
<223> OTHER INFORMATION: Light chain variable domain

<400> SEQUENCE: 194

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Phe
                20                  25                  30

Leu His Trp Tyr Gln Gln Lys Ser His Gly Ser Pro Arg Leu Leu Ile
            35                  40                  45

Lys Tyr Ser Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Thr Phe Pro Tyr
                85                  90                  95

Thr Phe Gly Gly Gly Thr Lys Leu Glu Ile Lys
            100                 105

<210> SEQ ID NO 195
<211> LENGTH: 113
<212> TYPE: PRT
<213> ORGANISM: Mus musculus
<220> FEATURE:
<223> OTHER INFORMATION: Light chain variable domain

<400> SEQUENCE: 195

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
                20                  25                  30

Ser Asn Gln Arg Asn Tyr Leu Asp Trp Tyr Gln Gln Lys Pro Gly Gln
            35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys

<210> SEQ ID NO 196
<211> LENGTH: 107
<212> TYPE: PRT
<213> ORGANISM: Mus musculus
<220> FEATURE:
<223> OTHER INFORMATION: Light chain variable domain

<400> SEQUENCE: 196

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Asn Pro Tyr
                85                  90                  95

Thr Phe Gly Gly Gly Thr Lys Leu Glu Ile Lys
            100                 105

<210> SEQ ID NO 197
<211> LENGTH: 106
<212> TYPE: PRT
<213> ORGANISM: Mus musculus
<220> FEATURE:
<223> OTHER INFORMATION: Light chain variable domain

<400> SEQUENCE: 197

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Thr Asn Pro Leu Thr
                85                  90                  95

Phe Gly Ala Gly Thr Lys Leu Asp Leu Lys
            100                 105

<210> SEQ ID NO 198
<211> LENGTH: 108
<212> TYPE: PRT
<213> ORGANISM: Mus musculus
<220> FEATURE:
<223> OTHER INFORMATION: Light chain variable domain

<400> SEQUENCE: 198

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Leu Glu
65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Leu Glu Ile Lys
            100                 105

<210> SEQ ID NO 199
<211> LENGTH: 107
<212> TYPE: PRT
<213> ORGANISM: Mus musculus
<220> FEATURE:
<223> OTHER INFORMATION: Light chain variable domain

<400> SEQUENCE: 199

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln Leu His Tyr Gly Thr Pro Tyr
                85                  90                  95

Thr Phe Gly Ser Gly Thr Lys Leu Glu Ile Lys
            100                 105

<210> SEQ ID NO 200
<211> LENGTH: 112
<212> TYPE: PRT
<213> ORGANISM: Mus musculus
<220> FEATURE:
<223> OTHER INFORMATION: Light chain variable domain

<400> SEQUENCE: 200

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Ala Gly Lys Thr Tyr Leu Asn Trp Leu Leu Gln Lys Ser Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

```
Ser Arg Val Glu Ala Glu Asp Leu Gly Val Tyr Tyr Cys Trp Gln Gly
            85                  90                  95

Thr His Phe Pro Trp Thr Phe Gly Gly Gly Thr Lys Leu Glu Ile Lys
            100                 105                 110

<210> SEQ ID NO 201
<211> LENGTH: 106
<212> TYPE: PRT
<213> ORGANISM: Mus musculus
<220> FEATURE:
<223> OTHER INFORMATION: Light chain variable domain

<400> SEQUENCE: 201

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
            50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Pro Thr
            85                  90                  95

Phe Gly Ala Gly Thr Lys Leu Glu Leu Lys
            100                 105

<210> SEQ ID NO 202
<211> LENGTH: 112
<212> TYPE: PRT
<213> ORGANISM: Mus musculus
<220> FEATURE:
<223> OTHER INFORMATION: Light chain variable domain

<400> SEQUENCE: 202

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asn Ile Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
            85                  90                  95

Thr His Val Pro Tyr Thr Phe Gly Gly Gly Thr Lys Leu Glu Ile Lys
            100                 105                 110

<210> SEQ ID NO 203
<211> LENGTH: 106
<212> TYPE: PRT
<213> ORGANISM: Mus musculus
<220> FEATURE:
<223> OTHER INFORMATION: Light chain variable domain
```

<400> SEQUENCE: 203

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Lys Lys Asn
            20                  25                  30

Ile Ala Trp Tyr Gln His Lys Pro Gly Lys Pro Arg Leu Leu Ile
        35                  40                  45

Trp Tyr Thr Ser Thr Leu Gln Pro Gly Ile Pro Ser Arg Phe Ser Gly
50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp His Leu Arg Thr
                85                  90                  95

Phe Gly Gly Gly Thr Lys Leu Glu Ile Lys
            100                 105

<210> SEQ ID NO 204
<211> LENGTH: 113
<212> TYPE: PRT
<213> ORGANISM: Mus musculus
<220> FEATURE:
<223> OTHER INFORMATION: Light chain variable domain

<400> SEQUENCE: 204

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Arg
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
                100                 105                 110

Lys

<210> SEQ ID NO 205
<211> LENGTH: 107
<212> TYPE: PRT
<213> ORGANISM: Mus musculus
<220> FEATURE:
<223> OTHER INFORMATION: Light chain variable domain

<400> SEQUENCE: 205

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Leu Lys Leu Leu Ile
        35                  40                  45

Tyr Ser Ala Ser Tyr Arg Tyr Ile Gly Val Pro Asp Arg Phe Thr Gly
50                  55                  60

```
Ser Gly Ser Gly Thr Asp Phe Thr Phe Thr Ile Asn Ser Val Gln Ala
 65                  70                  75                  80

Glu Asp Leu Ala Val Tyr Tyr Cys His Gln Tyr Tyr Ser Thr Pro Leu
                 85                  90                  95

Thr Phe Gly Thr Gly Thr Lys Leu Glu Leu Lys
            100                 105

<210> SEQ ID NO 206
<211> LENGTH: 107
<212> TYPE: PRT
<213> ORGANISM: Mus musculus
<220> FEATURE:
<223> OTHER INFORMATION: Light chain variable domain

<400> SEQUENCE: 206

Asp Ile Val Leu Thr Gln Ser Pro Ala Thr Leu Ser Val Thr Pro Gly
 1               5                  10                  15

Asp Arg Val Ser Leu Ser Cys Arg Ala Ser Gln Asn Ile Ser Asp Phe
                20                  25                  30

Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Pro
                 85                  90                  95

Thr Phe Gly Gly Gly Thr Lys Leu Glu Ile Lys
            100                 105

<210> SEQ ID NO 207
<211> LENGTH: 223
<212> TYPE: PRT
<213> ORGANISM: Homo sapiens
<220> FEATURE:
<223> OTHER INFORMATION: UCH-L1 isoform 1 amino acid sequence

<400> SEQUENCE: 207

Met Gln Leu Lys Pro Met Glu Ile Asn Pro Glu Met Leu Asn Lys Val
 1               5                  10                  15

Leu Ser Arg Leu Gly Val Ala Gly Gln Trp Arg Phe Val Asp Val Leu
                20                  25                  30

Gly Leu Glu Glu Glu Ser Leu Gly Ser Val Pro Ala Pro Ala Cys Ala
             35                  40                  45

Leu Leu Leu Leu Phe Pro Leu Thr Ala Gln His Glu Asn Phe Arg Lys
 50                  55                  60

Lys Gln Ile Glu Glu Leu Lys Gly Gln Glu Val Ser Pro Lys Val Tyr
 65                  70                  75                  80

Phe Met Lys Gln Thr Ile Gly Asn Ser Cys Gly Thr Ile Gly Leu Ile
                 85                  90                  95

His Ala Val Ala Asn Asn Gln Asp Lys Leu Gly Phe Glu Asp Gly Ser
                100                 105                 110

Val Leu Lys Gln Phe Leu Ser Glu Thr Glu Lys Met Ser Pro Glu Asp
            115                 120                 125

Arg Ala Lys Cys Phe Glu Lys Asn Glu Ala Ile Gln Ala Ala His Asp
        130                 135                 140

Ala Val Ala Gln Glu Gly Gln Cys Arg Val Asp Asp Lys Val Asn Phe
145                 150                 155                 160
```

```
His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
    210                 215                 220

<210> SEQ ID NO 208
<211> LENGTH: 236
<212> TYPE: PRT
<213> ORGANISM: Homo sapiens
<220> FEATURE:
<223> OTHER INFORMATION: UCH-L1 isoform 2 amino acid sequence

<400> SEQUENCE: 208

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Ala Leu Lys His Lys Gln Ser Ala Gln
        195                 200                 205

Leu Ser Thr Gly Pro Leu Trp Cys Glu Leu Gln Met Val Lys His Ser
    210                 215                 220

Pro Gln Cys Met Ser Cys Ile Arg Tyr Leu Thr Leu
225                 230                 235

<210> SEQ ID NO 209
<211> LENGTH: 164
<212> TYPE: PRT
<213> ORGANISM: Homo sapiens
<220> FEATURE:
<223> OTHER INFORMATION: UCH-L1 isoform 3 amino acid sequence
```

<400> SEQUENCE: 209

```
Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
            35                  40                  45

Leu Leu Leu Leu Phe Pro Leu Thr Ala Gln His Glu Asn Phe Arg Lys
50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
                100                 105                 110

Val Leu Lys Gln Phe Leu Ser Glu Thr Glu Lys Met Ser Pro Glu Asp
            115                 120                 125

Arg Ala Lys Cys Phe Glu Lys Asn Glu Ala Ile Gln Ala Ala His Asp
130                 135                 140

Ala Val Ala Gln Glu Gly Gln Cys Arg Val Asp Asp Lys Met Asp Glu
145                 150                 155                 160

Cys Leu Phe Arg
```

<210> SEQ ID NO 210
<211> LENGTH: 193
<212> TYPE: PRT
<213> ORGANISM: Homo sapiens
<220> FEATURE:
<223> OTHER INFORMATION: UCH-L1 isoform 4 amino acid sequence

<400> SEQUENCE: 210

```
Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
            35                  40                  45

Leu Leu Leu Leu Phe Pro Leu Thr Ala Gln His Glu Asn Phe Arg Lys
50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
                100                 105                 110

Val Leu Lys Gln Phe Leu Ser Glu Thr Glu Lys Met Ser Pro Glu Asp
            115                 120                 125

Arg Ala Lys Cys Phe Glu Lys Asn Glu Ala Ile Gln Ala Ala His Asp
130                 135                 140

Ala Val Ala Gln Glu Gly Gln Cys Arg Val Asp Asp Lys Thr Leu Pro
145                 150                 155                 160

Arg Ser Ala Glu Asn Ser Pro Ser Val Ser Lys Glu Lys Ser Ala Ser
                165                 170                 175
```

```
Leu Pro Trp Leu Ser Ala Arg Gln Pro Asn Ala Leu Trp Glu Gly Leu
            180                 185                 190

Cys

<210> SEQ ID NO 211
<211> LENGTH: 182
<212> TYPE: PRT
<213> ORGANISM: Homo sapiens
<220> FEATURE:
<223> OTHER INFORMATION: UCH-L1 isoform 5 amino acid sequence

<400> SEQUENCE: 211

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
130                 135                 140

Ala Val Ala Gln Glu Gly Gln Cys Arg Val Asp Asp Lys Thr Leu Pro
145                 150                 155                 160

Arg His Leu Ser Thr Ser Arg Val His Ser Cys Pro Leu Gly His Cys
                165                 170                 175

Gly Val Ser Phe Arg Trp
            180

<210> SEQ ID NO 212
<211> LENGTH: 432
<212> TYPE: PRT
<213> ORGANISM: Homo sapiens
<220> FEATURE:
<223> OTHER INFORMATION: GFAP isoform 1 amino acid sequence

<400> SEQUENCE: 212

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95
```

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
            115                 120                 125

Gln Leu Thr Ala Asn Ser Ala Arg Leu Glu Val Glu Arg Asp Asn Leu
130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
            195                 200                 205

Arg Glu Leu Gln Glu Gln Leu Ala Arg Gln Gln Val His Val Glu Leu
210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
            275                 280                 285

Leu Gln Ser Leu Thr Cys Asp Leu Glu Ser Leu Arg Gly Thr Asn Glu
290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
            355                 360                 365

Leu Leu Glu Gly Glu Glu Asn Arg Ile Thr Ile Pro Val Gln Thr Phe
370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430

<210> SEQ ID NO 213
<211> LENGTH: 431
<212> TYPE: PRT
<213> ORGANISM: Homo sapiens
<220> FEATURE:
<223> OTHER INFORMATION: GFAP isoform 2 amino acid sequence

<400> SEQUENCE: 213

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

```
Pro Gly Thr Arg Leu Ser Leu Ala Arg Met Pro Pro Leu Pro Thr
        35                  40                  45

Arg Val Asp Phe Ser Leu Ala Gly Ala Leu Asn Ala Gly Phe Lys Glu
 50                  55                  60

Thr Arg Ala Ser Glu Arg Ala Glu Met Met Glu Leu Asn Asp Arg Phe
 65                  70                  75                  80

Ala Ser Tyr Ile Glu Lys Val Arg Phe Leu Glu Gln Gln Asn Lys Ala
                 85                  90                  95

Leu Ala Ala Glu Leu Asn Gln Leu Arg Ala Lys Glu Pro Thr Lys Leu
                100                 105                 110

Ala Asp Val Tyr Gln Ala Glu Leu Arg Glu Leu Arg Leu Arg Leu Asp
                115                 120                 125

Gln Leu Thr Ala Asn Ser Ala Arg Leu Glu Val Glu Arg Asp Asn Leu
130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
                180                 185                 190

Leu Glu Glu Glu Ile Arg Phe Leu Arg Lys Ile His Glu Glu Glu Val
                195                 200                 205

Arg Glu Leu Gln Glu Gln Leu Ala Arg Gln Gln Val His Val Glu Leu
210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
                260                 265                 270

Glu Leu Leu Arg Gln Ala Lys His Glu Ala Asn Asp Tyr Arg Arg Gln
                275                 280                 285

Leu Gln Ser Leu Thr Cys Asp Leu Glu Ser Leu Arg Gly Thr Asn Glu
                290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
                340                 345                 350

Leu Asn Val Lys Leu Ala Leu Asp Ile Glu Ile Ala Thr Tyr Arg Lys
                355                 360                 365

Leu Leu Glu Gly Glu Glu Asn Arg Ile Thr Ile Pro Val Gln Thr Phe
                370                 375                 380

Ser Asn Leu Gln Ile Arg Gly Gly Lys Ser Thr Lys Asp Gly Glu Asn
385                 390                 395                 400

His Lys Val Thr Arg Tyr Leu Lys Ser Leu Thr Ile Arg Val Ile Pro
                405                 410                 415

Ile Gln Ala His Gln Ile Val Asn Gly Thr Pro Pro Ala Arg Gly
                420                 425                 430

<210> SEQ ID NO 214
<211> LENGTH: 438
```

```
<212> TYPE: PRT
<213> ORGANISM: Homo sapiens
<220> FEATURE:
<223> OTHER INFORMATION: GFAP isoform 3 amino acid sequence

<400> SEQUENCE: 214

Met Glu Arg Arg Arg Ile Thr Ser Ala Ala Arg Arg Ser Tyr Val Ser
1               5                   10                  15

Ser Gly Glu Met Met Val Gly Leu Ala Pro Gly Arg Arg Leu Gly
            20                  25                  30

Pro Gly Thr Arg Leu Ser Leu Ala Arg Met Pro Pro Pro Leu Pro Thr
            35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
            115                 120                 125

Gln Leu Thr Ala Asn Ser Ala Arg Leu Glu Val Glu Arg Asp Asn Leu
130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
            195                 200                 205

Arg Glu Leu Gln Glu Gln Leu Ala Arg Gln Gln Val His Val Glu Leu
210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
            275                 280                 285

Leu Gln Ser Leu Thr Cys Asp Leu Glu Ser Leu Arg Gly Thr Asn Glu
290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
            355                 360                 365

Leu Leu Glu Gly Glu Glu Asn Arg Ile Thr Ile Pro Val Gln Thr Phe
370                 375                 380
```

```
Ser Asn Leu Gln Ile Arg Gly Gln Tyr Ser Arg Ala Ser Trp Glu Gly
385                 390                 395                 400

His Trp Ser Pro Ala Pro Ser Ser Arg Ala Cys Arg Leu Leu Gln Thr
                405                 410                 415

Gly Thr Glu Asp Gln Gly Lys Gly Ile Gln Leu Ser Leu Gly Ala Phe
            420                 425                 430

Val Thr Leu Gln Arg Ser
            435

<210> SEQ ID NO 215
<211> LENGTH: 324
<212> TYPE: PRT
<213> ORGANISM: Mus musculus
<220> FEATURE:
<223> OTHER INFORMATION: Heavy chain constant domain

<400> SEQUENCE: 215

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300
```

```
Leu His Glu Gly Leu His Asn His His Thr Glu Lys Ser Leu Ser His
305                 310                 315                 320

Ser Pro Gly Lys

<210> SEQ ID NO 216
<211> LENGTH: 335
<212> TYPE: PRT
<213> ORGANISM: Mus musculus
<220> FEATURE:
<223> OTHER INFORMATION: Heavy chain constant domain

<400> SEQUENCE: 216

Ala Lys Thr Thr Ala Pro Ser Val Tyr Pro Leu Val Pro Val Cys Gly
1               5                   10                  15

Gly Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Leu Leu Gln Ser Gly Leu Tyr Thr Leu
        50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro His Gln
            100                 105                 110

Arg Val Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Val Leu
305                 310                 315                 320

His Asn His Leu Thr Thr Lys Thr Ile Ser Arg Ser Leu Gly Lys
                325                 330                 335
```

<210> SEQ ID NO 217
<211> LENGTH: 404
<212> TYPE: PRT
<213> ORGANISM: Mus musculus
<220> FEATURE:
<223> OTHER INFORMATION: Heavy chain constant domain

<400> SEQUENCE: 217

```
Lys Thr Thr Pro Pro Ser Val Tyr Pro Leu Ala Pro Gly Cys Gly Asp
1               5                   10                  15

Thr Thr Gly Ser Ser Val Thr Leu Gly Cys Leu Val Lys Gly Tyr Phe
            20                  25                  30

Pro Glu Ser Val Thr Val Thr Trp Asn Ser Gly Ser Leu Ser Ser Ser
        35                  40                  45

Val His Thr Phe Pro Ala Leu Leu Gln Ser Gly Leu Tyr Thr Met Ser
    50                  55                  60

Ser Ser Val Thr Val Pro Ser Ser Thr Trp Pro Ser Gln Thr Val Thr
65                  70                  75                  80

Cys Ser Val Ala His Pro Ala Ser Ser Thr Thr Val Asp Lys Lys Leu
                85                  90                  95

Glu Pro Ser Gly Pro Ile Ser Thr Ile Asn Pro Cys Pro Pro Cys Lys
            100                 105                 110

Glu Cys His Lys Cys Pro Ala Pro Asn Leu Glu Gly Gly Pro Ser Val
        115                 120                 125

Phe Ile Phe Pro Pro Asn Ile Lys Asp Val Leu Met Ile Ser Leu Thr
    130                 135                 140

Pro Lys Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Ile Arg Val Val Ser
            180                 185                 190

Thr Leu Pro Ile Gln His Gln Asp Trp Met Ser Gly Lys Glu Phe Lys
        195                 200                 205

Cys Lys Val Asn Asn Lys Asp Leu Pro Ser Pro Ile Glu Arg Thr Ile
    210                 215                 220

Ser Lys Ile Lys Gly Leu Val Arg Ala Pro Gln Val Tyr Ile Leu Pro
225                 230                 235                 240

Pro Pro Ala Glu Gln Leu Ser Arg Lys Asp Val Ser Leu Thr Cys Leu
                245                 250                 255

Val Val Gly Phe Asn Pro Gly Asp Ile Ser Val Glu Trp Thr Ser Asn
            260                 265                 270

Gly His Thr Glu Glu Asn Tyr Lys Asp Thr Ala Pro Val Leu Asp Ser
        275                 280                 285

Asp Gly Ser Tyr Phe Ile Tyr Ser Lys Leu Asn Met Lys Thr Ser Lys
    290                 295                 300

Trp Glu Lys Thr Asp Ser Phe Ser Cys Asn Val Arg His Glu Gly Leu
305                 310                 315                 320

Lys Asn Tyr Tyr Leu Lys Lys Thr Ile Ser Arg Ser Pro Gly Leu Asp
                325                 330                 335

Leu Asp Asp Ile Cys Ala Glu Ala Lys Asp Gly Glu Leu Asp Gly Leu
            340                 345                 350

Trp Thr Thr Ile Thr Ile Phe Ile Ser Leu Phe Leu Leu Ser Val Cys
        355                 360                 365
```

-continued

```
Tyr Ser Ala Ser Val Thr Leu Phe Lys Val Lys Trp Ile Phe Ser Ser
        370                 375                 380

Val Val Glu Leu Lys Gln Lys Ile Ser Pro Asp Tyr Arg Asn Met Ile
385                 390                 395                 400

Gly Gln Gly Ala

<210> SEQ ID NO 218
<211> LENGTH: 329
<212> TYPE: PRT
<213> ORGANISM: Homo sapiens
<220> FEATURE:
<223> OTHER INFORMATION: Heavy chain constant domain

<400> SEQUENCE: 218

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly
            325

<210> SEQ ID NO 219
<211> LENGTH: 106
<212> TYPE: PRT
<213> ORGANISM: Mus musculus
<220> FEATURE:
<223> OTHER INFORMATION: Light chain constant domain

<400> SEQUENCE: 219

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 220
<211> LENGTH: 105
<212> TYPE: PRT
<213> ORGANISM: Mus musculus
<220> FEATURE:
<223> OTHER INFORMATION: Light chain constant domain

<400> SEQUENCE: 220

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Lys Val Asp Gly Thr Pro Val
        35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
            100                 105

<210> SEQ ID NO 221
<211> LENGTH: 106
<212> TYPE: PRT
<213> ORGANISM: Homo sapiens
<220> FEATURE:
<223> OTHER INFORMATION: Light chain constant domain

<400> SEQUENCE: 221

Thr Val Ala Ala Pro Ser Val Phe Ile Phe Pro Pro Ser Asp Glu Gln
1               5                   10                  15

```
Leu Lys Ser Gly Thr Ala Ser Val Val Cys Leu Leu Asn Asn Phe Tyr
         20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
50                   55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 222
<211> LENGTH: 106
<212> TYPE: PRT
<213> ORGANISM: Homo sapiens
<220> FEATURE:
<223> OTHER INFORMATION: Light chain constant domain

<400> SEQUENCE: 222

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 223
<211> LENGTH: 454
<212> TYPE: PRT
<213> ORGANISM: Mus musculus
<220> FEATURE:
<223> OTHER INFORMATION: Heavy chain constant domain

<400> SEQUENCE: 223

Ser Gln Ser Phe Pro Asn Val Phe Pro Leu Val Ser Cys Glu Ser Pro
1               5                   10                  15

Leu Ser Asp Lys Asn Leu Val Ala Met Gly Cys Leu Ala Arg Asp Phe
            20                  25                  30

Leu Pro Ser Thr Ile Ser Phe Thr Trp Asn Tyr Gln Asn Asn Thr Glu
        35                  40                  45

Val Ile Gln Gly Ile Arg Thr Phe Pro Thr Leu Arg Thr Gly Gly Lys
    50                  55                  60

Tyr Leu Ala Thr Ser Gln Val Leu Leu Ser Pro Lys Ser Ile Leu Glu
65                  70                  75                  80

Gly Ser Asp Glu Tyr Leu Val Cys Lys Ile His Tyr Gly Gly Lys Asn
                85                  90                  95
```

-continued

Arg Asp Leu His Val Pro Ile Pro Ala Val Ala Glu Met Asn Pro Asn
            100                 105                 110

Val Asn Val Phe Val Pro Pro Arg Asp Gly Phe Ser Gly Pro Ala Pro
            115                 120                 125

Arg Lys Ser Lys Leu Ile Cys Glu Ala Thr Asn Phe Thr Pro Lys Pro
            130                 135                 140

Ile Thr Val Ser Trp Leu Lys Asp Gly Lys Leu Val Glu Ser Gly Phe
145                 150                 155                 160

Thr Thr Asp Pro Val Thr Ile Glu Asn Lys Gly Ser Thr Pro Gln Thr
                165                 170                 175

Tyr Lys Val Ile Ser Thr Leu Thr Ile Ser Glu Ile Asp Trp Leu Asn
            180                 185                 190

Leu Asn Val Tyr Thr Cys Arg Val Asp His Arg Gly Leu Thr Phe Leu
            195                 200                 205

Lys Asn Val Ser Ser Thr Cys Ala Ala Ser Pro Ser Thr Asp Ile Leu
            210                 215                 220

Thr Phe Thr Ile Pro Pro Ser Phe Ala Asp Ile Phe Leu Ser Lys Ser
225                 230                 235                 240

Ala Asn Leu Thr Cys Leu Val Ser Asn Leu Ala Thr Tyr Glu Thr Leu
            245                 250                 255

Asn Ile Ser Trp Ala Ser Gln Ser Gly Glu Pro Leu Glu Thr Lys Ile
            260                 265                 270

Lys Ile Met Glu Ser His Pro Asn Gly Thr Phe Ser Ala Lys Gly Val
            275                 280                 285

Ala Ser Val Cys Val Glu Asp Trp Asn Asn Arg Lys Glu Phe Val Cys
            290                 295                 300

Thr Val Thr His Arg Asp Leu Pro Ser Pro Gln Lys Lys Phe Ile Ser
305                 310                 315                 320

Lys Pro Asn Glu Val His Lys His Pro Pro Ala Val Tyr Leu Leu Pro
            325                 330                 335

Pro Ala Arg Glu Gln Leu Asn Leu Arg Glu Ser Ala Thr Val Thr Cys
            340                 345                 350

Leu Val Lys Gly Phe Ser Pro Ala Asp Ile Ser Val Gln Trp Leu Gln
            355                 360                 365

Arg Gly Gln Leu Leu Pro Gln Glu Lys Tyr Val Thr Ser Ala Pro Met
370                 375                 380

Pro Glu Pro Gly Ala Pro Gly Phe Tyr Phe Thr His Ser Ile Leu Thr
385                 390                 395                 400

Val Thr Glu Glu Glu Trp Asn Ser Gly Glu Thr Tyr Thr Cys Val Val
                405                 410                 415

Gly His Glu Ala Leu Pro His Leu Val Thr Glu Arg Thr Val Asp Lys
            420                 425                 430

Ser Thr Gly Lys Pro Thr Leu Tyr Asn Val Ser Leu Ile Met Ser Asp
            435                 440                 445

Thr Gly Gly Thr Cys Tyr
            450

<210> SEQ ID NO 224
<211> LENGTH: 452
<212> TYPE: PRT
<213> ORGANISM: Homo sapiens
<220> FEATURE:
<223> OTHER INFORMATION: Heavy chain constant domain

<400> SEQUENCE: 224

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400
```

```
Ser Glu Glu Glu Trp Asn Thr Gly Glu Thr Tyr Thr Cys Val Ala His
                405             410                 415

Glu Ala Leu Pro Asn Arg Val Thr Glu Arg Thr Val Asp Lys Ser Thr
            420             425                 430

Gly Lys Pro Thr Leu Tyr Asn Val Ser Leu Val Met Ser Asp Thr Ala
        435             440                 445

Gly Thr Cys Tyr
    450
```